US012453501B2

(12) United States Patent
Hatakeyama

(10) Patent No.: US 12,453,501 B2
(45) Date of Patent: Oct. 28, 2025

(54) BIO-ELECTRODE COMPOSITION, BIO-ELECTRODE, METHOD FOR MANUFACTURING BIO-ELECTRODE, AND REACTION COMPOSITE

(71) Applicant: SHIN-ETSU CHEMICAL CO., LTD., Tokyo (JP)

(72) Inventor: Jun Hatakeyama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1024 days.

(21) Appl. No.: 17/522,306

(22) Filed: Nov. 9, 2021

(65) Prior Publication Data

US 2022/0160281 A1 May 26, 2022

(30) Foreign Application Priority Data

Nov. 26, 2020 (JP) ................................ 2020-196158

(51) Int. Cl.

| | |
|---|---|
| ***C08K 3/04*** | (2006.01) |
| ***A61B 5/024*** | (2006.01) |
| ***A61B 5/257*** | (2021.01) |
| ***A61B 5/265*** | (2021.01) |
| ***A61B 5/268*** | (2021.01) |
| ***C08K 3/08*** | (2006.01) |
| ***C08L 83/04*** | (2006.01) |

(52) U.S. Cl.

CPC .......... *A61B 5/268* (2021.01); *A61B 5/02444* (2013.01); *A61B 5/257* (2021.01); *A61B 5/265* (2021.01); *C08K 3/041* (2017.05); *C08K 3/08* (2013.01); *C08L 83/04* (2013.01); *C08K 2003/0806* (2013.01); *C08K 2201/001* (2013.01)

(58) Field of Classification Search

CPC ........... C08K 3/04; C08K 3/041; C08K 3/042

See application file for complete search history.

(56) References Cited

U.S. PATENT DOCUMENTS

| | | | | |
|---|---|---|---|---|
| 5,981,680 | A | 11/1999 | Petroff et al. | |
| 2002/0177039 | A1 | 11/2002 | Lu et al. | |
| 2002/0188069 | A1 | 12/2002 | Sugo et al. | |
| 2012/0308891 | A1 | 12/2012 | Todoriki et al. | |
| 2015/0275060 | A1 | 10/2015 | Kuroda et al. | |
| 2016/0155530 | A1 | 6/2016 | Someya et al. | |
| 2017/0275510 | A1 | 9/2017 | Quan et al. | |
| 2018/0072930 | A1 | 3/2018 | Hatakeyama et al. | |
| 2018/0085019 | A1 | 3/2018 | Hatakeyama et al. | |
| 2018/0086948 | A1 | 3/2018 | Hatakeyama et al. | |
| 2018/0215876 | A1 | 8/2018 | Hatakeyama et al. | |
| 2018/0229024 | A1* | 8/2018 | Hatakeyama .......... | A61B 5/291 |
| 2018/0273811 | A1 | 9/2018 | Cura et al. | |
| 2019/0106528 | A1 | 4/2019 | Hatakeyama et al. | |
| 2019/0209740 | A1* | 7/2019 | Hatakeyama ........ | A61B 5/0531 |
| 2020/0113464 | A1* | 4/2020 | Hatakeyama ............ | A61B 5/25 |
| 2020/0317840 | A1 | 10/2020 | Hatakeyama et al. | |

FOREIGN PATENT DOCUMENTS

| | | | |
|---|---|---|---|
| CN | 111789585 | A | 10/2020 |
| EP | 3 718 471 | A1 | 10/2020 |
| JP | H05-095924 | A | 4/1993 |
| JP | 2002-332305 | A | 11/2002 |
| JP | 2003-225217 | A | 8/2003 |
| JP | 2004-033468 | A | 2/2004 |
| JP | 2004-527902 | A | 9/2004 |
| JP | 2005-320418 | A | 11/2005 |
| JP | 2011-079946 | A | 4/2011 |
| JP | 2015-019806 | A | 2/2015 |
| JP | 2015-100673 | A | 6/2015 |
| JP | 2015-193803 | A | 11/2015 |
| JP | 2016-011338 | A | 1/2016 |
| JP | 2016-065238 | A | 4/2016 |
| JP | 2018-044147 | A | 3/2018 |
| JP | 2018-059050 | A | 4/2018 |
| JP | 2018-059052 | A | 4/2018 |
| JP | 2018-123304 | A | 8/2018 |
| JP | 2018-130534 | A | 8/2018 |
| JP | 2019-503406 | A | 2/2019 |
| JP | 2019-070109 | A | 5/2019 |
| JP | 2020-002342 | A | 1/2020 |
| JP | 2020-140973 | A | 9/2020 |
| KR | 10-2020-0117878 | A | 10/2020 |
| WO | 2013/039151 | A1 | 3/2013 |

OTHER PUBLICATIONS

Long et al.; Polymer Electrolytes for Lithium Polymer Batteries; J. Mater. Chem. A; 2016; p. 10038-10069; vol. 4.

Snyder et al.; Ion Conductivity of Comb Polysiloxane Polyelectrolytes Containing Oligoether and Perfluoroether Sidechains; J. of the Electrochemical Society; 2003; pp. A1090-A1094; vol. 150, No. 8.

Tsubokawa et al.; "The Curing of Epoxy Resins by Carbon Black;" Kobunshi Ronbunshu (Japanese Journal of Polymer Science and Technology); 1984; pp. 597-603; vol. 41, No. 10.

May 13, 2022 Extended Search Report issued in European Patent Application No. 21209358.7.

Oct. 27, 2023 Office Action issued in Korean Patent Application No. 10-2021-0161535.

(Continued)

*Primary Examiner* — Margaret G Moore
(74) *Attorney, Agent, or Firm* — Oliff PLC

(57) ABSTRACT

A bio-electrode composition contains (A) a reaction composite of a monomer having an ionic functional group and a carbon particle. The component (A) contains the carbon particle bonded to the monomer having a structure selected from the group consisting of salts of ammonium, lithium, sodium, potassium, and silver formed with any of fluorosulfonic acid, fluorosulfonimide, and N-carbonyl-fluorosulfonamide. Thus, the present invention provides: a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried; a bio-electrode including a living body contact layer formed of the bio-electrode composition; and a method for manufacturing the bio-electrode.

23 Claims, 3 Drawing Sheets

(56) References Cited

OTHER PUBLICATIONS

Oct. 31, 2022 Office Action and Search Report issued in Taiwanese Patent Application No. 110143642.
May 4, 2023 Office Action Issued in European Patent Application No. 21 209 358.7.

* cited by examiner

[FIG. 1]
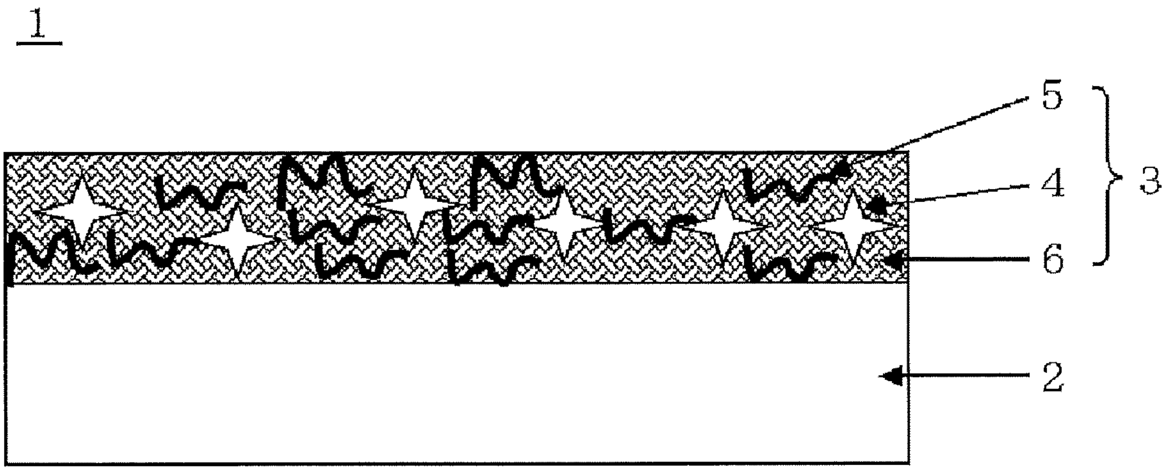
[FIG. 2]
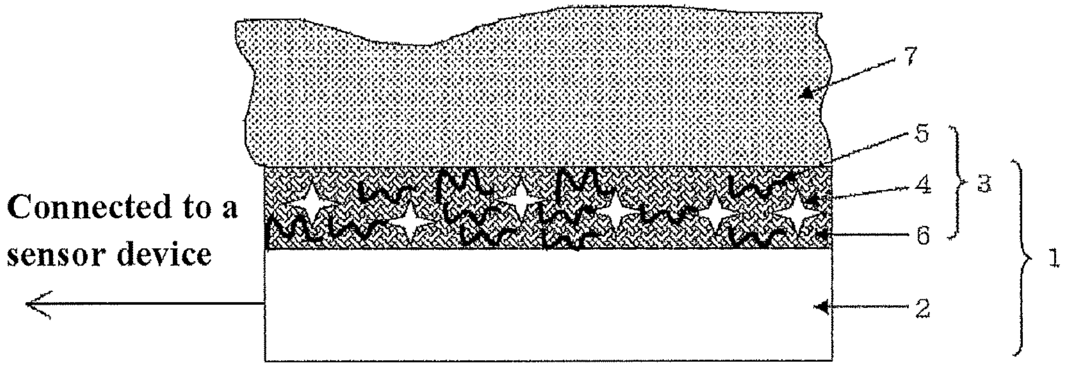

[FIG. 3]
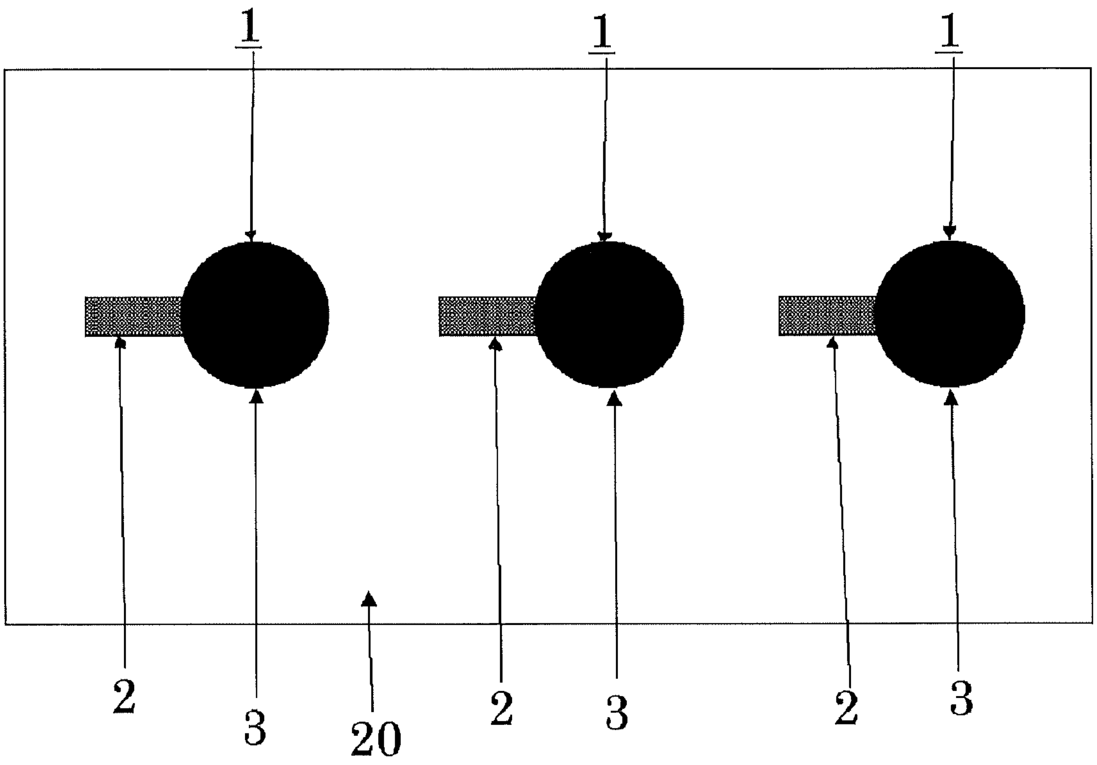
[FIG. 4]
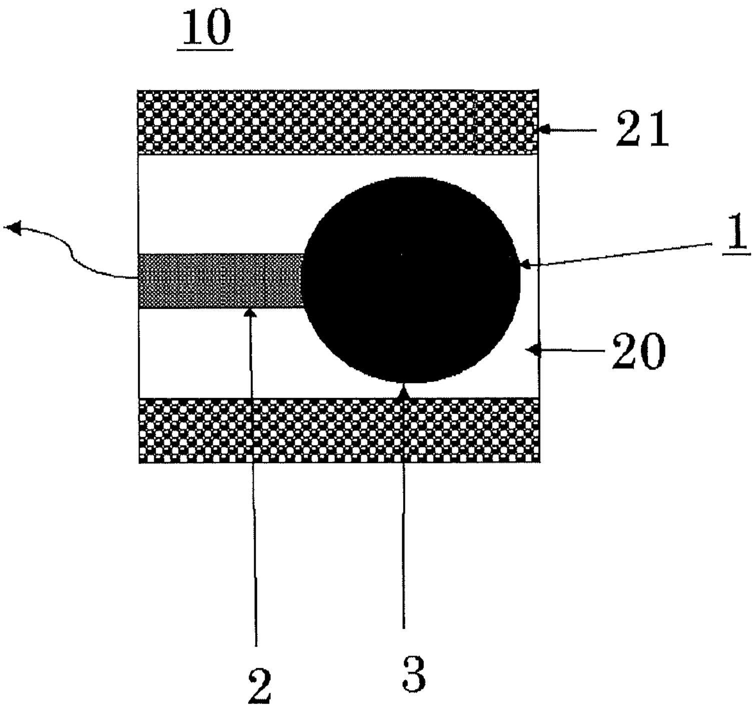

[FIG. 5]
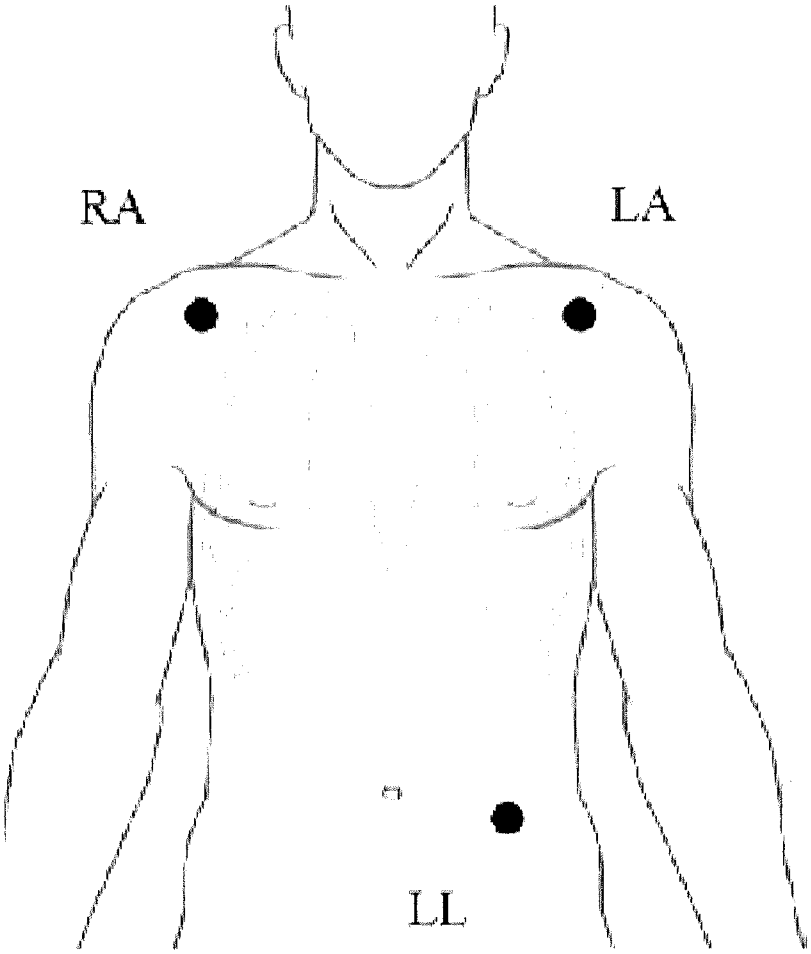
[FIG. 6]
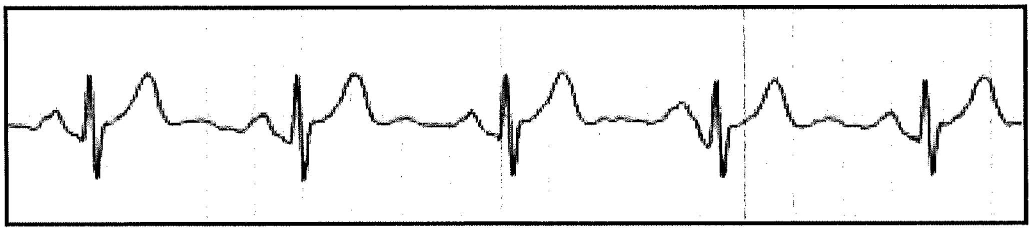

BIO-ELECTRODE COMPOSITION, BIO-ELECTRODE, METHOD FOR MANUFACTURING BIO-ELECTRODE, AND REACTION COMPOSITE

TECHNICAL FIELD

The present invention relates to: a bio-electrode that is used in contact with the skin of a living body and capable of detecting physical conditions such as heart rate by an electric signal transmitted from the skin; a method for manufacturing the bio-electrode; and a bio-electrode composition desirably used for a bio-electrode.

BACKGROUND ART

A recent growing popularity of Internet of Things (IoT) has accelerated the development of wearable devices, such as watches and eye-glasses that allow for Internet access. Even in the fields of medicine and sports, wearable devices for constantly monitoring the user's physical state are increasingly demanded, and such technological development is expected to be further encouraged.

In the field of medicine, use of wearable devices has been examined for monitoring the state of human organs by sensing extremely weak current, such as an electrocardiogram which detects an electric signal to measure the motion of the heart. The electrocardiogram measurement is conducted by attaching an electrode coated with an electro-conductive paste to a body, but this is a single (not continuous), short-time measurement. On the other hand, development of the above medical wearable device is aimed at device for continuously monitoring the health condition for a few weeks. Accordingly, a bio-electrode used in a medical wearable device is required to make no changes in electric conductivity even in long-time use and cause no skin allergy. In addition to these, it is also required that a bio-electrode is light-weight and can be produced at low cost.

Medical wearable devices are classified into two types: a type which is directly attached to body and a type which is incorporated into clothes. As the type which is attached to a body, it has been proposed a bio-electrode using water-soluble gel containing water and electrolyte, which are materials of the foregoing electro-conductive paste (Patent Document 1). The water-soluble gel contains sodium, potassium, or calcium as the electrolyte in a water-soluble polymer for retaining water, and converts changes of ion concentration from skin into electricity. On the other hand, as the type which is incorporated into clothes, it has been proposed a means to use cloth in which an electro-conductive polymer such as PEDOT-PSS (poly-3,4-ethylenedioxythiophene-polystyrenesulfonate) or silver paste is incorporated into the fibers for electrodes (Patent Document 2).

However, the use of the hydrophilic gel containing water and electrolytes unfortunately brings about loss of electric conductivity due to water evaporation in drying process. Meanwhile, the use of a higher-ionization-tendency metal such as copper can cause some users to suffer from skin allergy. The use of an electro-conductive polymer such as PEDOT-PSS can also cause skin allergy due to the strong acidity of the electro-conductive polymer, and further cause peeling of the electro-conductive polymer from fibers during washing.

By taking advantage of excellent electric conductivity, the use of metal nanowire, carbon black, carbon nanotube, and the like as electrode materials has been examined (Patent Documents 3, 4, and 5). With higher contact probability among metal nanowires, the wires can conduct electricity even when added in small quantities. The metal nanowire, however, can cause skin allergies since they are thin material with sharp tips. Even if these electrode materials themselves cause no allergic reaction in the manners described above, the biocompatibility may be degraded depending on the shape of a material and its inherent stimulation, thereby making it hard to satisfy both electric conductivity and biocompatibility.

Although metal films seem to function as excellent bio-electrodes thanks to extremely high electric conductivity, this is not always the case. Upon heartbeat, the human skin releases not only extremely weak current, but also sodium ion, potassium ion, and calcium ion. It is thus necessary to convert changes in ion concentration into current. Noble metals, however, are difficult to ionize and are inefficient in converting ions from skin to current. Therefore, the resulting bio-electrode using a noble metal is characterized by high impedance and high resistance to the skin during electrical conduction.

Meanwhile, the use of a battery containing an ionic liquid has been examined (Patent Document 6). Advantageously, the ionic liquid is thermally and chemically stable, and has excellent electric conductivity, providing wider battery applications. However, an ionic liquid having smaller molecular weight as shown in Patent Document 6 unfortunately dissolves into water. When a bio-electrode containing such an ionic liquid is used, the ionic liquid is extracted from the bio-electrode by sweating, which not only lowers the electric conductivity, but also causes rough dry skin as a result of the skin soaking with the liquid.

Batteries using a lithium salt of polymer type sulfonimide have also been examined (Non-Patent Document 1). Lithium has been applied to batteries because of their high ionic mobility. However, this is not a bio-compatible material. Additionally, lithium salts of fluorosulfonate have been examined in a form of a pendant on silicone (Non-Patent Document 2).

The bio-electrode fails to obtain biological information if it is apart from the skin. A change in contact area solely affects the quantity of electricity traveling through the electrode, and hence affects the baseline of an electrocardiogram (electric signal). Accordingly, in order to stably detect electric signals from the body, the bio-electrode is required to be in constant contact with the skin and make no changes in contact area. For this reason, the bio-electrode is preferably adherent. Moreover, the bio-electrode is required to have stretchability and flexibility so that the bio-electrode can follow changes in skin expansion or folding.

There has been examined a bio-electrode composed of: silver chloride at a portion which comes into contact with skin; and silver deposited at a portion through which electricity is conducted to a device. Solid silver chloride has neither adhesive strength to skin nor stretchability, so that the ability to collect biological signals is lowered particularly when the user moves. For this reason, a laminate film of silver chloride and silver is used as a bio-electrode with a water-soluble gel deposited between the bio-electrode and the skin. In this case, the aforementioned deterioration occurs when the gel is dried.

It has been reported that when an epoxy resin is mixed with carbon black, the curing reaction proceeds at lower temperature than when an epoxy resin is alone. This is because the reaction between the epoxy group and carboxyl group present on the surface of the carbon black allows the crosslinking reaction to proceed at lower temperature (Non-Patent Document 3).

A lithium ion battery using graphene oxide as a conduction auxiliary agent is reported (Patent Document 7). In this case, graphene oxide is used as a binder for improving the dispersibility and electric conductivity of the positive electrode material such as lithium cobaltate. Both ion battery and bio-electrode are required to have high ionic conductivity.

CITATION LIST

Patent Literature

Patent Document 1: WO 2013-039151 A1
Patent Document 2: JP 2015-100673 A
Patent Document 3: JP H05-095924 A
Patent Document 4: JP 2003-225217 A
Patent Document 5: JP 2015-019806 A
Patent Document 6: JP 2004-527902 A
Patent Document 7: JP 2020-140973 A

Non Patent Literature

Non-Patent Document 1: J. Mater. Chem. A, 2016, 4, p10038-10069
Non-Patent Document 2: J. of the Electrochemical Society, 150(8), A1090-A1094 (2003)
Non-Patent Document 3: Kobunshi Ronbunshu (Japanese Journal of Polymer Science and Technology), Vol. 41, No. 10, pp. 597-603 (1984)

SUMMARY OF INVENTION

Technical Problem

The present invention has been made to solve the above problems. An object of the present invention is to provide: a bio-electrode composition capable of forming a living body contact layer for a bio-electrode which is excellent in electric conductivity and biocompatibility, light-weight, and manufacturable at low cost, and which prevents significant reduction in the electric conductivity even when the bio-electrode is wetted with water or dried; a bio-electrode including a living body contact layer formed of the bio-electrode composition; and a method for manufacturing the bio-electrode.

Solution to Problem

To achieve the object, the present invention provides a bio-electrode composition comprising (A) a reaction composite comprising a monomer having an ionic functional group and a carbon particle, wherein the component (A) comprises the carbon particle bonded to the monomer having a structure selected from the group consisting of salts of ammonium, lithium, sodium, potassium, and silver formed with any of fluorosulfonic acid, fluorosulfonimide, and N-carbonyl-fluoro sulfonamide.

Such a bio-electrode composition is a bio-electrode composition capable of forming a living body contact layer for a bio-electrode which is excellent in electric conductivity and biocompatibility, light-weight, and manufacturable at low cost, and which prevents significant reduction in the electric conductivity even when wetted with water or dried.

The carbon particle is preferably selected from the group consisting of carbon black, carbon nanotube, graphite (black lead), and graphene.

Such carbon particles are suitably usable in the present invention.

The monomer having a structure selected from the group consisting of salts of ammonium, lithium, sodium, potassium, and silver formed with any of fluorosulfonic acid, fluorosulfonimide, and N-carbonyl-fluorosulfonamide preferably comprises a structure shown by any of the following general formulae (1)-1 to (1)-4, (1)-1

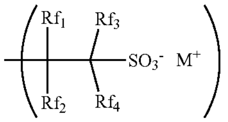

(1)-2

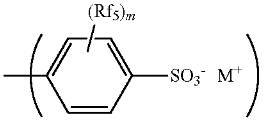

(1)-3

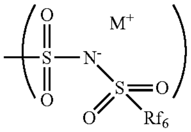

(1)-4

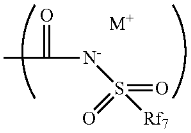

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; "m" represents an integer of 1 to 4; and $M^+$ represents an ion selected from the group consisting of an ammonium ion, a lithium ion, a sodium ion, a potassium ion, and a silver ion.

In this case, the monomer having a structure selected from the group consisting of salts of ammonium, lithium, sodium, potassium, and silver formed with any of fluorosulfonic acid, fluorosulfonimide, and N-carbonyl-fluorosulfonamide is preferably shown by any of the following general formulae (2)-1 to (2)-4, (2)-1

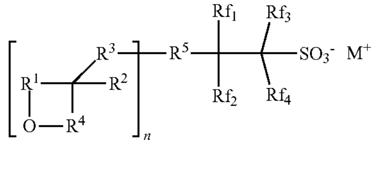

-continued (2)-2

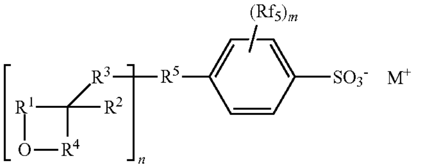

(2)-3

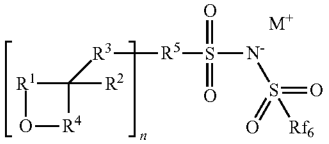

(2)-4

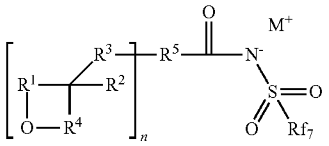

wherein $R^1$ represents an alkylene group having 1 to 8 carbon atoms, optionally bonded to $R^3$ to form a ring, and optionally having an ether group; $R^2$ represents a hydrogen atom, or an alkyl group having 1 to 4 carbon atoms; $R^3$ represents a single bond, or a linear, branched, or cyclic alkylene group having 1 to 20 carbon atoms, and optionally has an aromatic group, an ether bond, an ester bond, a hydroxy group, or a nitrogen atom; $R^4$ represents a single bond or a methylene group; $R^5$ represents a single bond, or a hydrocarbon group with a valency of (n+1) having 1 to 10 carbon atoms and optionally having an ether group or an ester group; "n" represents 1 or 2; and $Rf_1$ to $Rf_7$, $M^+$, and "m" are as defined above.

More preferably, the component (A) is a reaction product between 100 parts by mass of the carbon particle and 5 parts by mass or more of the monomer having an ionic functional group.

Further preferably, the component (A) comprises an ammonium ion shown by the following general formula (3) as an ammonium ion for forming the ammonium salts, (3)

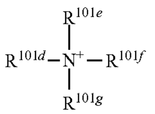

wherein $R^{101d}$, $R^{101e}$, $R^{101f}$, and $R^{101g}$ each represent a hydrogen atom, a linear, branched, or cyclic alkyl group having 1 to 13 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

Such bio-electrode compositions have a pendant of a monomer having an ionic functional group on the carbon particle, so that both of the ionic conductivity and electron conductivity are improved, and the sensitivity of the resulting bio-electrode is improved. Besides, it is possible to prevent the monomer having an ionic functional group from being extracted out of the bio-electrode film, and decrease in the sensitivity to biological signals due to the extraction can be prevented. Further, the permeability through skin and the stimulus to the skin are reduced. This makes it possible to more surely prevent the compositions from permeating the skin and causing allergies.

The bio-electrode composition preferably further comprises a component (B) which is an adhesive resin.

In this case, the component (B) is preferably one or more selected from the group consisting of a silicone resin, a (meth)acrylate resin, and a urethane resin.

Such materials enable constant adhesion to skin and stable electric-signal collection for a long time.

More preferably, the component (B) comprises diorganosiloxane having an alkenyl group, and organohydrogenpolysiloxane having an SiH group.

In this case, the component (B) preferably further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

Such materials can be suitably used in the bio-electrode composition.

The bio-electrode composition preferably further comprises a component (C) which is a polymer compound having an ionic repeating unit.

In this case, the ionic repeating unit of the component (C) preferably comprises a repeating unit having a structure selected from the group consisting of salts of ammonium, lithium, sodium, potassium, and silver formed with any of fluorosulfonic acid, fluorosulfonimide, and N-carbonyl-fluorosulfonamide.

When the bio-electrode composition contains a polymer compound having such repeating units, the effects of the present invention can be further enhanced.

The bio-electrode composition preferably further comprises a component (D) which is a carbon powder and/or a metal powder.

In this case, the carbon powder is preferably one or both of carbon black and carbon nanotube.

The metal powder is preferably a powder of a metal selected from the group consisting of gold, silver, platinum, copper, tin, titanium, nickel, aluminum, tungsten, molybdenum, ruthenium, chromium, and indium.

In this case, the metal powder is preferably a silver powder.

Such materials further improve the electric conductivity.

The bio-electrode composition preferably further comprises a component (E) which is an organic solvent.

Such a material makes the coating property of the bio-electrode composition further favorable.

Moreover, the present invention provides a bio-electrode comprising an electro-conductive base material and a living body contact layer formed on the electro-conductive base material, wherein the living body contact layer is a cured product of the above-described bio-electrode composition.

The inventive bio-electrode is excellent in electric conductivity and biocompatibility, light-weight, and manufacturable at low cost. Even when wetted with water or dried, the bio-electrode prevents significant reduction in the electric conductivity.

The electro-conductive base material preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive bio-electrode, such electro-conductive base materials are particularly suitably usable.

Further, the present invention provides a method for manufacturing a bio-electrode having an electro-conductive base material and a living body contact layer formed on the electro-conductive base material, comprising:

applying the above-described bio-electrode composition onto the electro-conductive base material; and curing the bio-electrode composition to form the living body contact layer.

According to the inventive method for manufacturing a bio-electrode, it is possible to easily manufacture a bio-electrode which is excellent in electric conductivity and biocompatibility, light-weight, and manufacturable at low cost, and which prevents significant reduction in the electric conductivity even when the bio-electrode is wetted with water or dried.

The electro-conductive base material to be used preferably comprises one or more selected from the group consisting of gold, silver, silver chloride, platinum, aluminum, magnesium, tin, tungsten, iron, copper, nickel, stainless steel, chromium, titanium, carbon, and electro-conductive polymer.

In the inventive method for manufacturing a bio-electrode, such electro-conductive base materials are particularly suitably usable.

Furthermore, the present invention provides a reaction composite comprising a monomer having an ionic functional group and a carbon particle, wherein the reaction composite comprises the carbon particle bonded to the monomer having a structure selected from the group consisting of salts of ammonium, lithium, sodium, potassium, and silver formed with any of fluorosulfonic acid, fluorosulfonimide, and N-carbonyl-fluorosulfonamide.

The carbon particle is preferably selected from the group consisting of carbon black, carbon nanotube, graphite (black lead), and graphene.

Through modification of such carbon particles with a monomer having an ionic functional group, the resulting particles become a particularly useful component of a bio-electrode composition capable of forming a living body contact layer for a bio-electrode which enables high-sensitive and efficient conduction of ions released from skin and electric signals to a device (i.e., excellent in electric conductivity), which causes no allergy even when the bio-electrode is attached to skin for a long period (i.e., excellent in biocompatibility), and which prevents significant reduction in the electric conductivity even when the bio-electrode is wetted with water or dried.

Advantageous Effects of Invention

As described above, the inventive bio-electrode composition containing a carbon particle having an ionic functional group-containing monomer bonded thereto (i.e., reaction composite of the carbon particle and the monomer having an ionic functional group) makes it possible to form a living body contact layer for a bio-electrode that is capable of efficiently conducting electric signals from skin to a device (i.e., excellent in electric conductivity), free from the risk of causing allergies even when the bio-electrode is worn on skin for a long period (i.e., excellent in biocompatibility), light-weight, manufacturable at low cost, and free from significant reduction of the electric conductivity even when the bio-electrode is wetted with water or dried. The electric conductivity can be further enhanced by additionally adding an ionic polymer compound and/or an electro-conductive powder (carbon powder, metal powder). A bio-electrode having particularly high adhesive strength and high stretchability can be produced by the combination with a resin that has adhesion and stretchability. Moreover, the stretchability and the adhesion to skin can be enhanced using additives, etc. The stretchability and the adhesion can also be adjusted by appropriately controlling the composition of the resin or the thickness of the living body contact layer.

With the above-described carbon particles having an ionic functional group-containing monomer bonded thereto, the inventive bio-electrode is allowed to achieve both of electric conductivity and biocompatibility, and is also allowed to have adhesion. Thus, it is possible to keep the contact area with skin constant and to stably obtain electric signals from skin with high sensitivity.

Additionally, the inventive method for manufacturing a bio-electrode enables simple and low-cost manufacturing of the inventive bio-electrode, which is excellent in electric conductivity and biocompatibility, light-weight, and free from significant reduction of the electric conductivity even when it is wetted with water or dried.

BRIEF DESCRIPTION OF DRAWINGS

FIG. 1 is a schematic sectional view showing an example of the inventive bio-electrode;

FIG. 2 is a schematic sectional view showing an example of the inventive bio-electrode worn on a living body;

FIG. 3 is a schematic view of printed bio-electrodes prepared in Examples of the present invention;

FIG. 4 is a schematic view of one of the bio-electrodes prepared in Examples of the present invention, the bio-electrode being cut out and provided with an adhesive layer and an electro-conductive line thereon;

FIG. 5 is a view showing locations where electrodes and earth are attached on a human body in measuring biological signals in Examples of the present invention; and FIG. 6 shows one of electrocardiogram waveforms obtained using the bio-electrodes in Examples of the present invention.

DESCRIPTION OF EMBODIMENTS

As noted above, it has been desired to develop: a bio-electrode composition that can form a living body contact layer for a bio-electrode which is excellent in biocompatibility and electric conductivity so as to detect biological signals with high sensitivity but low noise, which is light-weight and manufacturable at low cost, and which prevents significant reduction in the electric conductivity even when wetted with water or dried and prevents residue from remaining on skin after peeling from the skin; a bio-electrode including a living body contact layer formed from the bio-electrode composition; and a method for manufacturing the bio-electrode.

The surface of skin releases ions of sodium, potassium, and calcium in accordance with heartbeat. A bio-electrode has to convert the increase and decrease of these ions released from skin to electric signals. Accordingly, the bio-electrode requires a material that is excellent in ionic conductivity to transmit the increase and decrease of ions. The electric potential on the skin surface also varies in accordance with heartbeat. This variation of the electric potential is so small that the bio-electrode also requires electron conductivity to transmit extremely weak current to a device.

Water-soluble gels containing sodium chloride or potassium chloride have high ionic conductivity and electron conductivity. However, when the water is dried up, the electric conductivity is lost. Additionally, the electric conductivity is lowered by elution of sodium chloride or potassium chloride from the bio-electrode while the user takes a bath or shower, too.

A bio-electrode using a metal such as gold or silver detects only extremely weak current and has low ionic conductivity, and the sensitivity as a bio-electrode is low. Like metals, carbon has electron conductivity, but the electron conductivity is lower than those of metals, so that the sensitivity as a bio-electrode is lower than those of metals.

Electro-conductive polymers represented by PEDOT-PSS have both electron conductivity and ionic conductivity. Nevertheless, since the polarity is low, the ionic conductivity is not so high.

Salts of fluorosulfonic acid, fluorosulfonimide, and N-carbonyl-fluorosulfonamide have high polarity and high ionic conductivity. The present invention aims to combine such a salt with a carbon particle to achieve both high ionic conductivity and high electron conductivity.

To stably obtain biological signals after attachment to skin, a bio-electrode film needs to have adhesion. Meanwhile, if a residue remains on skin when a bio-electrode is peeled after long-time attachment, the residue may cause rash or rough skin. The present invention has been devised, considering that the bio-electrode needs to incorporate an ionic monomer bonded to a carbon particle to prevent such residue.

The present inventor and colleagues herein propose: a bio-electrode composition which contains an ionic polymer bonded to a carbon particle; and a bio-electrode including the cured bio-electrode composition.

In neutralized salts formed from highly acidic acids, the ions are strongly polarized to improve the ionic conductivity. This is why lithium salts of bis(trifluoromethanesulfonyl)imidic acid and tris(trifluoromethanesulfonyl)methide acid show high ionic conductivity as a lithium ion battery. On the other hand, the higher acidity of the acid before the neutral salt formation results in a problem that the salt has stronger irritation to a body. That is, ionic conductivity and irritation to a body are in relation of trade-off. However, a salt applied to a bio-electrode has to achieve both higher ionic conductivity and lower irritation to a body.

An ion compound decreases its permeability through skin and irritation to the skin as the molecular weight is larger. Accordingly, an ion compound is preferably in a form of a polymer with higher molecular weight or bonded to a particle of carbon, silica, etc. Thus, the present inventor and colleagues have conceived that adding a composite of an ionic monomer bonded to a carbon powder prevents residue after the long-time attachment on the skin and peeling therefrom.

Further, when this salt is mixed with, for example, a silicone-based, acrylic-based, or urethane-based adhesive (resin), the use of this mixture enables constant adhesion to skin and stable electric-signal collection for a long term.

Both of high ionic conductivity and high electron conductivity are important to form a bio-electrode of high sensitivity. To increase the electron conductivity, adding a metal powder and/or a carbon powder is effective.

In sum, the present invention is a bio-electrode composition comprising (A) a reaction composite comprising a monomer having an ionic functional group and a carbon particle, wherein the component (A) comprises the carbon particle bonded to the monomer having a structure selected from the group consisting of salts of ammonium, lithium, sodium, potassium, and silver formed with any of fluorosulfonic acid, fluorosulfonimide, and N-carbonyl-fluorosulfonamide.

Hereinafter, the present invention will be described in detail, but the present invention is not limited thereto.

<Bio-Electrode Composition>

The inventive bio-electrode composition contains (A) a reaction composite of a monomer having an ionic functional group (ionic monomer) and a carbon particle, and preferably contains (B) an adhesive resin. Hereinbelow, each component will be described in more details.

[(A) Reaction Composite (Salt) of Monomer with Ionic Functional Group and Carbon Particle]

In the inventive bio-electrode composition, the reaction composite (A) of a monomer having an ionic functional group and a carbon particle (ionic monomer-particle composite salt) is in a particulate form made of carbon bonding to the monomer which has a structure selected from the group consisting of salts of ammonium, lithium, sodium, potassium, and silver formed with any of fluorosulfonic acid, fluorosulfonimide, and N-carbonyl-fluorosulfonamide. The reaction composite (A) is preferably a material in which a monomer having an oxirane group or an oxetane group in addition to the ionic structure is bonded to the carbon particle by reaction.

The structure selected from the group consisting of salts of ammonium, lithium, sodium, potassium, and silver formed with any of fluorosulfonic acid, fluorosulfonimide, and N-carbonyl-fluorosulfonamide is preferably shown by any of the following general formulae (1)-1 to (1)-4.

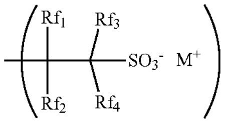

(1)-1

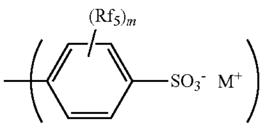

(1)-2

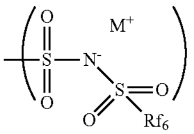

(1)-3

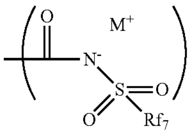

(1)-4

In the formulae, $Rf_1$ and $Rf_2$ each represent a hydrogen atom, a fluorine atom, an oxygen atom, a methyl group, or a trifluoromethyl group. When $Rf_1$ and $Rf_2$ represent an oxygen atom, the single oxygen atom represented by $Rf_1$ and $Rf_2$ bonds to a single carbon atom to form a carbonyl group. $Rf_3$ and $Rf_4$ each represent a hydrogen atom, a fluorine atom, or a trifluoromethyl group. At least one of $Rf_1$ to $Rf_4$ is a fluorine atom or a trifluoromethyl group. $Rf_5$, $Rf_6$, and $Rf_7$ each represent a fluorine atom, or a linear or branched alkyl group having 1 to 4 carbon atoms, and have at least one fluorine atom. "m" represents an integer of 1 to 4. $M^+$ represents an ion selected from the group consisting of an ammonium ion, a lithium ion, a sodium ion, a potassium ion, and a silver ion.

The monomer having a structure selected from the group consisting of salts of ammonium, lithium, sodium, potassium, and silver formed with any of fluorosulfonic acid, fluorosulfonimide, and N-carbonyl-fluorosulfonamide is preferably a monomer having an oxirane group or an oxetane group in addition to these structures, and more preferably shown by any of the following general formulae (2)-1 to (2)-4.

(2)-1

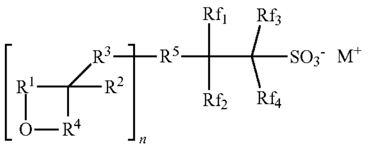

(2)-2

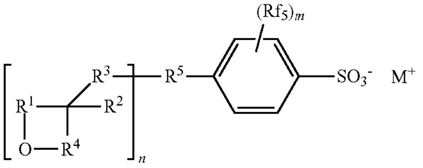

(2)-3

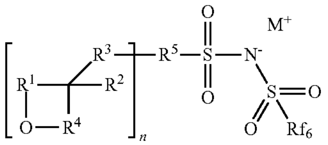

(2)-4

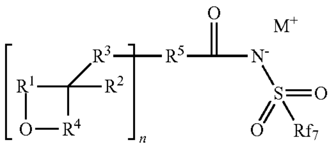

In the formulae, $R^1$ represents an alkylene group having 1 to 8 carbon atoms optionally bonded to $R^3$ to form a ring, and optionally having an ether group. $R^2$ represents a hydrogen atom, or an alkyl group having 1 to 4 carbon atoms. $R^3$ represents a single bond, or a linear, branched, or cyclic alkylene group having 1 to 20 carbon atoms, and optionally has an aromatic group, an ether bond, an ester bond, a hydroxy group, or a nitrogen atom. $R^4$ represents a single bond or a methylene group. $R^5$ represents a single bond, or a hydrocarbon group with a valency of (n+1) having 1 to 10 carbon atoms and optionally having an ether group or an ester group. "n" represents 1 or 2. $Rf_1$ to $Rf_7$, $M^+$, and "m" are as defined above.

$Rf_1$ to $Rf_7$ are preferably a fluorine atom, a hydrogen atom, or a trifluoromethyl group.

Specific examples of the monomer shown by the general formula (2)-1 can include the following.

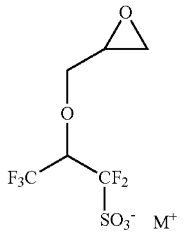

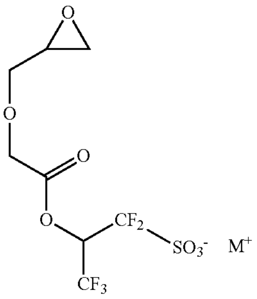

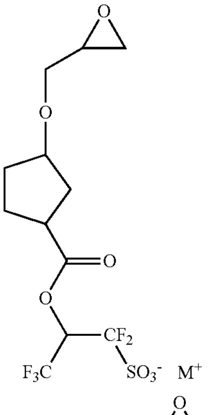

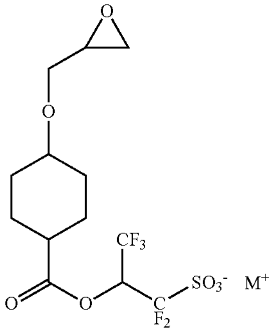

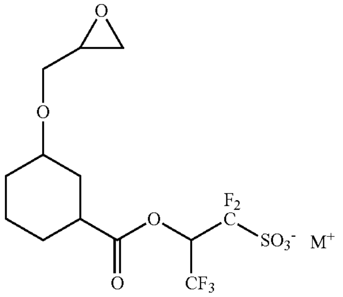

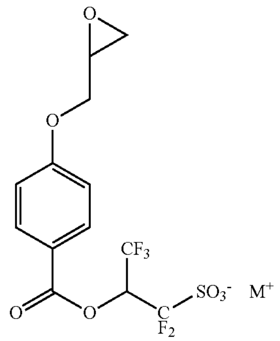

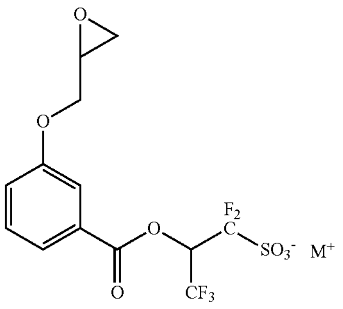

-continued
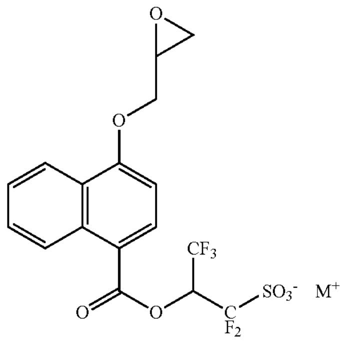
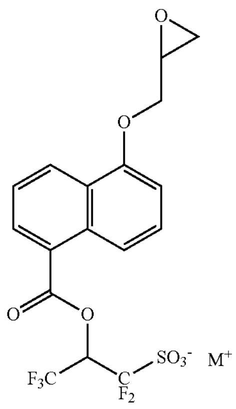
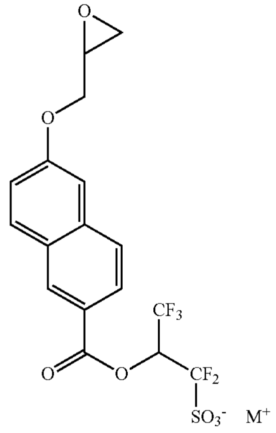
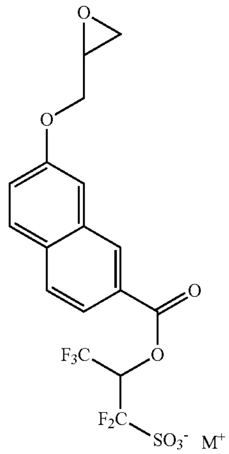
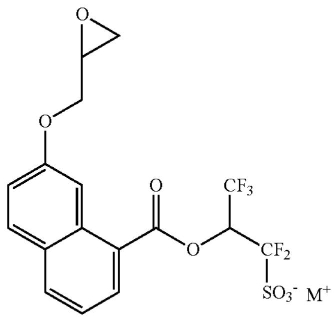
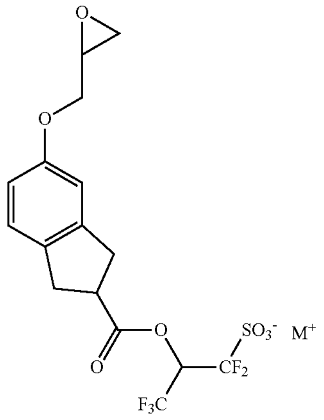
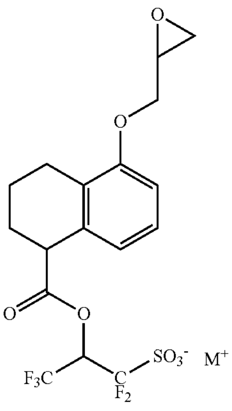
-continued
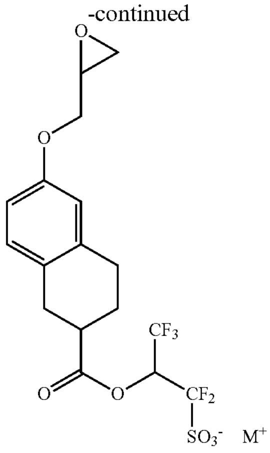
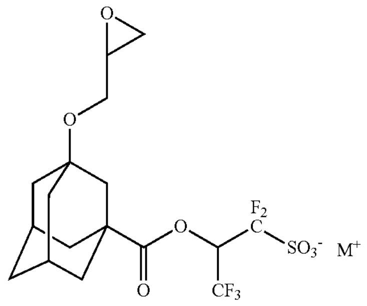
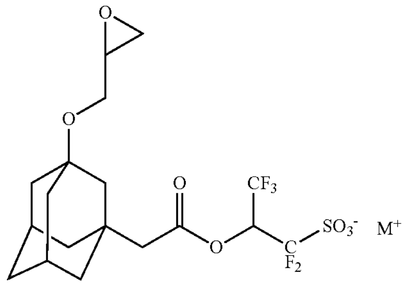
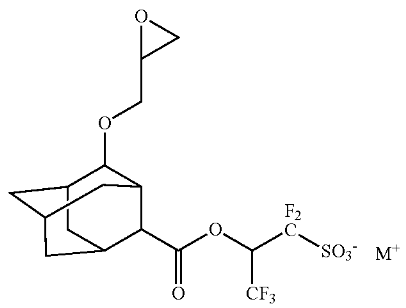
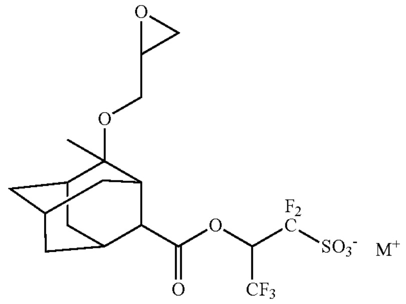

-continued
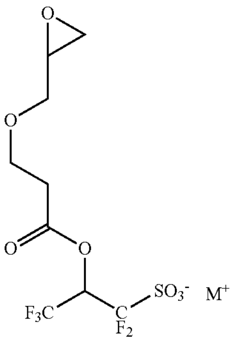
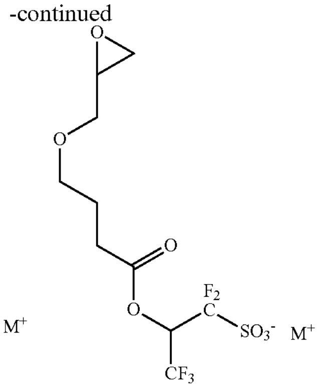
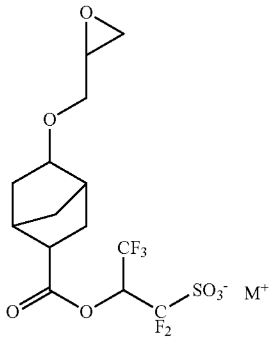
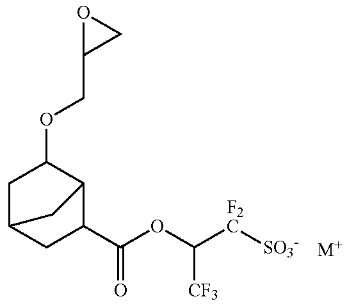
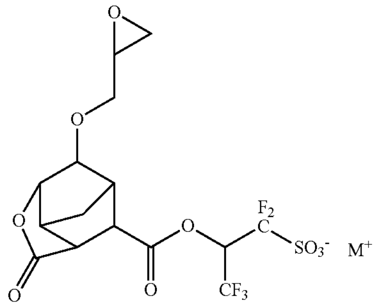
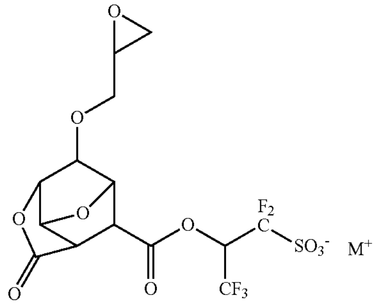
-continued
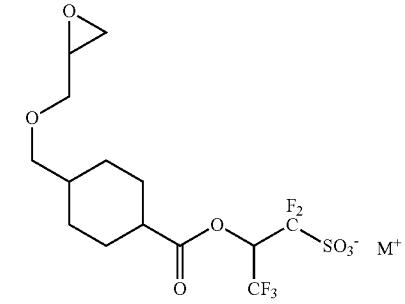
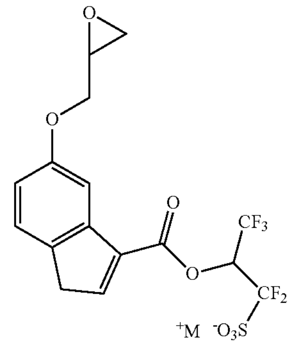
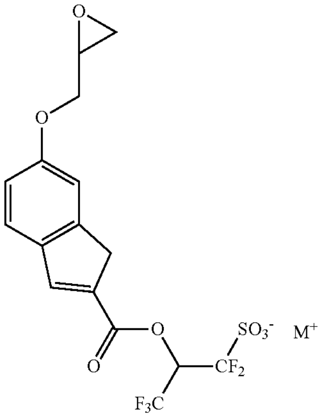
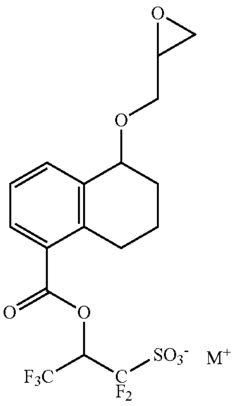
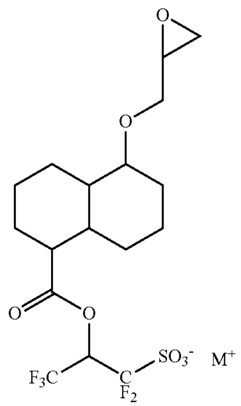

-continued
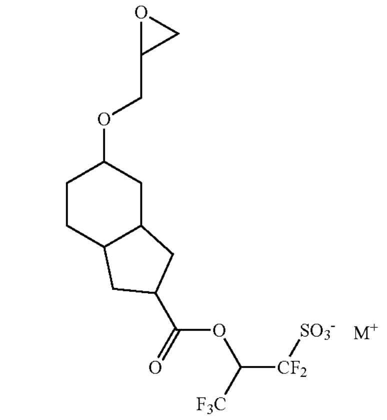
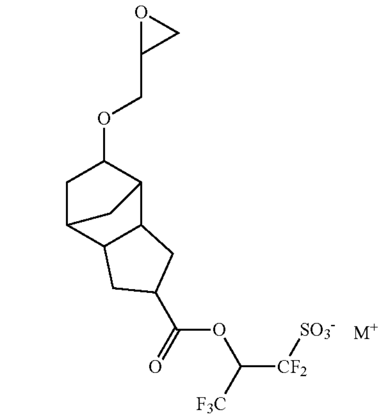
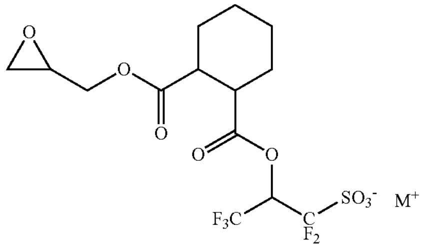
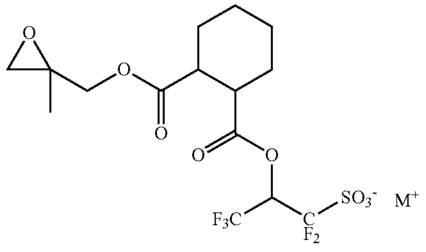
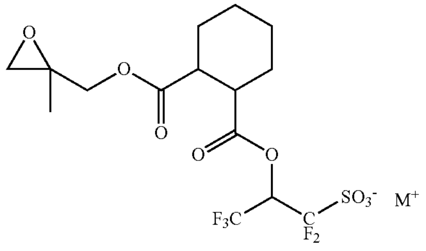
-continued
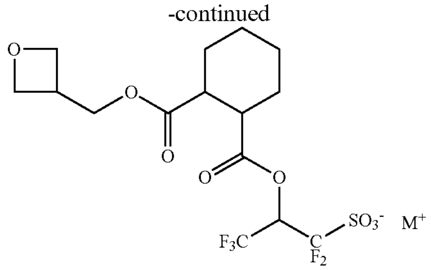
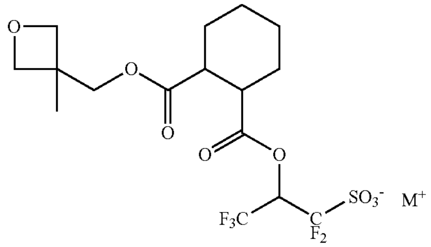
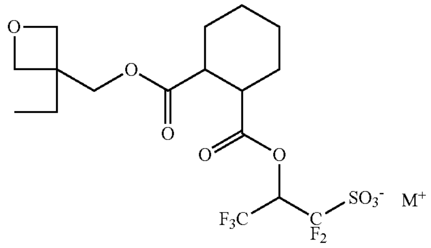
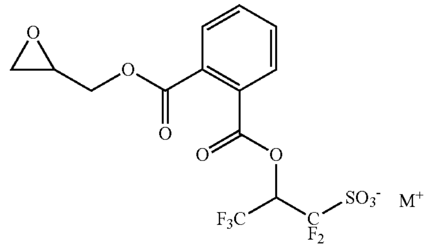
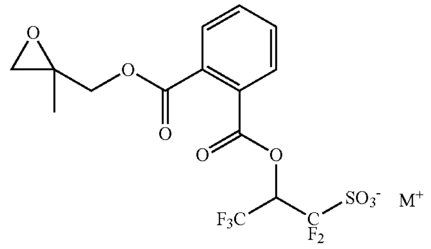
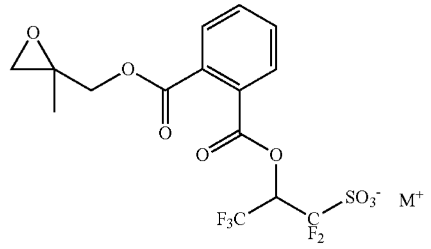
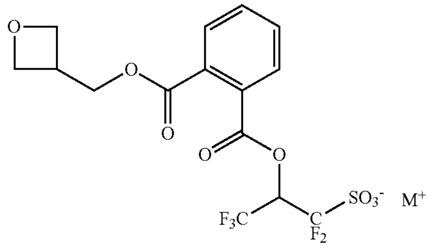

-continued
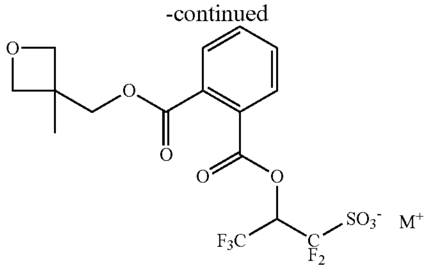
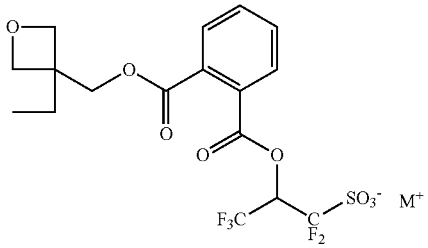
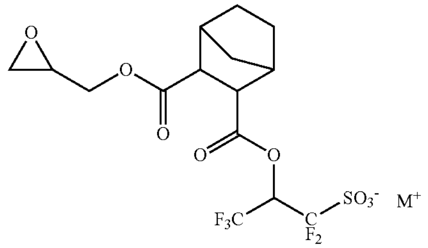
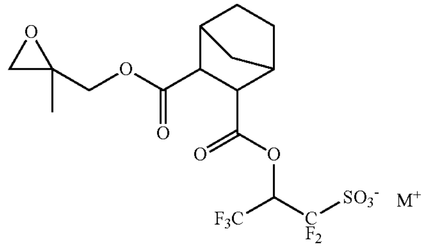
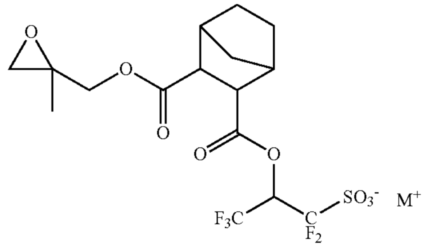
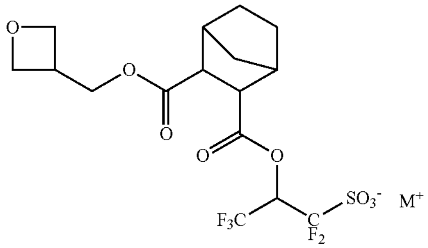
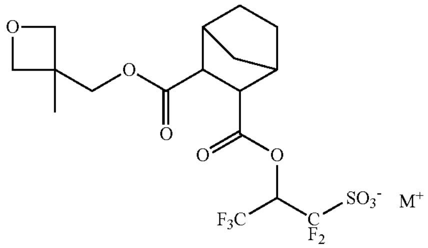
-continued
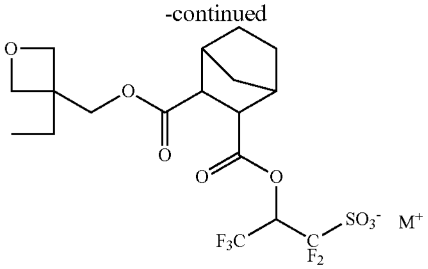
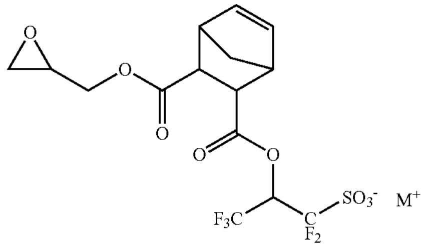
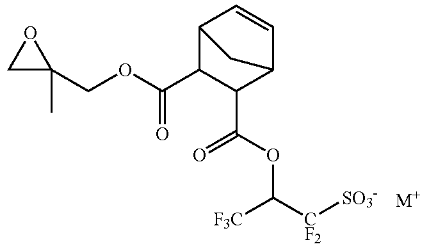
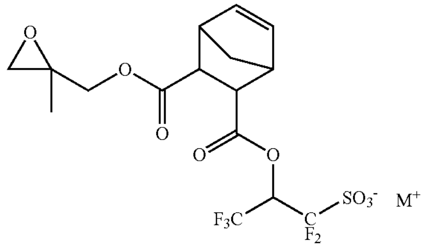
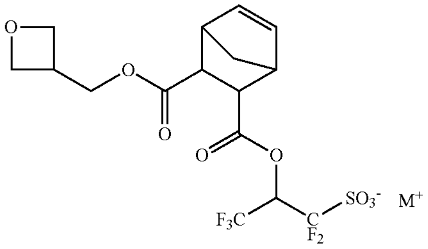
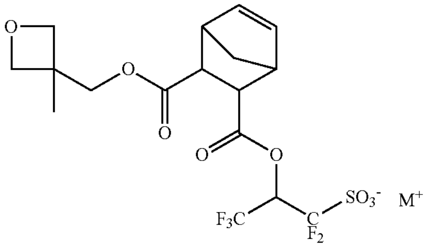
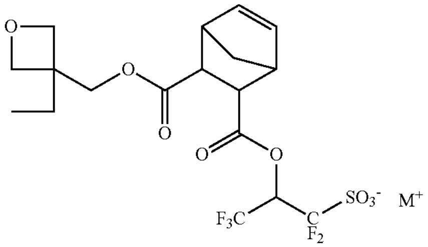

-continued
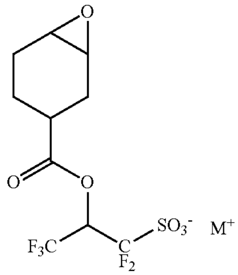
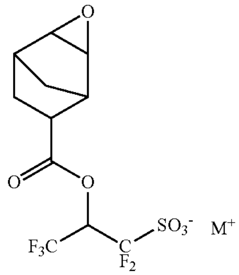
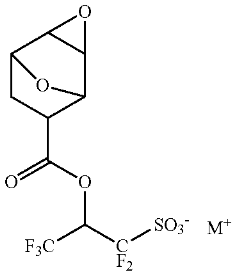
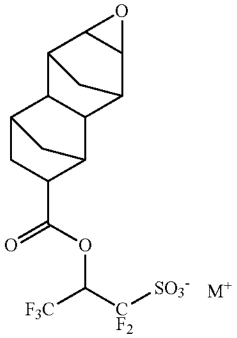
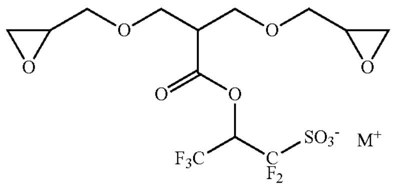
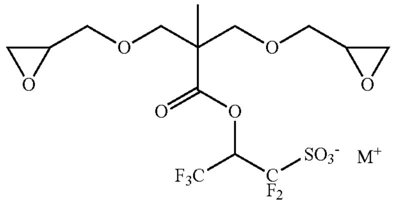
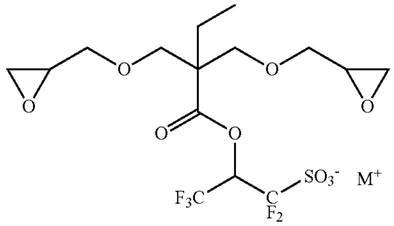
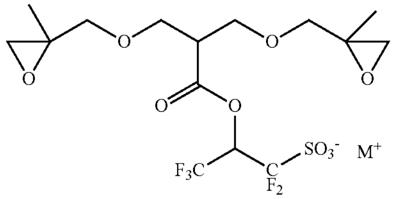
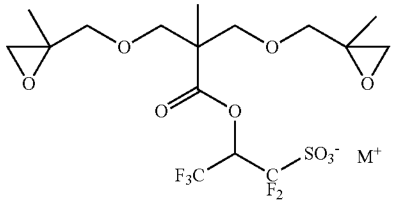
-continued
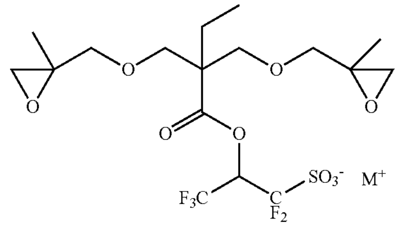
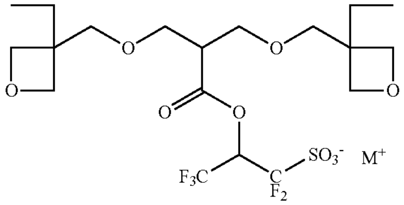
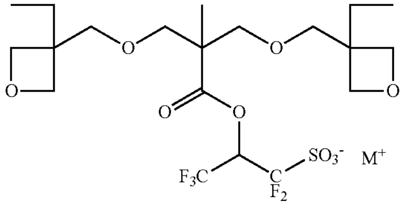
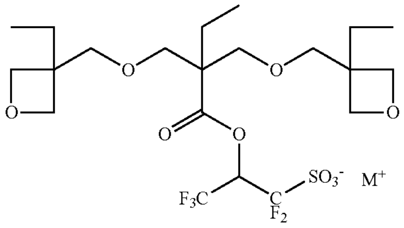
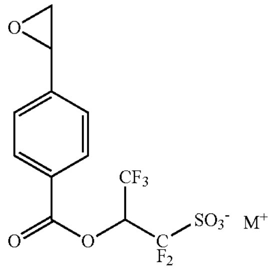
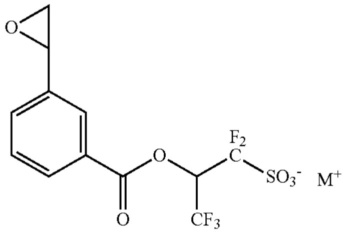
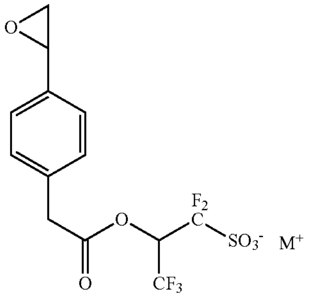

-continued
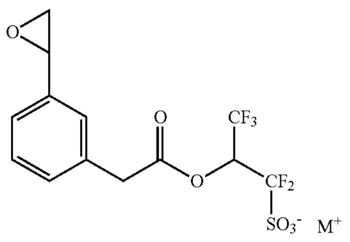
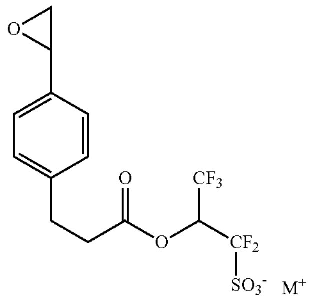
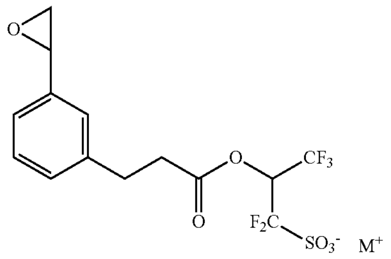
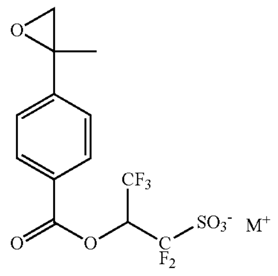
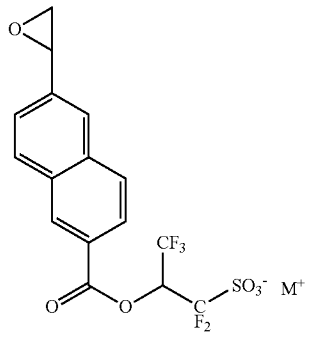
-continued
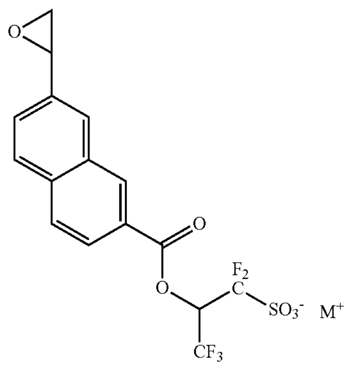
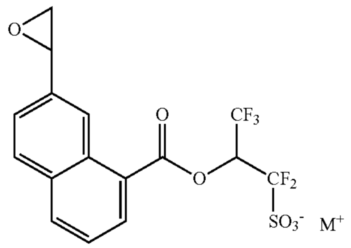
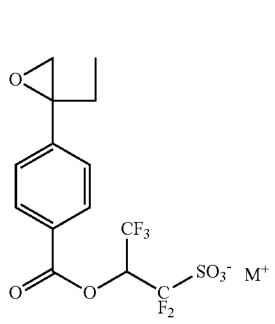
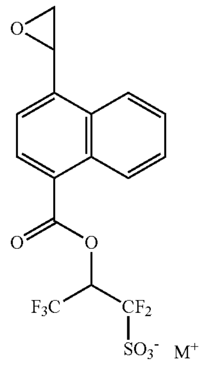
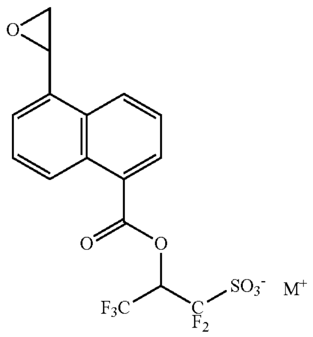
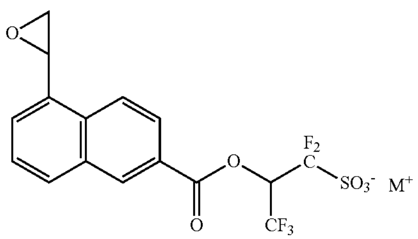

-continued
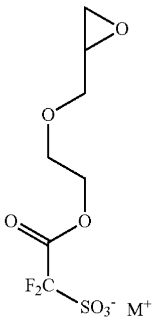
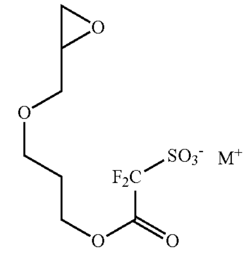
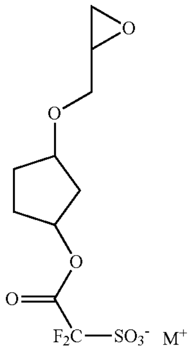
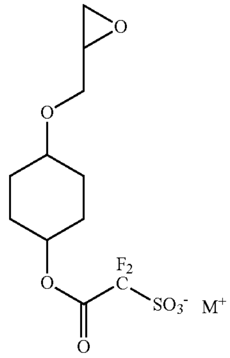
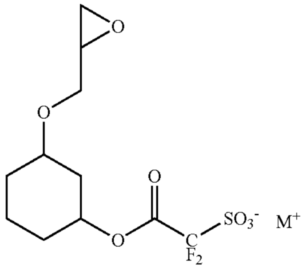
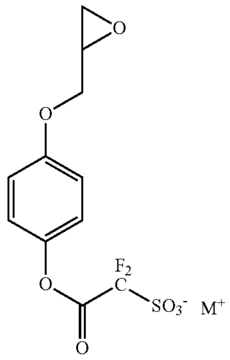
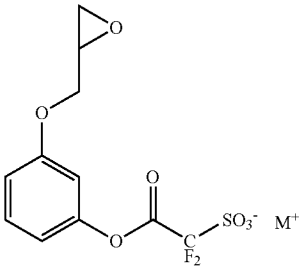
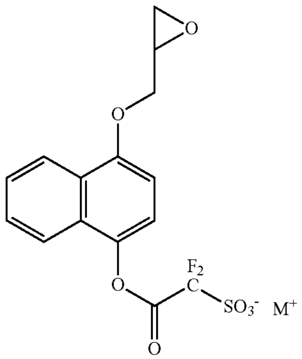
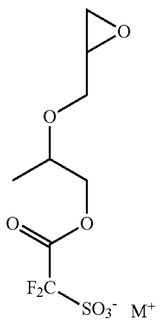
-continued
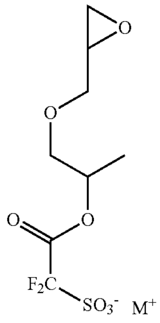
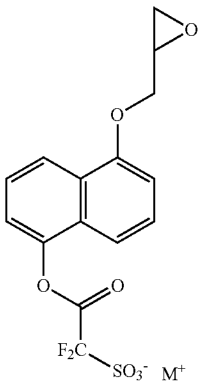
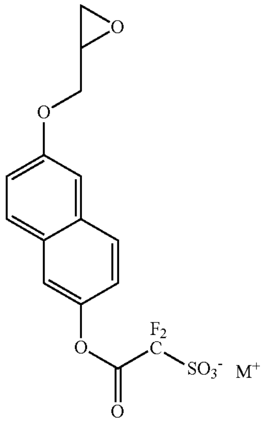
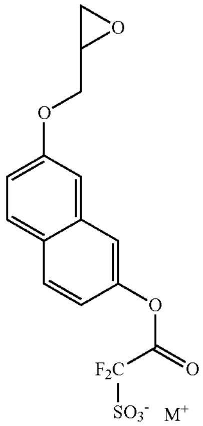
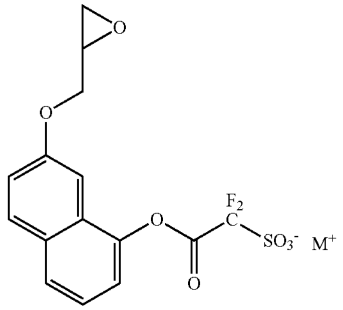
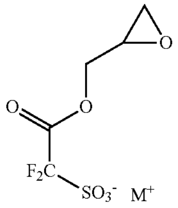
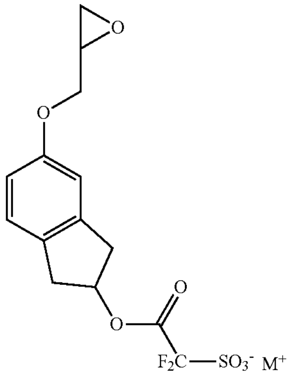

-continued
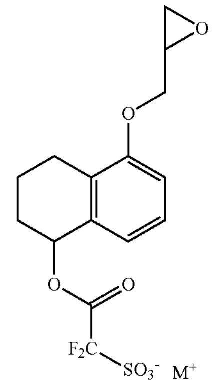
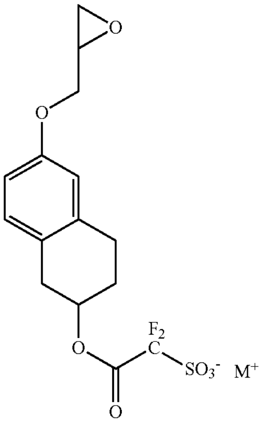
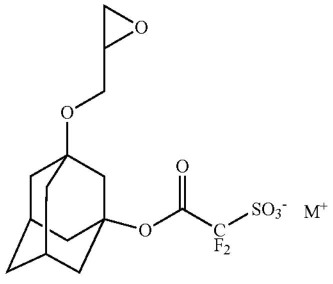
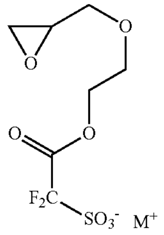
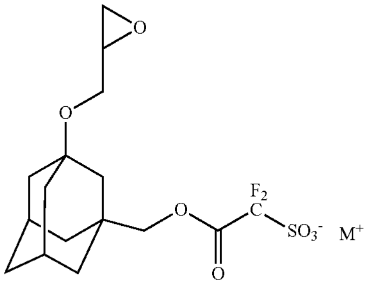
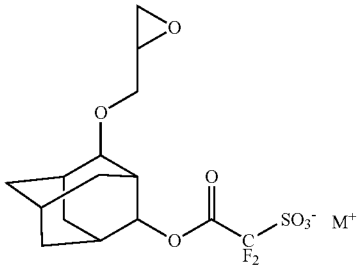
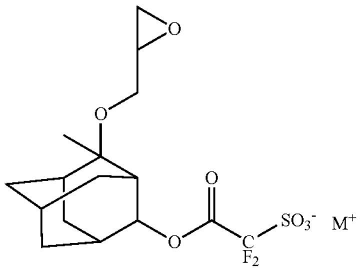
-continued
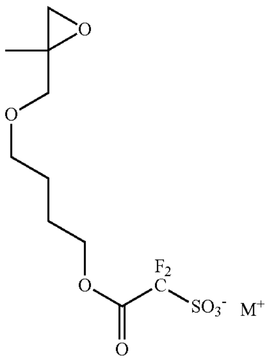
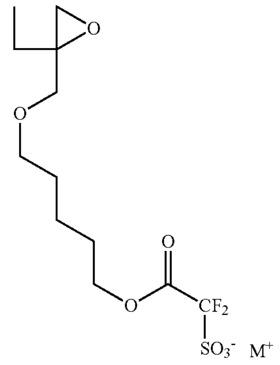
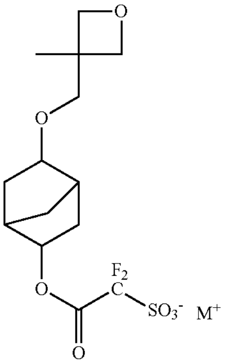
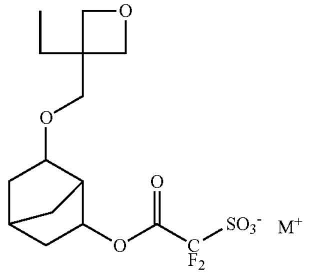
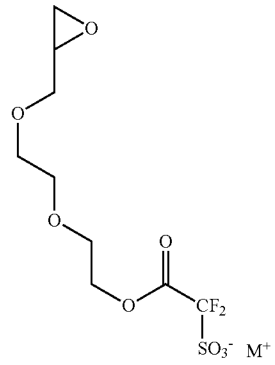
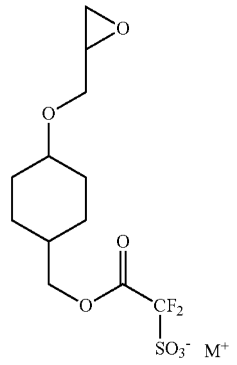
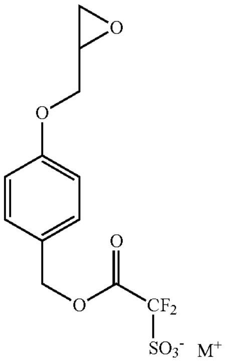
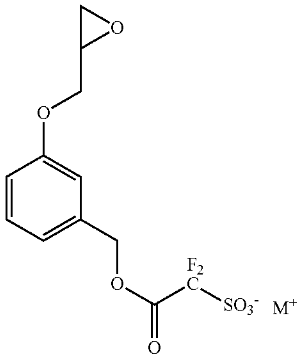

-continued
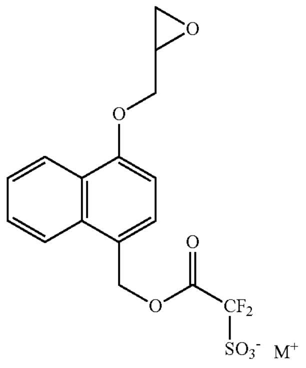
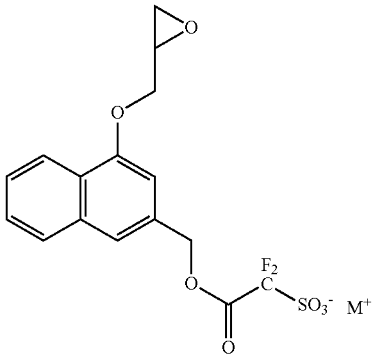
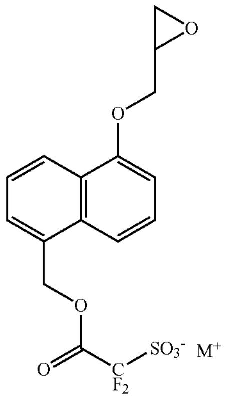
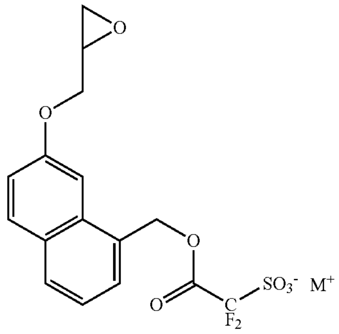
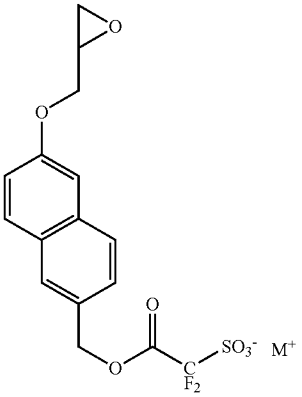
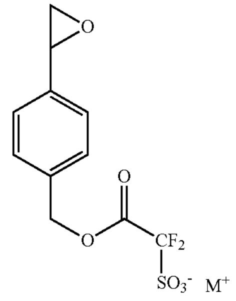
-continued
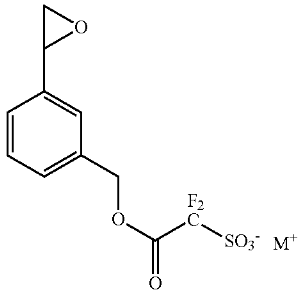
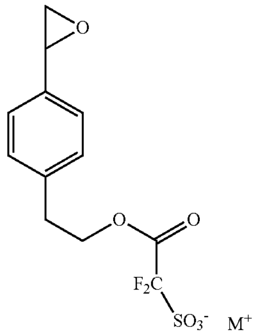
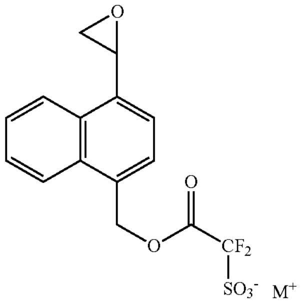
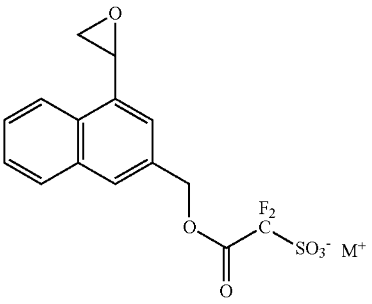
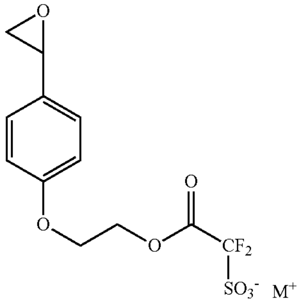
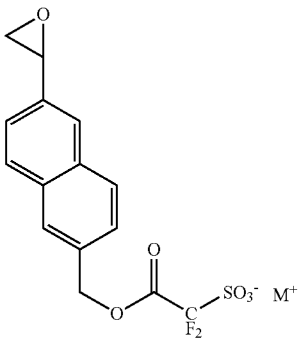

-continued
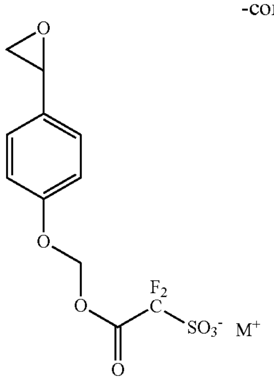
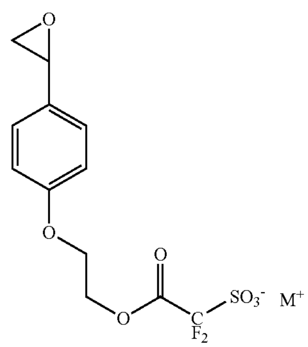
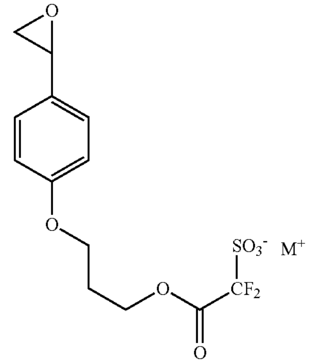
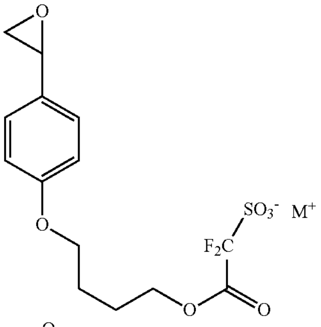
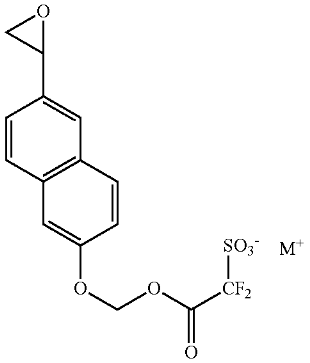
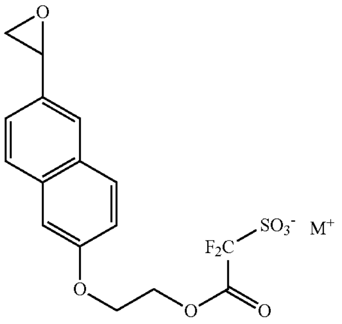
-continued
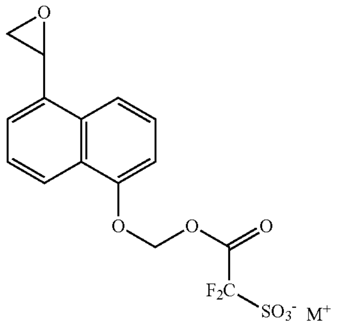
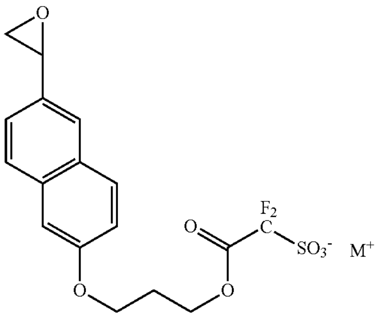
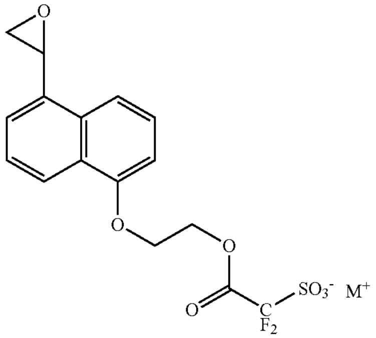
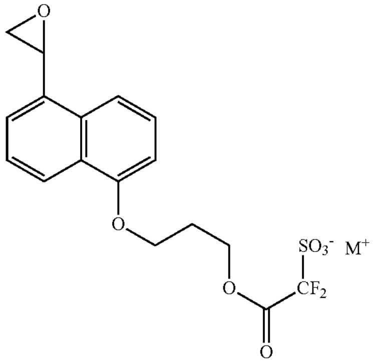
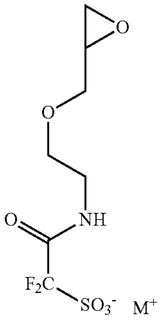
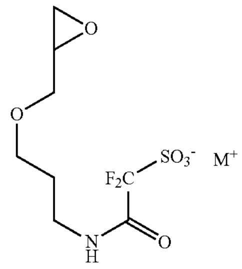

-continued
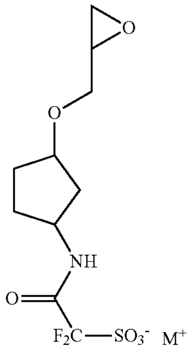
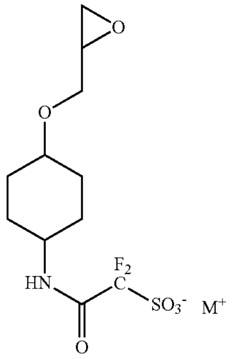
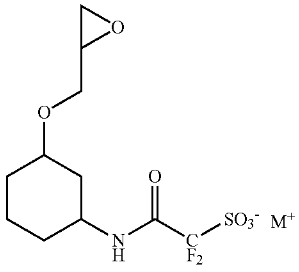
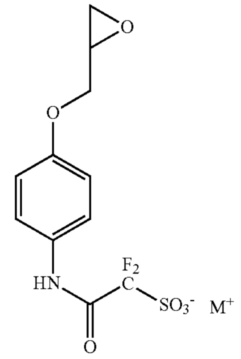
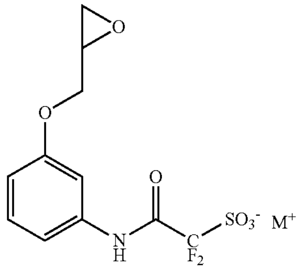
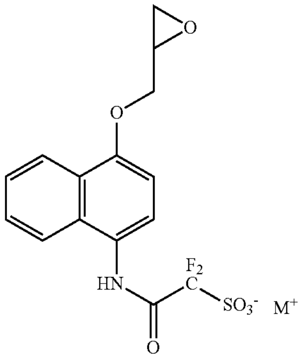
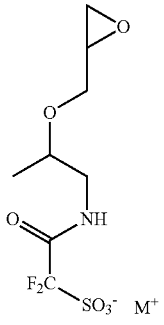
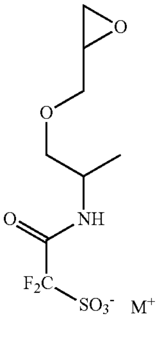
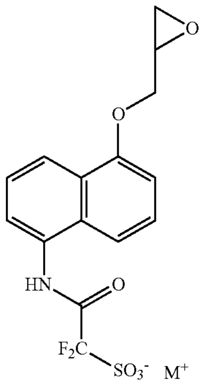
-continued
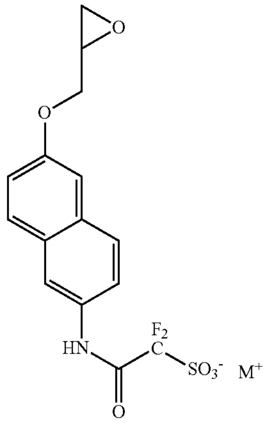
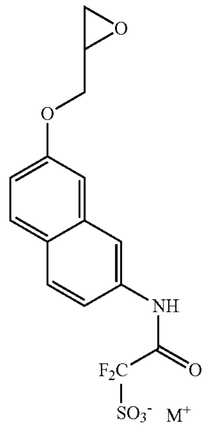
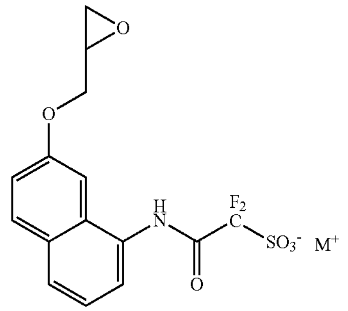
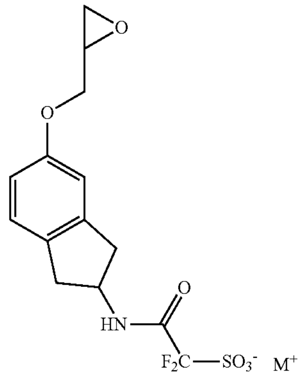
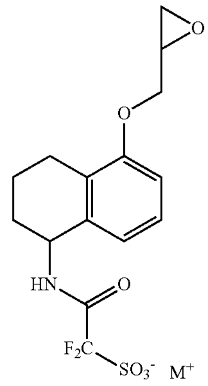
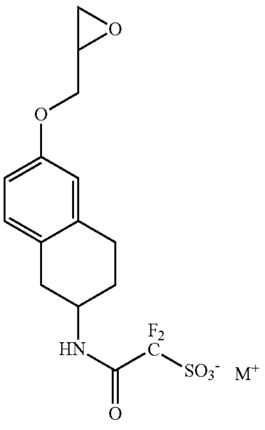

-continued
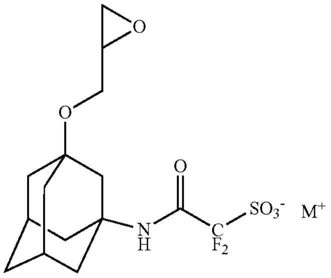
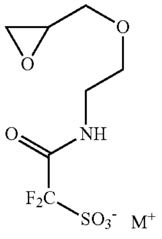
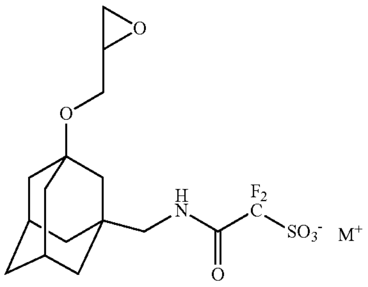
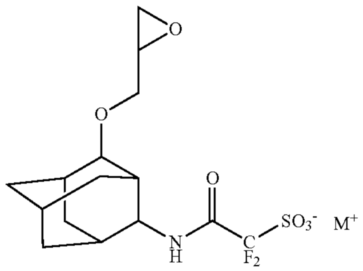
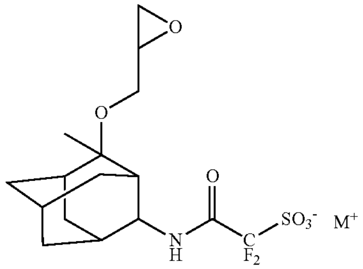
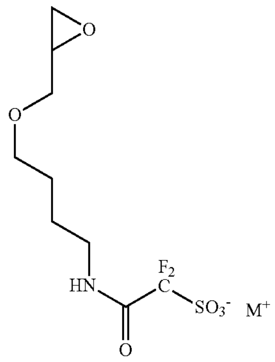
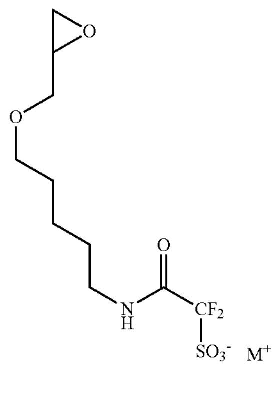
-continued
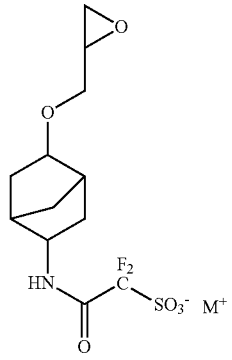
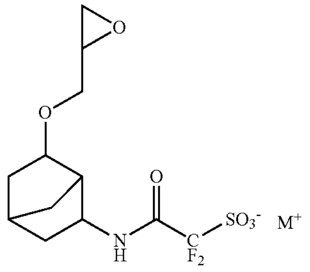
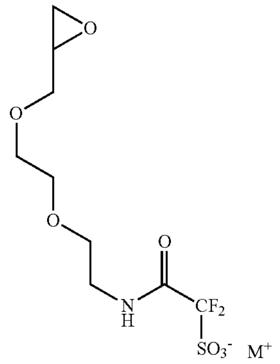
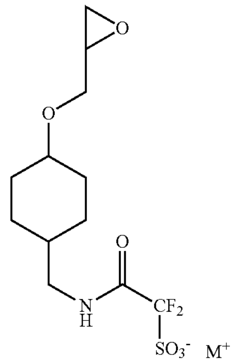
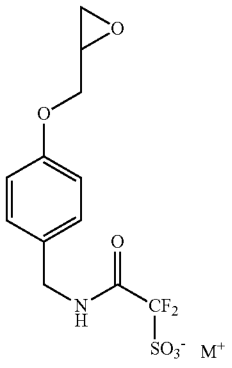
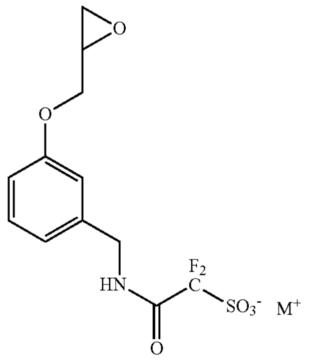
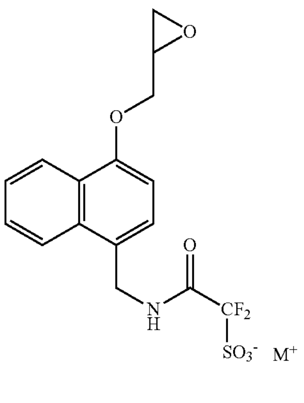

-continued
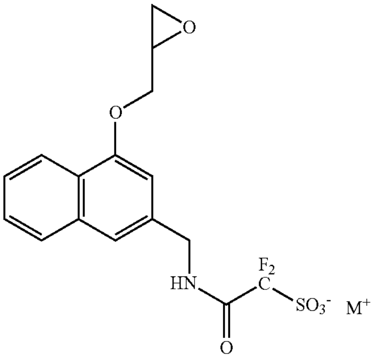
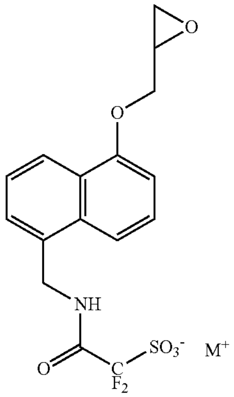
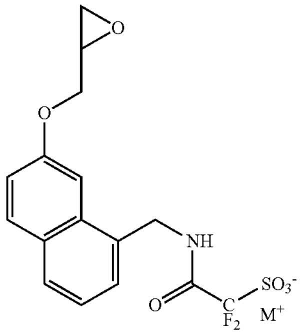
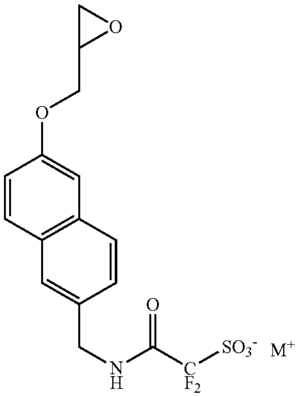
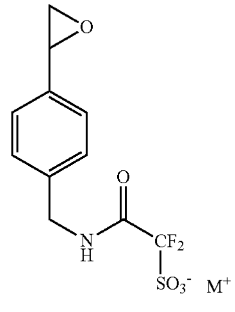
-continued
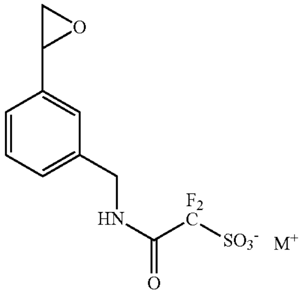
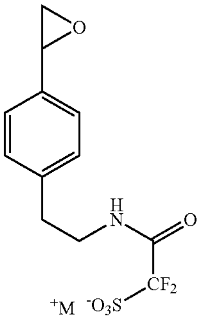
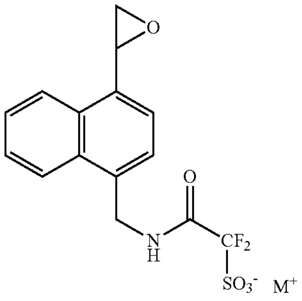
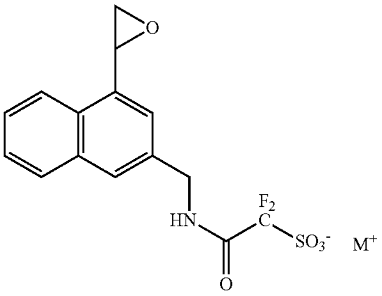
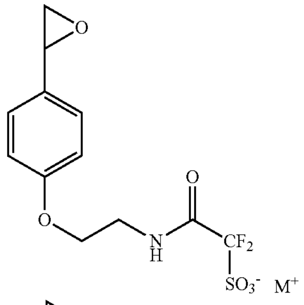
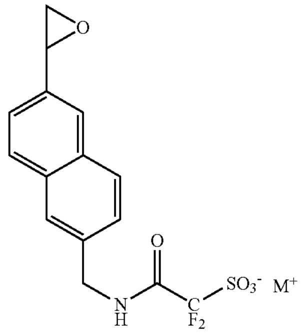

-continued
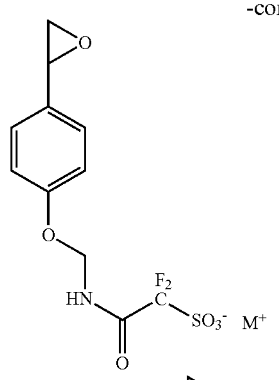
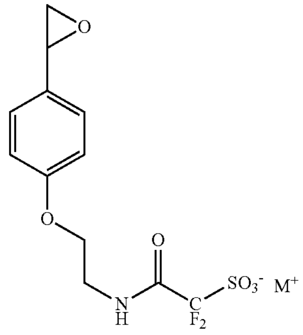
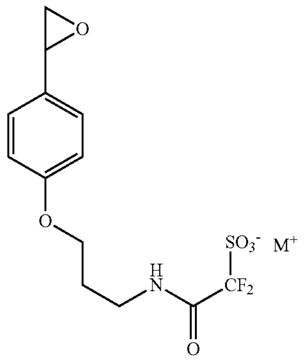
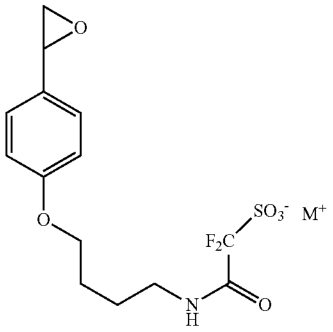
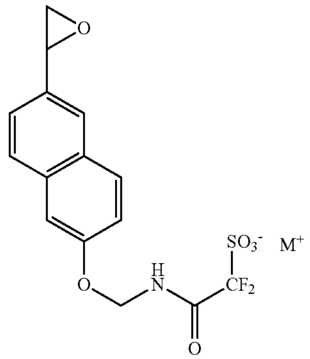
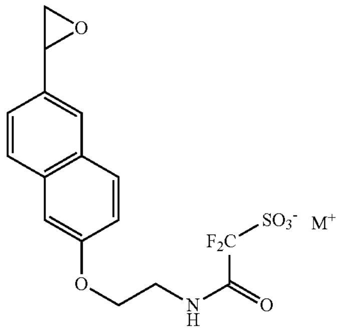
-continued
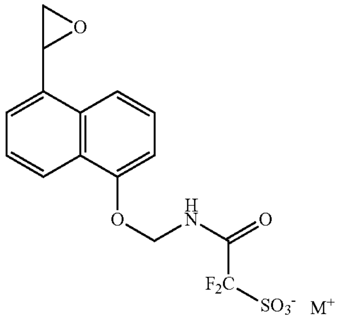
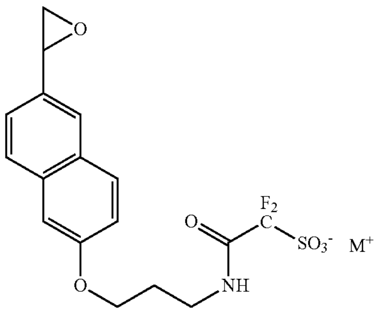
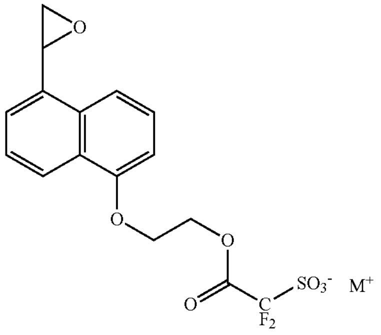
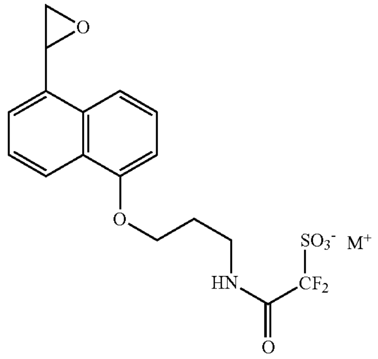
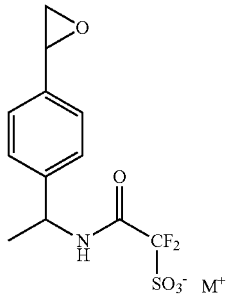
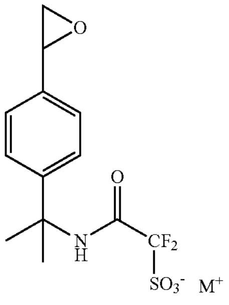

-continued
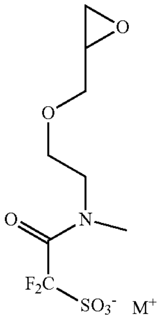
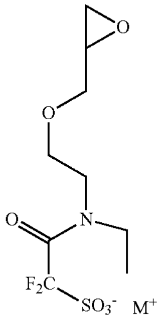
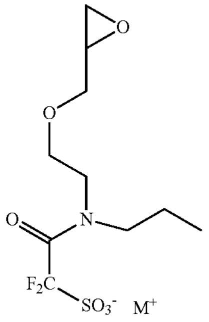
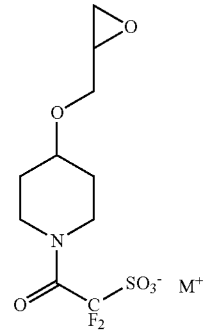
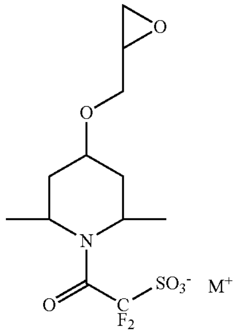
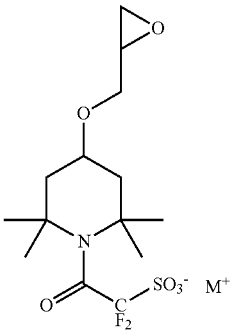
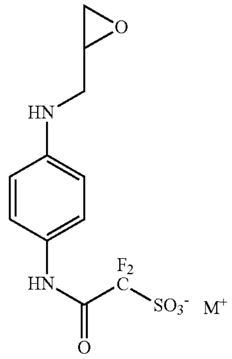
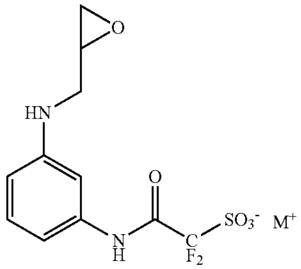
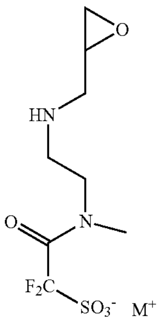
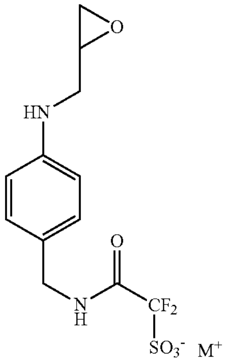
-continued
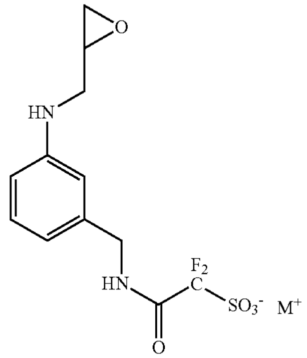
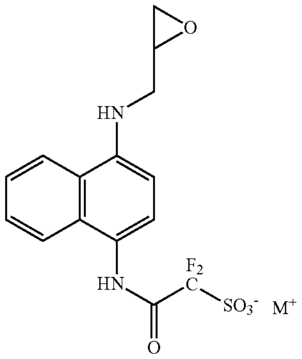
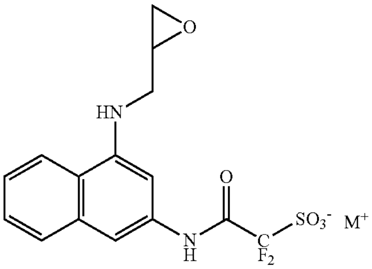
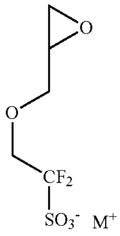
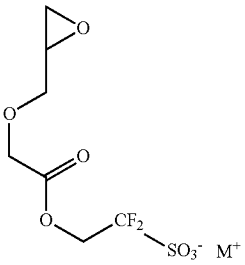
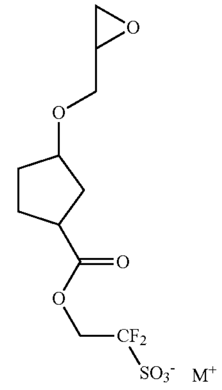
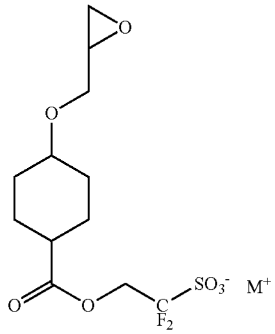

-continued
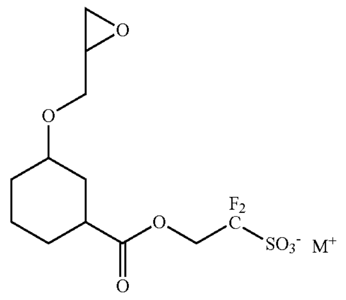
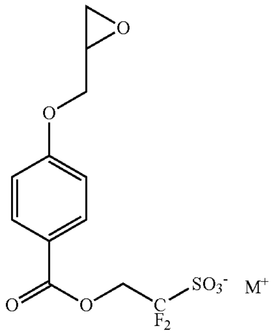
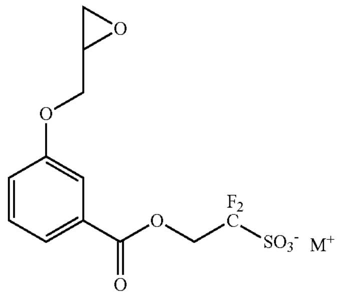
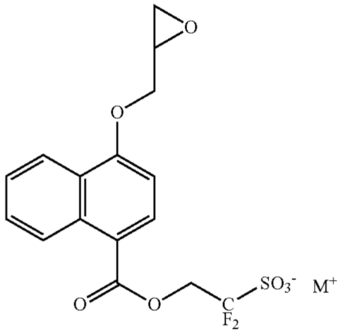
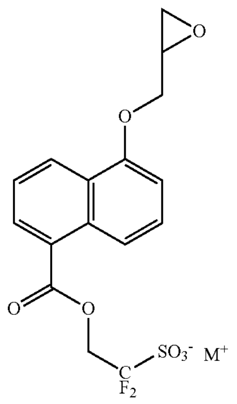
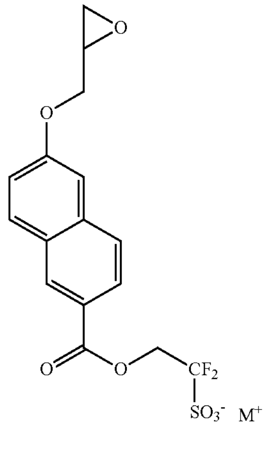
-continued
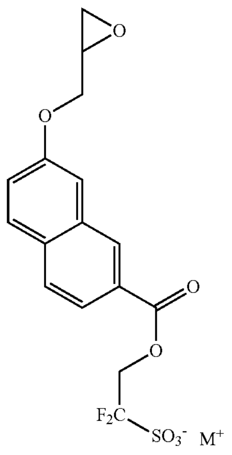
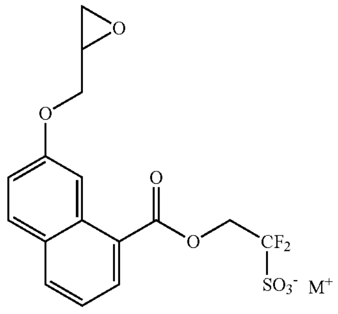
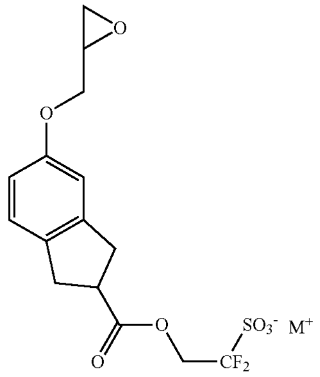
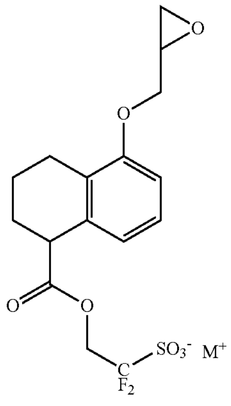
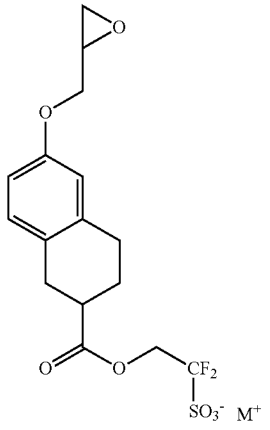
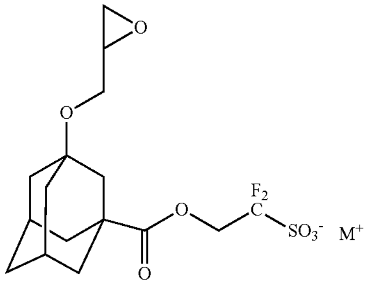

-continued
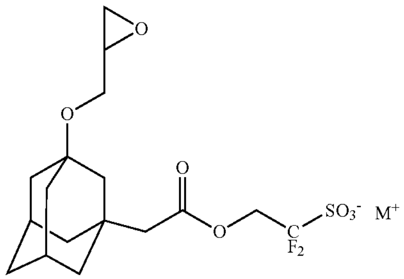
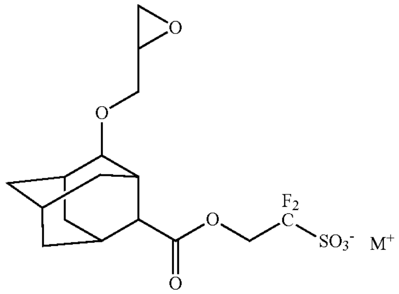
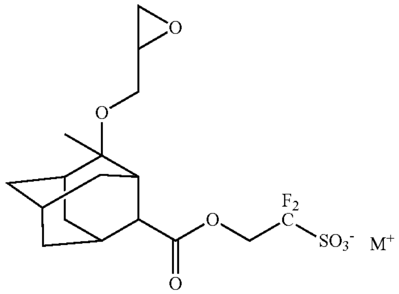
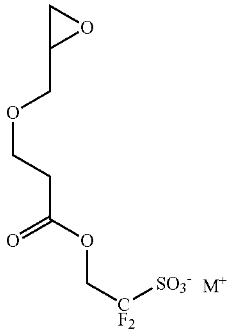
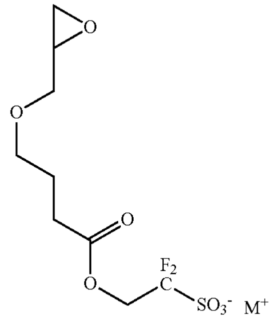
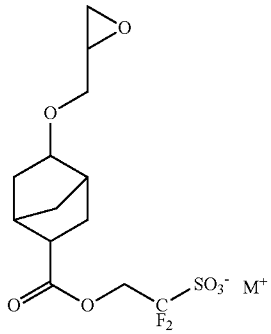
-continued
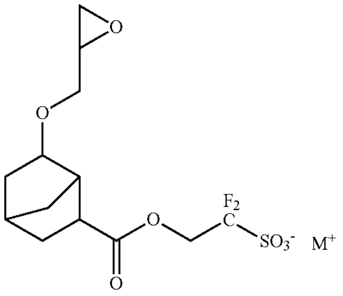
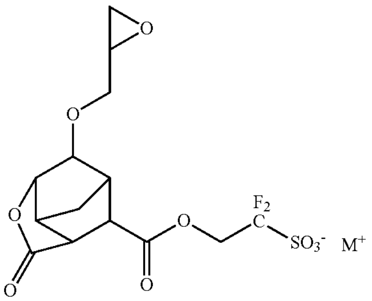
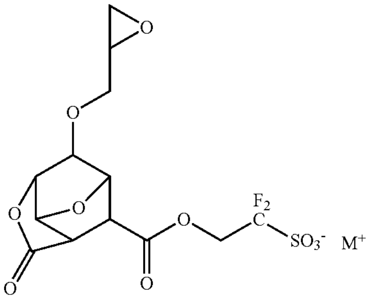
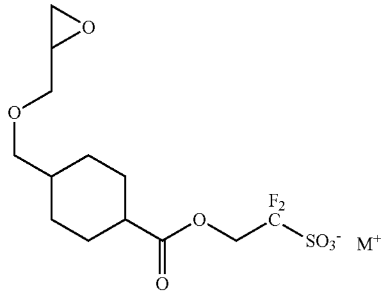
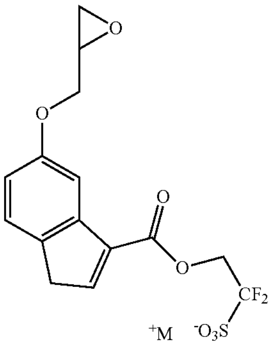

-continued
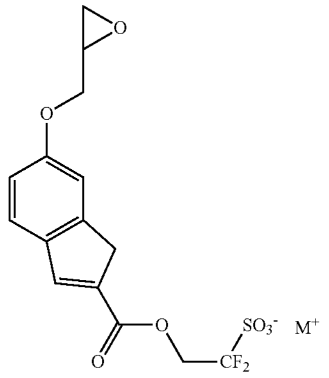
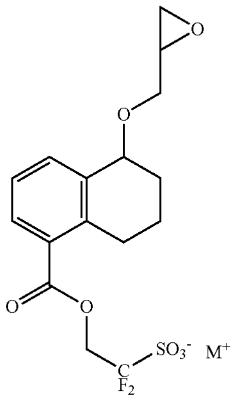
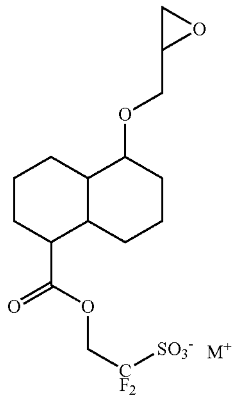
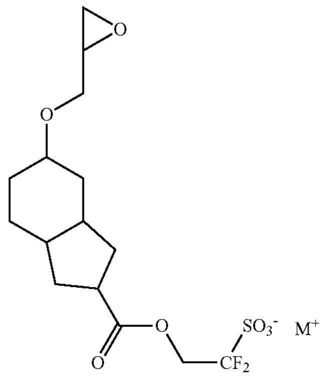
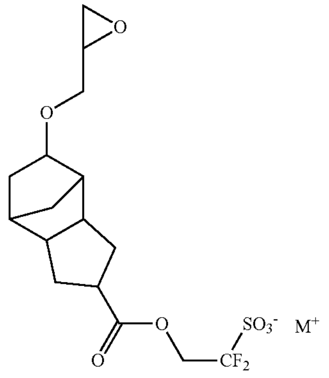
-continued
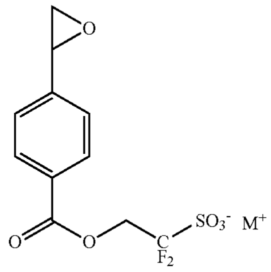
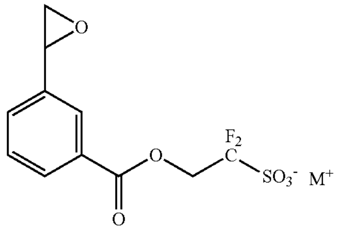
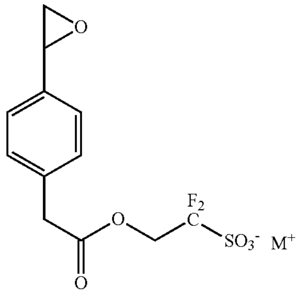
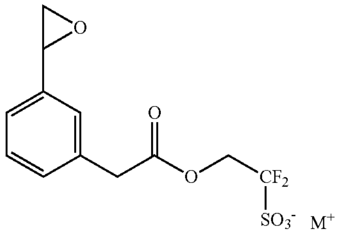
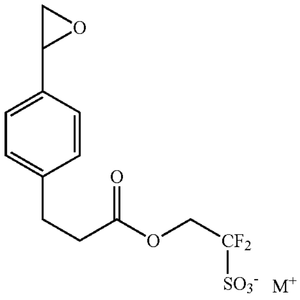
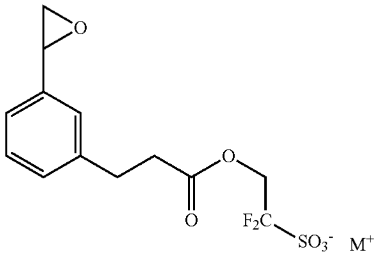

-continued
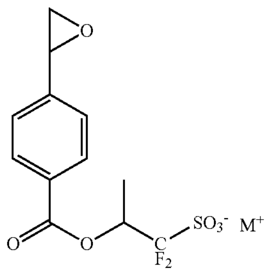
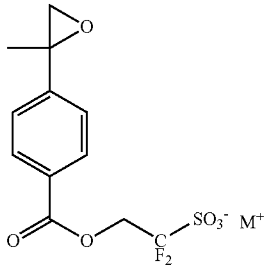
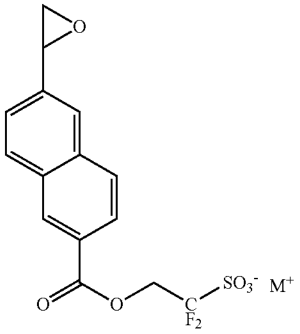
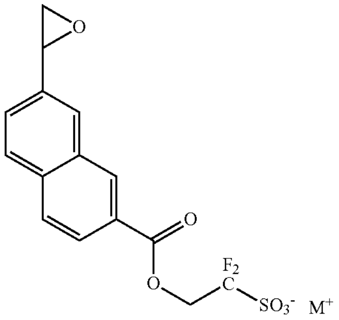
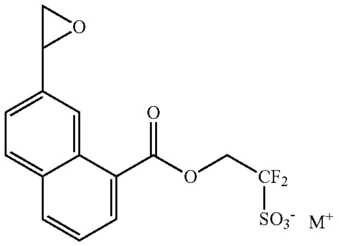
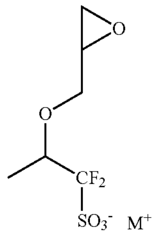
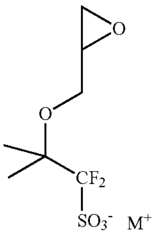
-continued
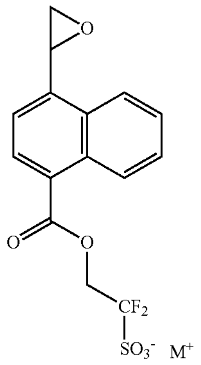
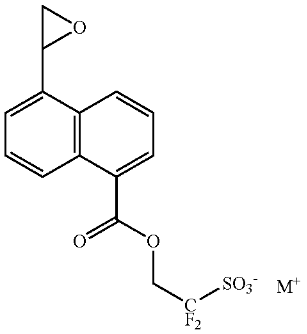
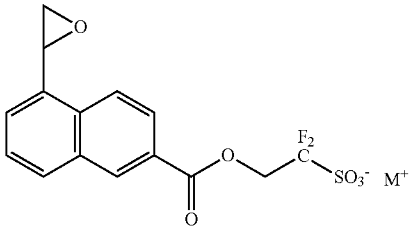
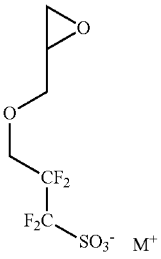
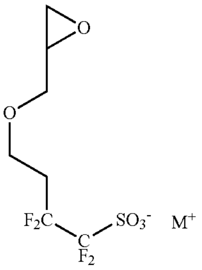
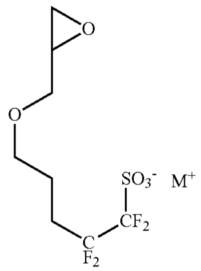
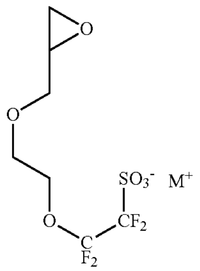
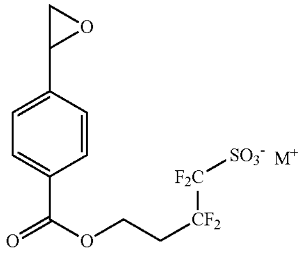
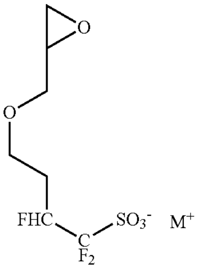

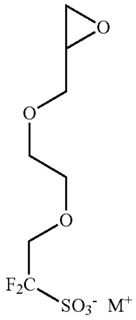
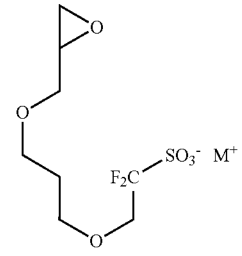
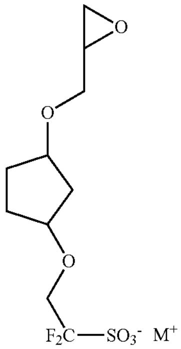
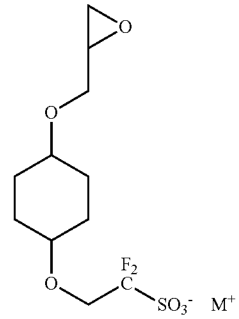
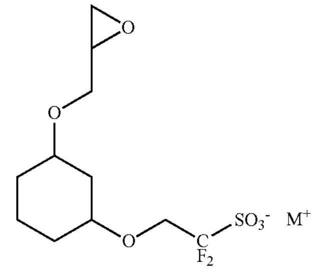
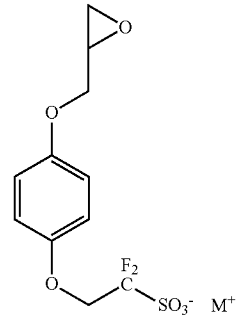
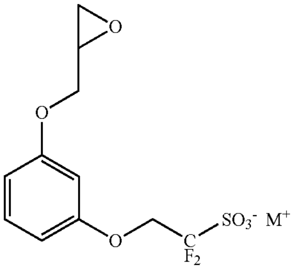
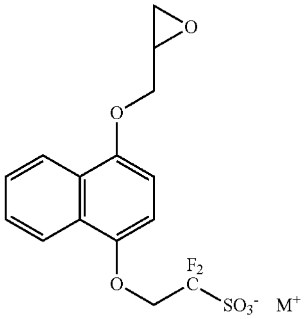
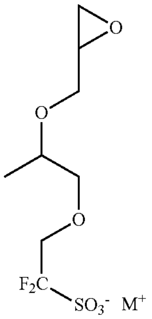
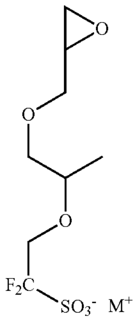
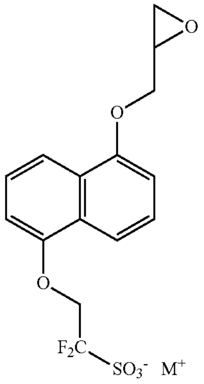
-continued
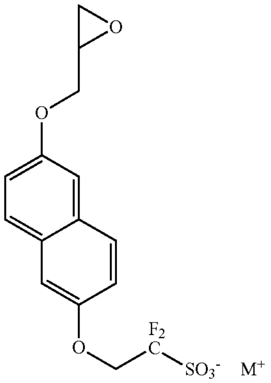
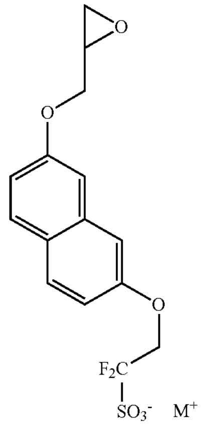
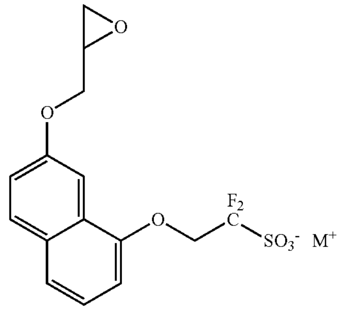
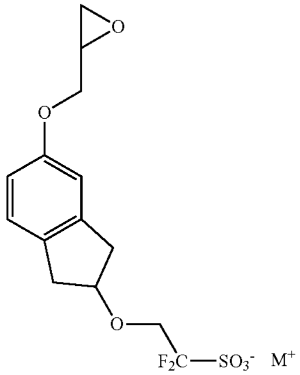
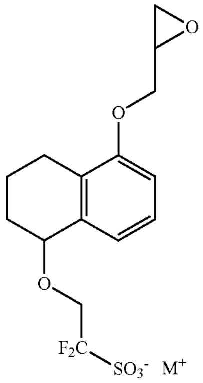
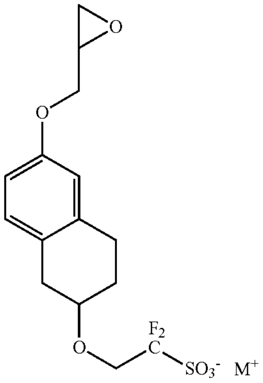

-continued
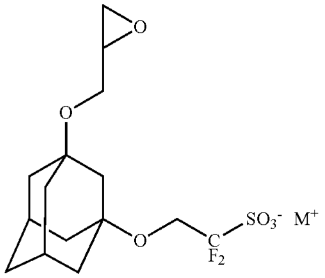
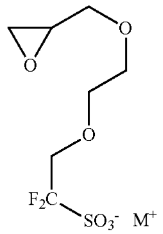
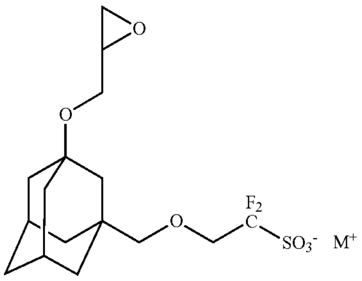
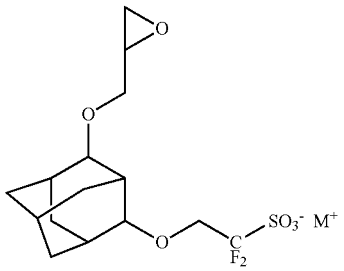
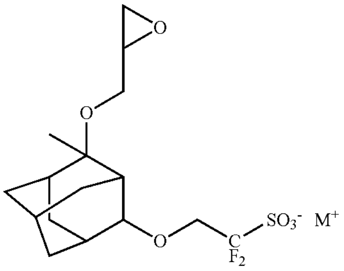
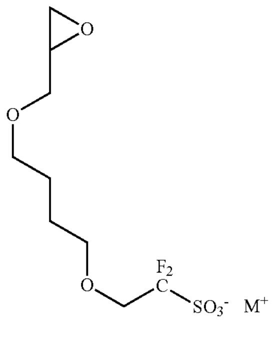
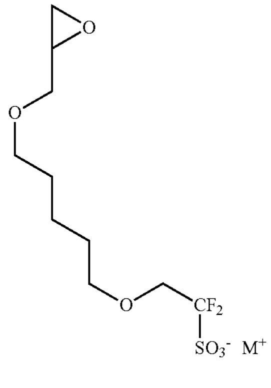
-continued
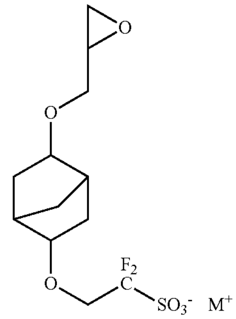
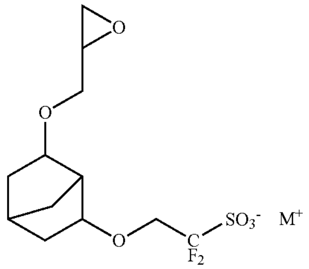
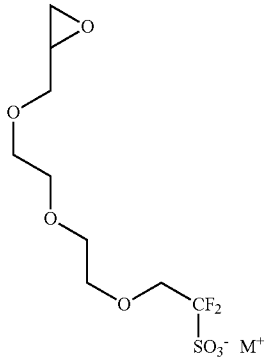
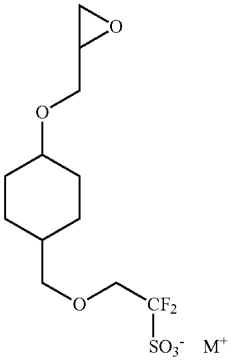
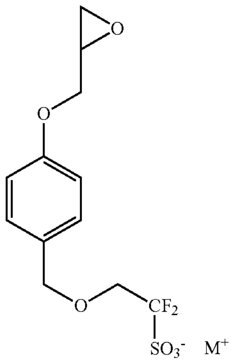
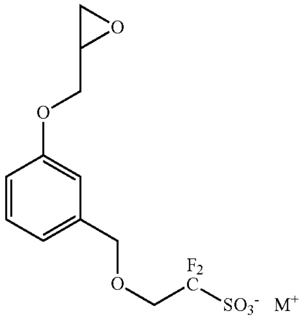
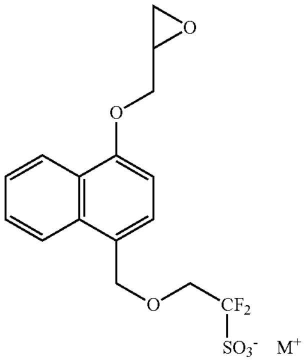
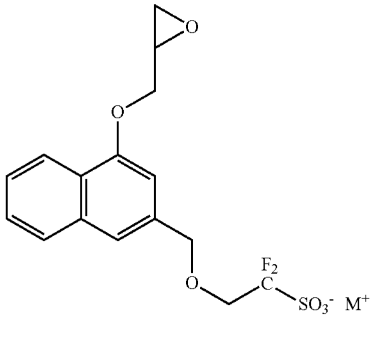

-continued
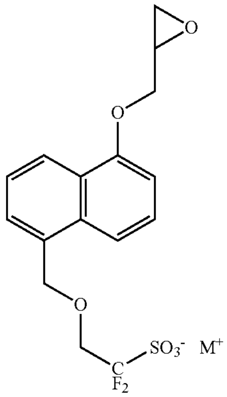
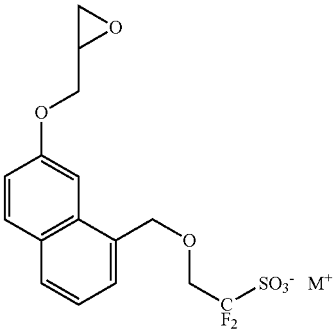
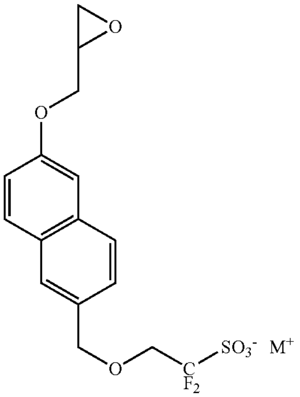
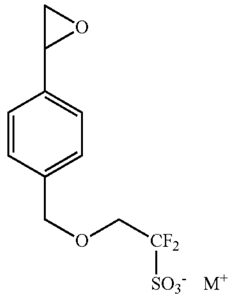
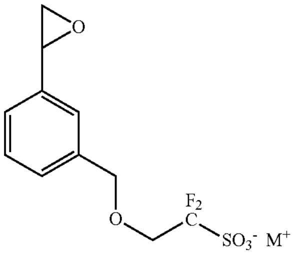
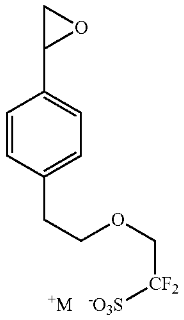
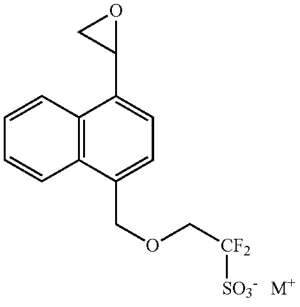
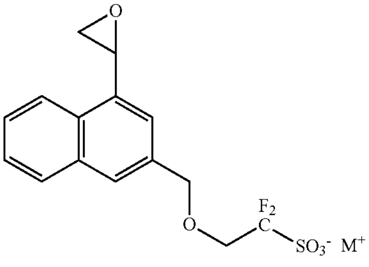
-continued
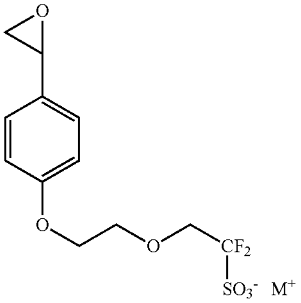
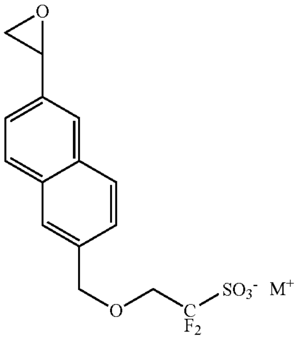
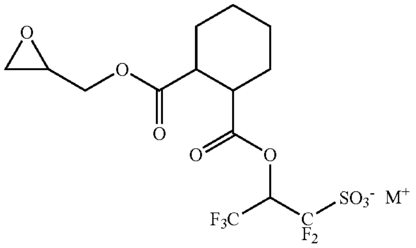
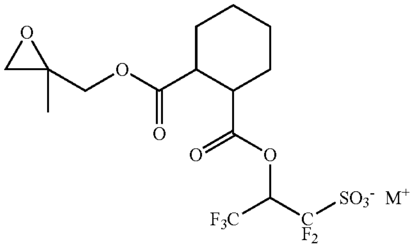
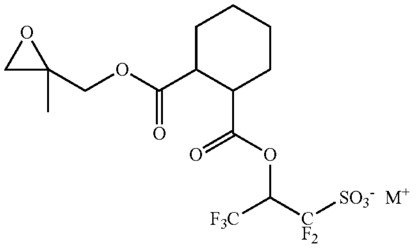
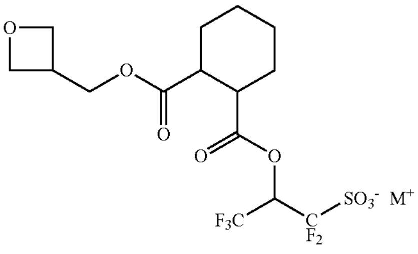

-continued
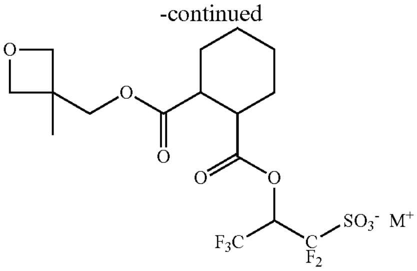
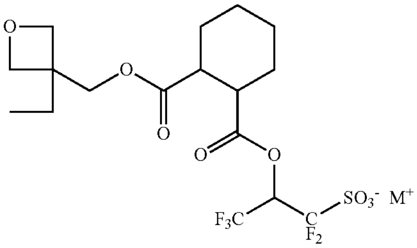
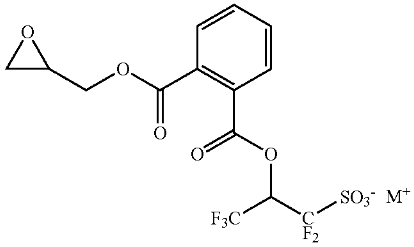
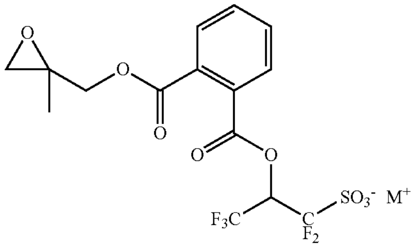
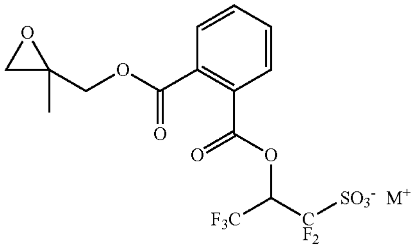
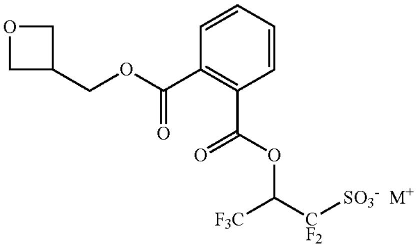
-continued
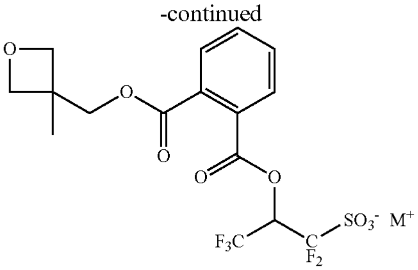
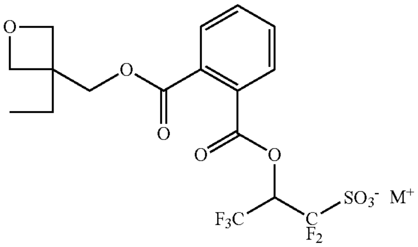
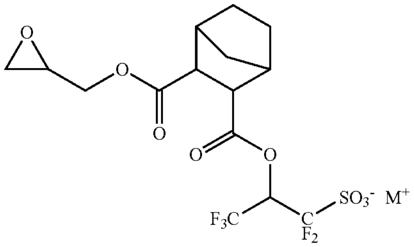
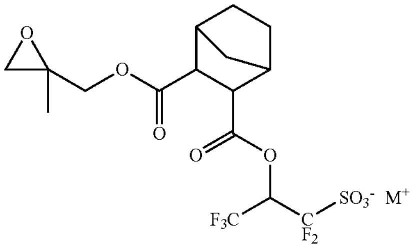
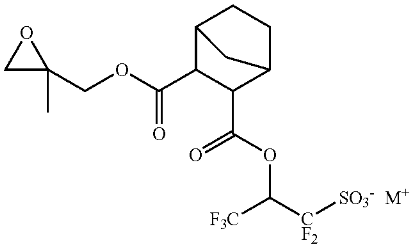
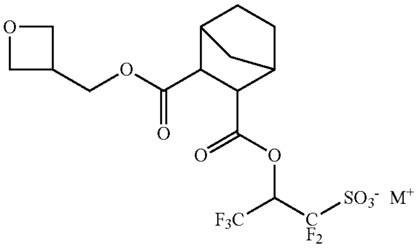

-continued
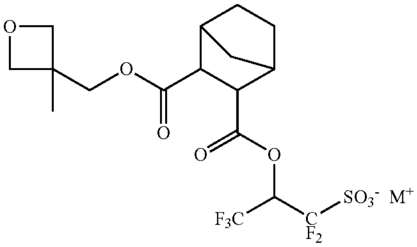
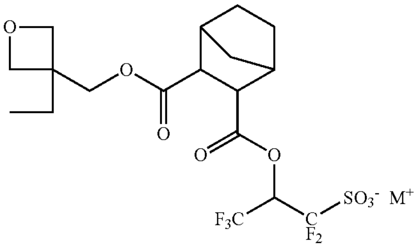
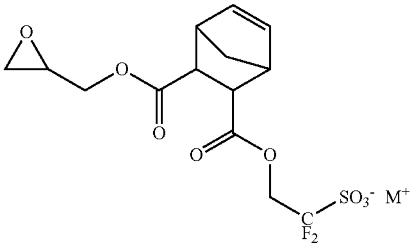
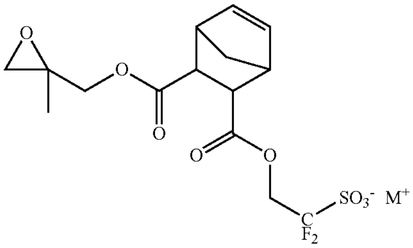
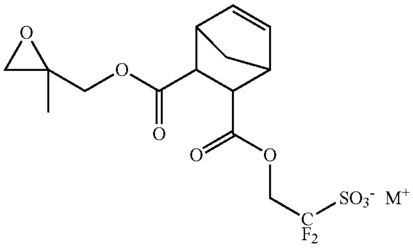
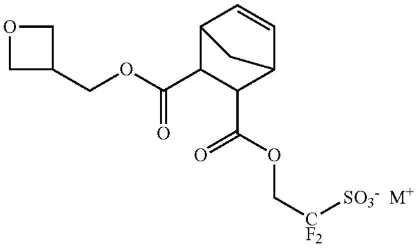
-continued
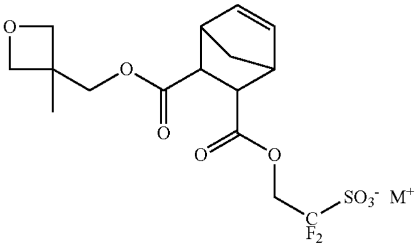
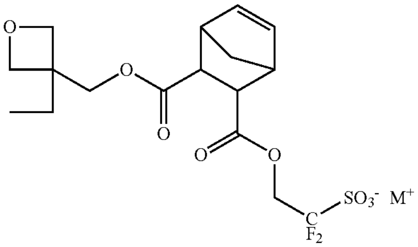
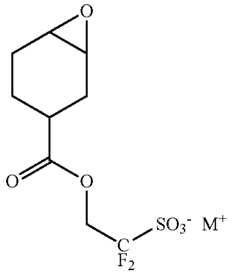
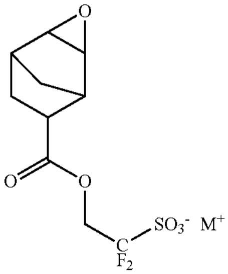
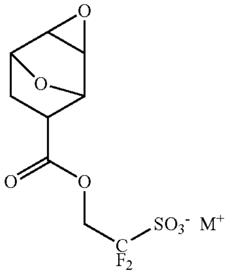
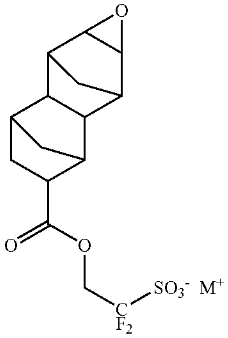
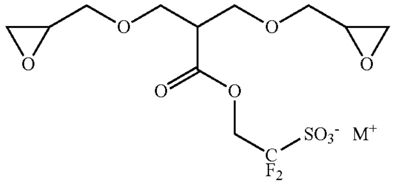

-continued
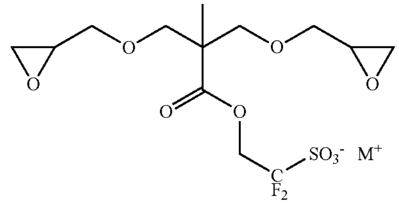
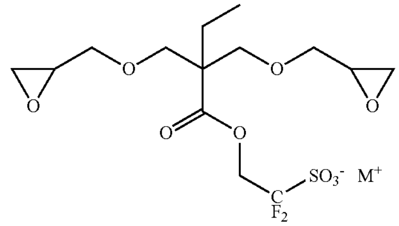
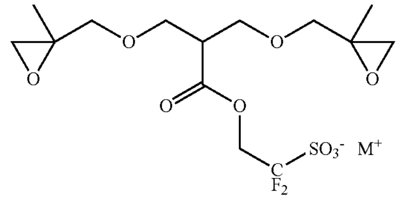
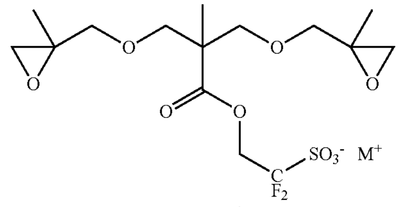
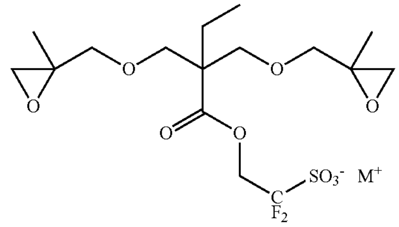
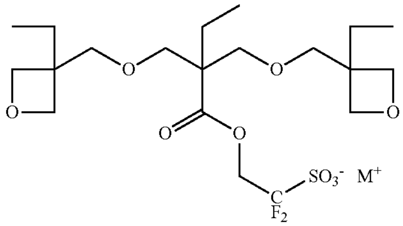
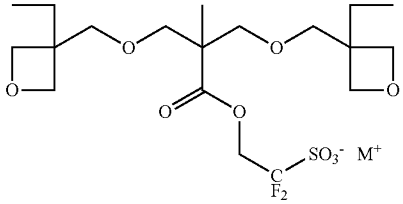
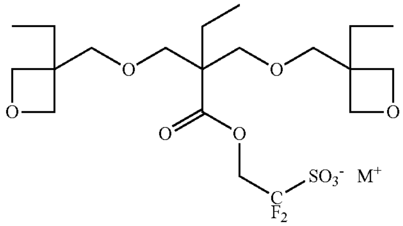
-continued
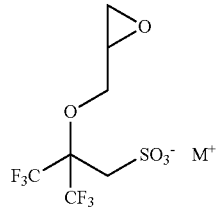
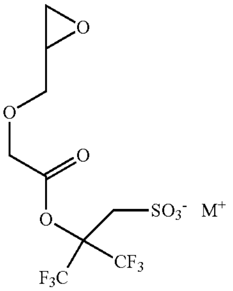
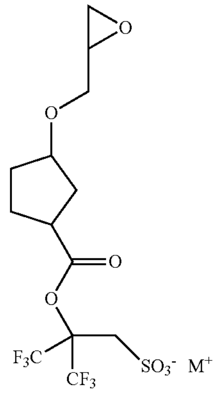
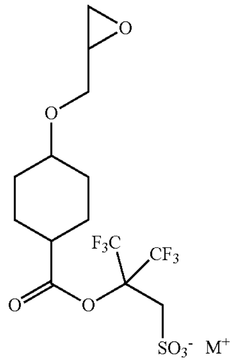
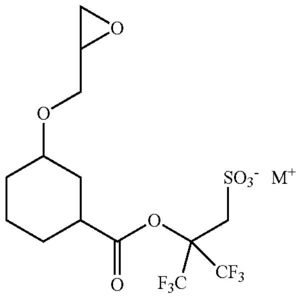
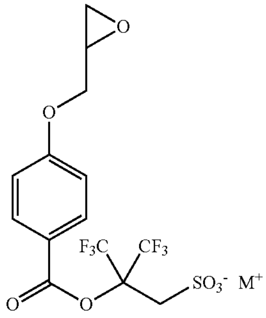
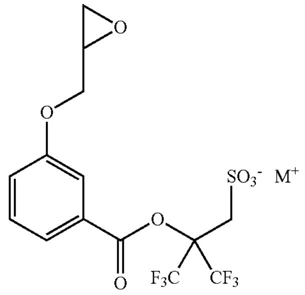
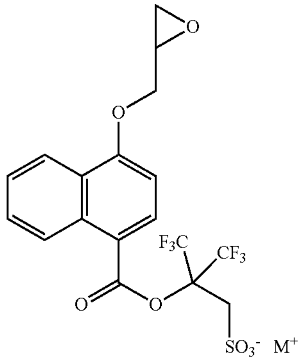
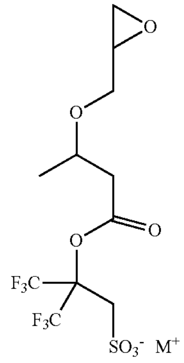

-continued
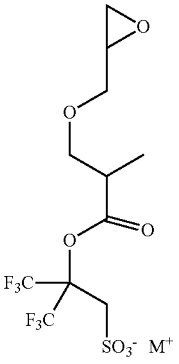
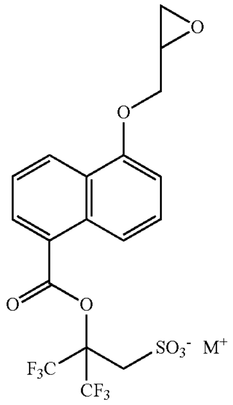
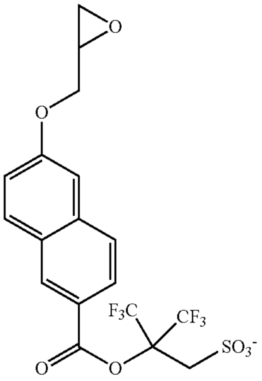
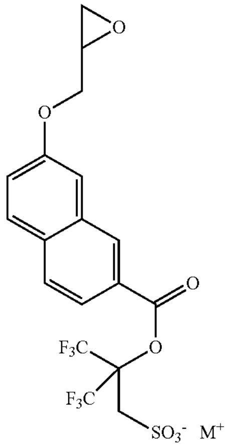
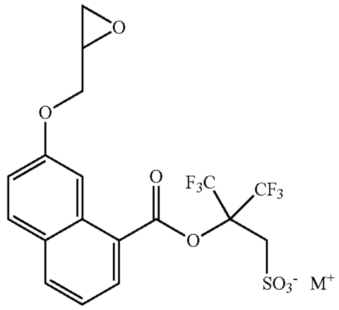
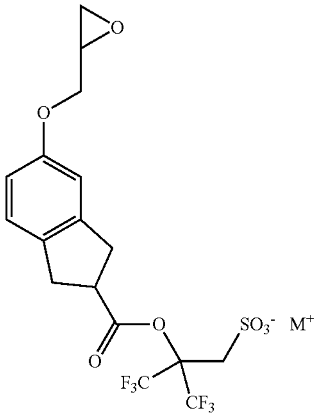
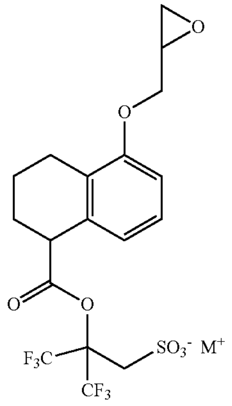
-continued
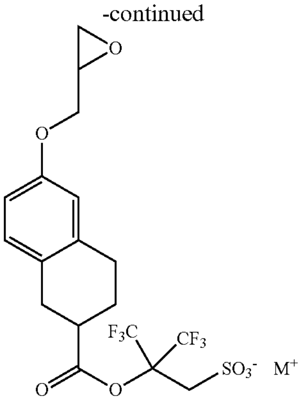
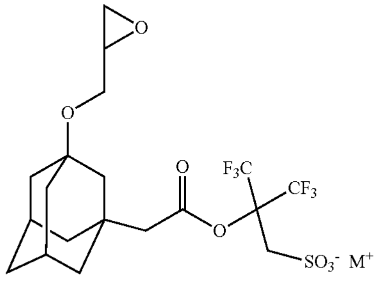
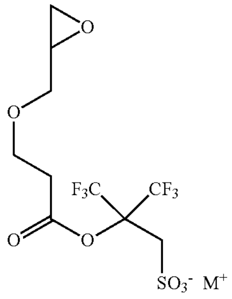
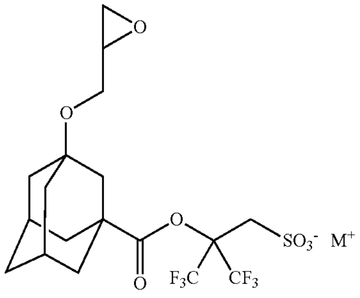
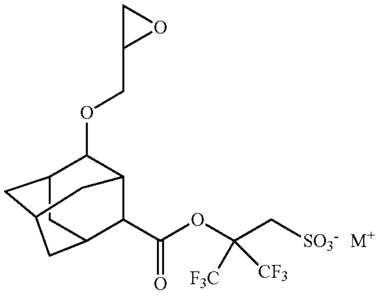

-continued
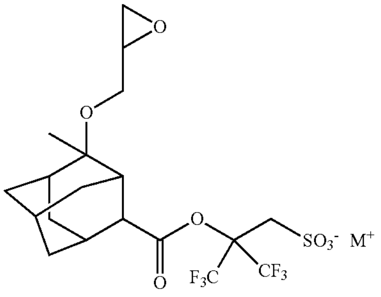
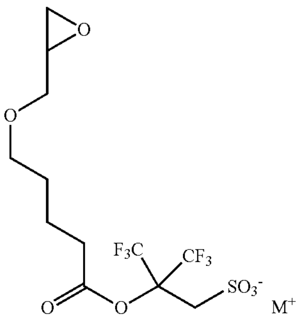
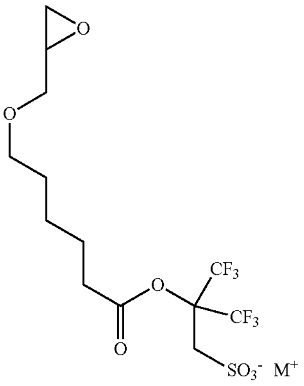
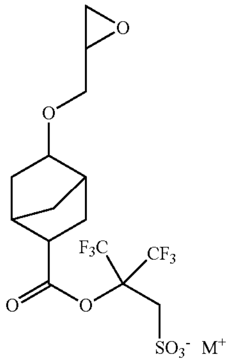
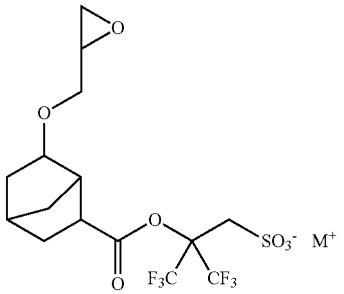
-continued
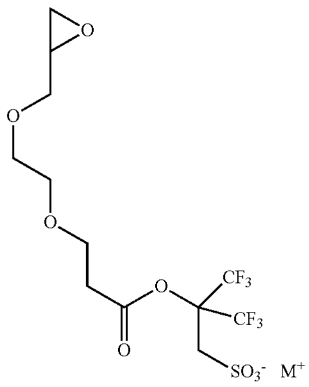
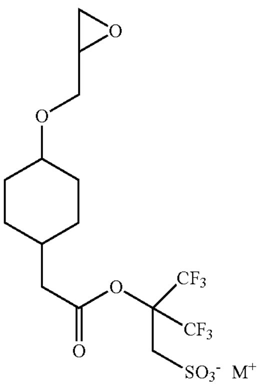
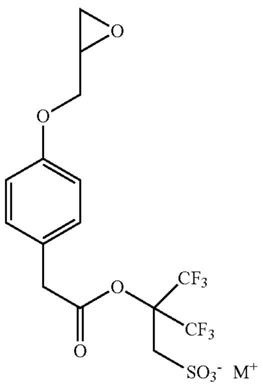
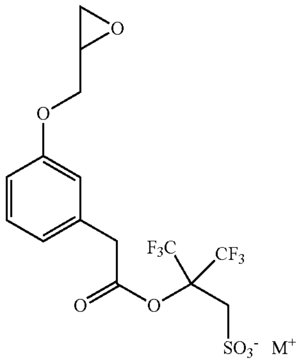
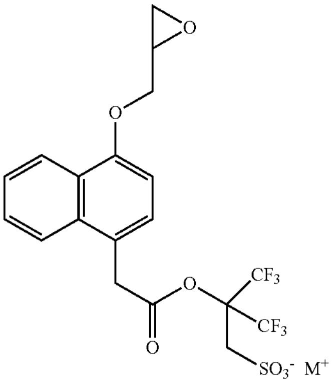

-continued
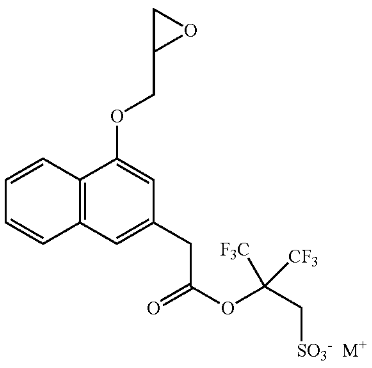
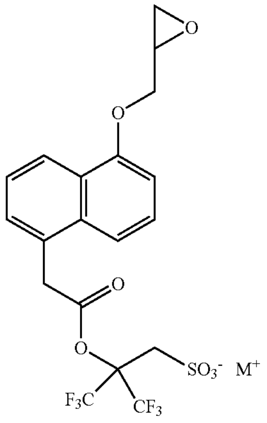
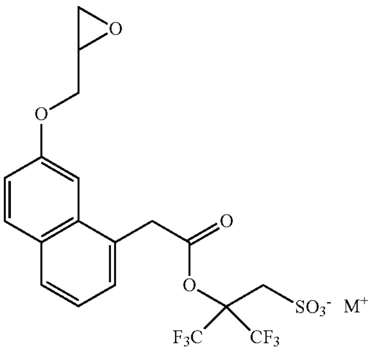
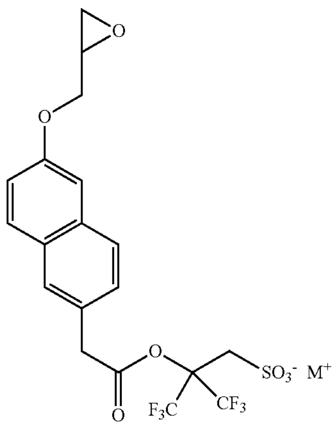
-continued
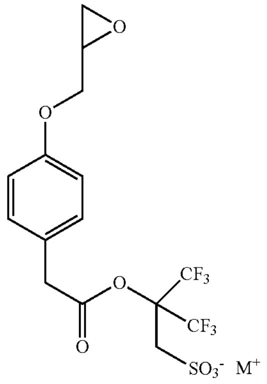
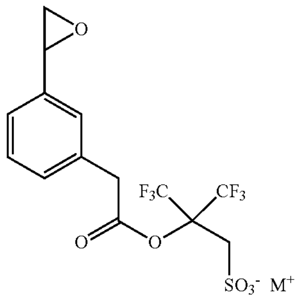
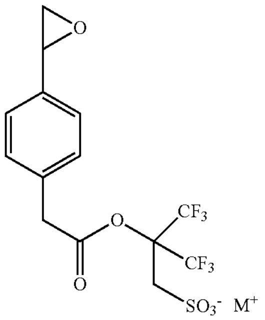
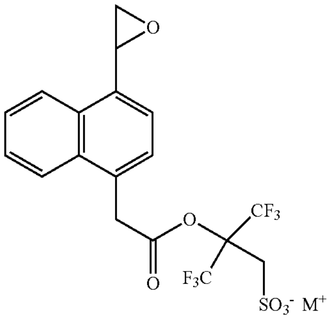
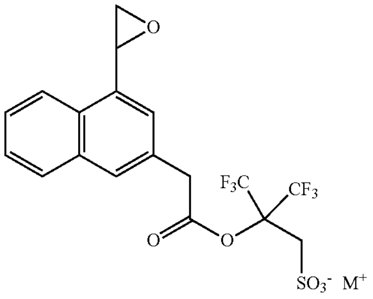
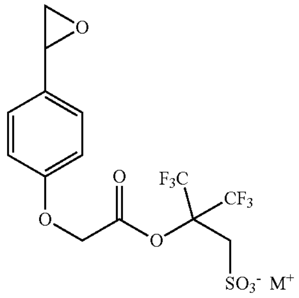

-continued
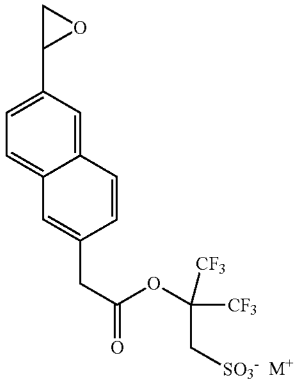
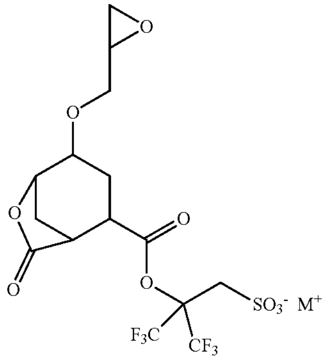
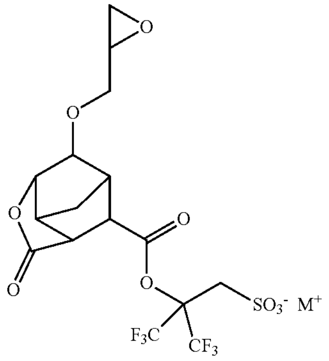
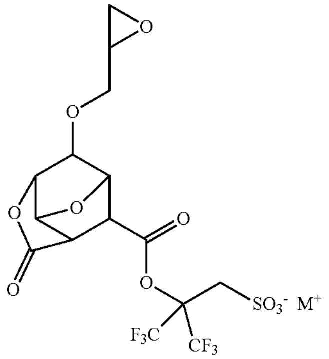
-continued
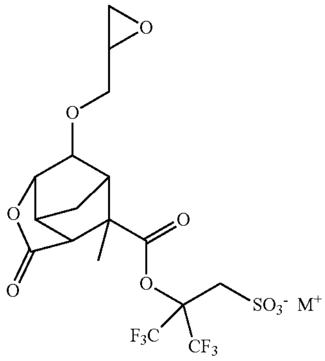
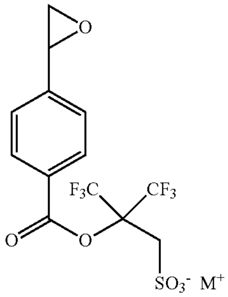
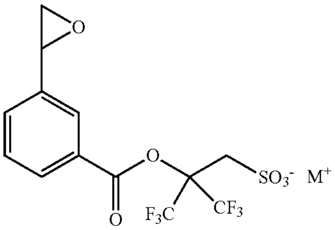
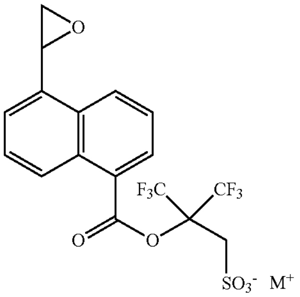
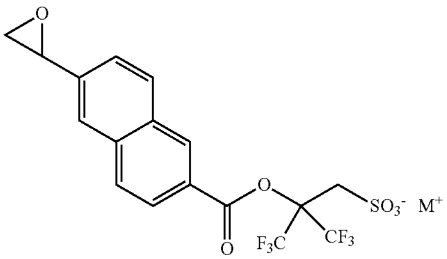
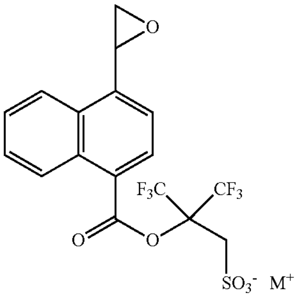

-continued
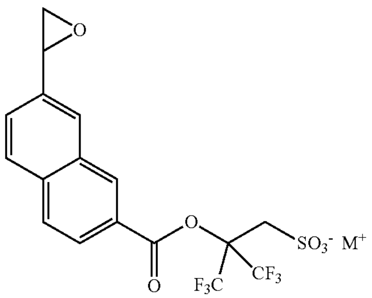
Specific examples of the monomer shown by the general formula (2)-2 can include the following.
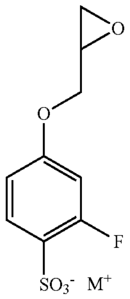
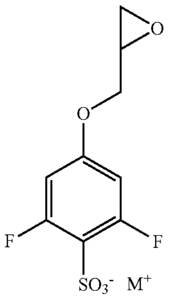
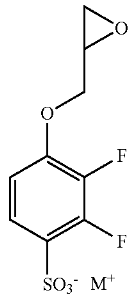
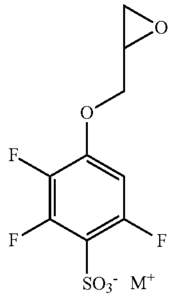
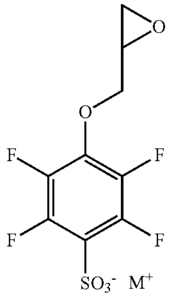
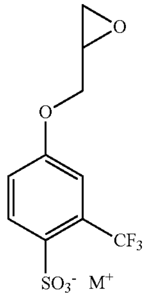
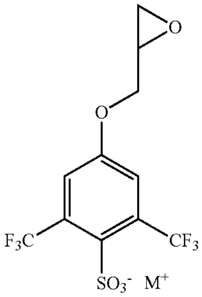
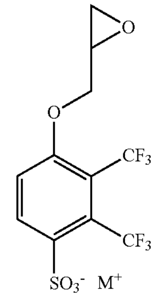
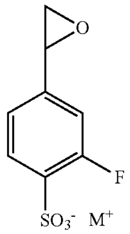
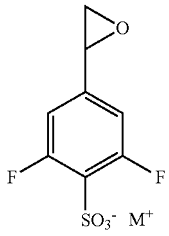
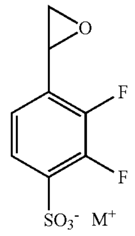
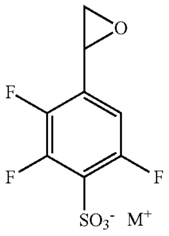
-continued
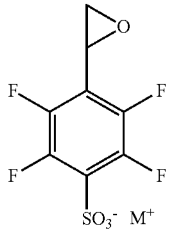
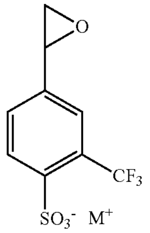
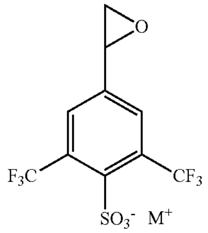
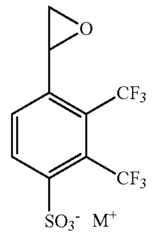
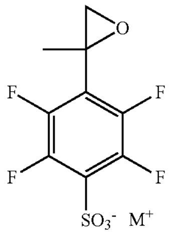
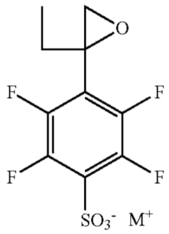
Specific examples of the monomer shown by the general formula (2)-3 can include the following.
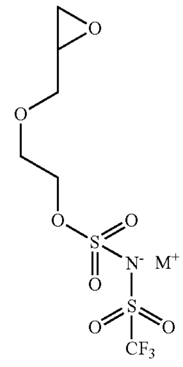
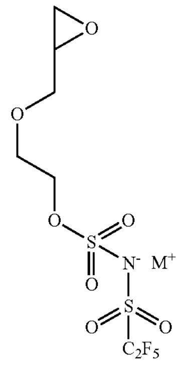
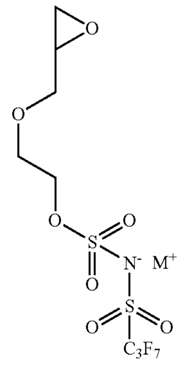
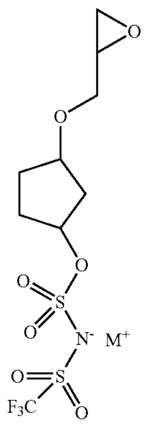
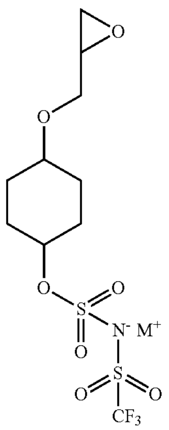
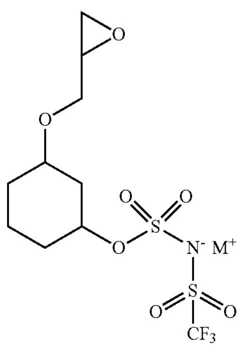

-continued
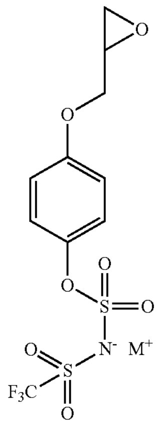
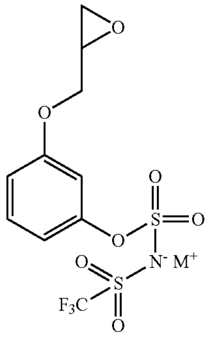
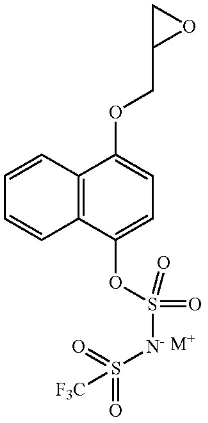
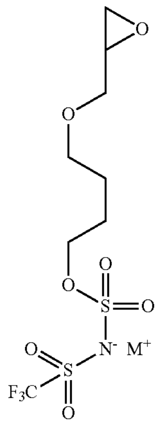
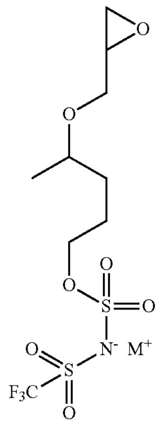
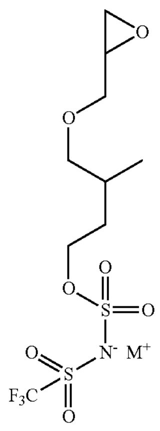
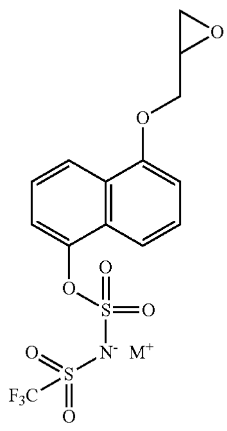
-continued
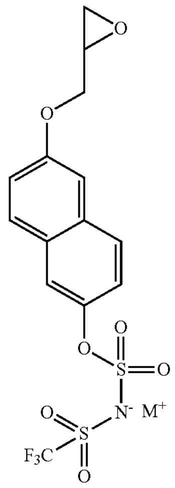
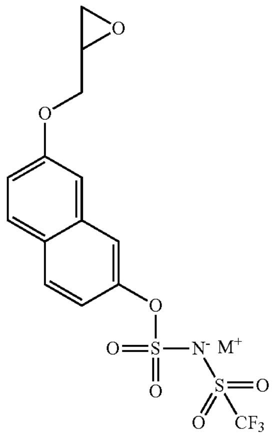
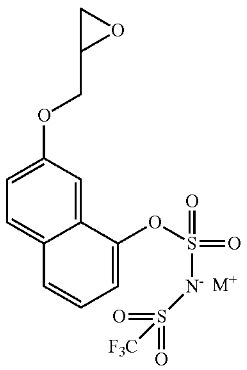
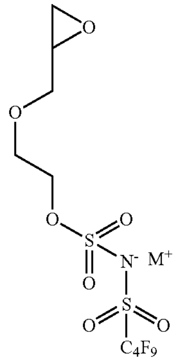
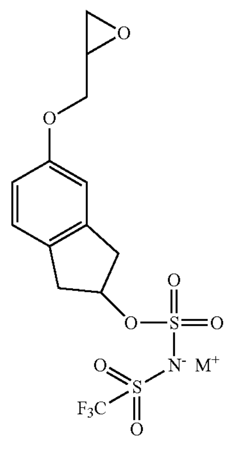
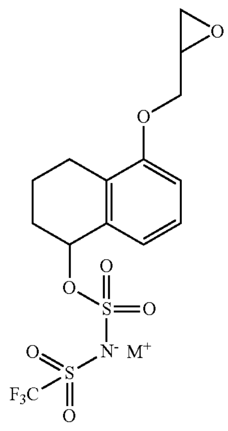

-continued
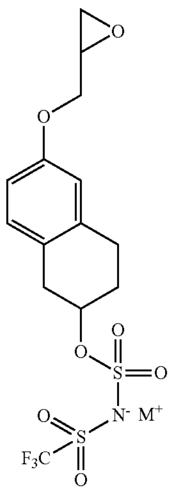
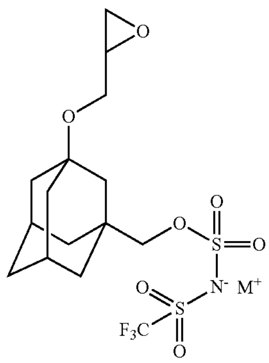
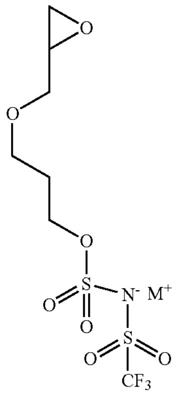
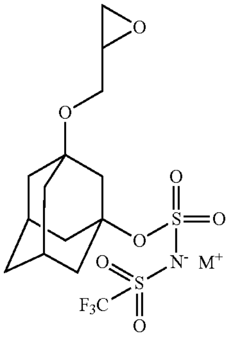
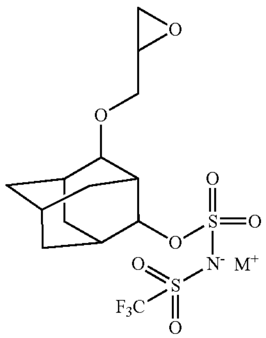
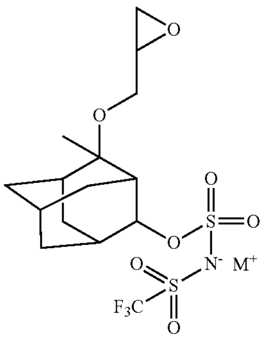
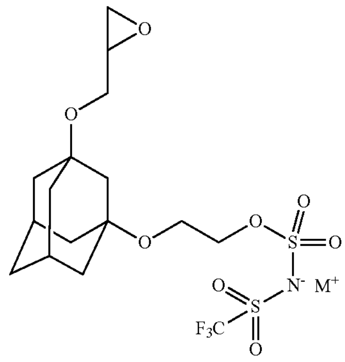
-continued
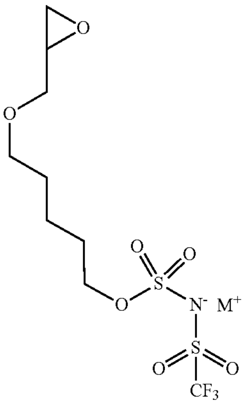
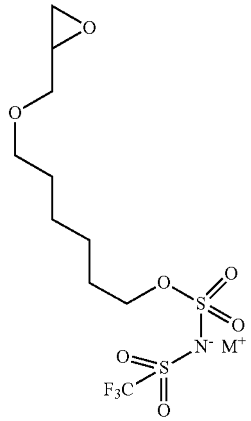
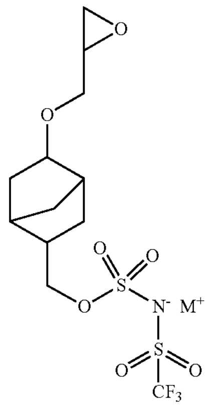
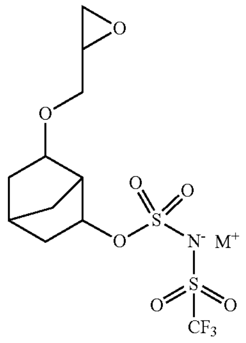
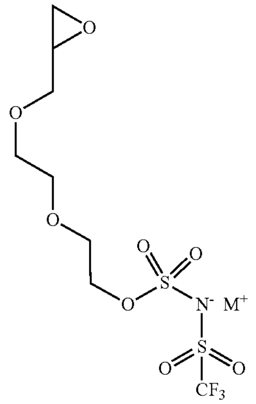
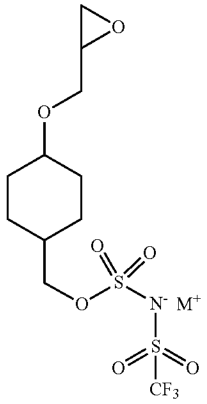
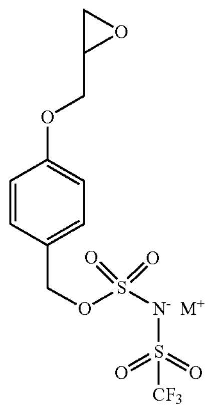
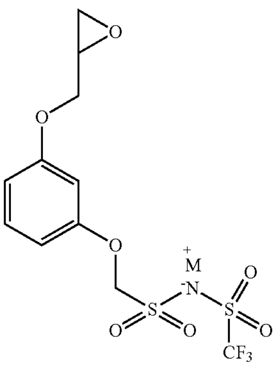

-continued
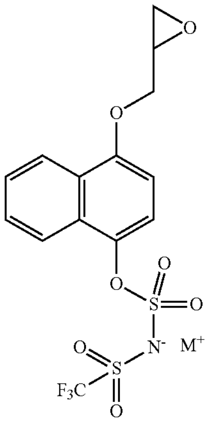
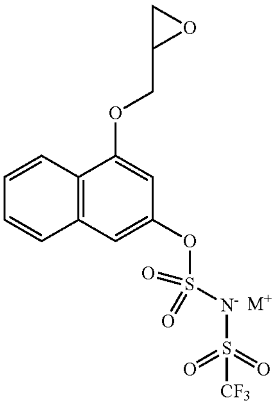
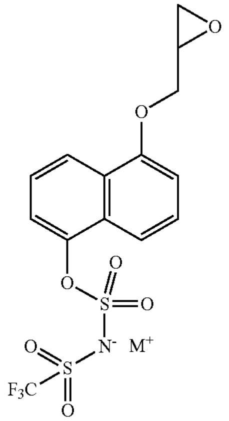
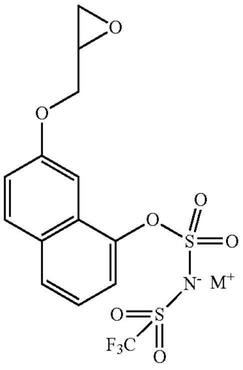
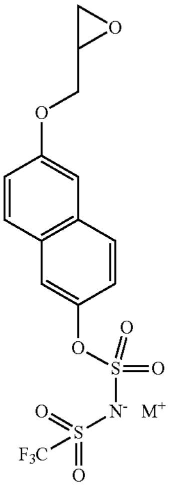
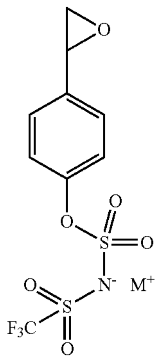
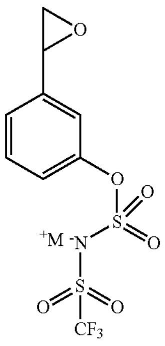
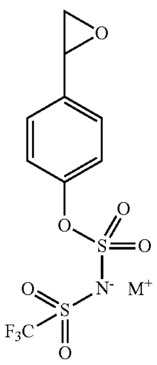
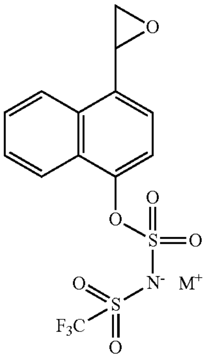
-continued
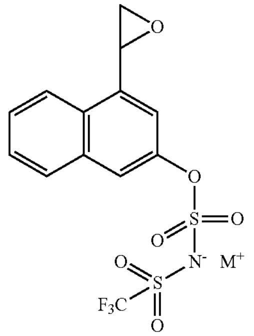
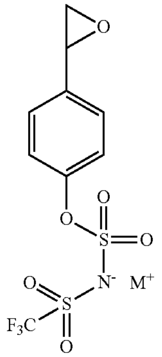
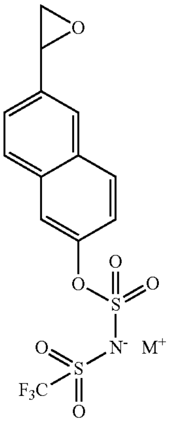
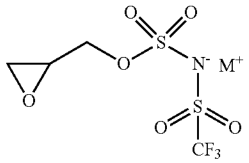
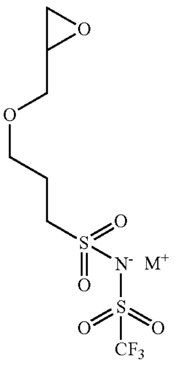
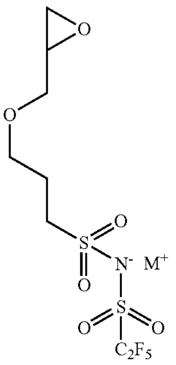
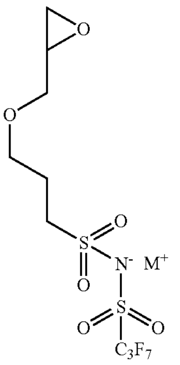
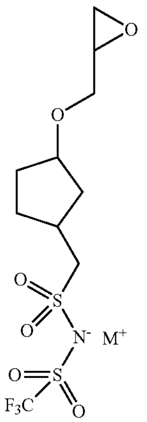
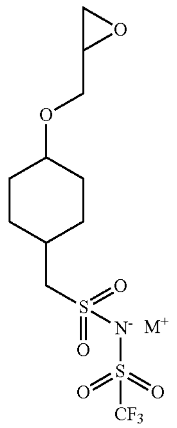
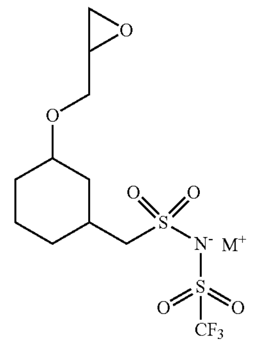

-continued
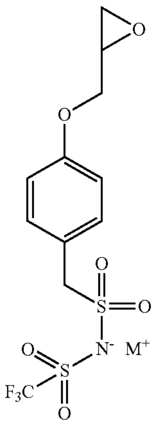
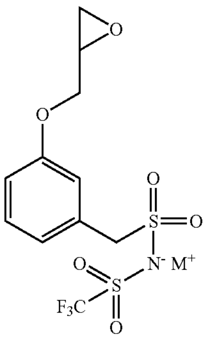
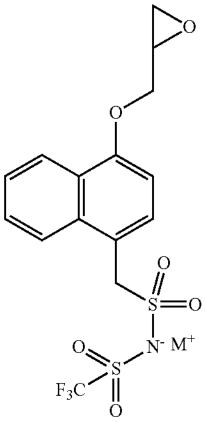
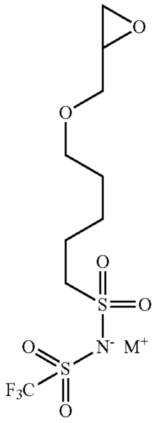
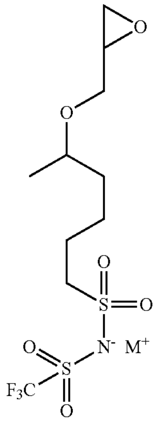
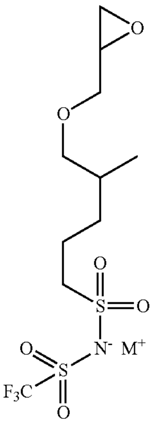
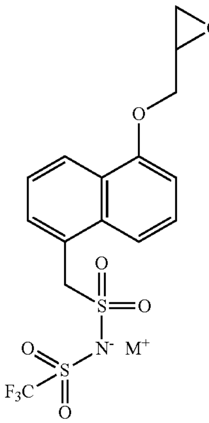
-continued
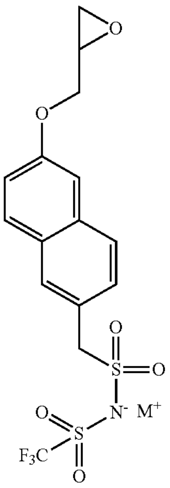
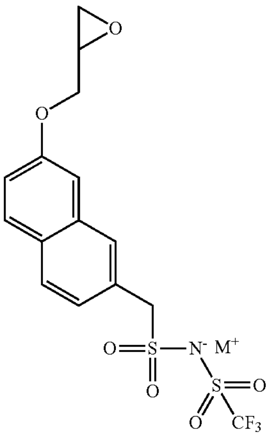
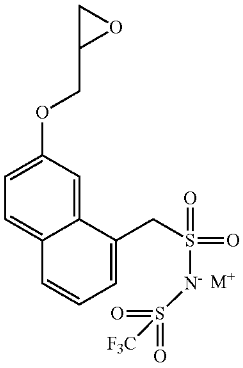
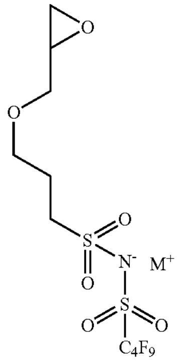
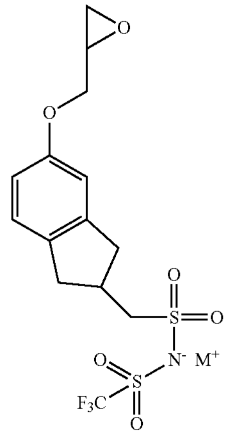
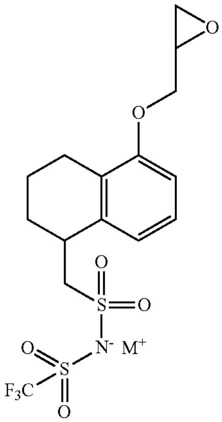

-continued
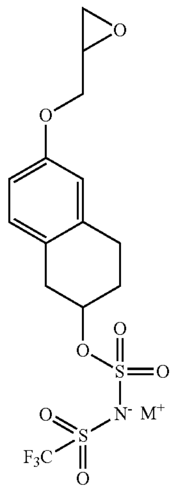
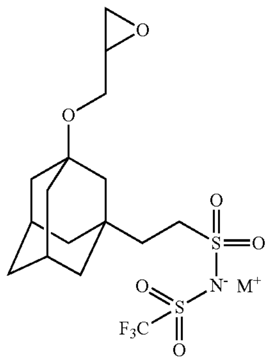
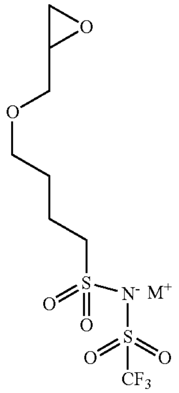
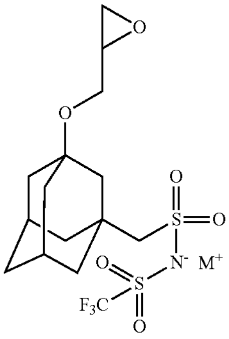
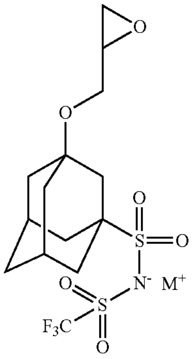
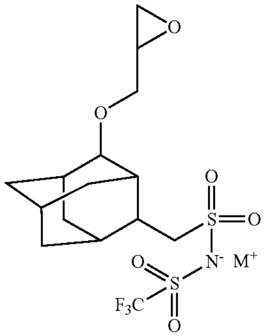
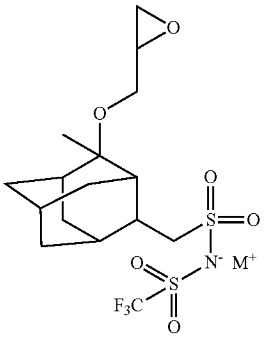
-continued
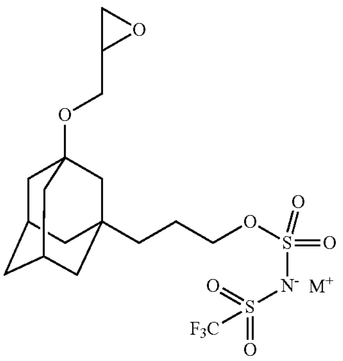
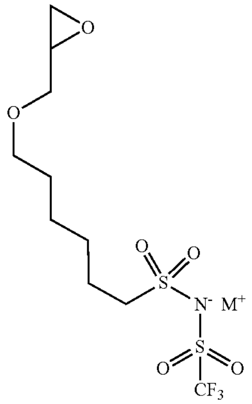
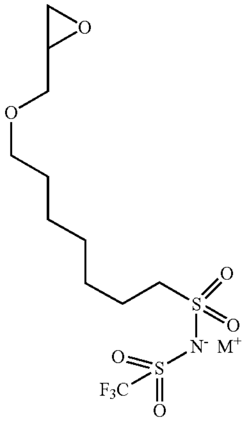
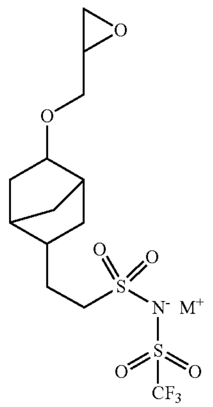
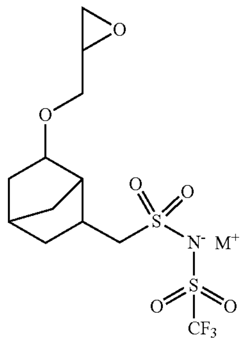
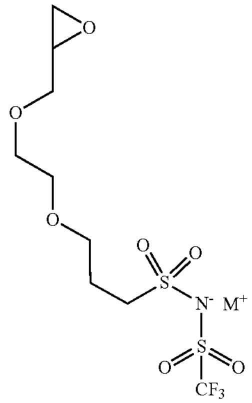
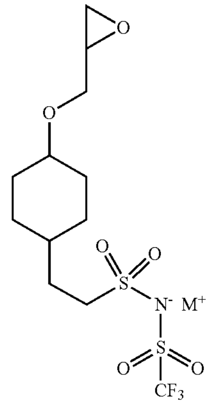

-continued
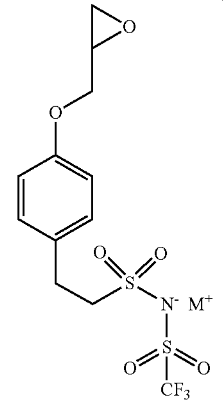
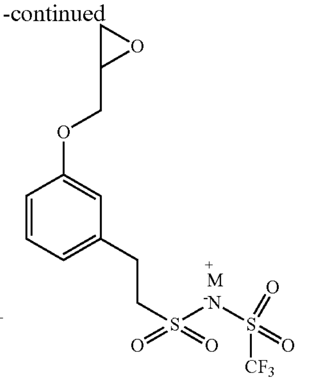
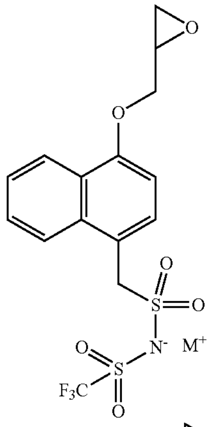
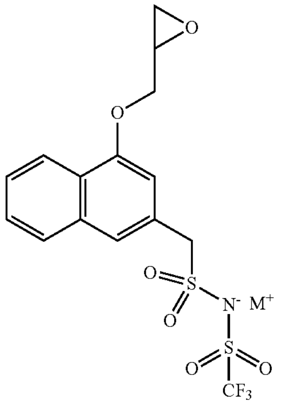
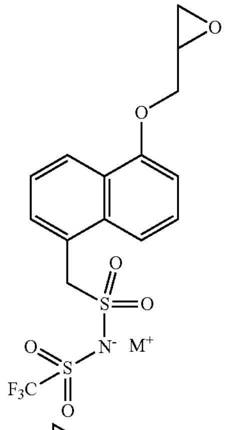
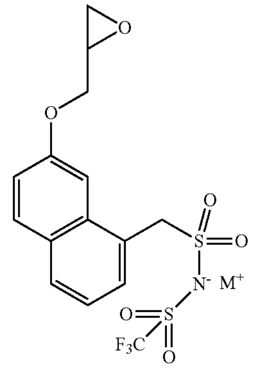
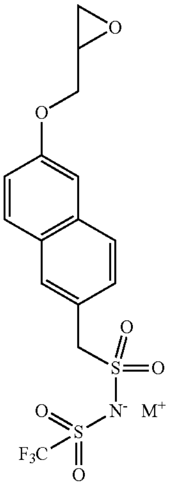
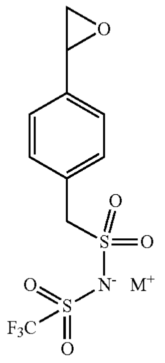
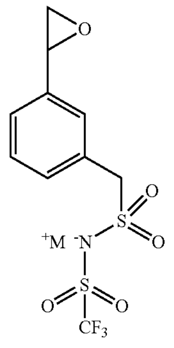
-continued
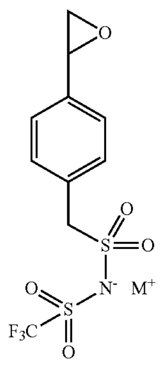
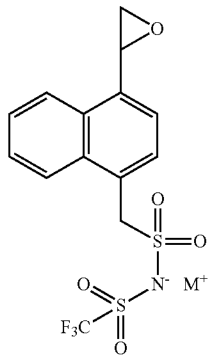
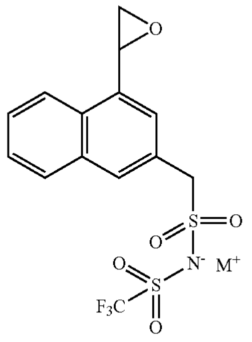
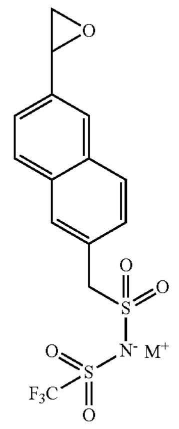
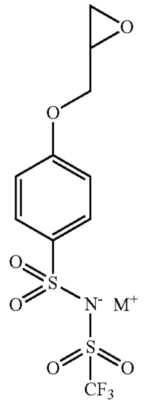
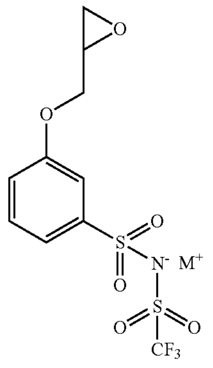
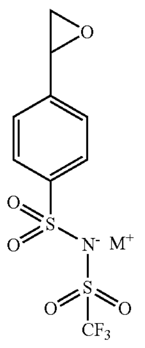
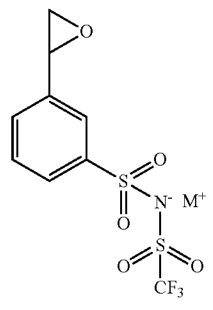
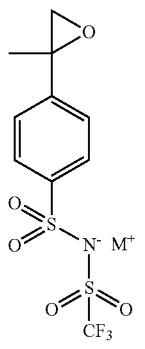
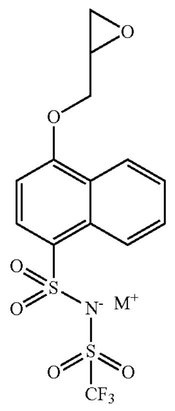

-continued
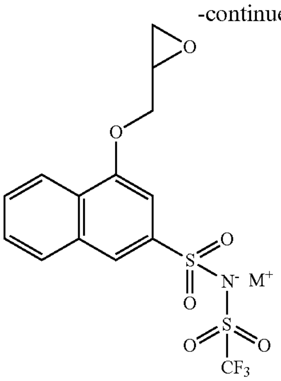
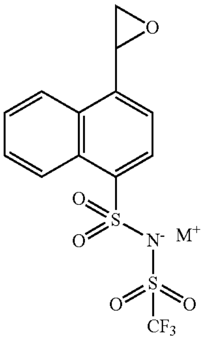
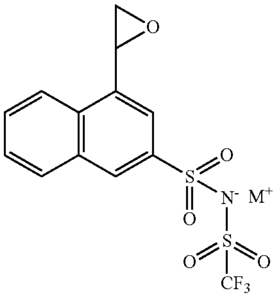
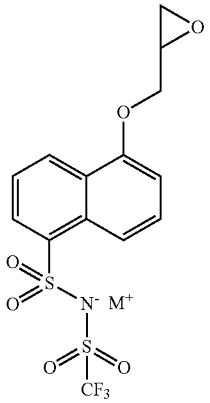
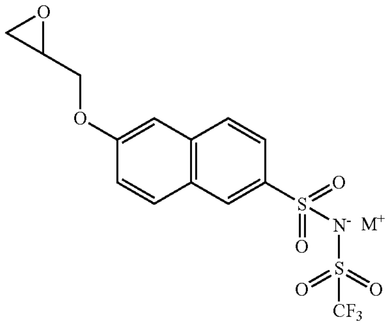
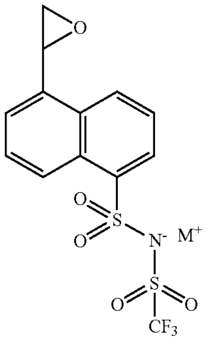
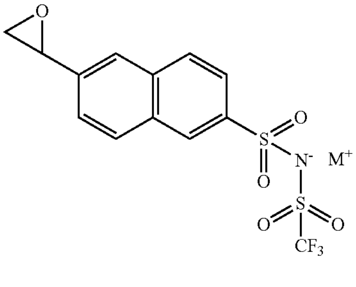
-continued
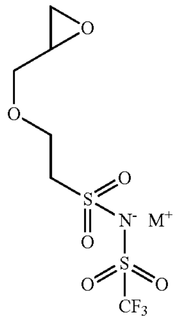
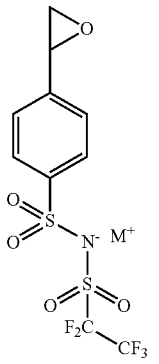
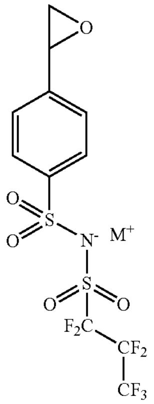
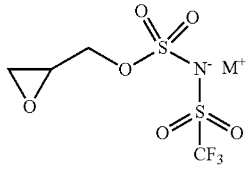
Specific examples of the monomer shown by the general formula (2)-4 can include the following.
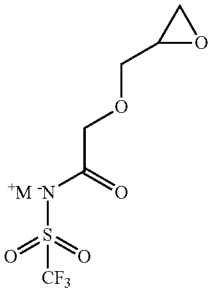
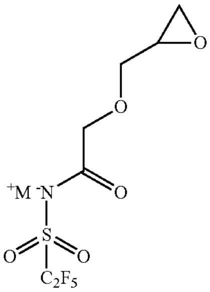
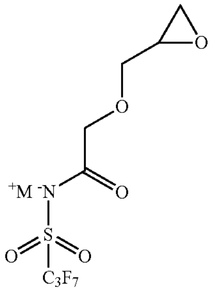
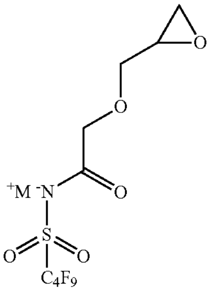
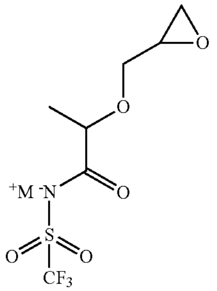
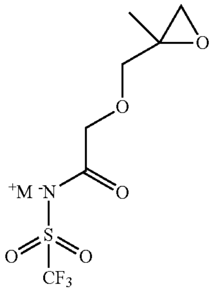

-continued
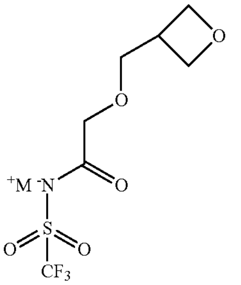
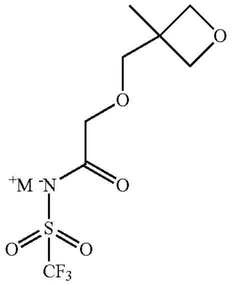
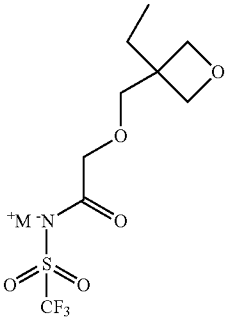
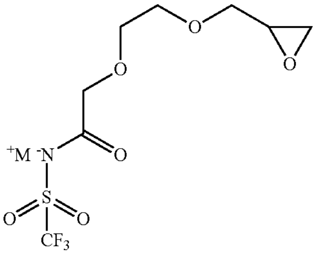
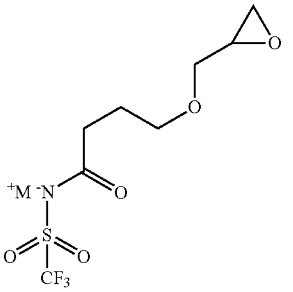
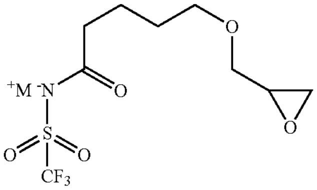
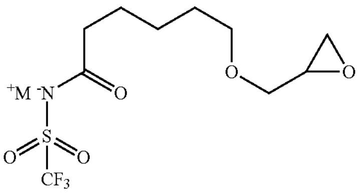
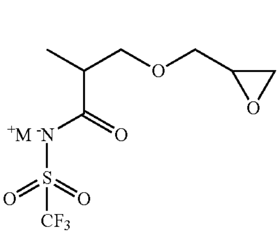
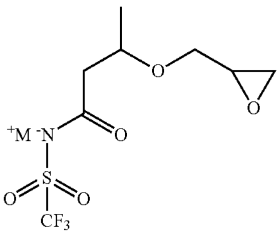
-continued
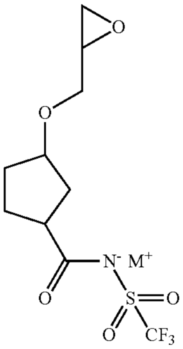
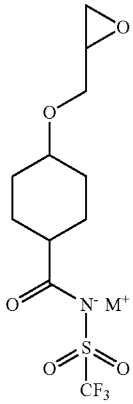
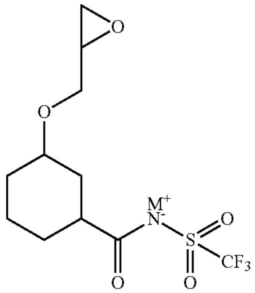
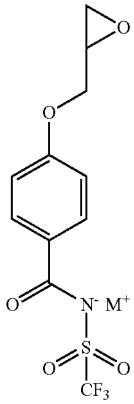
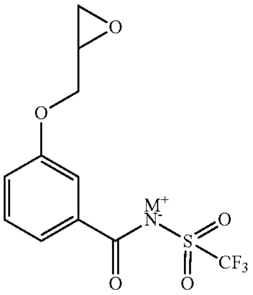
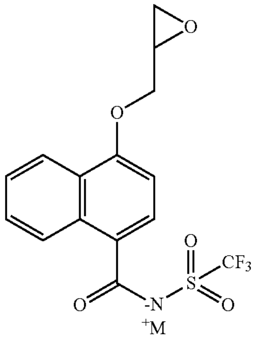
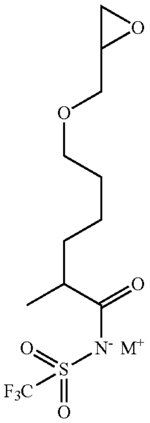
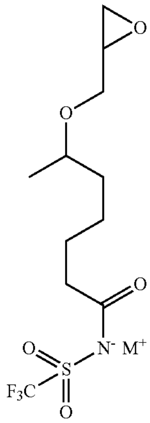
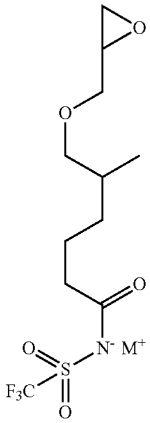

-continued
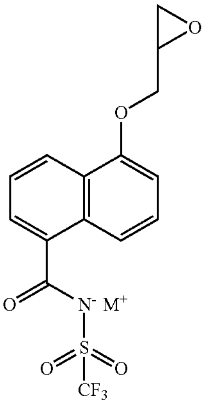
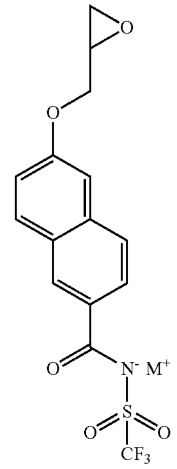
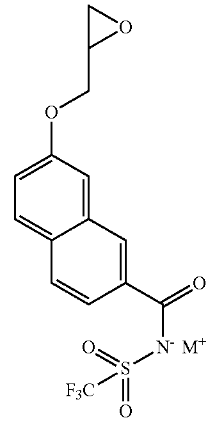
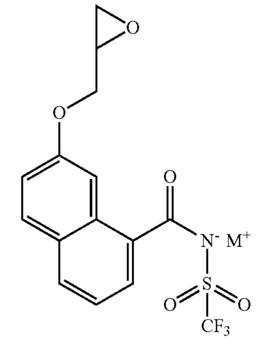
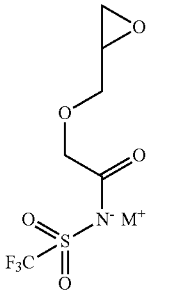
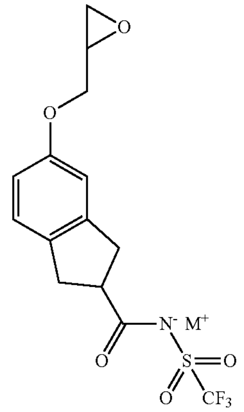
-continued
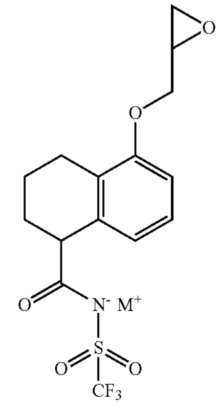
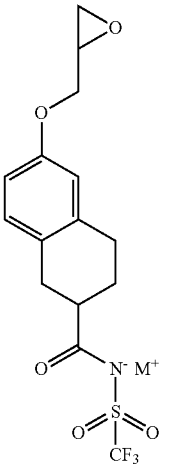
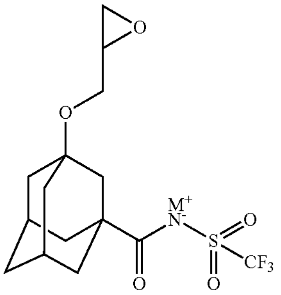
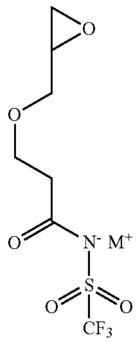
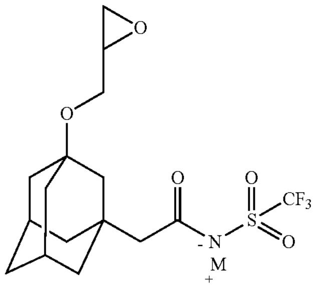
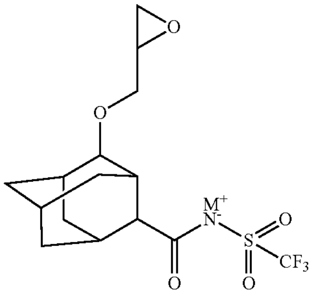
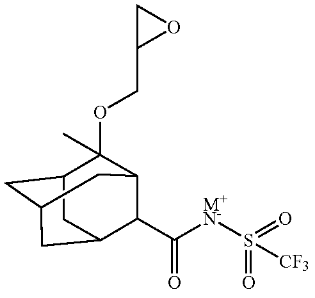

-continued
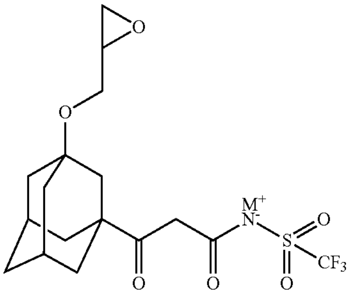
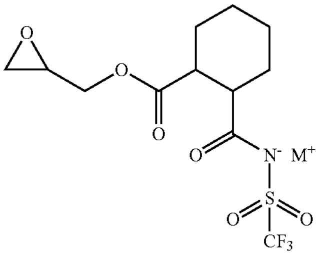
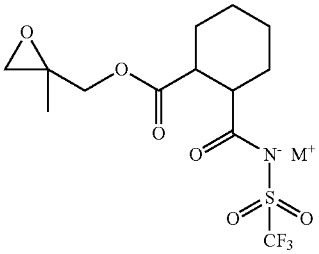
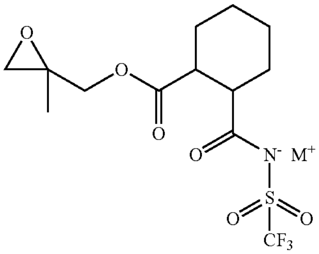
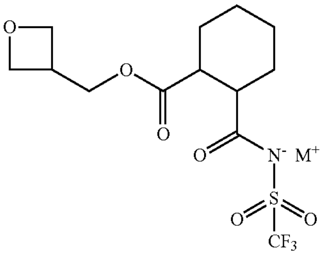
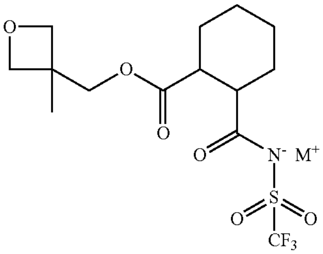
-continued
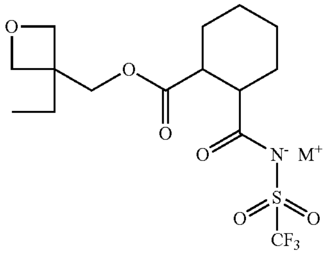
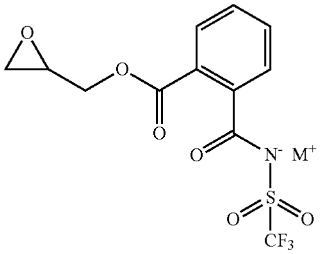
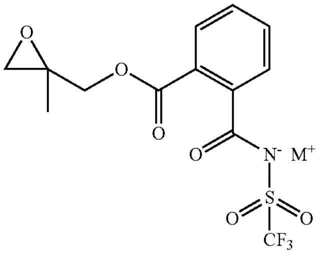
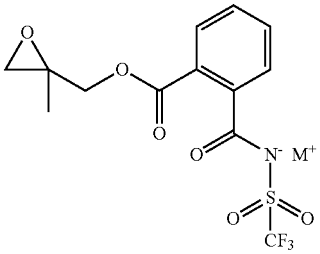
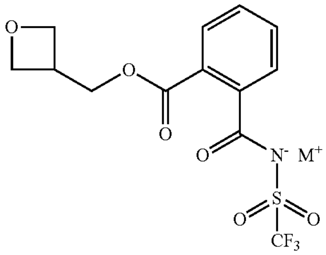
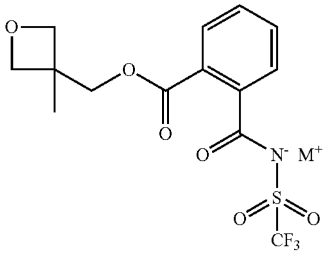

-continued
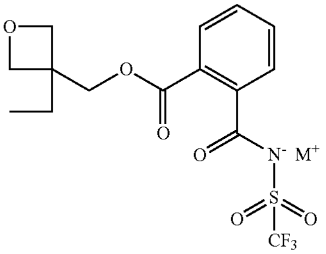
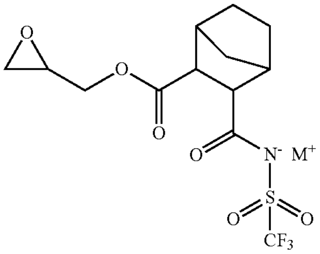
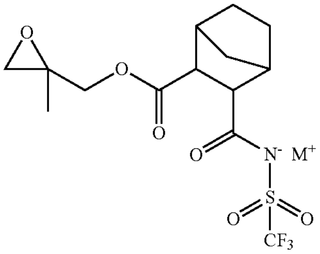
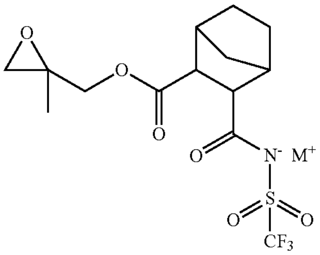
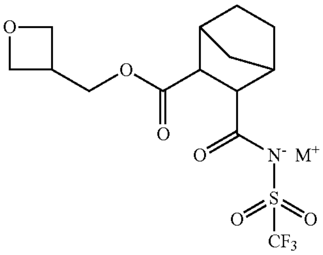
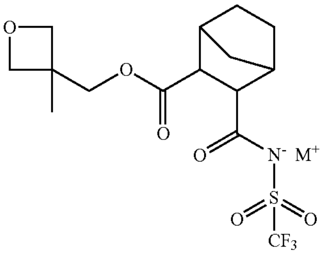
-continued
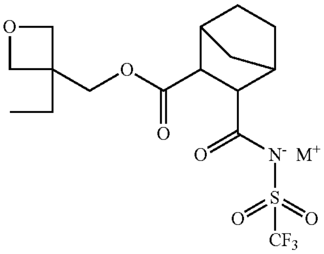
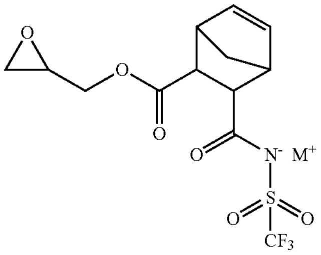
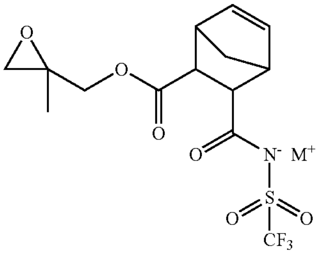
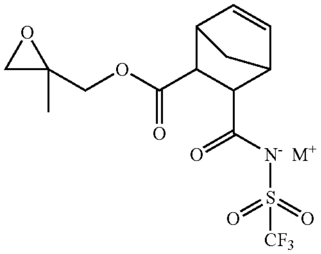
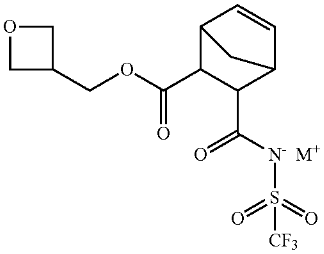
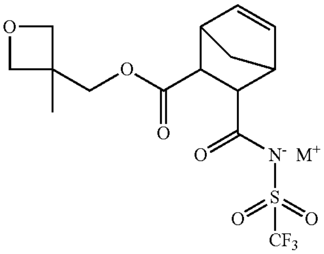

-continued
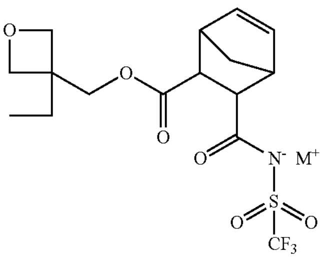
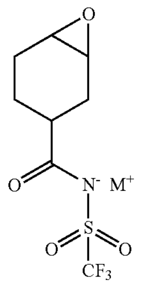
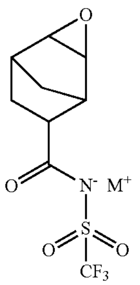
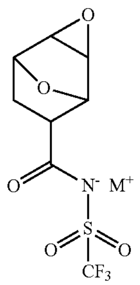
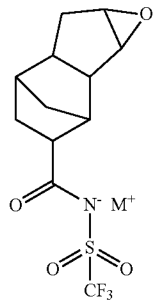
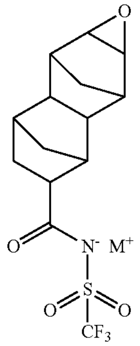
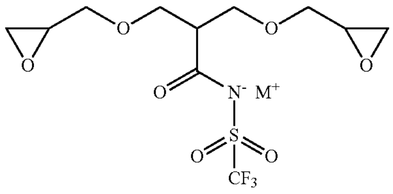
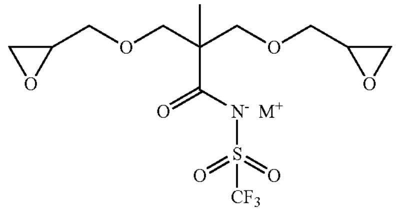
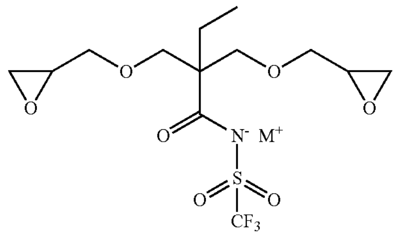
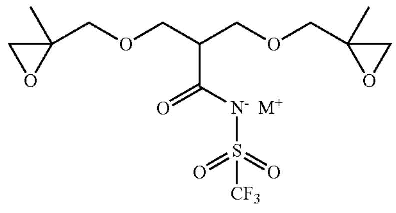
-continued
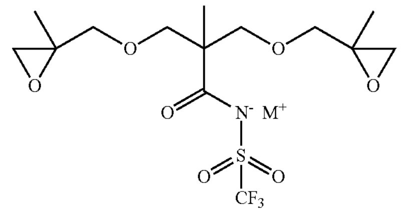
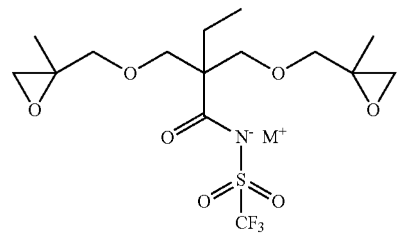
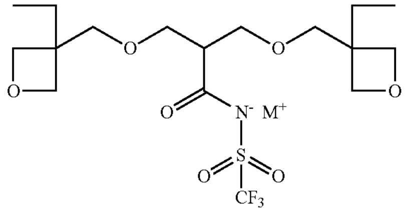
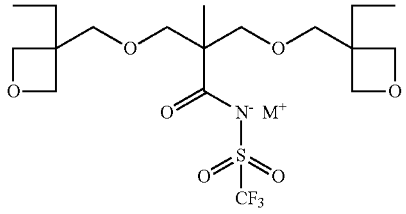
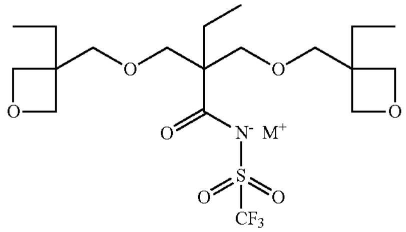
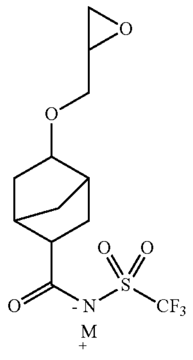
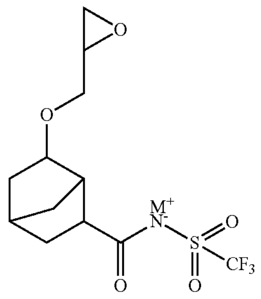

-continued

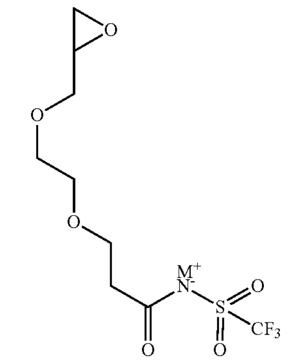

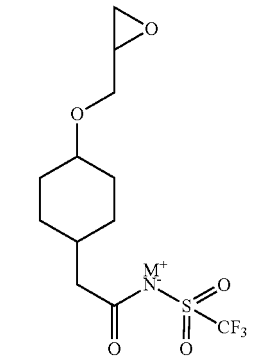

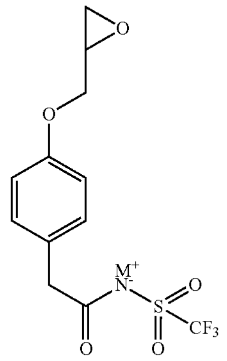

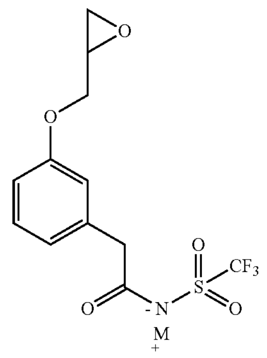

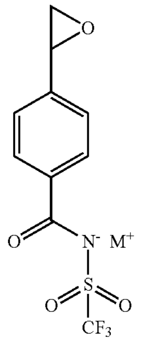

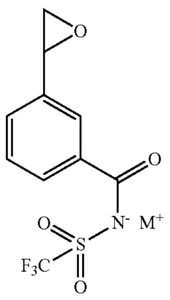

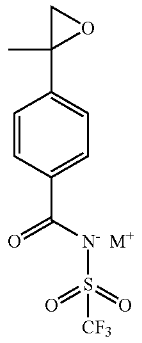

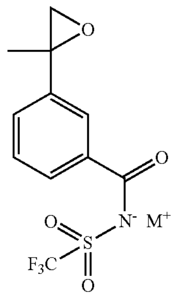

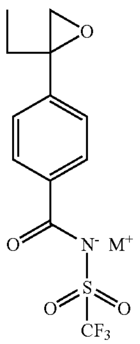

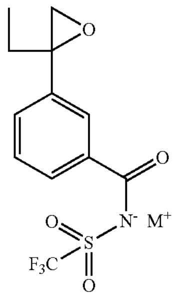

-continued

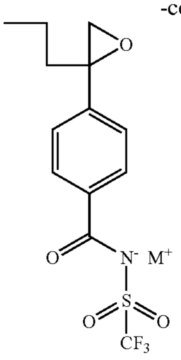

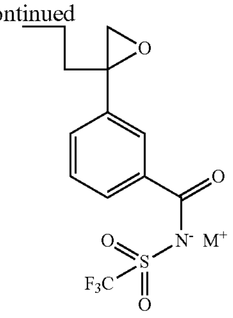

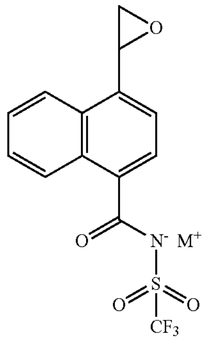

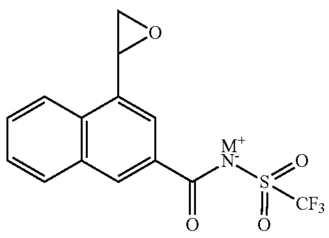

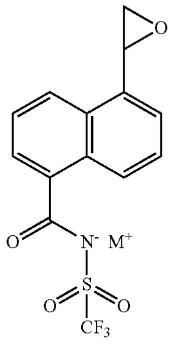

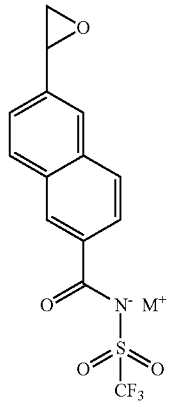

In the formulae, $M^+$ is as defined above.

The component (A) preferably contains an ammonium ion (ammonium cation) shown by the following general formula (3) as an ammonium ion for forming the ammonium salts, particularly as $M^+$ in the monomers shown by the general formulae (2)-1 to (2)-4.

(3)

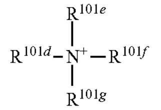

In the formula, $R^{101d}$, $R^{101e}$, $R^{101f}$, and $R^{101g}$ each represent a hydrogen atom, a linear, branched, or cyclic alkyl group having 1 to 13 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom.

$R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

Specific examples of the ammonium ion shown by the general formula (3) can include the following.

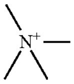
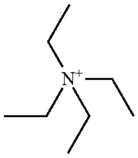
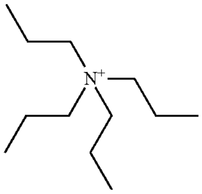
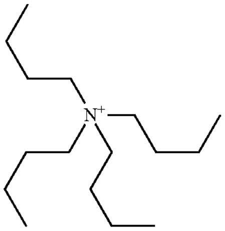
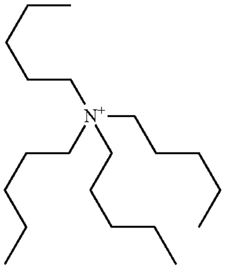
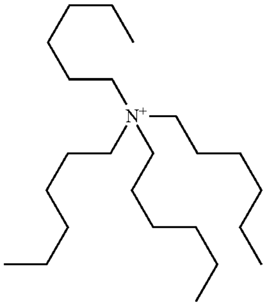
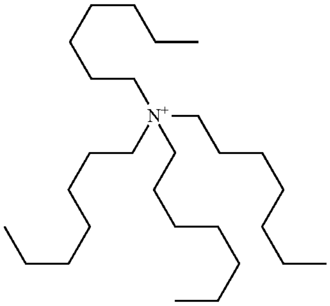
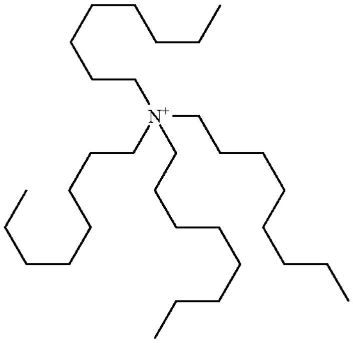

-continued

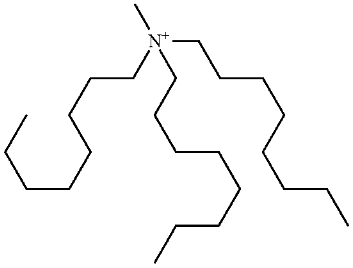
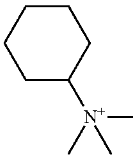
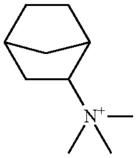
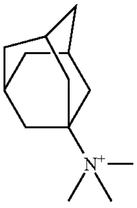
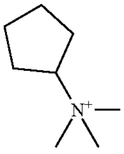
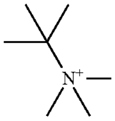
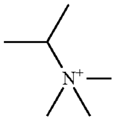
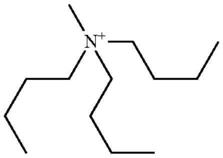
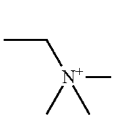
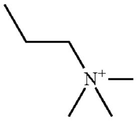
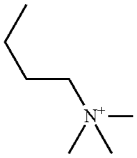
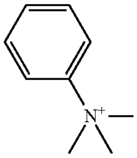
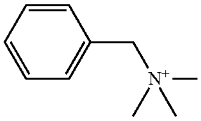
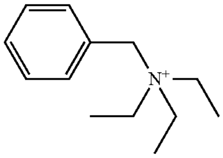
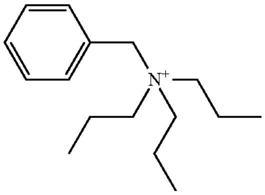
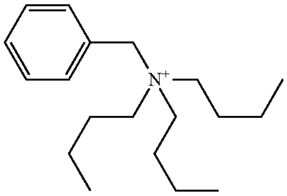
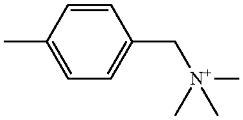
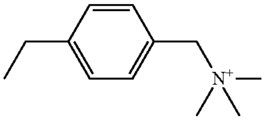
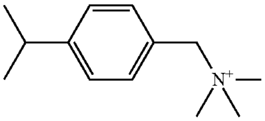
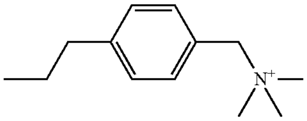
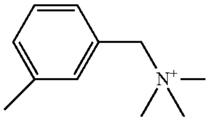
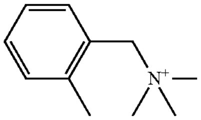
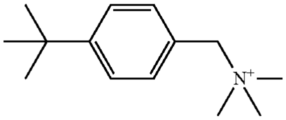

-continued
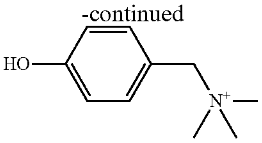
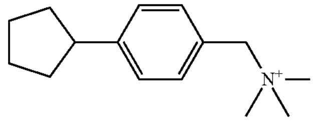
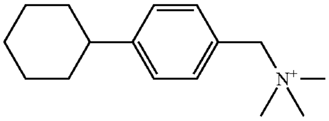
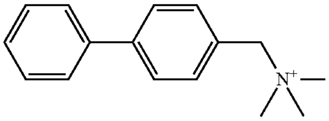
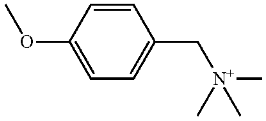
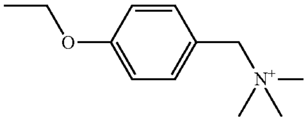
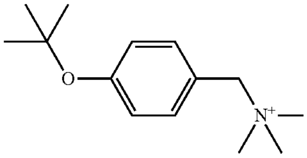
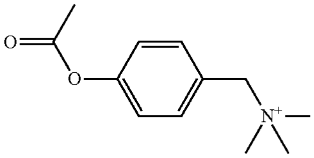
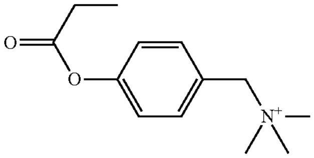
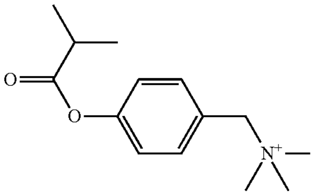
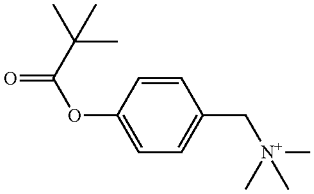
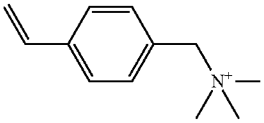
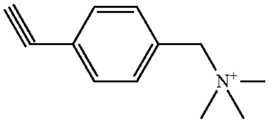
-continued
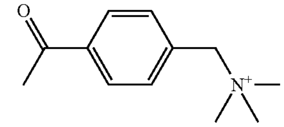
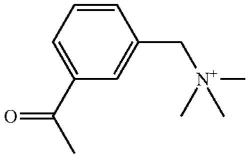
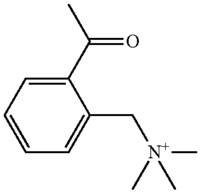
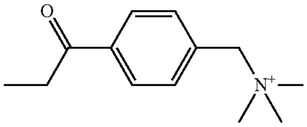
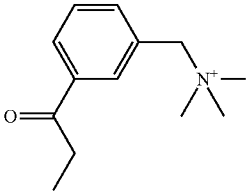
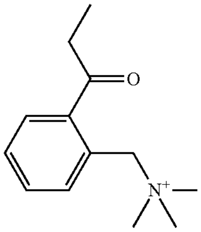
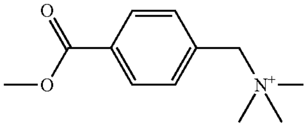
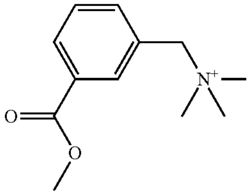
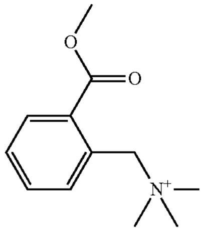
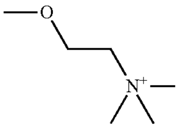
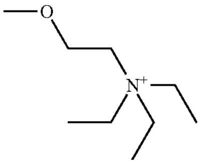
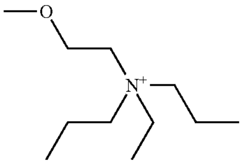
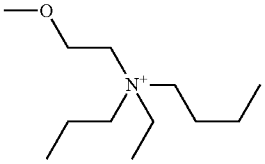
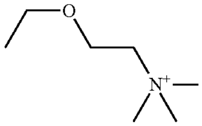
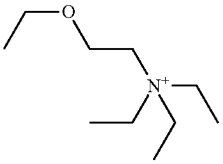
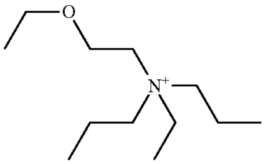
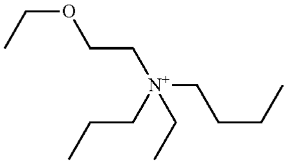
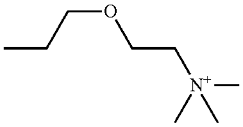

-continued
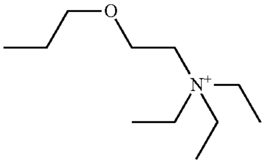
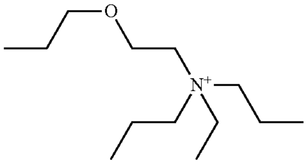
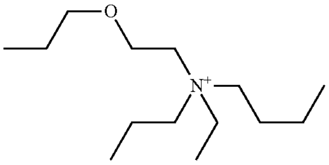
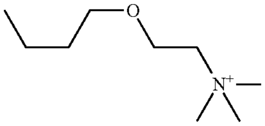
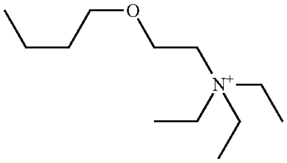
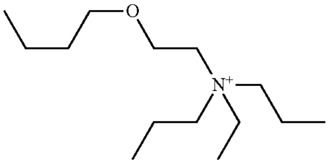
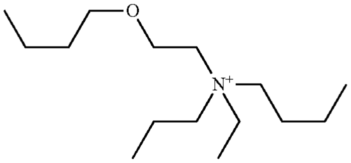
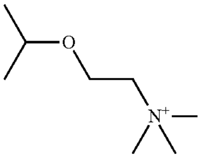
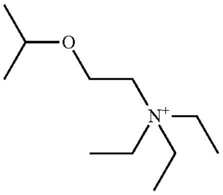
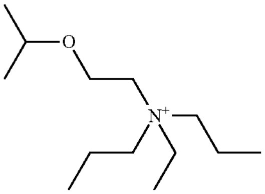
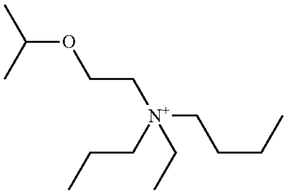
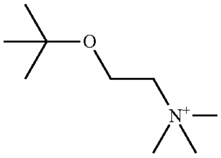
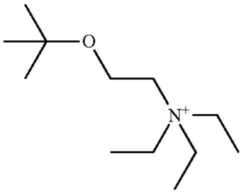
-continued
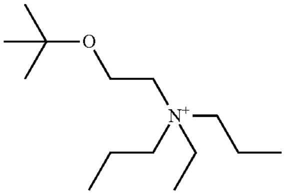
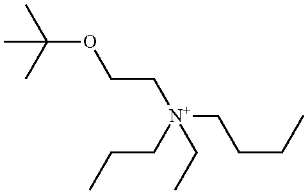
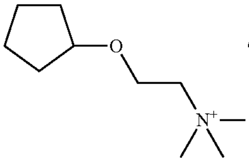
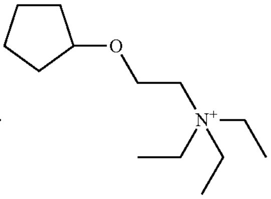
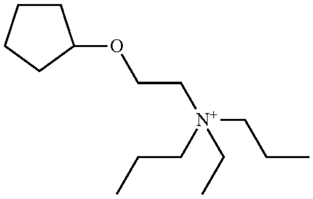
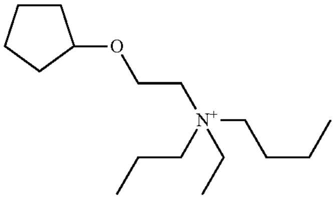
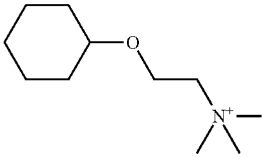
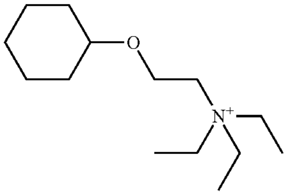
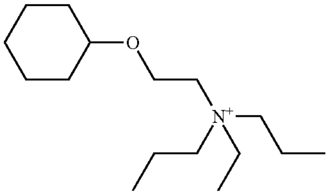
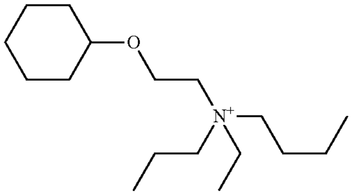

-continued
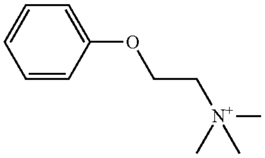
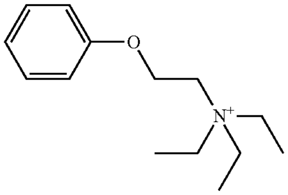
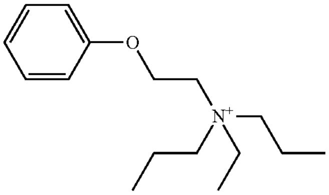
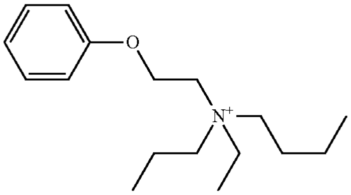
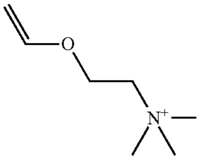
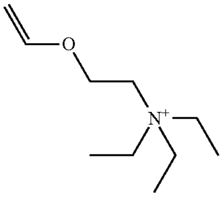
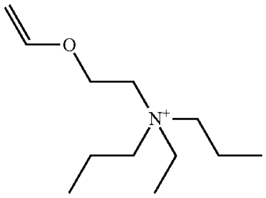
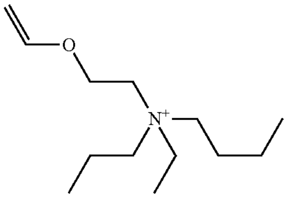
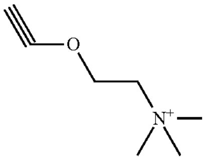
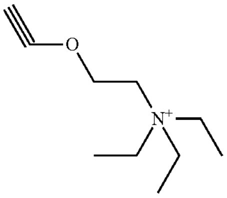
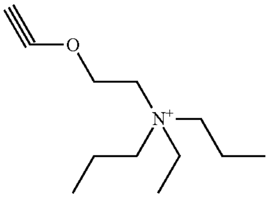
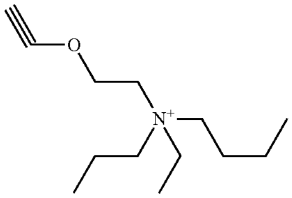
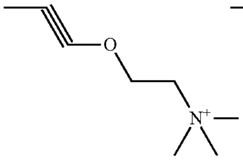
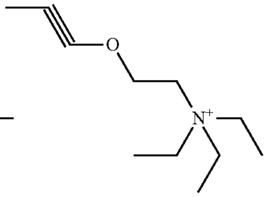
-continued
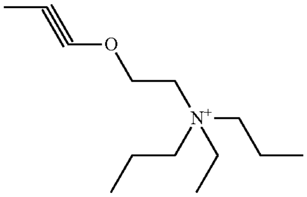
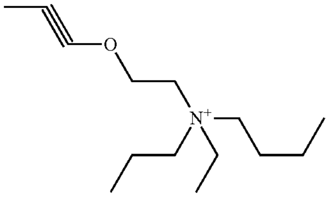
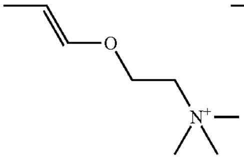
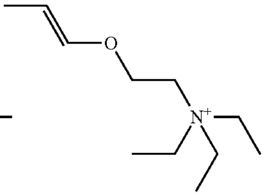
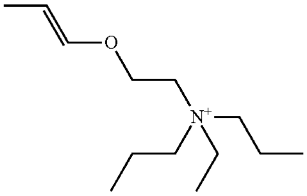
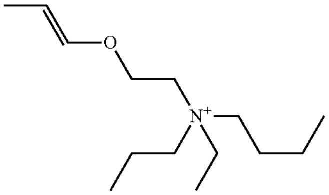
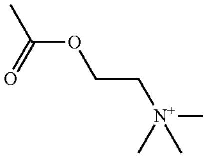
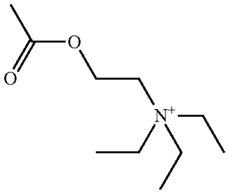
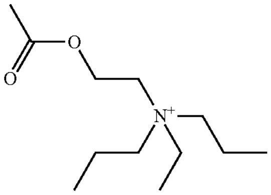
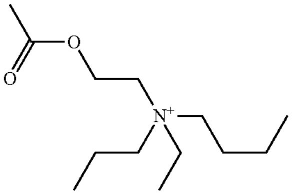
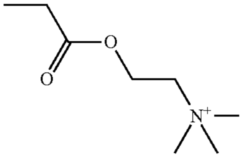
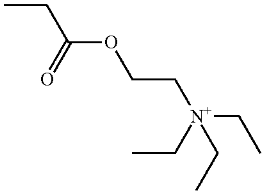

-continued
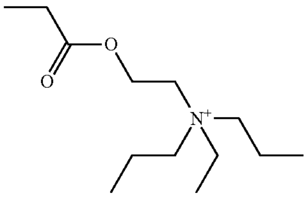
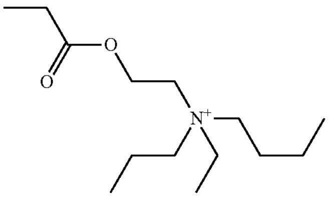
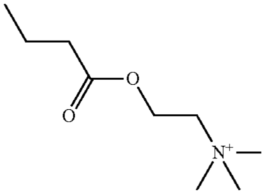
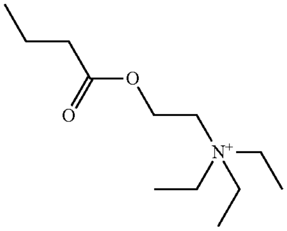
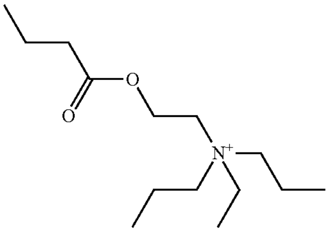
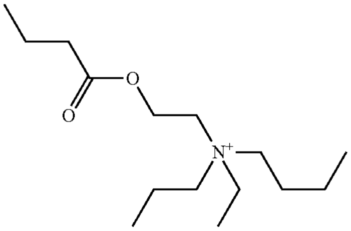
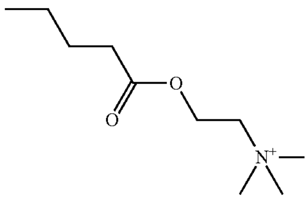
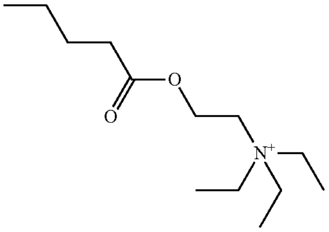
-continued
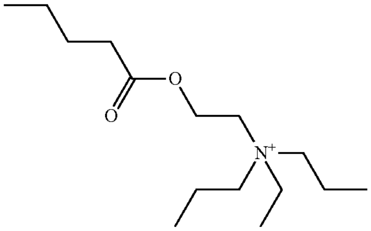
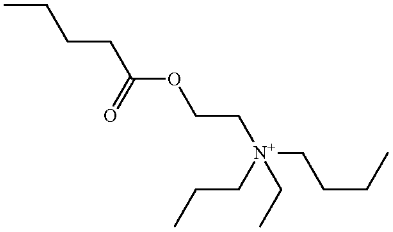
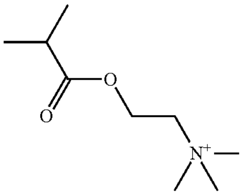
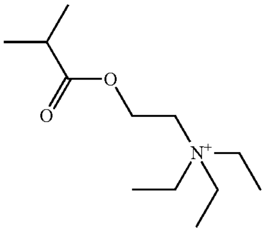
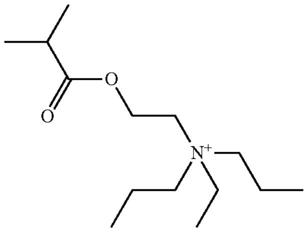
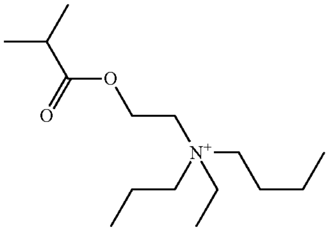
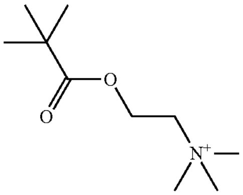
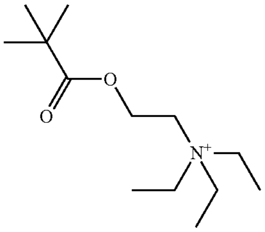
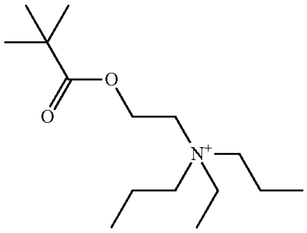

-continued
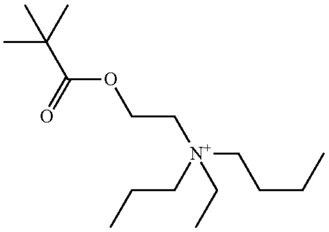
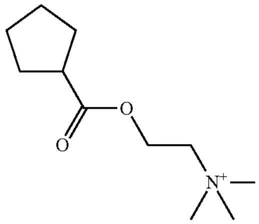
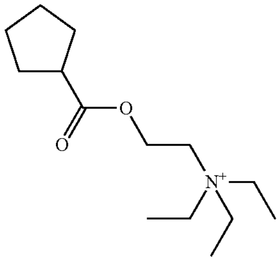
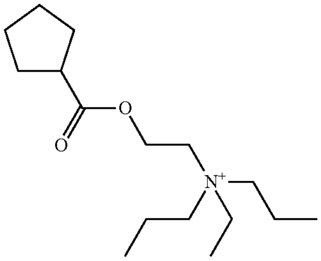
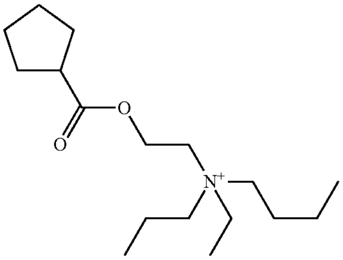
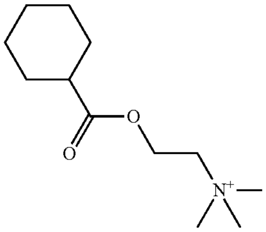
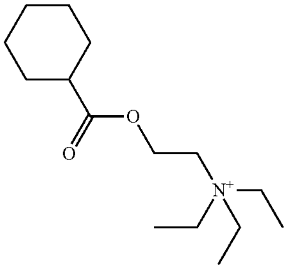
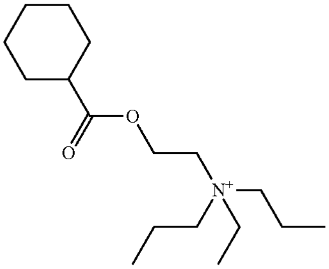
-continued
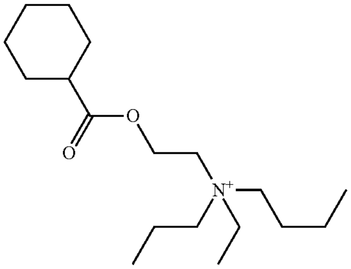
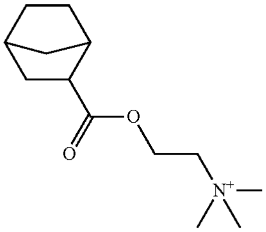
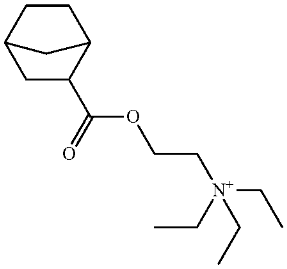
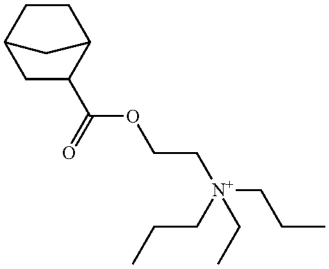
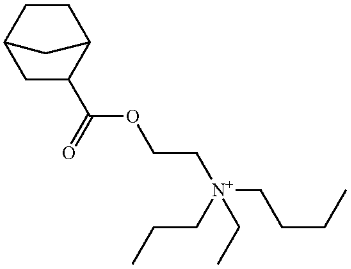
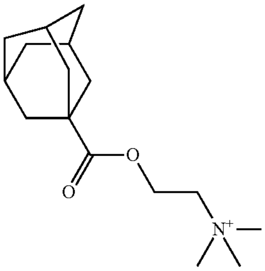
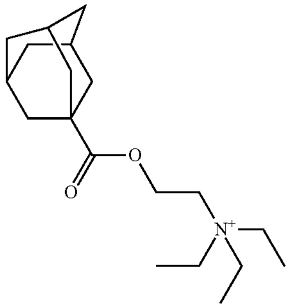
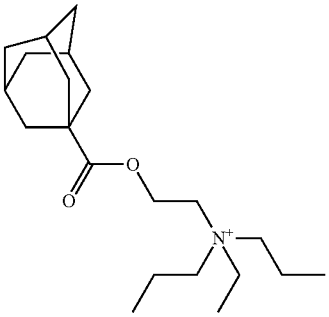

-continued
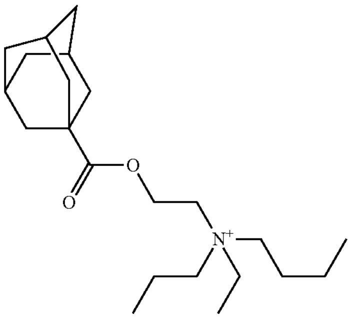
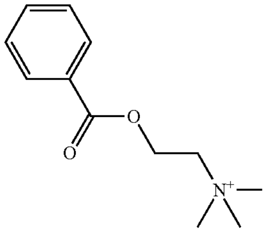
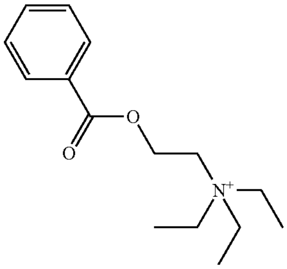
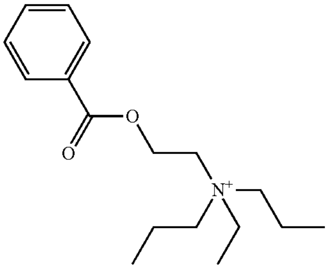
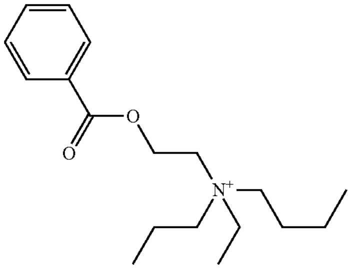
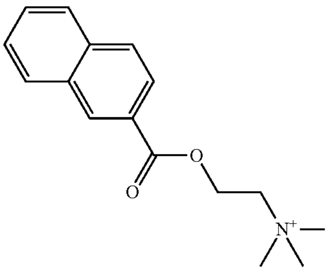
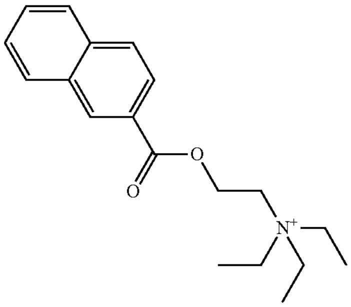
-continued
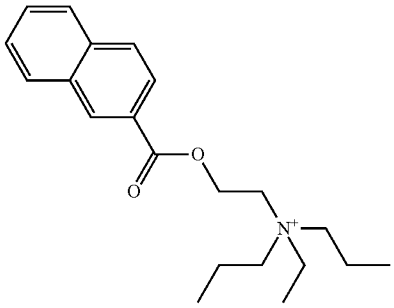
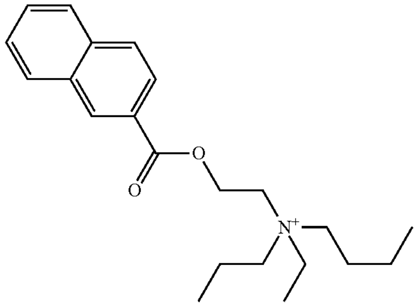
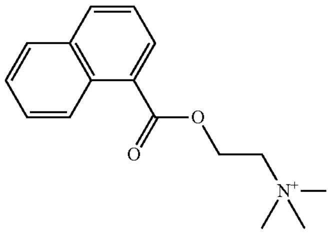
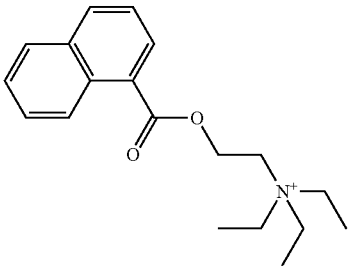
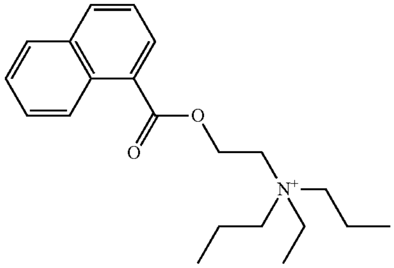
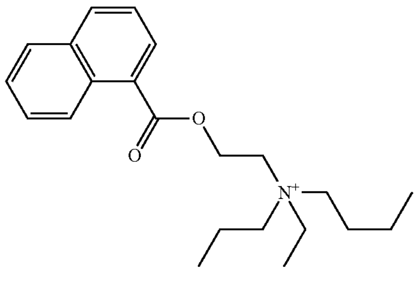

-continued
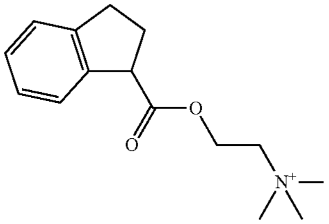
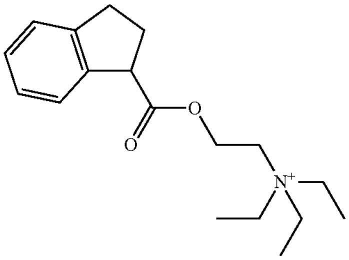
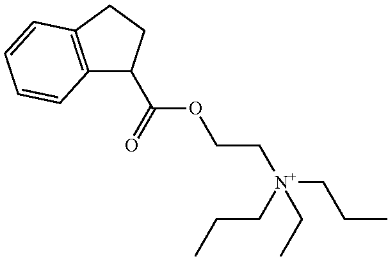
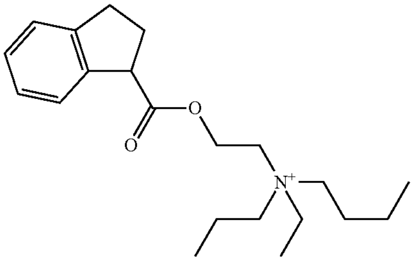
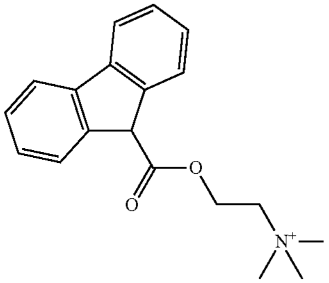
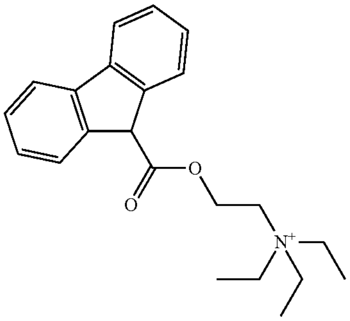
-continued
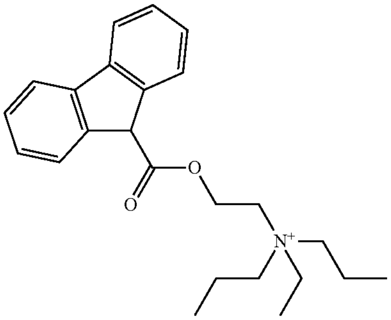
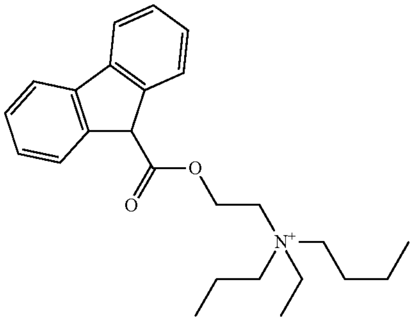
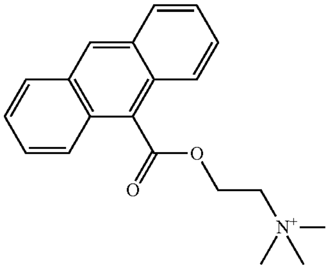
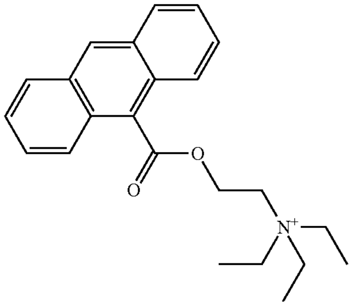
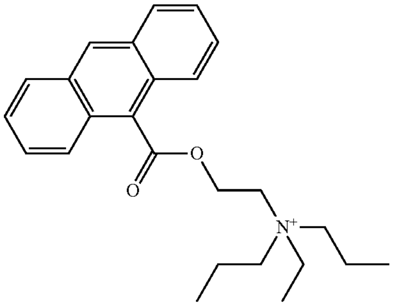

-continued
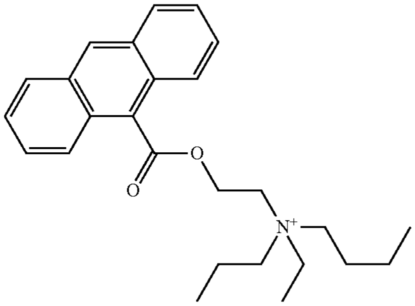
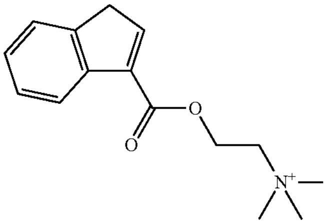
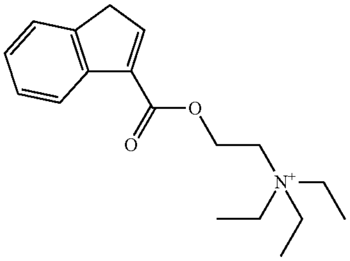
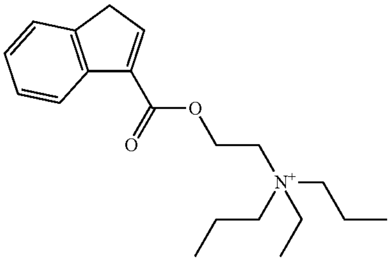
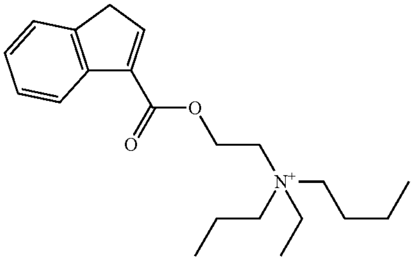
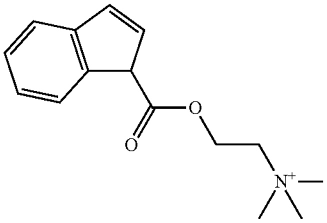
-continued
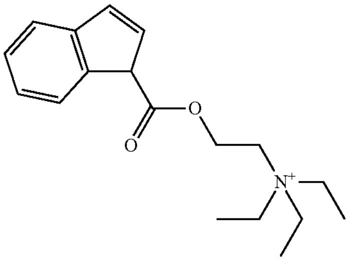
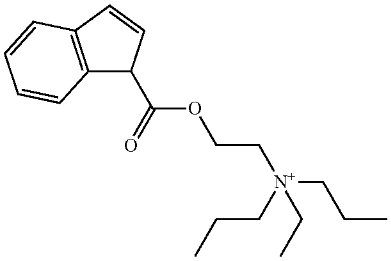
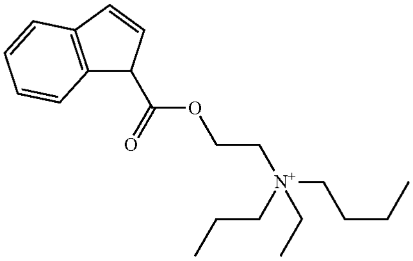
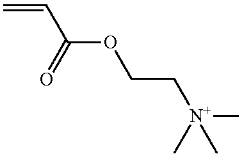
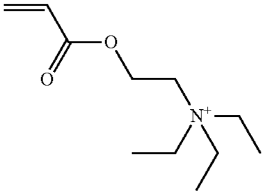
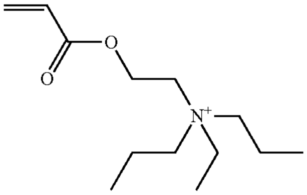
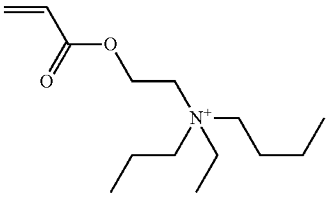
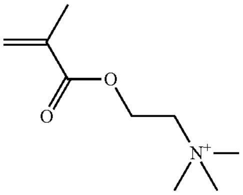
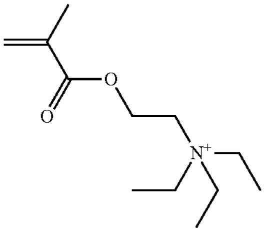

-continued
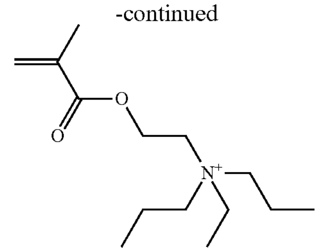
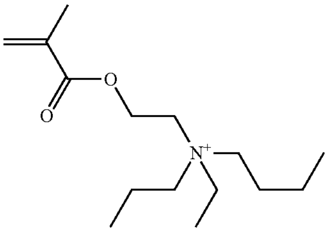
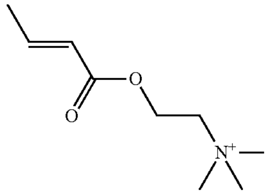
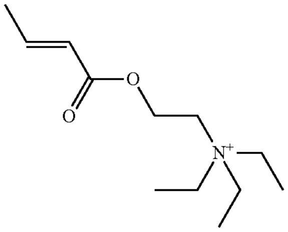
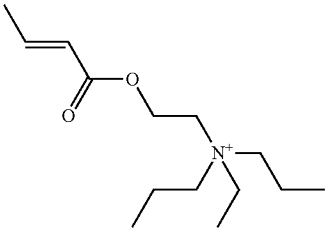
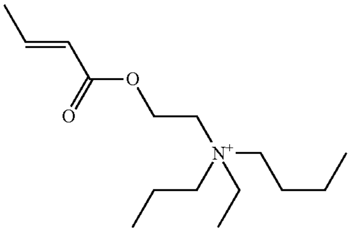
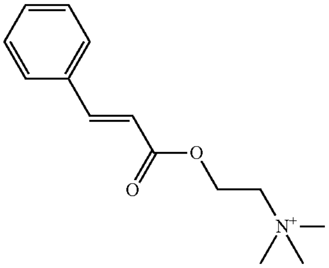
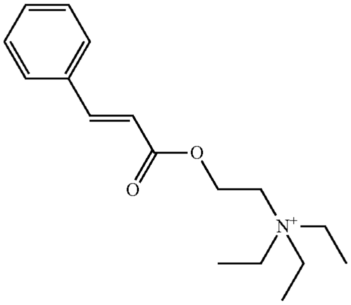
-continued
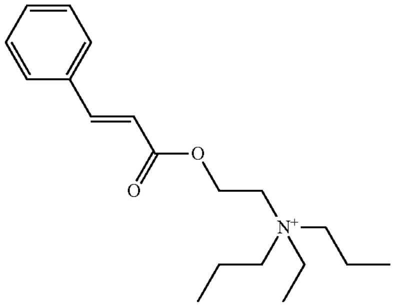
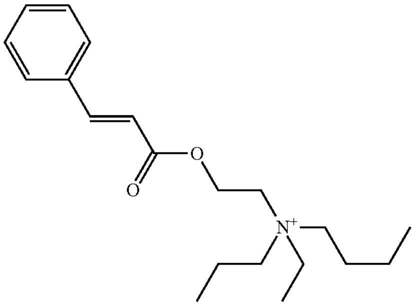
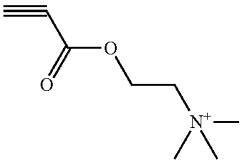
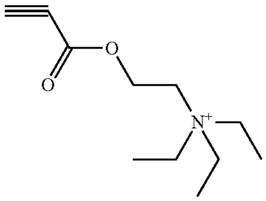
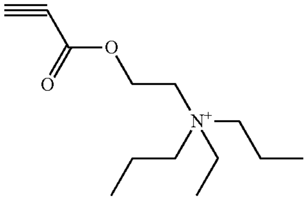
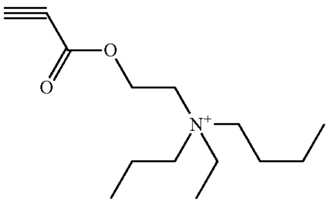
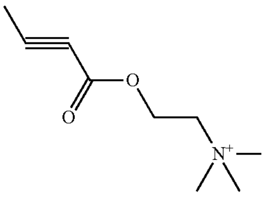
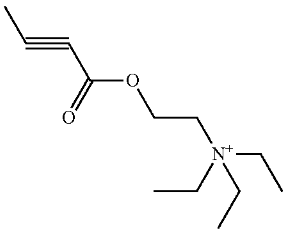
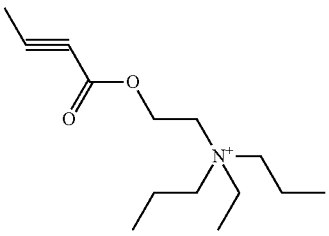

-continued
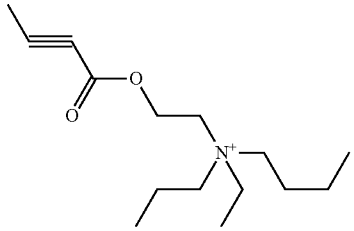
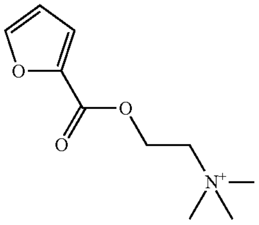
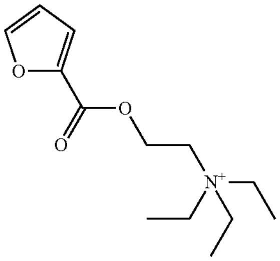
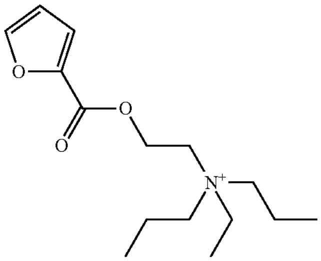
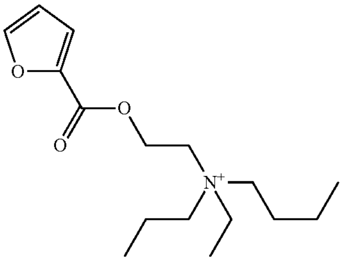
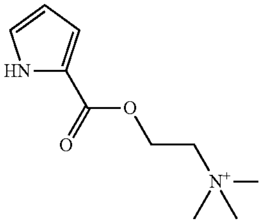
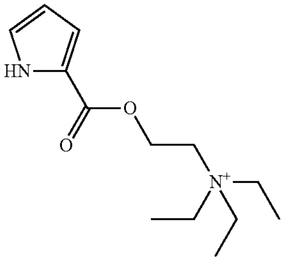
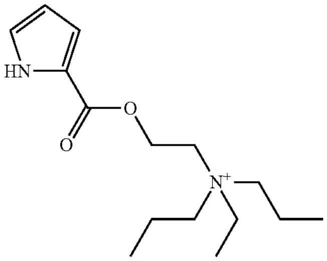
-continued
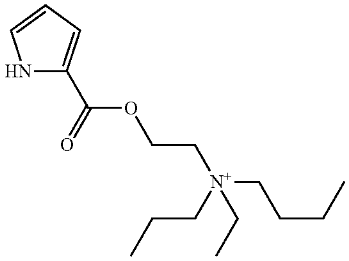
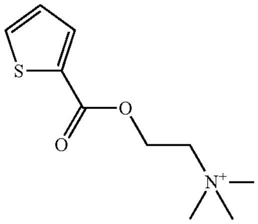
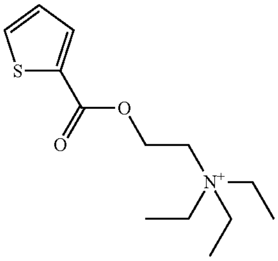
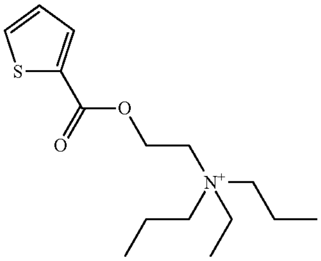
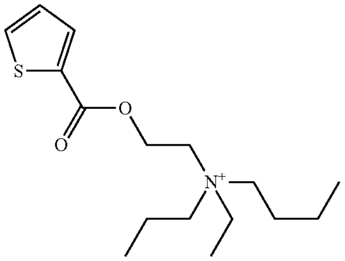
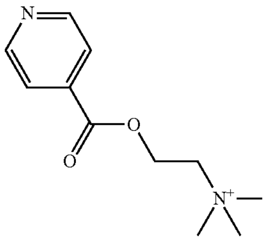
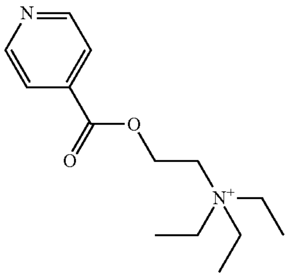
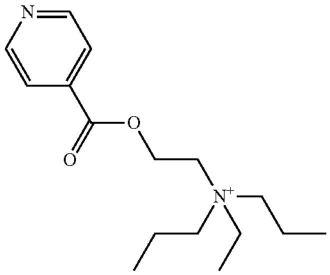

-continued
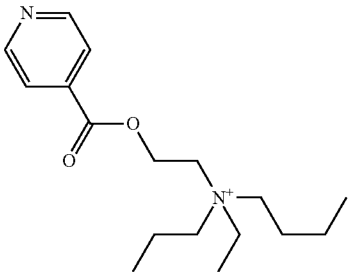
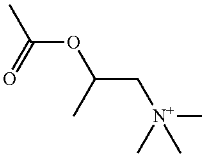
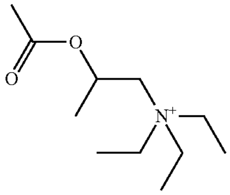
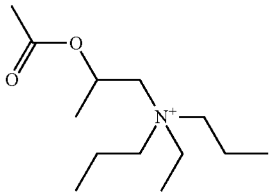
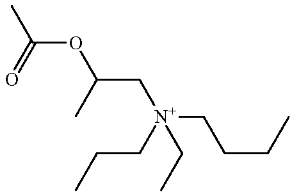
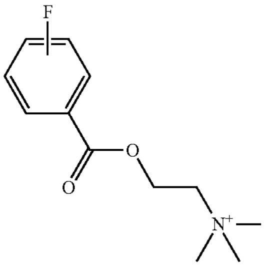
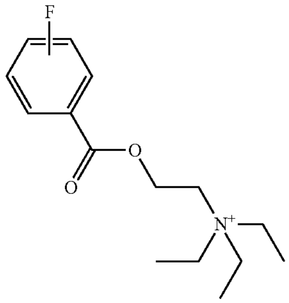
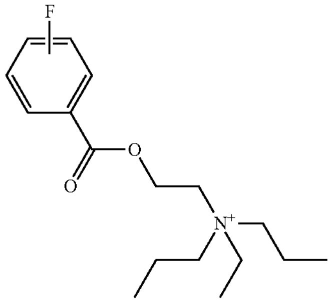
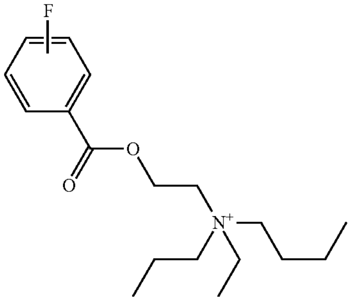
-continued
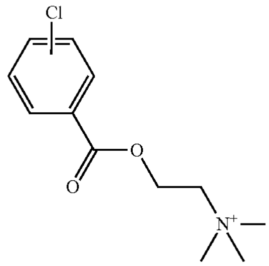
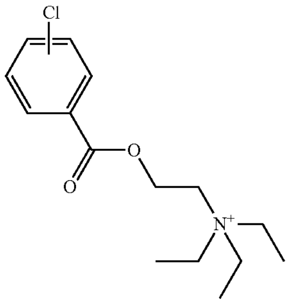
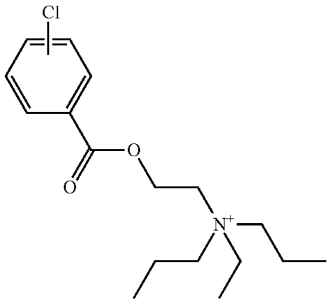
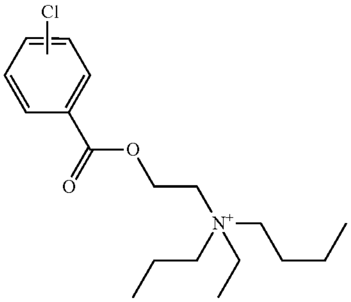
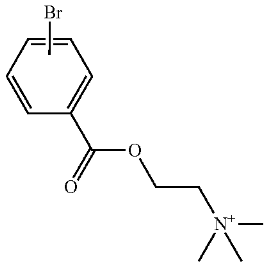
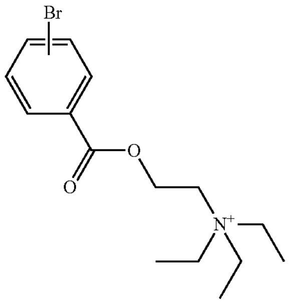
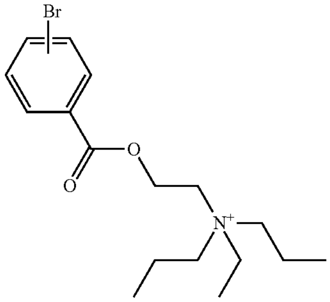

-continued
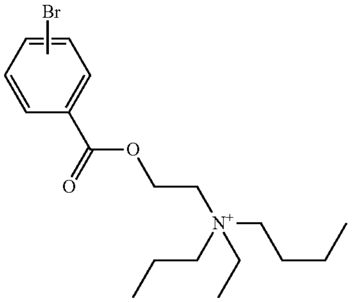
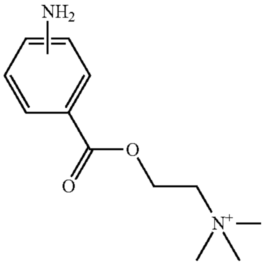
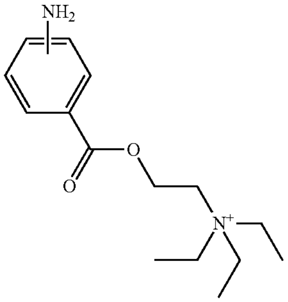
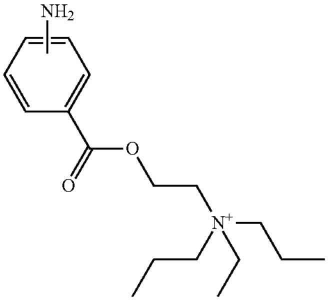
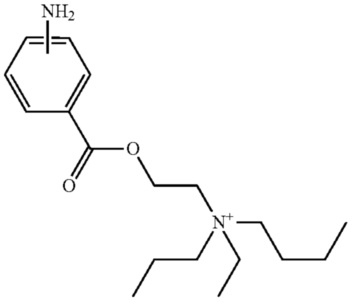
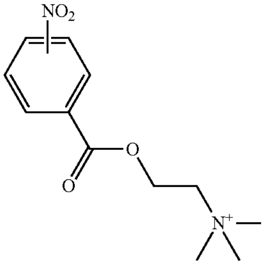
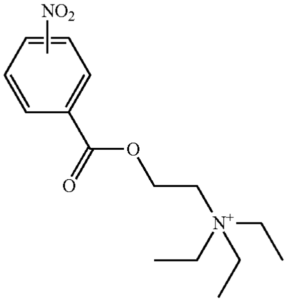
-continued
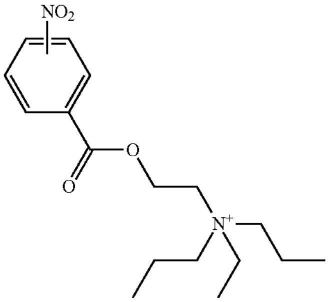
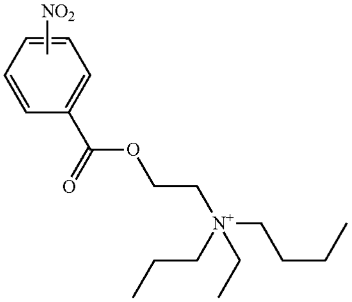
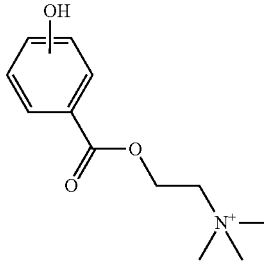
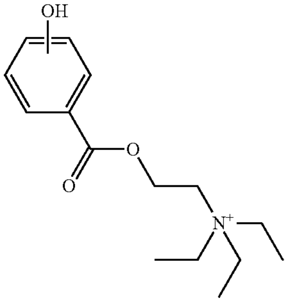
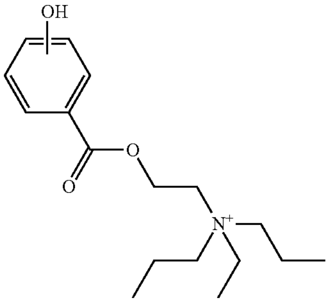
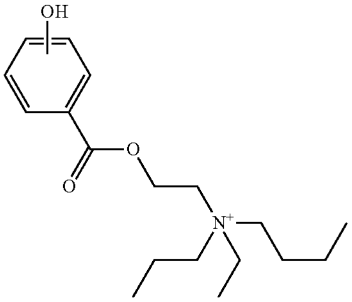

-continued
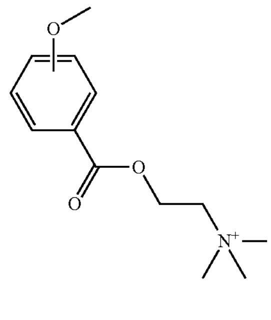
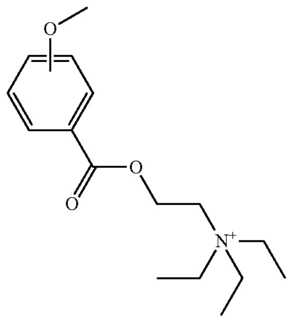
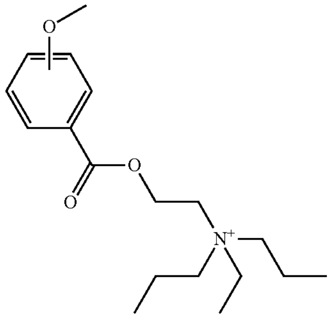
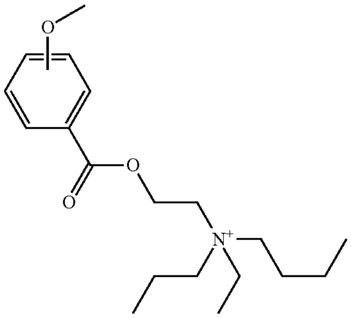
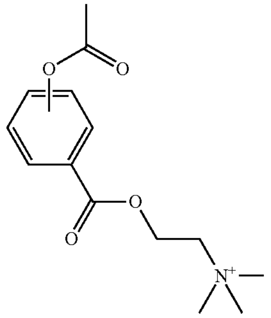
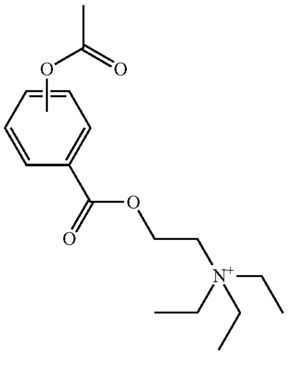
-continued
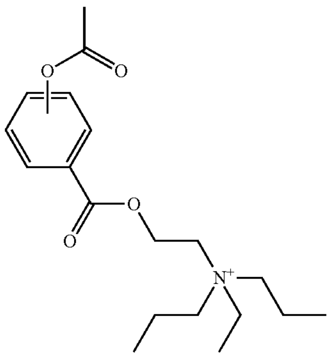
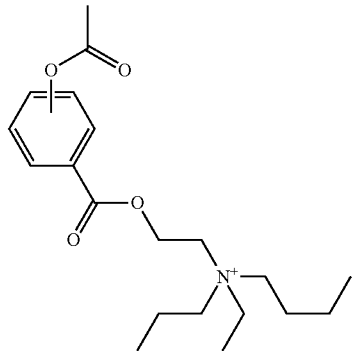
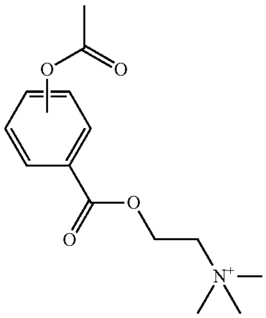
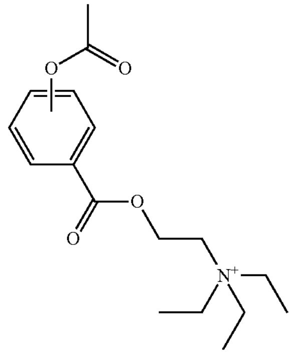
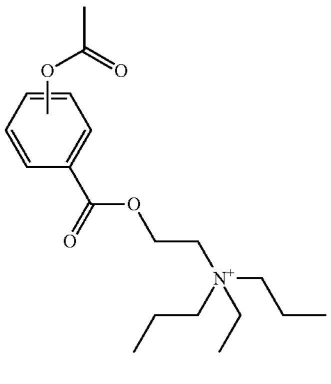

-continued
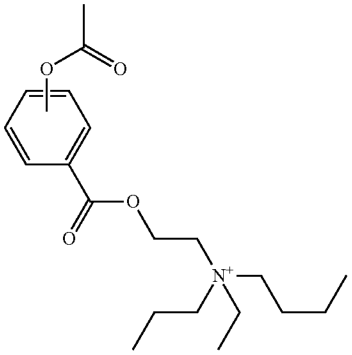
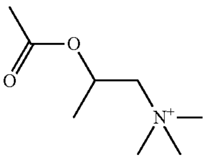
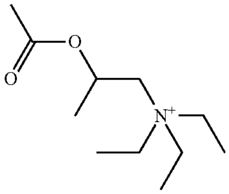
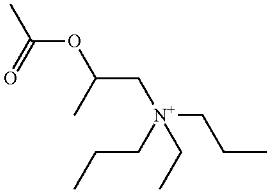
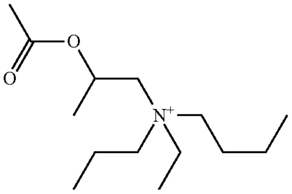
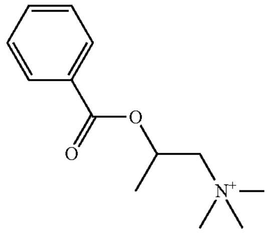
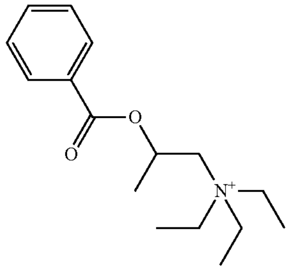
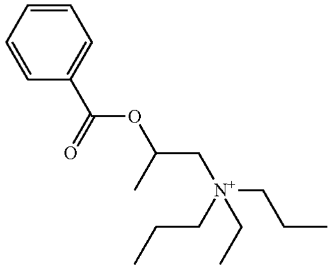
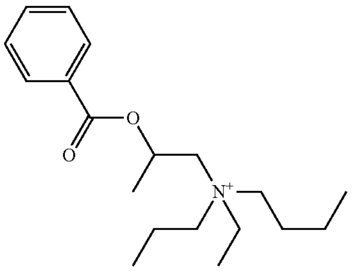
-continued
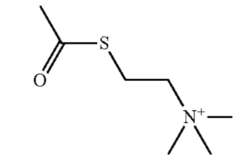
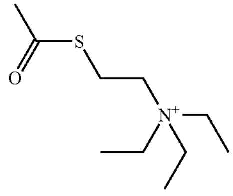
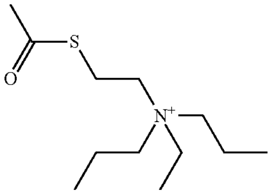
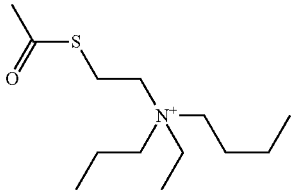
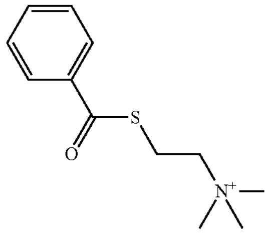
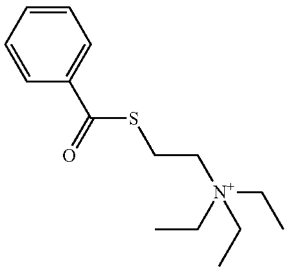
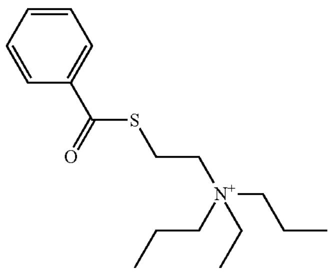
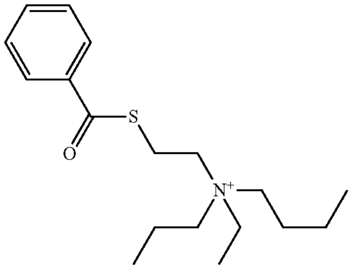
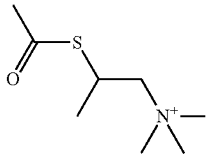
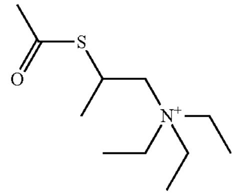
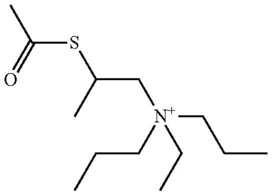
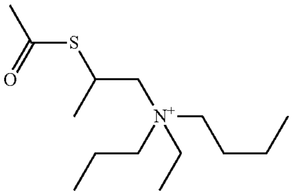

-continued
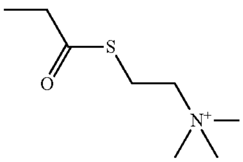
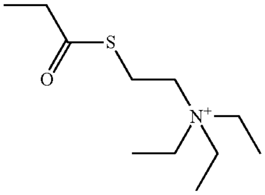
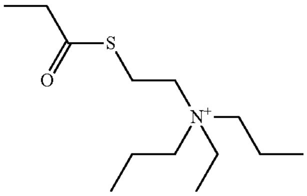
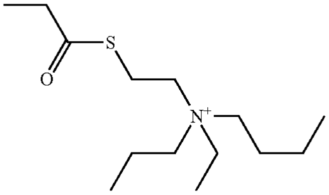
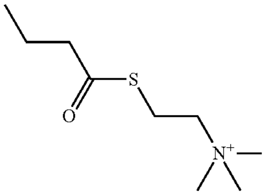
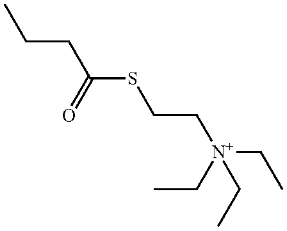
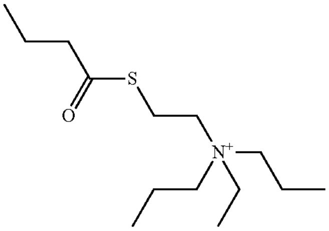
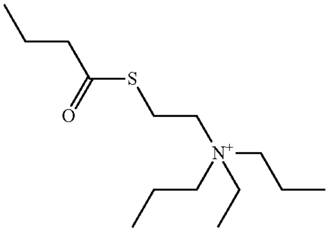
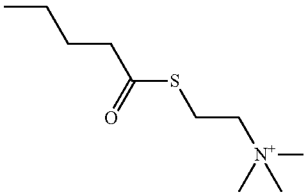
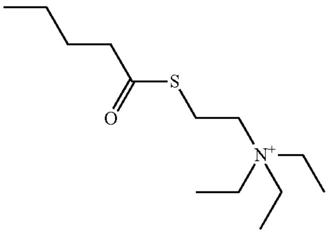
-continued
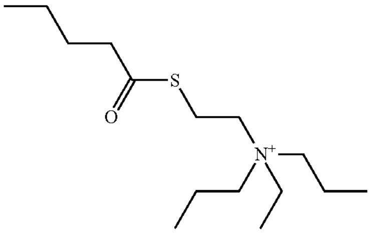
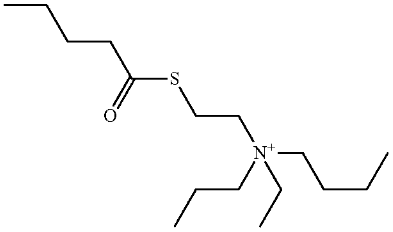
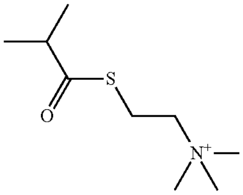
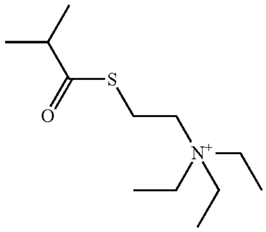
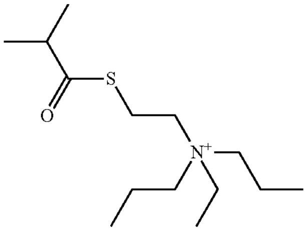
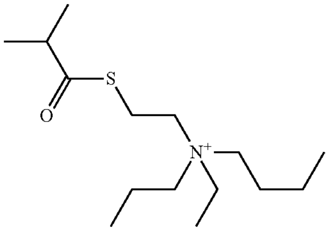
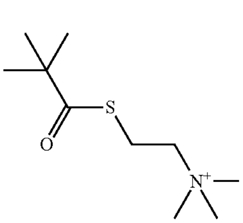
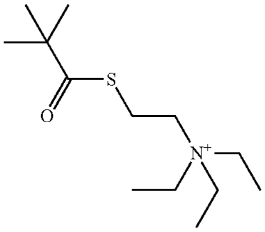
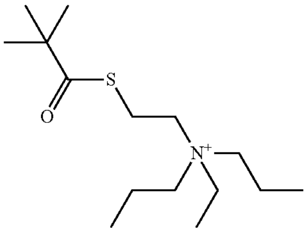

-continued
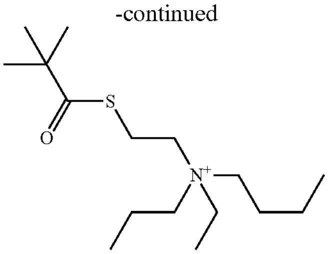
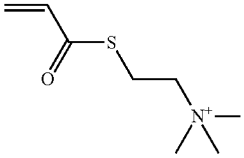
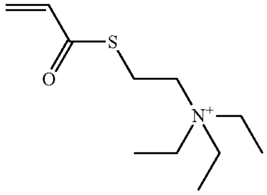
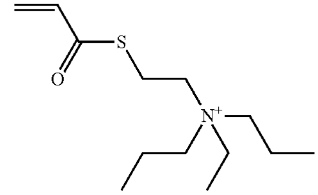
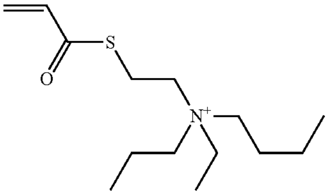
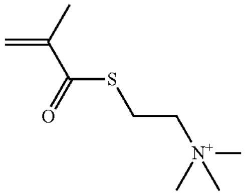
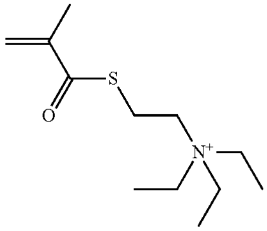
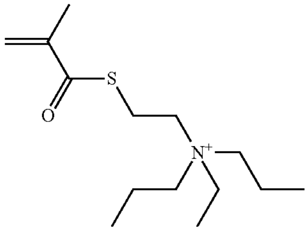
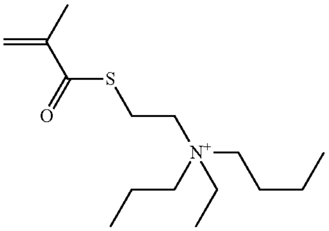
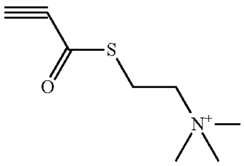
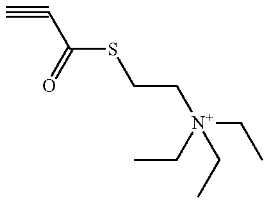
-continued
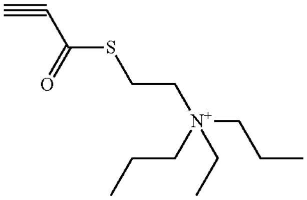
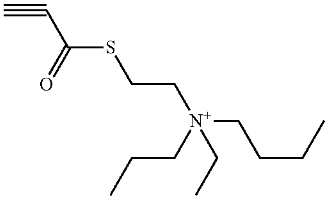
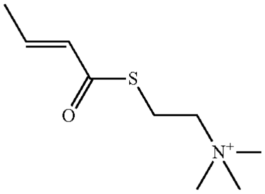
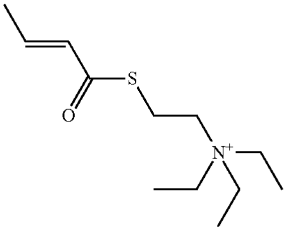
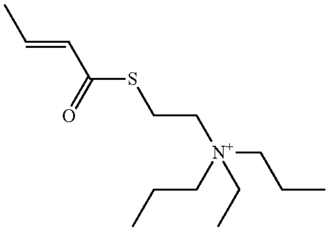
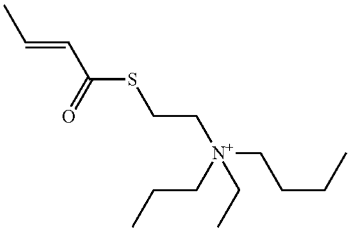
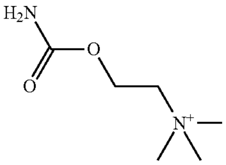
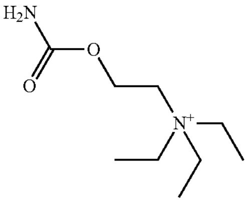
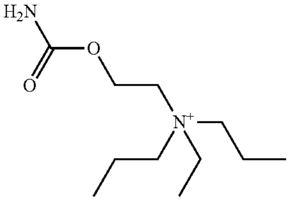
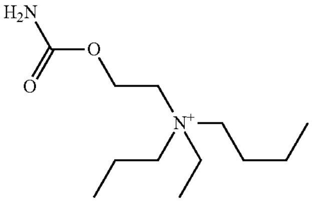

-continued
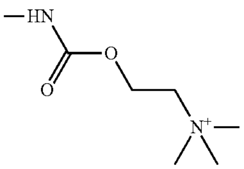
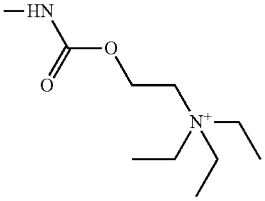
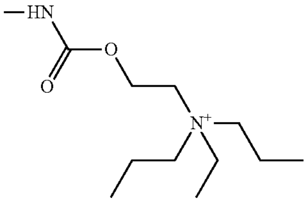
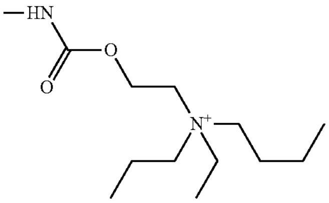
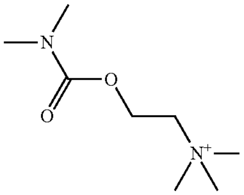
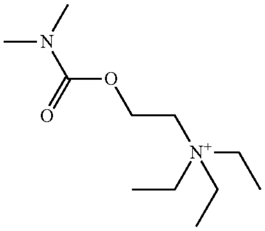
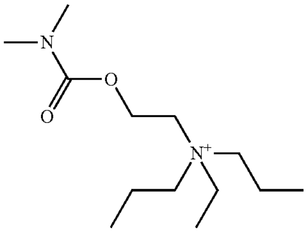
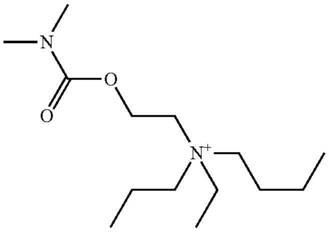
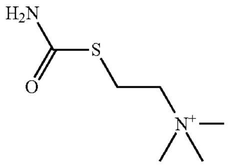
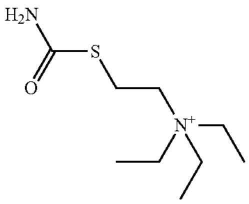
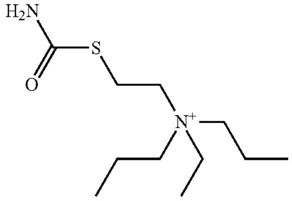
-continued
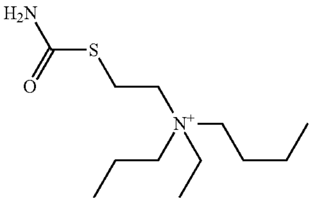
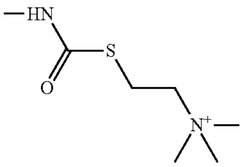
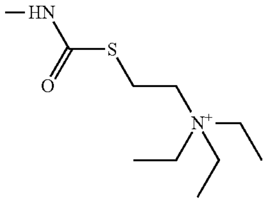
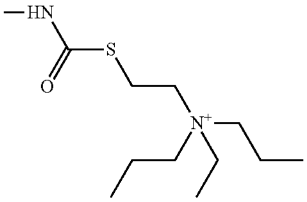
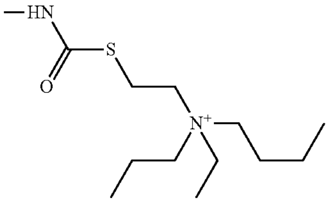
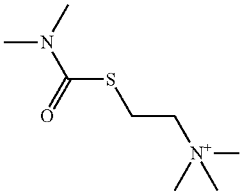
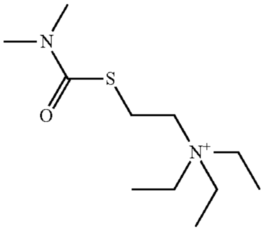
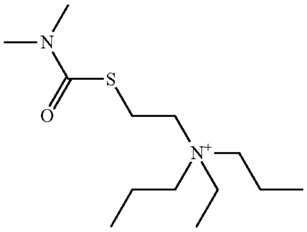
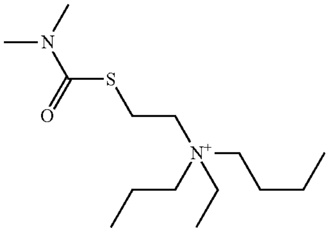
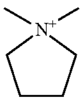
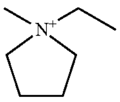
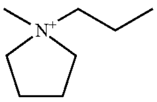
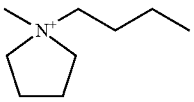
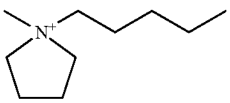
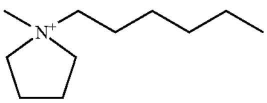

-continued
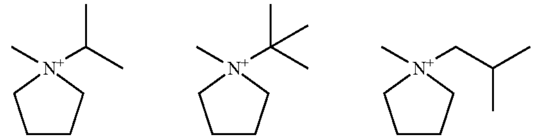
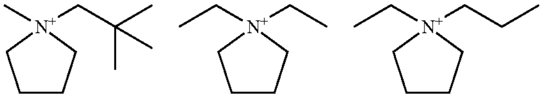
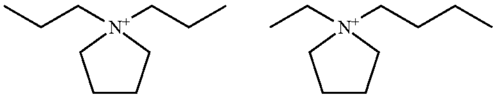
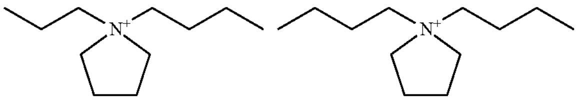
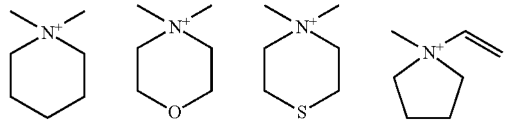
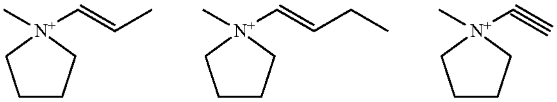
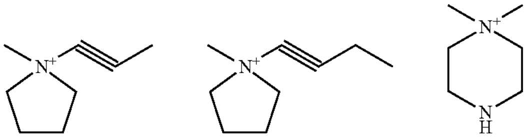
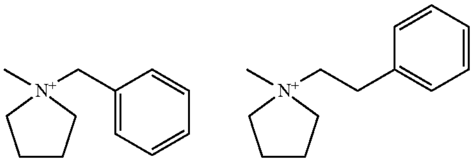
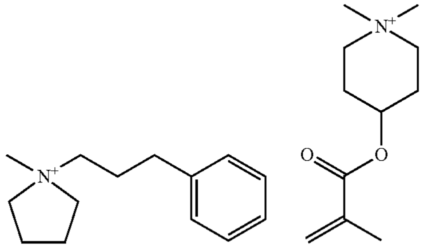
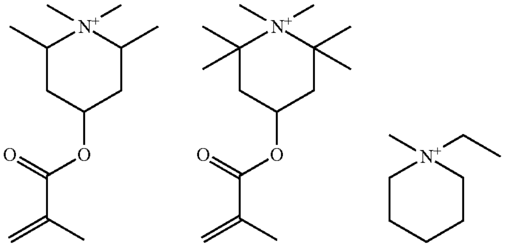
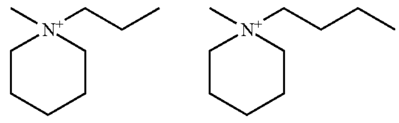
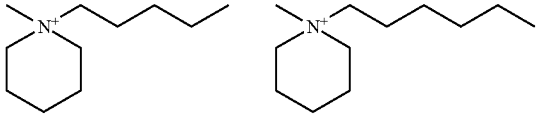
-continued
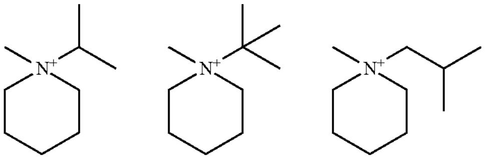
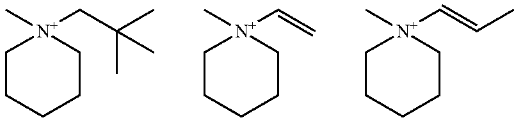
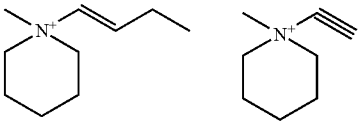
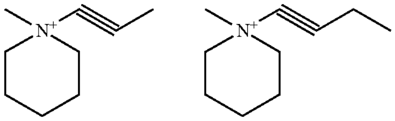
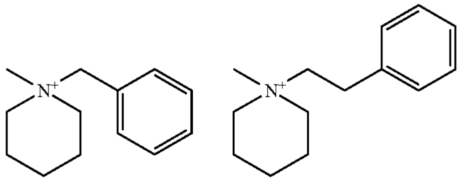
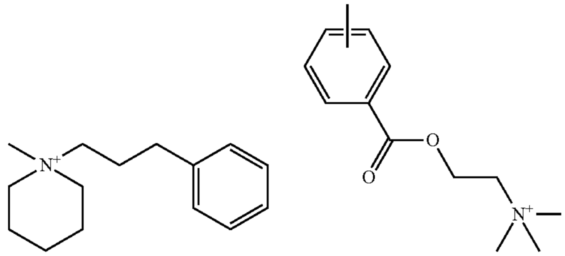
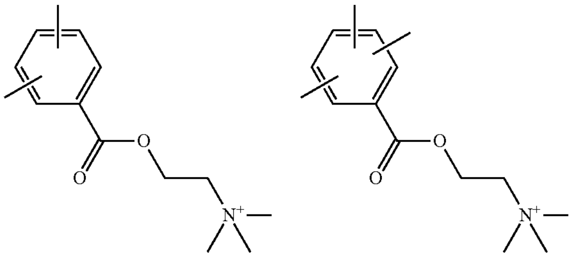
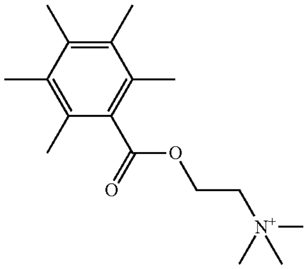

-continued
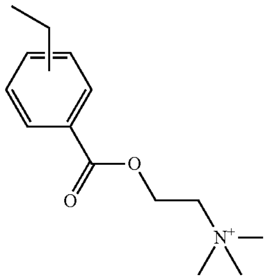
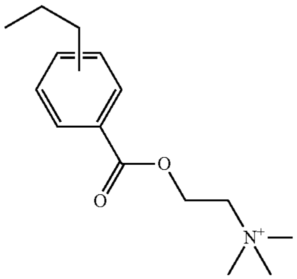
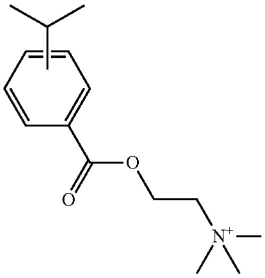
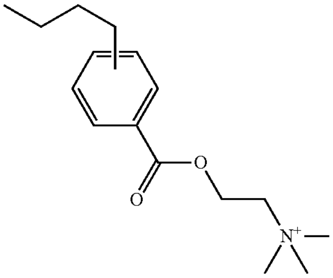
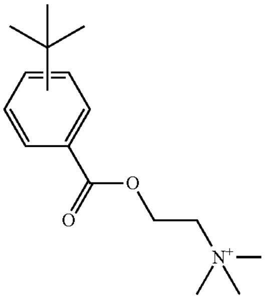
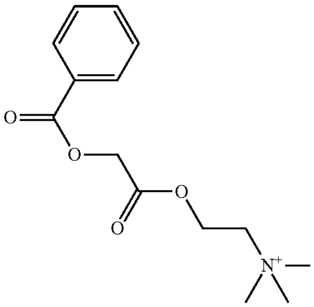
-continued
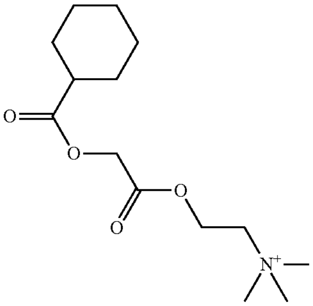
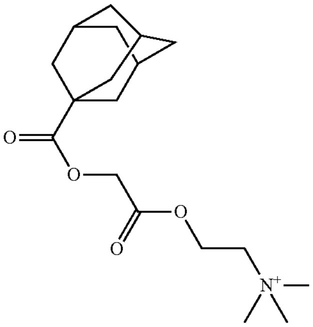
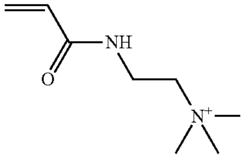
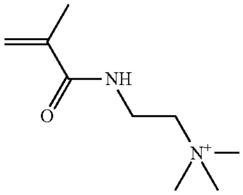
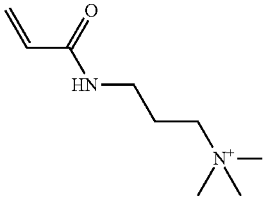
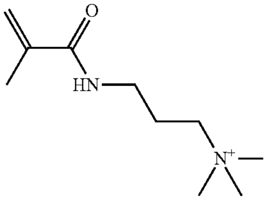
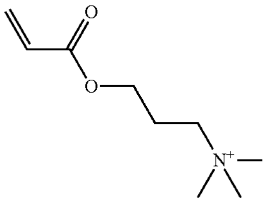
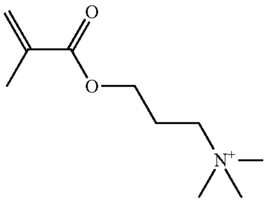
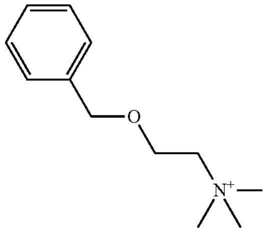
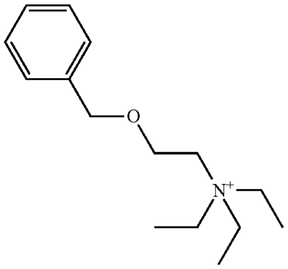

-continued
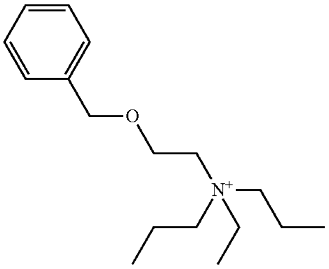
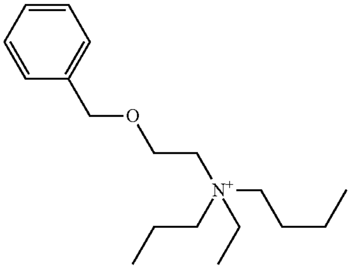
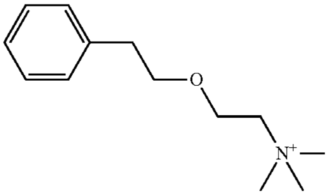
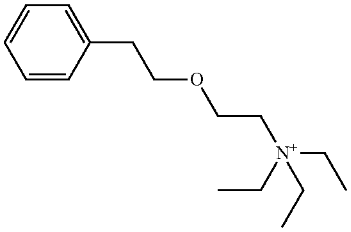
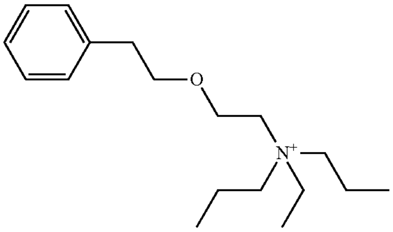
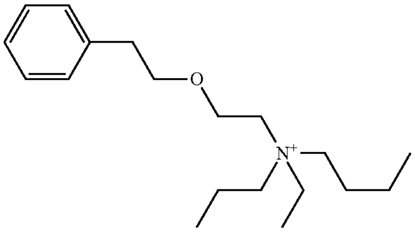
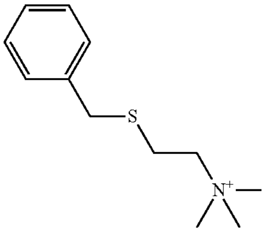
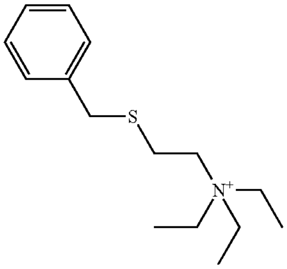
-continued
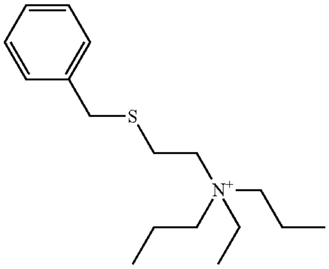
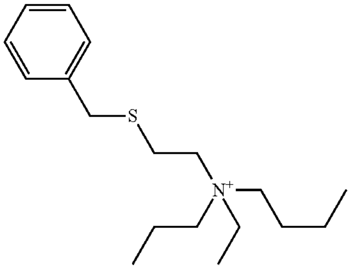
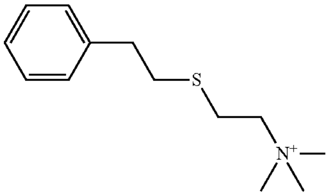
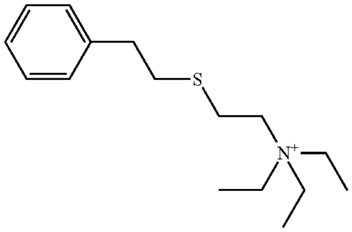
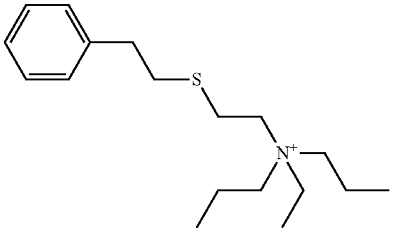
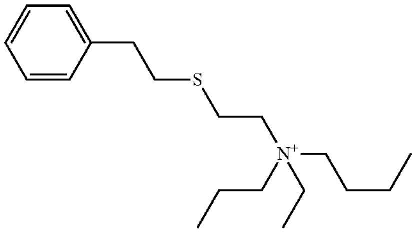
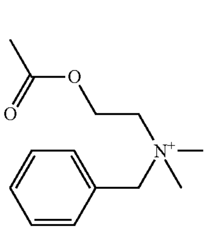
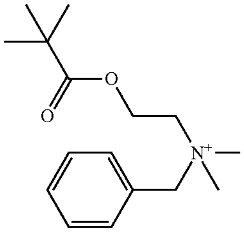

-continued
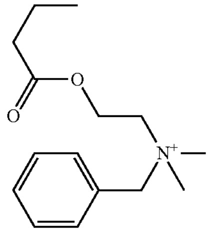
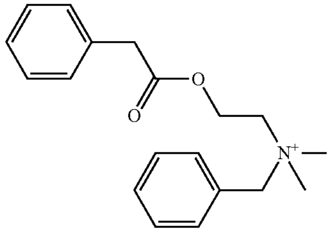
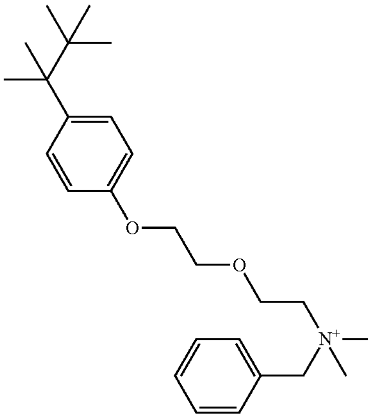
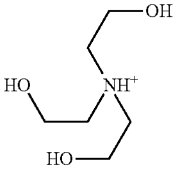
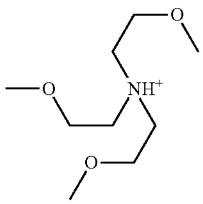
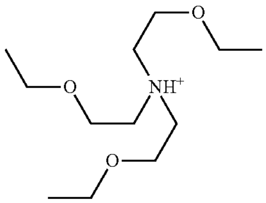
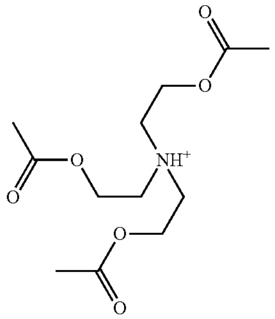
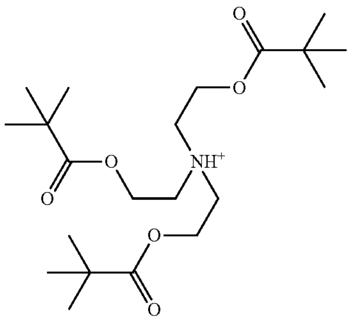
-continued
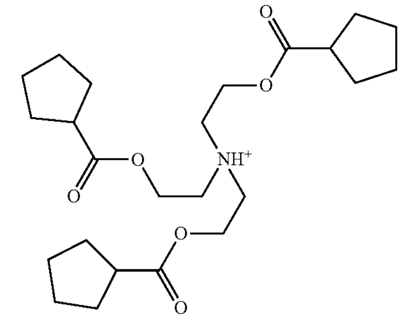
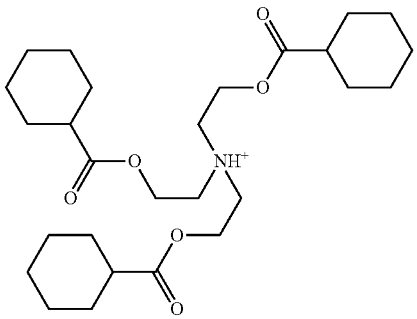
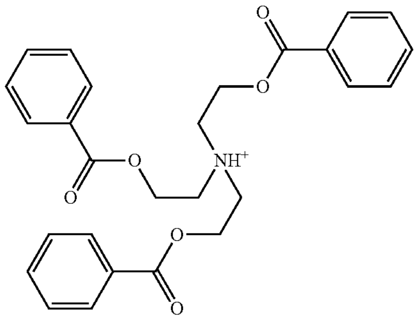
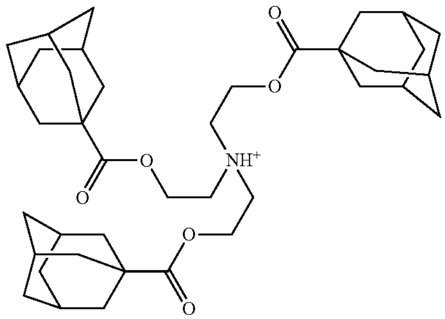
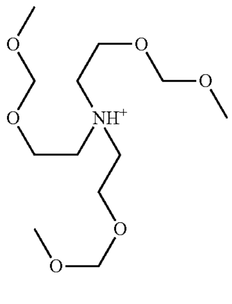
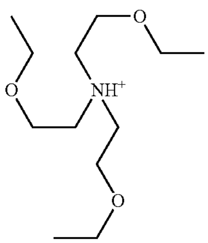

-continued
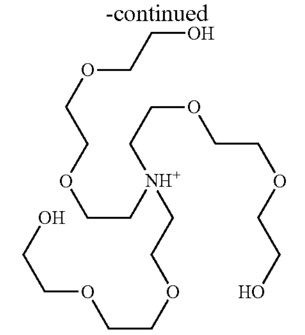
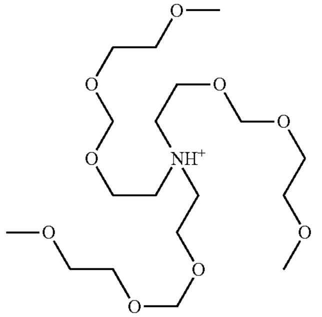
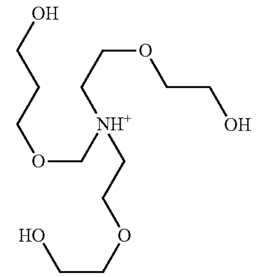
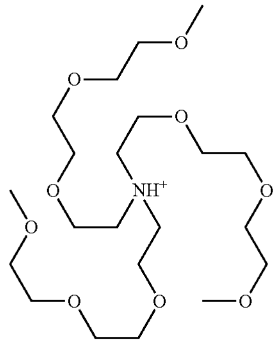
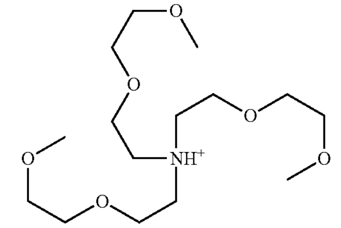
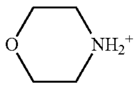
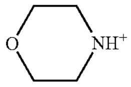
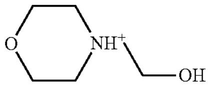
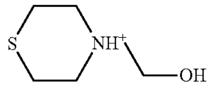
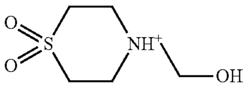
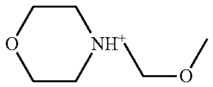
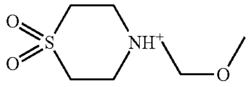
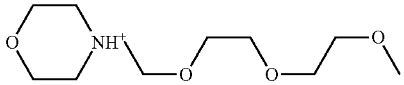
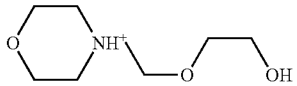
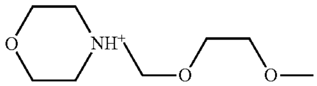
-continued
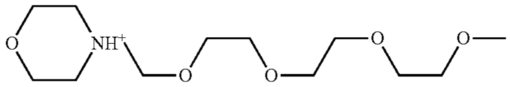
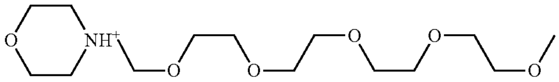
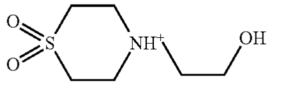
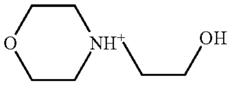
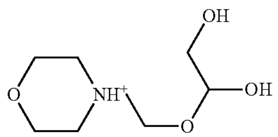
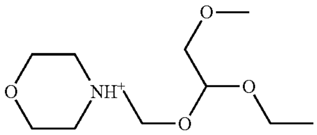
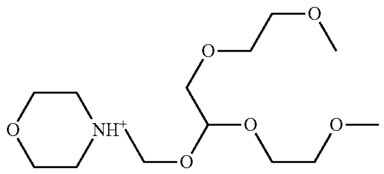
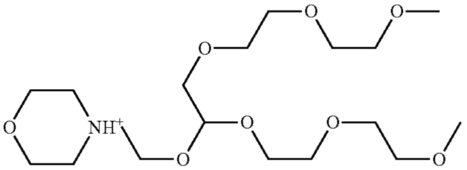
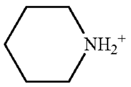
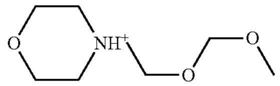
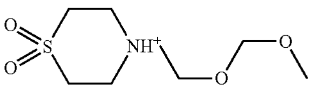
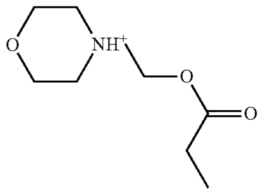
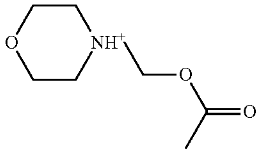
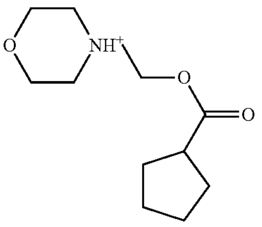
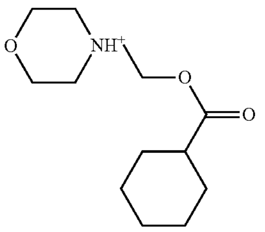
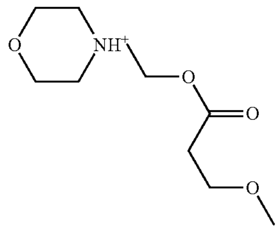

-continued

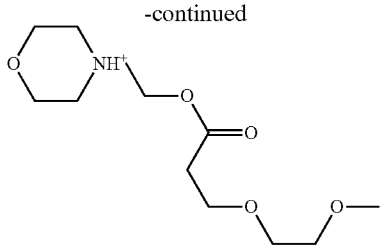

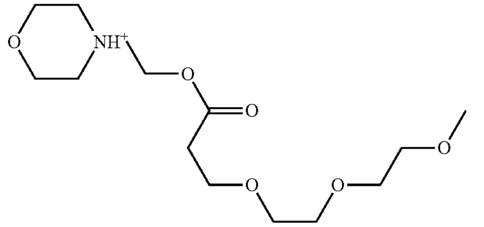

The ammonium ion shown by the general formula (3) is particularly preferably a tertiary or quaternary ammonium ion.

Examples of the carbon particle (carbon powder) which reacts with the monomer having an ionic functional group (ionic monomer) (particularly, the monomers of the general formulae (2)-1 to (2)-4) include carbon black, carbon nanotube, graphite (black lead), and graphene. The carbon nanotube and graphene may be single layer or may have a multilayer structure. Further, the carbon particle preferably has a reactive group, such as a hydroxy group, a carboxyl group, and an amino group.

The ionic monomer in the component (A) preferably has an oxirane group or an oxetane group. Such a group reacts with and bonds to a hydroxy group, a carboxyl group, or an amino group on the surface of the carbon particle.

The component (A) is preferably a reaction product between 100 parts by mass of the carbon particle and 5 parts by mass or more of the ionic monomer (particularly, the monomers of the general formulae (2)-1 to (2)-4).

Having the ionic monomer in a pendant form on the carbon powder enhances both the ionic conductivity and electron conductivity, and thus enhances the sensitivity of the resulting bio-electrode. Furthermore, it is possible to prevent extraction of the ionic monomer out of the bio-electrode film, and prevent a decrease in the sensitivity to biological signals due to the extraction. Further, the permeability through skin is also reduced, and the irritation to the skin is reduced. Thus, the composition can be more surely prevented from permeating the skin and causing allergies.

When the ionic monomer reacts with the carbon powder, the ionic monomer adheres to the carbon powder surface by chemical bonding.

The reaction for forming the composite of an ionic monomer and carbon powder is performed after the ionic monomer and the carbon powder are mixed, and the reaction proceeds at room temperature or by heating. The reaction can be promoted by heating. Nevertheless, if the heating temperature is too high, the ionic monomer breaks down. Thus, the heating temperature is preferably 300° C. or less.

A catalyst for promoting the reaction can also be added. When the ionic monomer has an oxirane group or an oxetane group and the carbon powder has a carboxyl group, it is possible to use pyridine, 2-ethylimidazole, a tertiary amine, or a metal compound, such as zinc 2-ethylhexanoate and acetylacetonato aluminum, for example.

In the inventive bio-electrode composition, the component (A) is blended in an amount of preferably 0.1 to 300 parts by mass, more preferably 1 to 200 parts by mass, relative to 100 parts by mass of the component (B) to be described below. Additionally, one kind of the component (A) may be used alone, or two or more kinds thereof may be used in mixture.

In some cases, not all molecules of the monomer containing an ion component shown by any of the general formulae (2)-1 to (2)-4 and an oxirane group or an oxetane group are consumed in the reaction with the carbon powder. In such a case, the unreacted monomer can be removed by washing the carbon powder with a solvent. In a case where a polymer compound is formed through cationic polymerization of the oxirane group or oxetane group, the performance as a bio-electrode is not lowered, and the irritation to skin is not increased.

[(B) Adhesive Resin]

The adhesive resin (B) to be blended in the inventive bio-electrode composition is a component compatibilized (well mixed) with and holds the ionic carbon powder (A). The adhesive resin (B) also holds an electric conductivity improver such as metal powder, carbon powder, silicon powder, and lithium titanate powder, and an additive such as ionic polymer and moisturizer, and exhibits adhesion. Note that the resin as the component (B) is preferably either or both of a thermosetting resin and a photo-curable resin, particularly preferably one or more selected from the group consisting of silicone-based resin (silicone resin), acrylic-based resin ((meth)acrylate resin), and urethane-based resin (urethane resin).

Examples of the adherent (adhesive) silicone-based resin include an addition reaction-curable (addition-curable) type and a radical crosslinking reaction-curable (radical curable) type. As the addition reaction-curable type, it is possible to use one that contains diorganosiloxane having an alkenyl group(s), an MQ resin having $R_3SiO_{0.5}$ and $SiO_2$ units, organohydrogenpolysiloxane having multiple SiH groups, a platinum catalyst, an addition-reaction inhibitor, and an organic solvent, for example, described in JP 2015-193803A. As the radical crosslinking reaction-curable type, it is possible to use one that contains diorganopolysiloxane with or without an alkenyl group, an MQ resin having $R_3SiO_{0.5}$ and $SiO_2$ units, organic peroxide, and an organic solvent, for example, described in JP 2015-193803A. Here, R represents a substituted or unsubstituted monovalent hydrocarbon group having 1 to 10 carbon atoms.

It is also possible to use a polysiloxane-resin integrated compound that is formed by condensation reaction of an MQ resin and polysiloxane having silanol at the terminal or the side chain of the polymer. The MQ resin contains many silanols, and improves adhesive strength by addition of it, but does not bind to the polysiloxane in molecular level because it is not crosslinkable. The adhesive strength can be increased by integrating the polysiloxane and the resin as described above.

The silicone-based resin may contain modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring. The addition of the modified siloxane improves dispersibility of the component (A) in the silicone resin. The modified siloxane may be modified at any part such as one terminal, both terminals, or a side chain of the siloxane.

As the adherent acrylic-based resin, it is possible to use one having hydrophilic (meth)acrylic ester and hydrophobic long chain (meth)acrylic ester as the repeating units described in JP 2016-011338A, for example. In some cases, it is also possible to copolymerize (meth)acrylic ester having a functional group or (meth)acrylic ester having a siloxane bond.

As the adherent urethane-based resin, it is possible to use one having a urethane bond with a polyether bond, a polyester bond, a polycarbonate bond, or a siloxane bond described in JP 2016-065238A, for example.

In the inventive bio-electrode composition, the resin of the component (B) preferably has high compatibility with the component (A) to prevent lowering of the electric conductivity due to separation of the component (A) from the resulting living body contact layer. In the inventive bio-electrode composition, the resin of the component (B) preferably has high adhesion to the electro-conductive base material to prevent peeling of the living body contact layer from the electro-conductive base material. In order to increase the adhesion to the electro-conductive base material and the compatibility with the salt, a use of a resin with high polarity as the resin of the component (B) is effective. Examples of such a resin include resin having one or more moieties selected from an ether bond, an ester bond, an amide bond, an imide bond, a urethane bond, a thiourethane bond, and a thiol group; a polyacrylic resin, a polyamide resin, a polyimide resin, a polyurethane resin, a polythiourethane resin; etc. On the other hand, the living body contact layer is to be contacted with a living body, thereby being susceptible to perspiration. Accordingly, in the inventive bio-electrode composition, the resin of the component (B) preferably has high repellency and is hardly hydrolyzed. To make the resin of the component (B) be highly repellent and hardly hydrolyzed, the use of a silicon-containing resin is effective.

The silicon atom-containing polyacrylic resin includes a polymer that has a silicone main chain and a polymer that has a silicon atom(s) on the side chain, either of which can be suitably used. As the polymer that has a silicone main chain, siloxane, silsesquioxane, or the like having a (meth)acrylpropyl group can be used. In this case, an addition of a photoradical generator allows the (meth)acryl moiety to polymerize to cure.

As the silicon atom-containing polyamide resin, it is possible to suitably use polyamide silicone resins described in JP 2011-079946A and U.S. Pat. No. 5,981,680B, for example. Such polyamide silicone resins can be synthesized by combining, for example, a silicone or non-silicone compound having amino groups at both terminals and a non-silicone or silicone compound having carboxyl groups at both terminals.

It is also possible to use polyamic acid before cyclization thereof, which is obtained by reacting carboxylic anhydride and amine. The carboxyl group of the polyamic acid may be crosslinked by using a crosslinking agent such as an epoxy type and an oxetane type. It is also possible to esterify the carboxyl group with hydroxyethyl (meth)acrylate to perform photoradical crosslinking of the (meth)acrylate moiety.

As the silicon atom-containing polyimide resin, it is possible to suitably use polyimide silicone resins described in JP 2002-332305A, for example. Although polyimide resins have very high viscosity, the viscosity can be decreased by blending a (meth)acrylic monomer as a solvent and a crosslinking agent.

Examples of the silicon atom-containing polyurethane resin include polyurethane silicone resins. Such polyurethane silicone resins can be crosslinked through urethane bond by blending a compound having isocyanate groups at both terminals and a compound having a hydroxy group(s) at the terminal(s), followed by heating. In this case, a silicon atom(s) (siloxane bond) have to be contained in either or both of the compound having isocyanate groups at both terminals and the compound having a hydroxy group(s) at the terminal(s). Alternatively, polysiloxane and a urethane (meth)acrylate monomer can be blended and photo-crosslinked as described in JP 2005-320418A. It is also possible to photo-crosslink a polymer having both of a siloxane bond(s) and a urethane bond(s), with the terminal having a (meth)acrylate group(s). Particularly, a material having a polyurethane main chain with a silicone chain on a side chain as described in JP 2018-123304A and JP 2019-70109A is preferable because of the properties of high strength and high stretchability.

The silicon atom-containing polythiourethane resin can be obtained by reaction of a compound having a thiol group(s) and a compound having an isocyanate group(s), provided that at least one of them contains a silicon atom(s). It can also be photo-cured if (meth)acrylate groups are contained at the terminals.

The silicone-based resin can be improved in compatibility with the foregoing salt by adding modified siloxane that has a functional group selected from the group consisting of an amino group, an oxirane group, an oxetane group, a polyether group, a hydroxy group, a carboxyl group, a mercapto group, a methacryl group, an acryl group, a phenol group, a silanol group, a carboxylic anhydride group, an aryl group, an aralkyl group, an amide group, an ester group, and a lactone ring, in addition to the diorganosiloxane having an alkenyl group(s), the MQ resin having $R_3SiO_{0.5}$ and $SiO_2$ units, and the organohydrogenpolysiloxane having multiple SiH groups.

The diorganosiloxane having an alkenyl group(s) and the organohydrogenpolysiloxane having multiple SiH groups can be crosslinked through an addition reaction with a platinum catalyst.

Examples of the platinum catalyst include platinum-based catalysts such as chloroplatinic acid, alcohol solution of chloroplatinic acid, reaction product of chloroplatinic acid and alcohol, reaction product of chloroplatinic acid and an olefin compound, reaction product of chloroplatinic acid and vinyl group-containing siloxane, a platinum-olefin complex, and a complex of platinum and vinyl group-containing siloxane; platinum group metal-based catalysts such as a rhodium complex and a ruthenium complex; etc. These catalysts may be used after dissolved or dispersed in alcohol solvent, hydrocarbon solvent, or siloxane solvent.

Note that the platinum catalyst is added in an amount preferably within 5 to 2,000 ppm, particularly preferably 10 to 500 ppm, relative to 100 parts by mass of the resin of the component (B).

In the inventive bio-electrode composition, the component (B) is blended in an amount of preferably 0 to 10000 parts by mass, more preferably 10 to 5000 parts by mass, relative to 100 parts by mass of the ion carbon powder of the component (A). Moreover, one kind of the component (B) may be used singly, or two or more kinds thereof may be used in mixture.

When the addition-curable silicone resin is used, an addition-reaction inhibitor may be added. This addition-reaction inhibitor is added as a quencher to prevent the action of the platinum catalyst in the solution and under a low temperature circumstance after forming the coating film and before heat curing. Specific examples of the addition-reaction inhibitor include 3-methyl-1-butyn-3-ol, 3-methyl-1-pentyn-3-ol, 3,5-dimethyl-1-hexyn-3-ol, 1-ethynylcyclohexanol, 3-methyl-3-trimethylsiloxy-1-butyne, 3-methyl-3-trimethylsiloxy-1-pentyne, 3,5-dimethyl-3-trimethylsiloxy-1-hexyne, 1-ethynyl-1-trimethylsiloxycyclohexane, bis(2,2-dimethyl-3-butynoxy)dimethylsilane, 1,3,5,7-tetramethyl-1,3,5,7-tetravinylcyclotetrasiloxane, 1,1,3,3-tetramethyl-1,3-divinyldisiloxane, etc.

The addition-reaction inhibitor is added in an amount preferably within 0 to 10 parts by mass, particularly preferably 0.05 to 3 parts by mass, relative to 100 parts by mass of the resin of the component (B).

Above all, the resin of the component (B) more preferably contains diorganosiloxane having an alkenyl group, and organohydrogenpolysiloxane having an SiH group. Particularly preferably, the resin of the component (B) further contains a silicone resin having an $SiO_2$ unit and an $R_xSiO_{(4-x)/2}$ unit, where R represents a substituted or unsubstituted monovalent hydrocarbon group having 1 to 10 carbon atoms, and "x" represents a number in a range of 2.5 to 3.5.

As will be described later, the living body contact layer is a cured product of the bio-electrode composition. The curing improves the adhesion of the living body contact layer to both of skin and the electro-conductive base material. The curing means is not particularly limited, and common means can be used, including crosslinking reaction by either or both of heat and light, or with an acid catalyst or a base catalyst, for example. The crosslinking reaction can be performed, for example, by appropriately selecting methods described in "Kakyou han-nou handbook (handbook of crosslinking reaction)", Chapter 2, pages 51-371, Yasuharu Nakayama, Maruzen Publishing Co., Ltd. (2013).

[(C) Ionic Polymer]

The inventive bio-electrode composition can also contain, as a component (C), a polymer compound having an ionic repeating unit, preferably, an ionic polymer containing a repeating unit having a structure selected from the group consisting of salts of ammonium, lithium, sodium, potassium, and silver formed with any of fluorosulfonic acid, fluorosulfonimide, and N-carbonyl-fluorosulfonamide. As the repeating unit of the ionic polymer, it is possible to employ ones described in paragraphs 0058 to 0130 of JP 2020-002342A. The ionic polymer is preferably added in an amount within 0.1 to 100 parts by mass relative to 100 parts by mass of the resin of the component (B).

[(D) Electro-Conductive Powder]

[Metal Powder]

The inventive bio-electrode composition may contain a metal powder as the component (D) in order to improve electron conductivity. The metal powder is a powder of a metal selected from the group consisting of gold, silver, platinum, copper, tin, titanium, nickel, aluminum, tungsten, molybdenum, ruthenium, chromium, and indium. The metal powder is added in an amount preferably within 1 to 50 parts by mass relative to 100 parts by mass of the resin of the component (B).

As the kind of the metal powder, gold, silver, and platinum are preferable from the viewpoint of electric conductivity; and silver, copper, tin, titanium, nickel, aluminum, tungsten, molybdenum, ruthenium, and chromium are preferable from the viewpoint of cost. From the viewpoint of biocompatibility, noble metals are preferable. From comprehensive viewpoint including the above, silver is most preferable.

The metal powder may have any shape, such as a spherical shape, a disk shape, a flaky shape, and a needle shape. The addition of flaky powder brings highest electric conductivity and is preferable thereby. The metal powder is preferably a flake having relatively lower density and larger specific surface area with a size of 100 μm or less, a tapped density of not more than 5 $g/cm^3$, and a specific surface area of not less than 0.5 $m^2/g$.

[Carbon Powder]

A carbon material (carbon powder) other than that in the component (A) can be added as an electric conductivity improver. Examples of the carbon material include carbon black, black lead, carbon nanotube, carbon fiber, etc. The carbon nanotube may be either single layer or multilayer, and the surface may be modified with an organic group(s). The carbon material is added in an amount preferably within 1 to 50 parts by mass relative to 100 parts by mass of the resin of the component (B).

[Silicon Powder]

The inventive bio-electrode composition may contain a silicon powder to enhance ion reception sensitivity. Examples of the silicon powder include powders of silicon, silicon monoxide, or silicon carbide. The particle diameter of the powder is preferably smaller than 100 μm, more preferably 1 μm or less. Since finer particles have a larger surface area, the resulting bio-electrode can receive a larger amount of ions and has higher sensitivity. The silicon powder is added in an amount preferably within 1 to 50 parts by mass relative to 100 parts by mass of the resin of the component (B).

[Lithium Titanate Powder]

The inventive bio-electrode composition may contain a lithium titanate powder to enhance ion reception sensitivity. Examples of the lithium titanate powder include powders containing a compound shown by molecular formulae $Li_2TiO_3$, $LiTiO_2$, or $Li_4Ti_5O_{12}$ with a spinel structure. The lithium titanate powder preferably has a spinel structure. It is also possible to use carbon-incorporated lithium titanate particles. The particle diameter of the powder is preferably smaller than 100 μm, more preferably 1 μm or less. Since finer particles have a larger surface area, the bio-electrode can receive a larger amount of ions, and has higher sensitivity. The aforementioned powders may be composite powders with carbon. The lithium titanate powder is added in an amount preferably within 1 to 50 parts by mass relative to 100 parts by mass of the resin of the component (B).

[(E) Organic Solvent]

Further, the inventive bio-electrode composition may contain the component (E), which is an organic solvent. Specific examples of the organic solvent include: aromatic hydrocarbon solvents, such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethyltoluene, 1,2,4,5-tetramethyltoluene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, pentamethylbenzene, hexamethylbenzene, hexylbenzene, and 1,3,5-triethylbenzene;

aliphatic hydrocarbon solvents, such as n-heptane, isoheptane, 3-methylhexane, 2,3-dimethylpentane, 3-ethylpentane, 1,6-heptadiene, 5-methyl-1-hexyne, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1-hexene, 4,4-dimethyl-1-hexene, 2-ethyl-1-hexene, 2-methyl-1-heptene, 1-octene, 2-octene, 3-octene, 4-octene, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1-ethyl-3-methylcyclohexane, 1-ethyl-4-methylcyclohexane, propylcyclohexane, isopropylcyclohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.$0^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, and isoparaffins, such as ISOPAR C, ISOPAR E, ISOPAR G, ISOPAR H, ISOPAR L, ISOPAR M, and ISOPAR V; ketone solvents, such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvents, such as 3-methoxybutanol, 3-methyl-3-methoxybutanol, 1-methoxy-2-propanol, and 1-ethoxy-2-propanol; ether solvents, such as propylene glycol monomethyl ether, ethylene glycol monomethyl ether, propylene glycol monoethyl ether, ethylene glycol monoethyl ether, propylene glycol dimethyl ether, diethylene glycol monomethyl ether, diethylene glycol monoethyl ether, diethylene glycol monopropyl ether, diethylene glycol monobutyl ether, diethylene glycol monopentyl ether, diethylene glycol monoheptyl ether, diethylene glycol diethyl ether, diethylene glycol dipropyl ether, diethylene glycol dibutyl ether, diisopropyl ether, diisobutyl ether, diisopentyl ether, di-n-pentyl ether, methyl cyclopentyl ether, methyl cyclohexyl ether, di-n-butyl ether, di-sec-butyl ether, diisopentyl ether, di-sec-pentyl ether, di-tert-amyl ether, di-n-hexyl ether, and anisole; ester solvents, such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactone solvents, such as γ-butyrolactone; water; etc.

Note that the organic solvent is added in an amount preferably within 10 to 50,000 parts by mass relative to 100 parts by mass of the resin of the component (B).

[(F) Other Additives]

The inventive bio-electrode composition can be mixed with a crosslinking agent, a crosslinking catalyst, and an ionic additive, and further with silica particles, polyether silicone, and polyglycerin silicone, besides the platinum catalyst and addition-reaction inhibitor described for the component (B). Silica particles have hydrophilic surfaces and favorable compatibility with the hydrophilic ion polymer, polyether silicone, and polyglycerin silicone, and can improve the dispersibility of the ionic polymer, polyether silicone, and polyglycerin silicone in the hydrophobic silicone adhesive. The silica particles may be either dry type or wet type both of which are preferably usable.

[Crosslinking Agent]

The inventive bio-electrode composition may contain an epoxy-type crosslinking agent. This crosslinking agent is a compound having multiple epoxy groups or oxetane groups in one molecule. The amount of the crosslinking agent added is preferably 1 to 30 parts by mass relative to 100 parts by mass of the resin of the component (B).

[Crosslinking Catalyst]

The inventive bio-electrode composition may also contain a catalyst for crosslinking the epoxy groups or the oxetane groups. As this catalyst, ones described in paragraphs 0027 to 0029 of JP 2019-503406A can be used. The amount of the catalyst added is preferably 0.01 to 10 parts by mass relative to 100 parts by mass of the resin of the component (B).

[Ionic Additive]

The inventive bio-electrode composition may contain an ionic additive to enhance the ionic conductivity. In consideration of biocompatibility, examples of the ionic additive include sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, betaine, and salts disclosed in JP 2018-44147A, JP 2018-59050A, JP 2018-59052A, and JP 2018-130534A.

[Silicone Compound having Polyglycerin Structure]

The inventive bio-electrode composition may contain a silicone compound having a polyglycerin structure to enhance the sensitivity to ions released from skin and the ionic conductivity by enhancing the moisture-holding property of the film. The silicone compound having a polyglycerin structure is blended in an amount of preferably 0.01 to 100 parts by mass, more preferably 0.5 to 60 parts by mass, relative to 100 parts by mass of a total of the components (A) and (B). Additionally, one kind of the silicone compound having a polyglycerin structure may be used singly, or two or more kinds thereof may be used in mixture.

The silicone compound having a polyglycerin structure is preferably shown by any of the following general formulae (4)' and (5)'.

(4)'

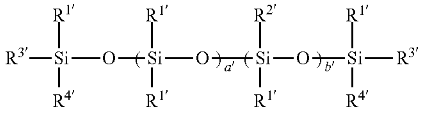

(4)'-1

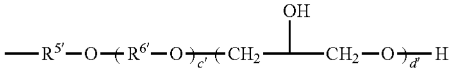

(4)'-2

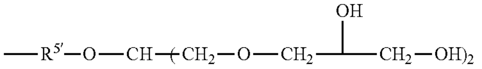

(5)'

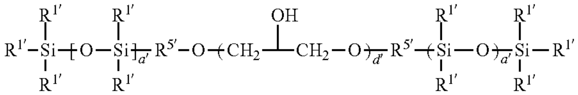

(6)'

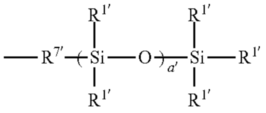

In the formulae (4)' and (5)', each $R^{1'}$ is identical to or different from one another, and independently represents a hydrogen atom, a phenyl group, a linear or branched alkyl group having 1 to 50 carbon atoms, or a silicone chain shown by a general formula (6)', and optionally contains an ether group. $R^{2'}$ represents a group having a polyglycerin group structure shown by the formula (4)'-1 or (4)'-2. Each $R^{3'}$ is identical to or different from the other, and independently represents the $R^{1'}$ group or the $R^{2'}$ group. Each $R^{4'}$ is identical to or different from the other, and independently represents the $R^{1'}$ group, the $R^{2'}$ group, or an oxygen atom. When $R^{4'}$ represents an oxygen atom, the two $R^{4'}$ moieties bond to each other and optionally constitute an ether group to form a ring together with silicon atoms. Each a' is identical to or different from one another and represents 0 to 100, b' represents 0 to 100, and a'+b' is 0 to 200. Nevertheless, when b' is 0, at least one $R^{3'}$ is the $R^{2'}$ group. In the formulae (4)'-1, (4)'-2, (5)', and (6)', $R^{5'}$ represents an alkylene group having 2 to 10 carbon atoms or an aralkylene group having 7 to 10 carbon atoms; $R^{6'}$ and $R^{7'}$ each represent an alkylene group having 2 to 6 carbon atoms, but $R^{7'}$ may represent an ether bond. c' represents 0 to 20. d' represents 1 to 20.

Examples of such a silicone compound having a polyglycerin structure can include the following.

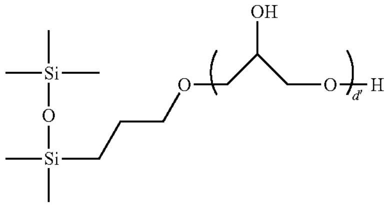

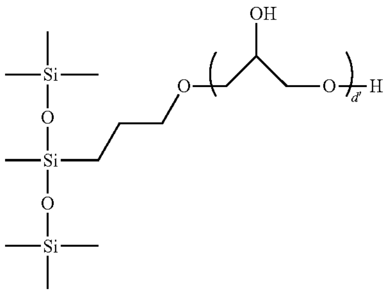

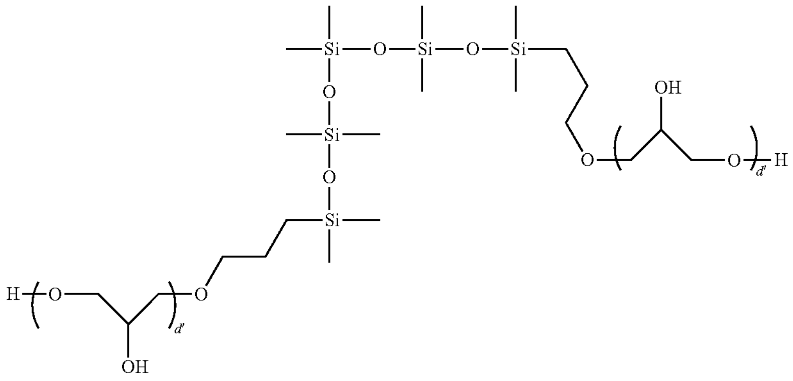

-continued
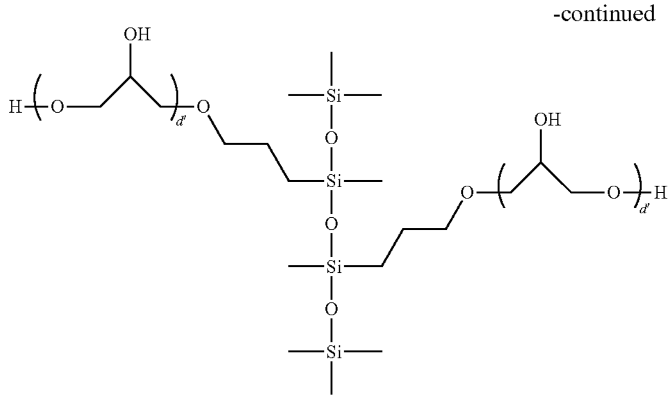
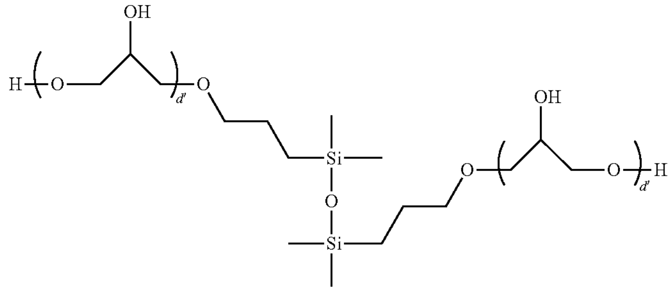
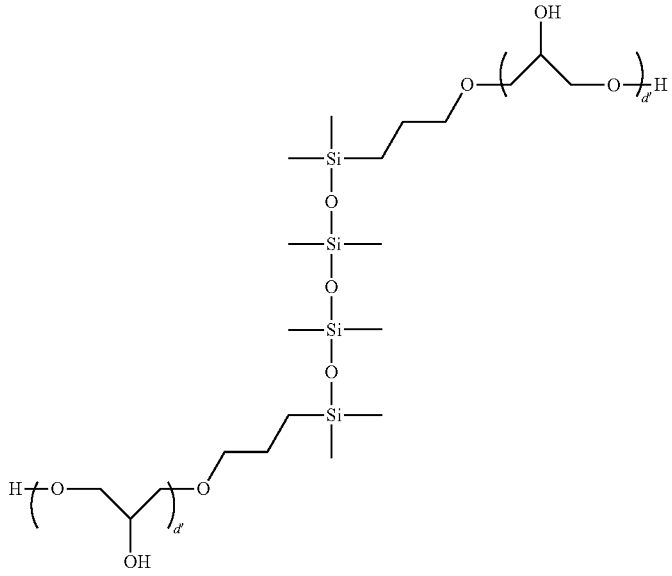
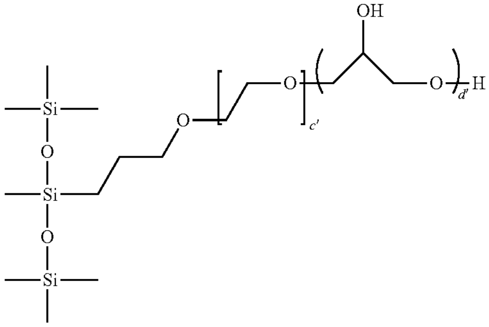
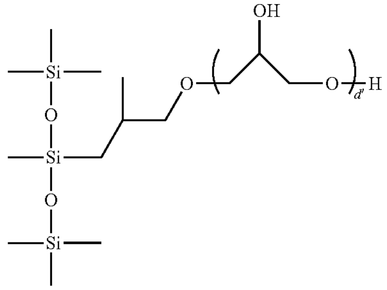
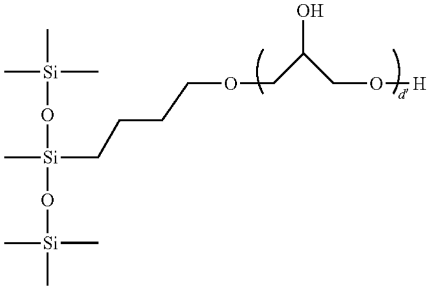

-continued
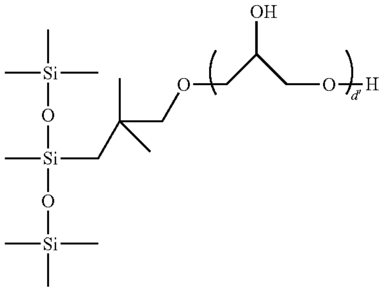
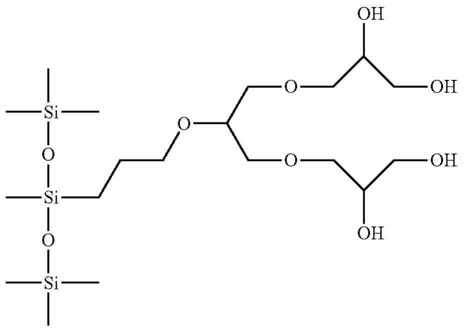
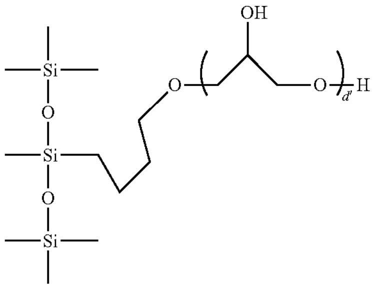
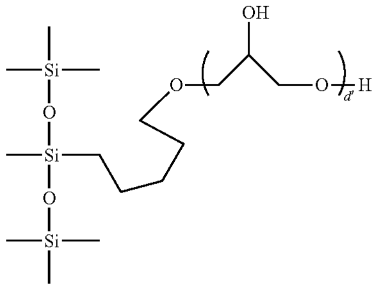
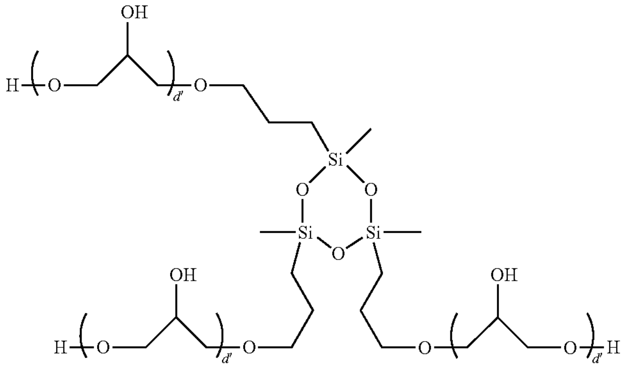
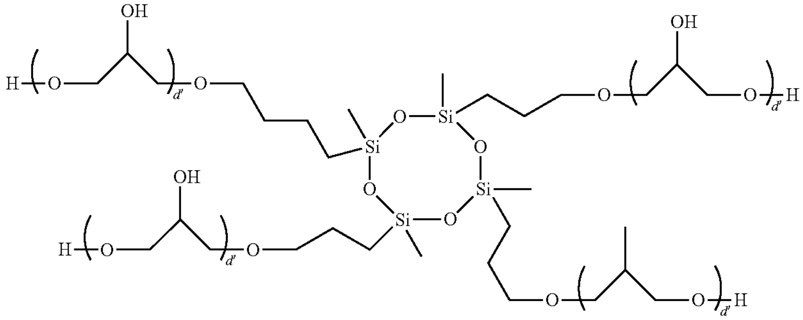
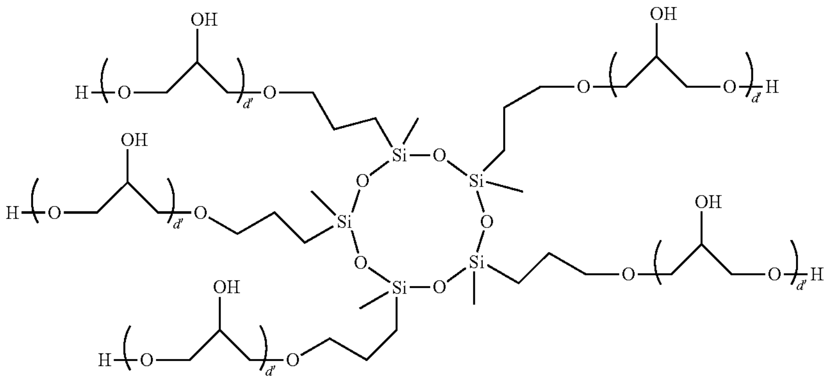

-continued
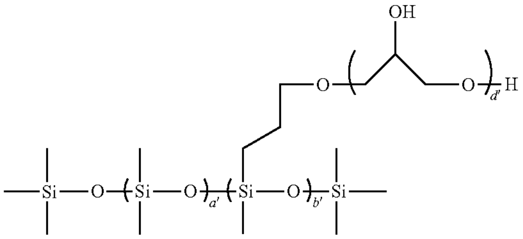
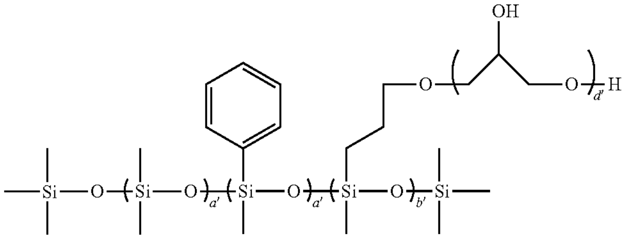
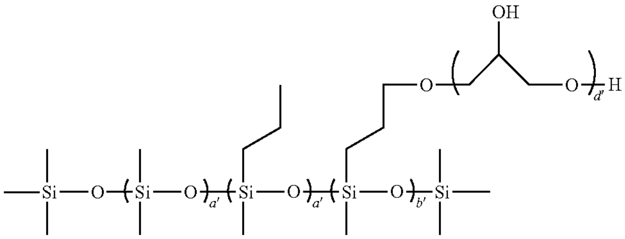
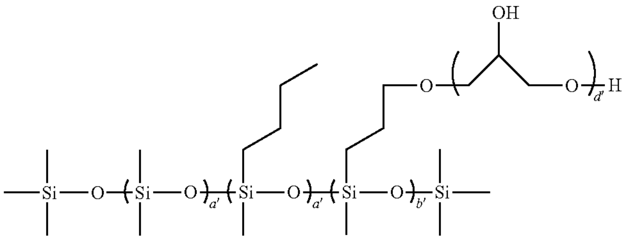
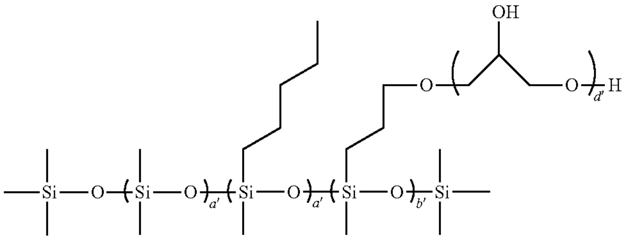
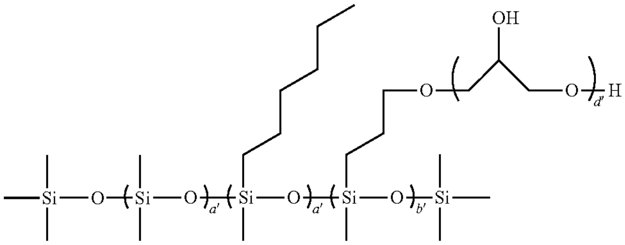
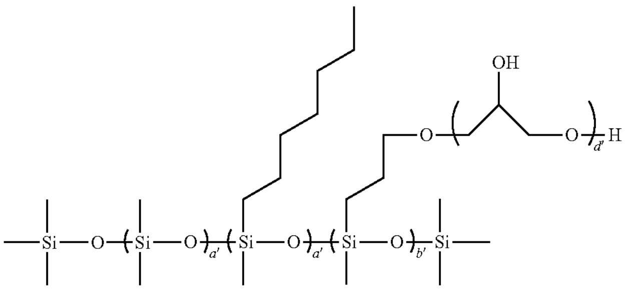

-continued
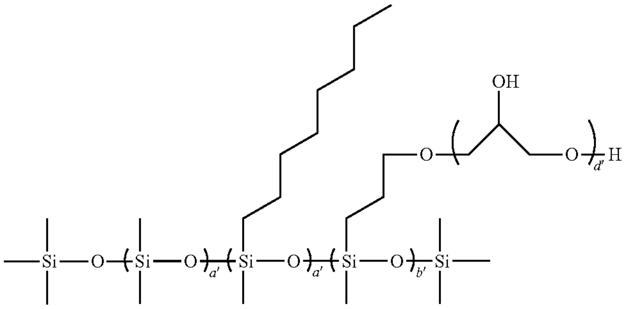
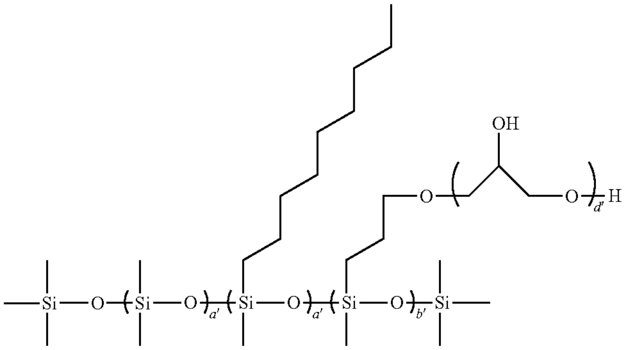
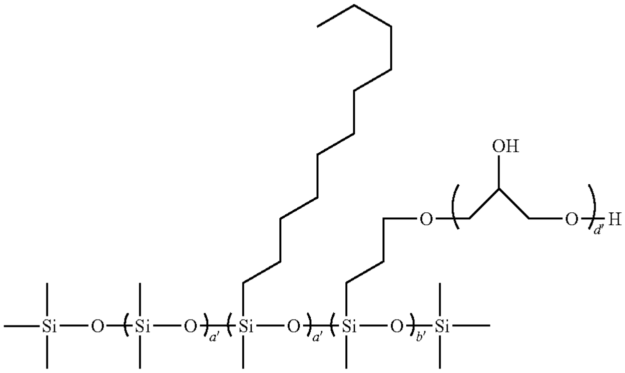
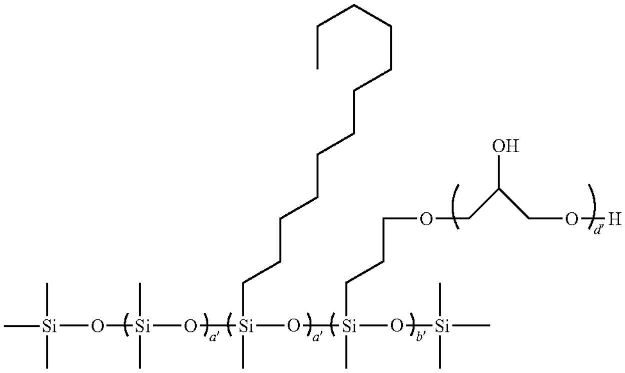

-continued
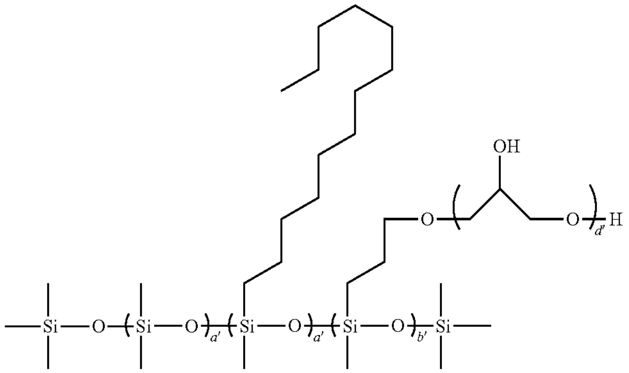
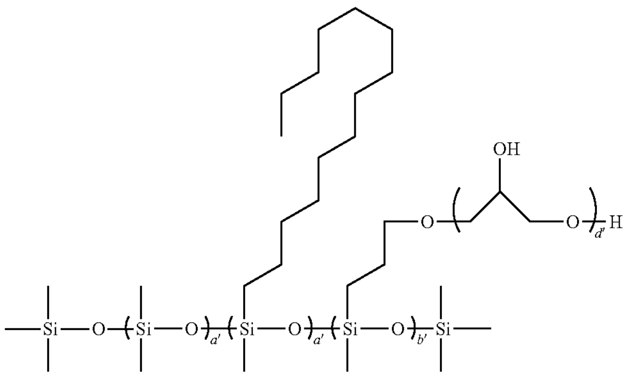
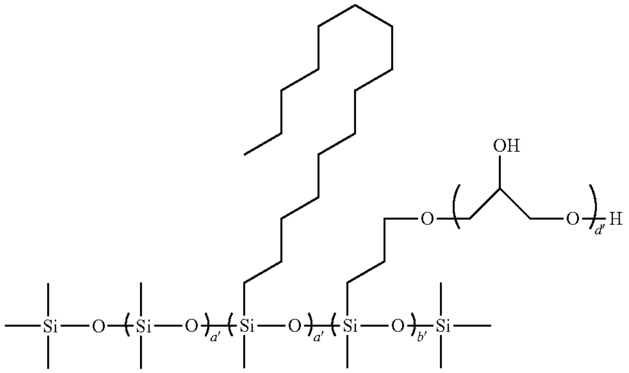
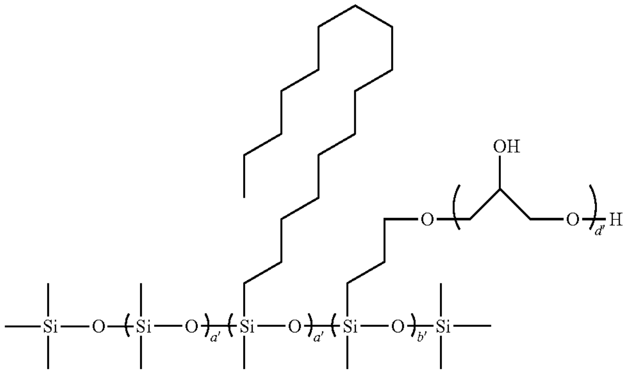

-continued
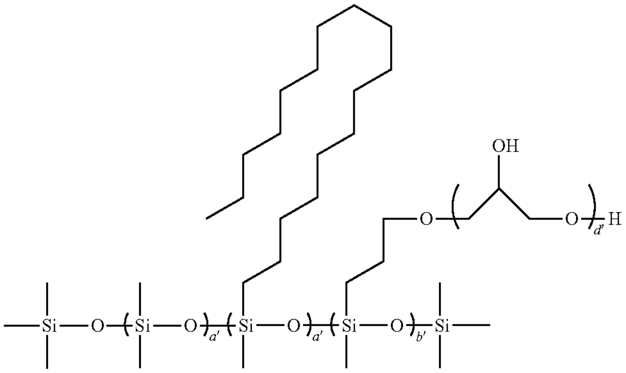
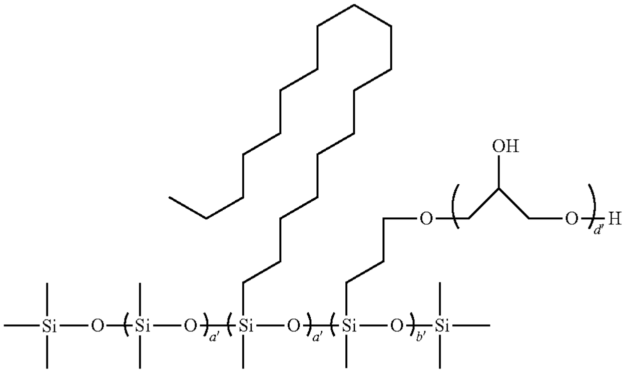
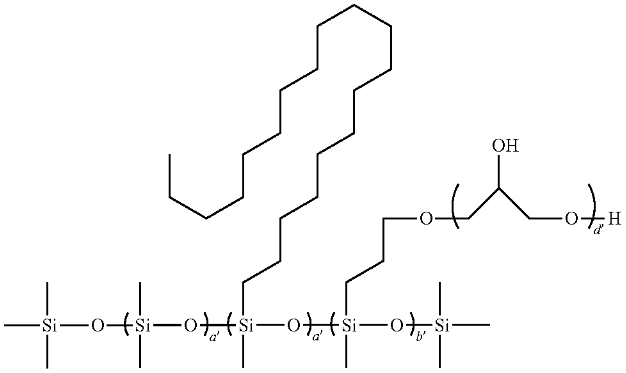
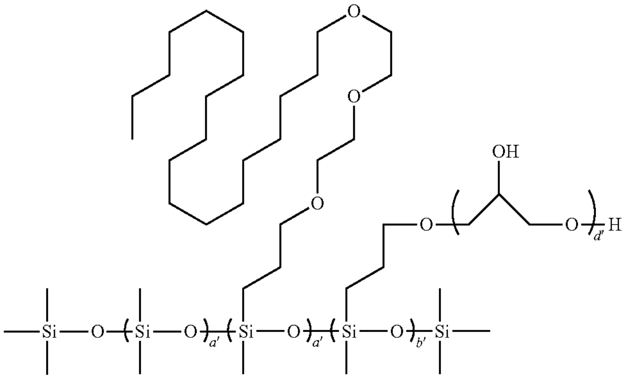

-continued
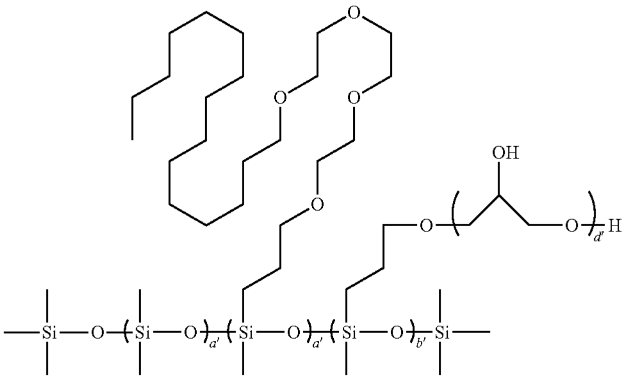
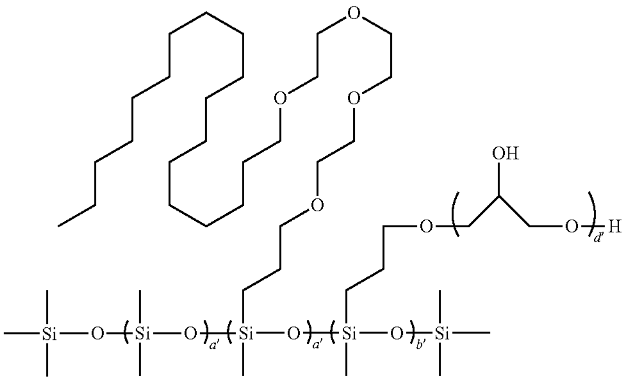
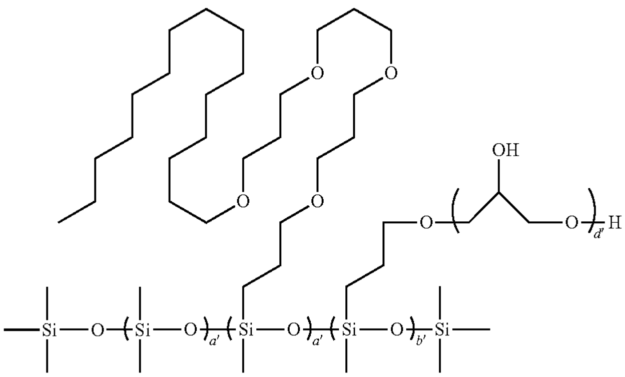
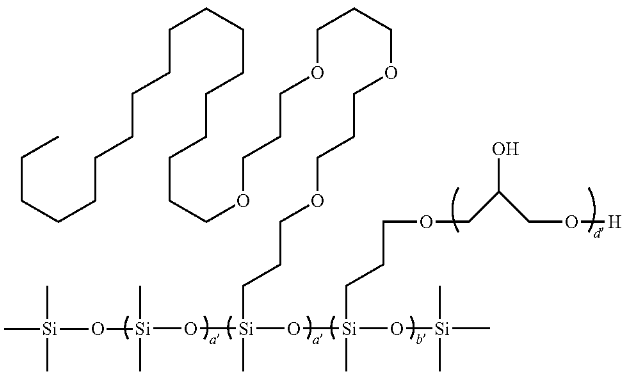

-continued
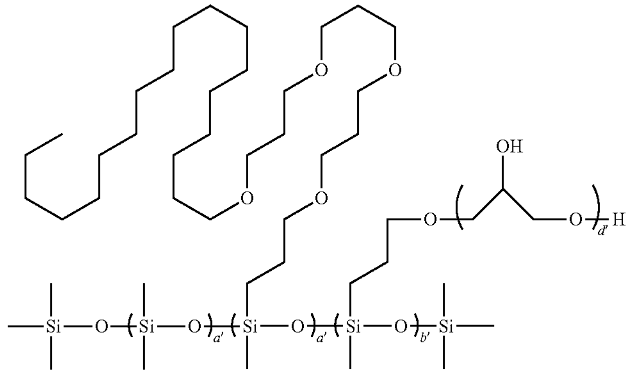
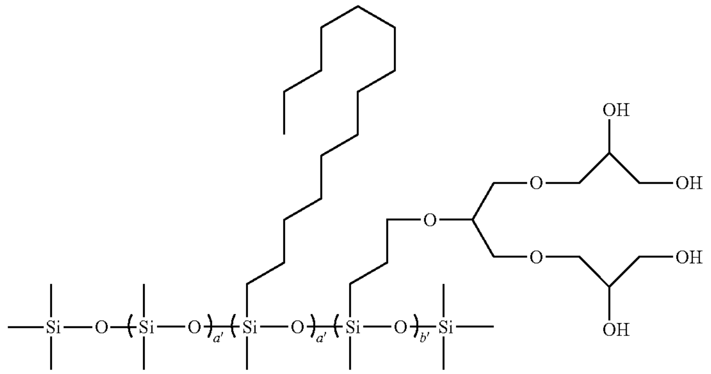
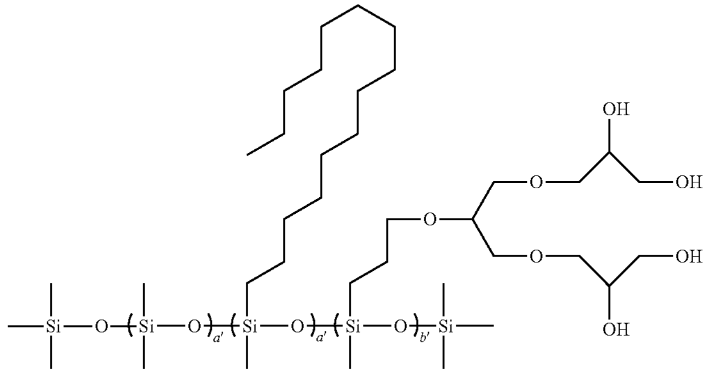
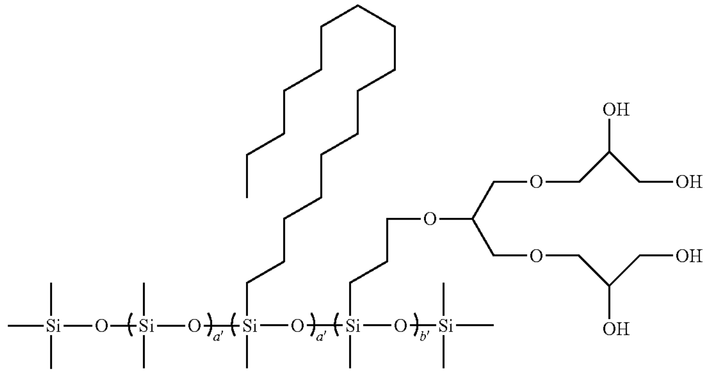

-continued
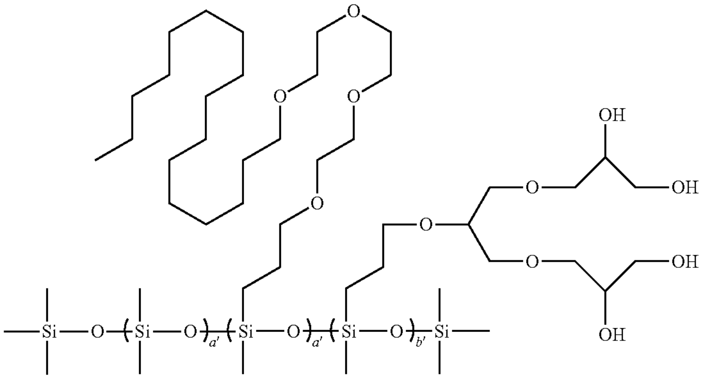
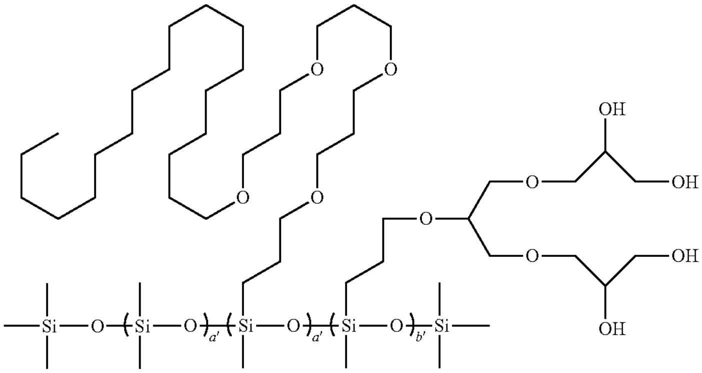
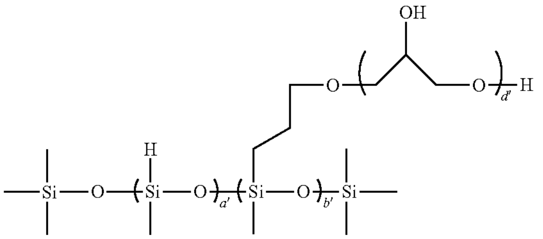
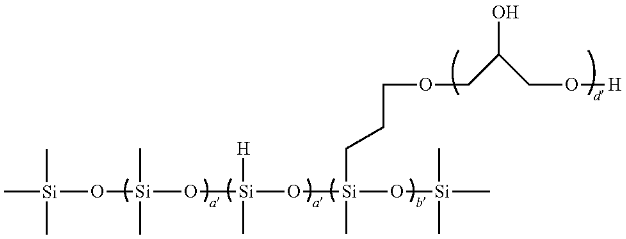
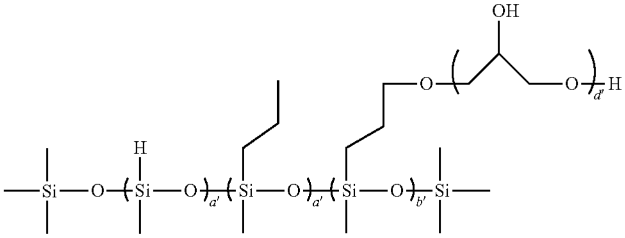
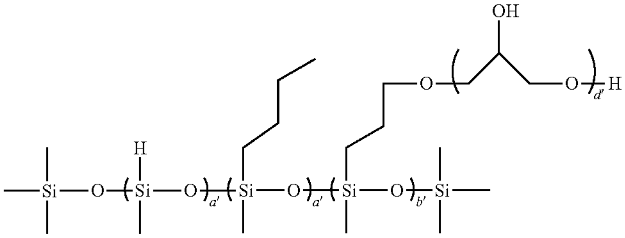
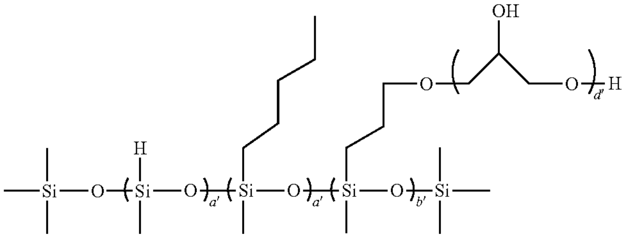

-continued
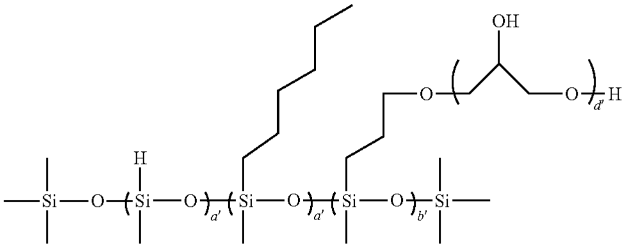
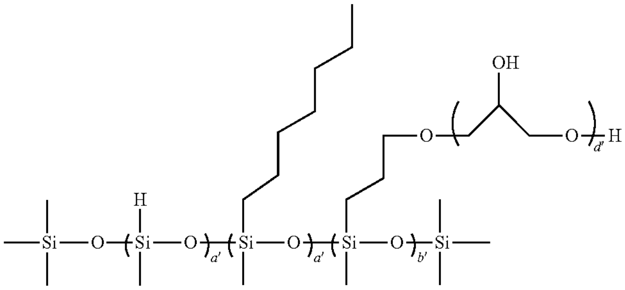
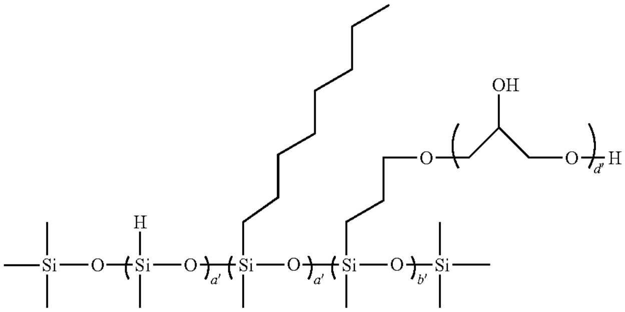
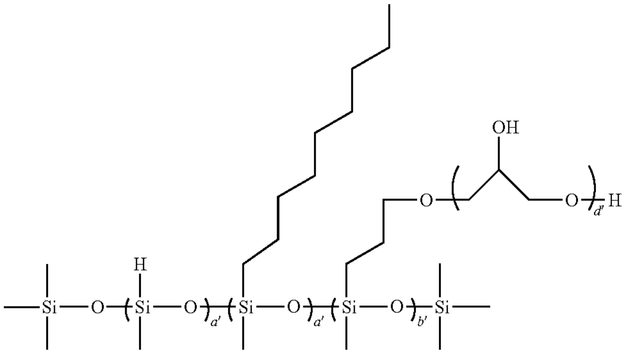
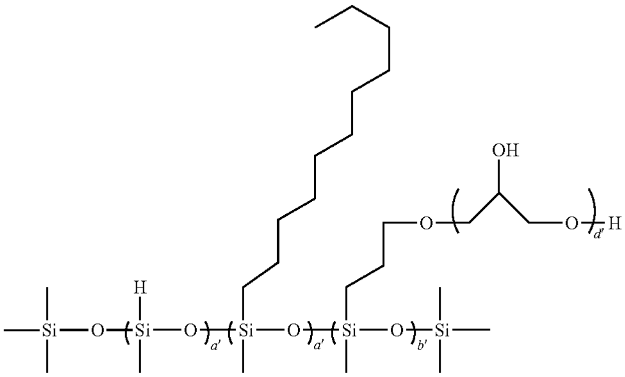

-continued
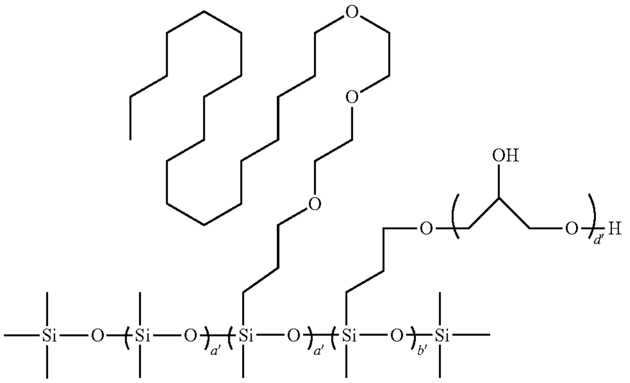
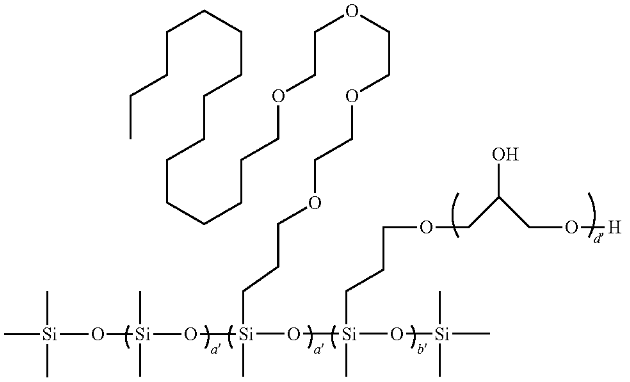
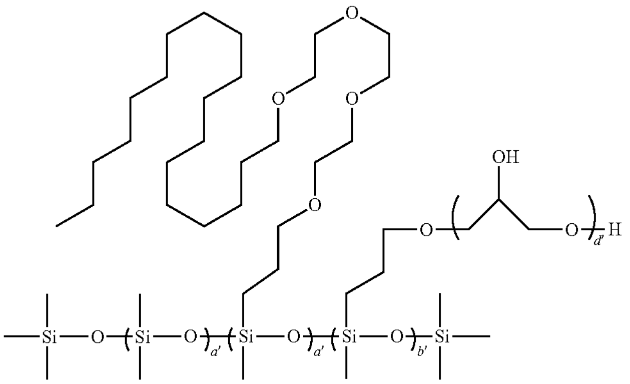
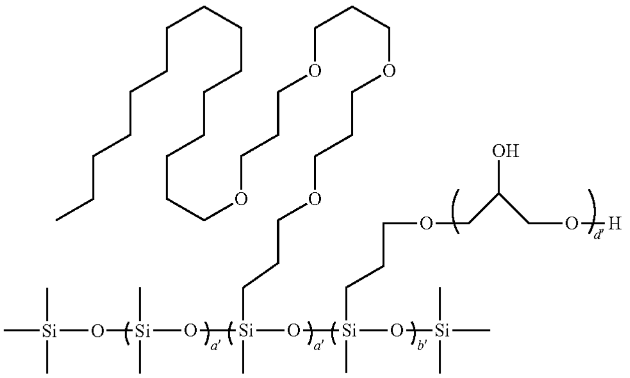

-continued
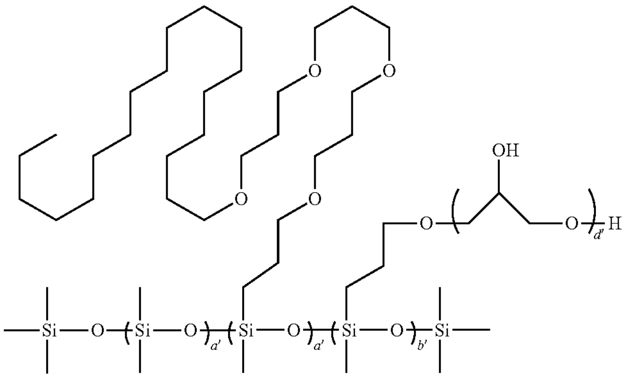
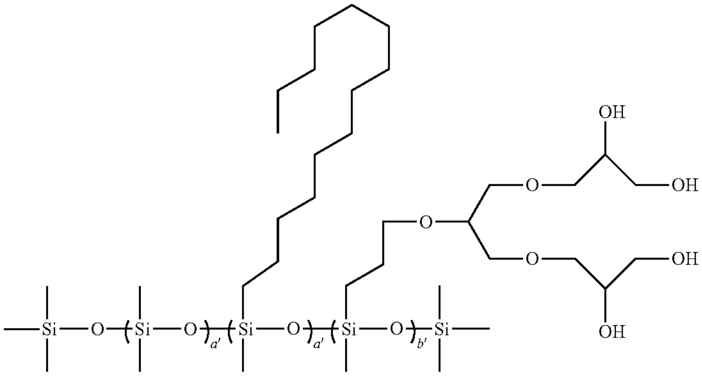
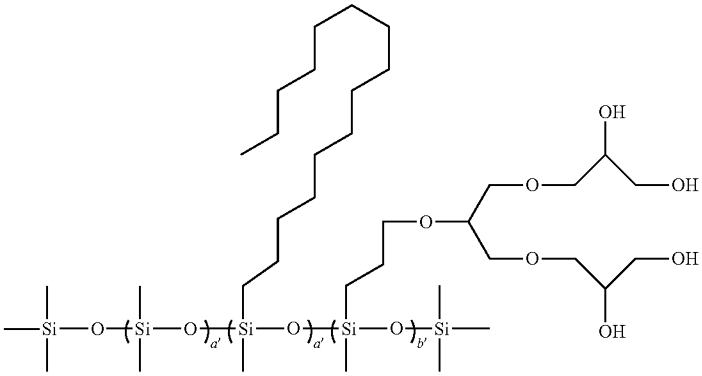
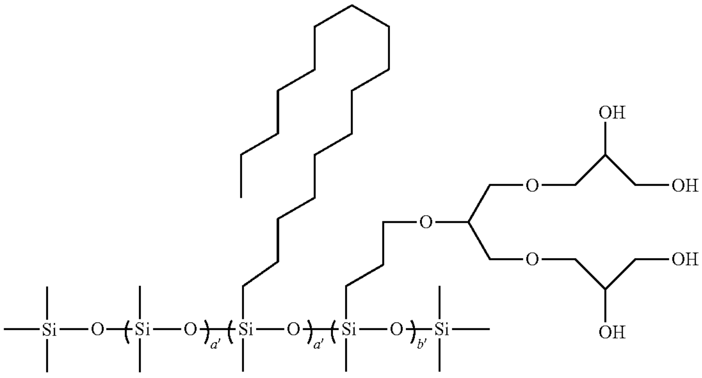

-continued
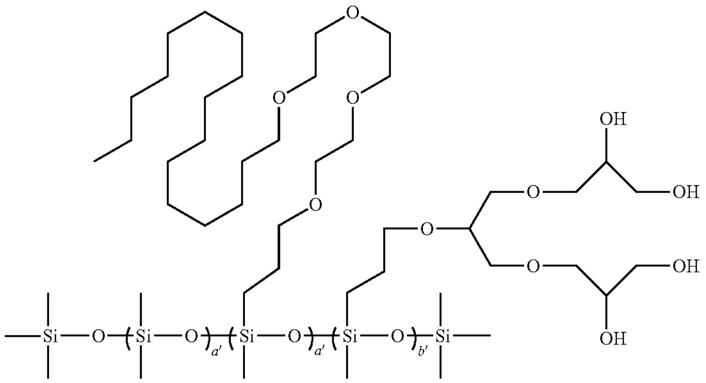
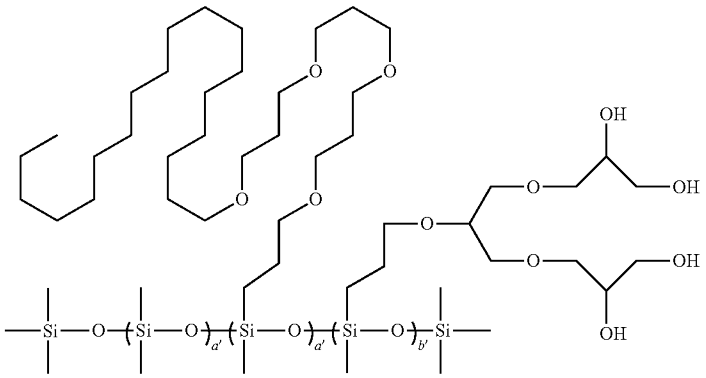
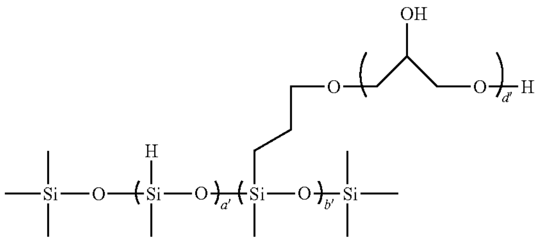
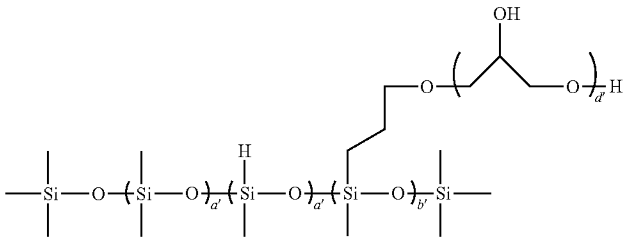
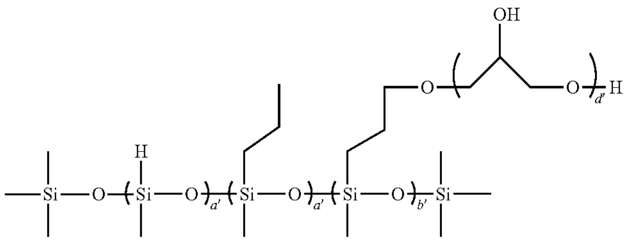
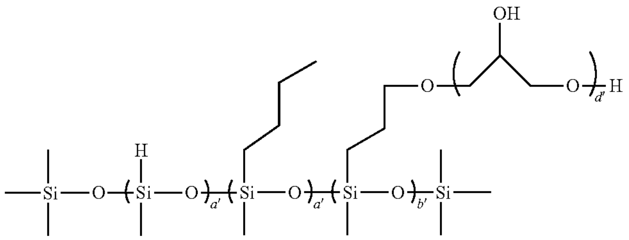
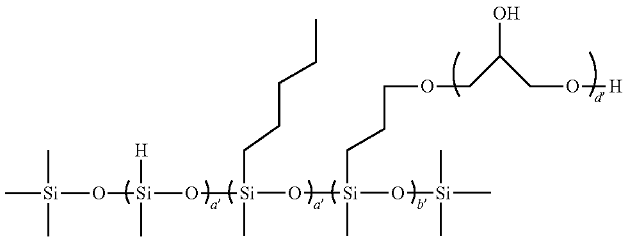

-continued
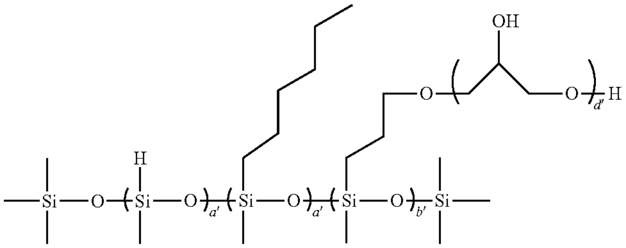
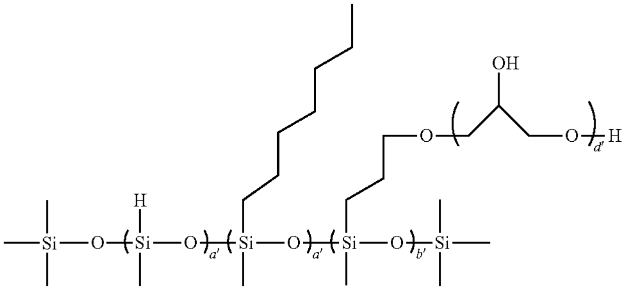
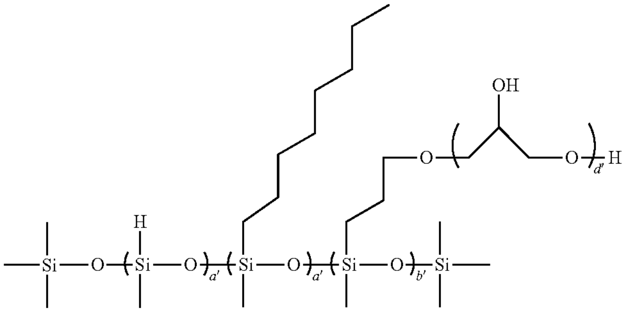
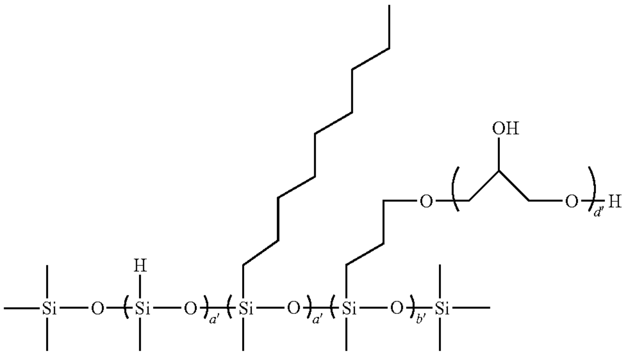
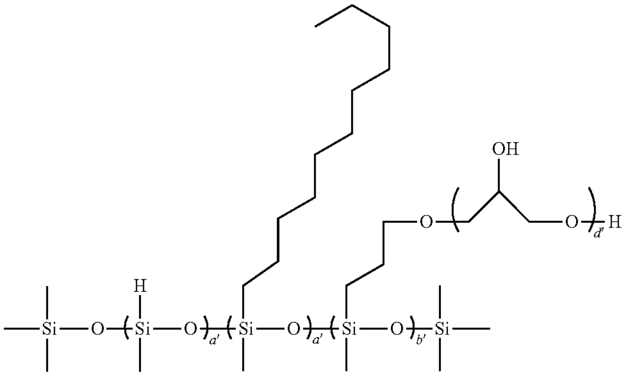

-continued
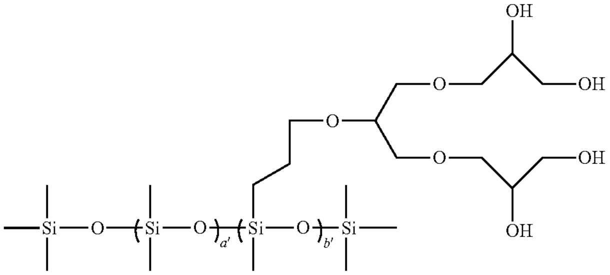
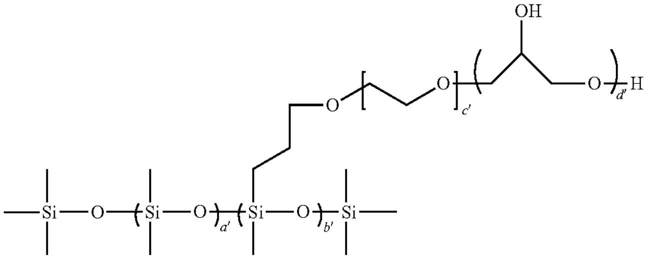
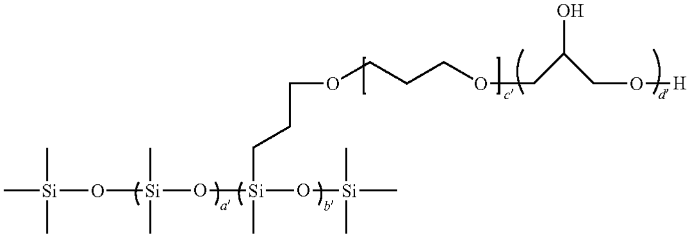
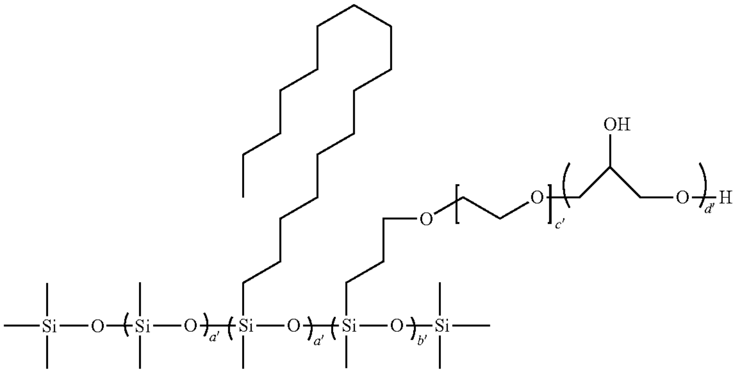
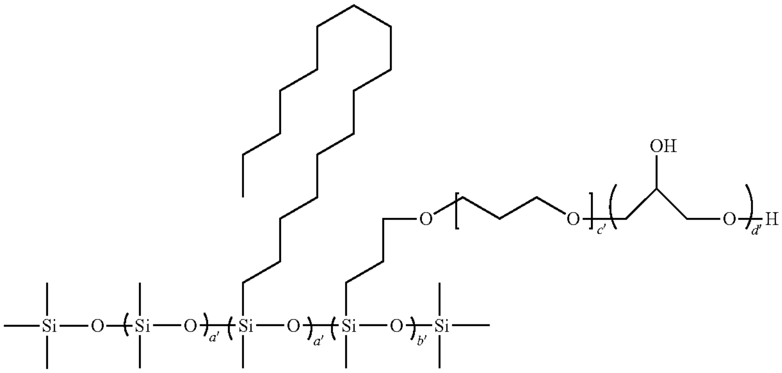

-continued
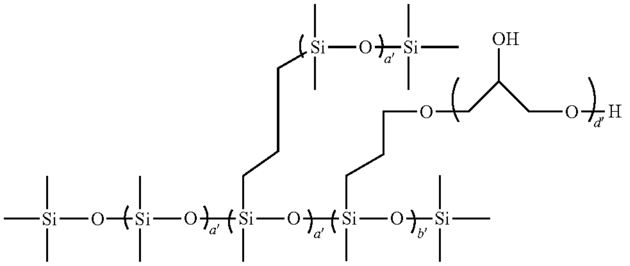
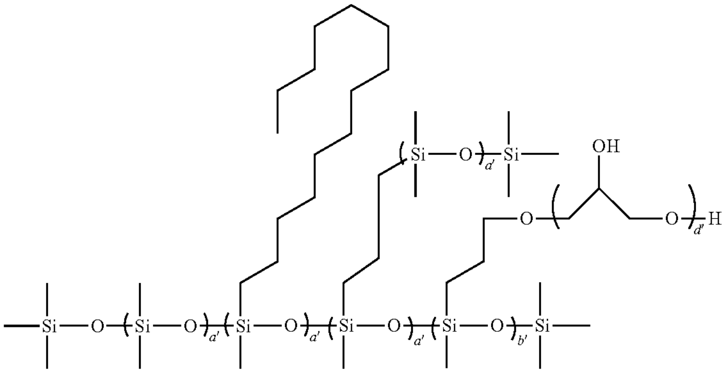
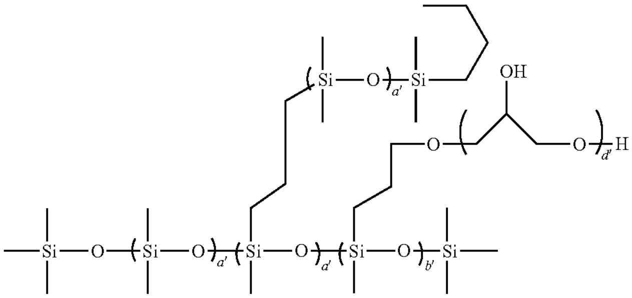
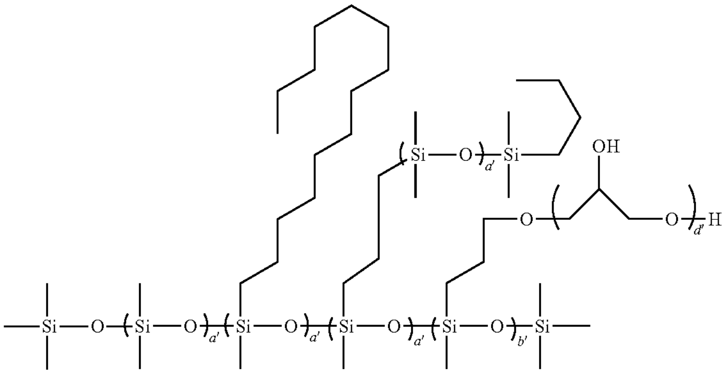
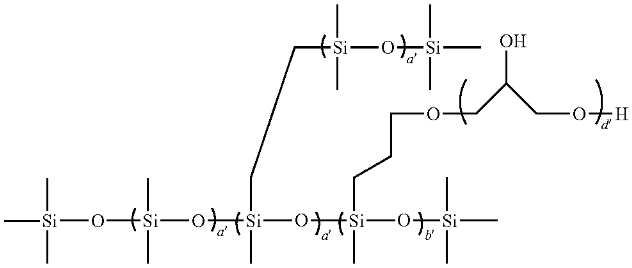

-continued
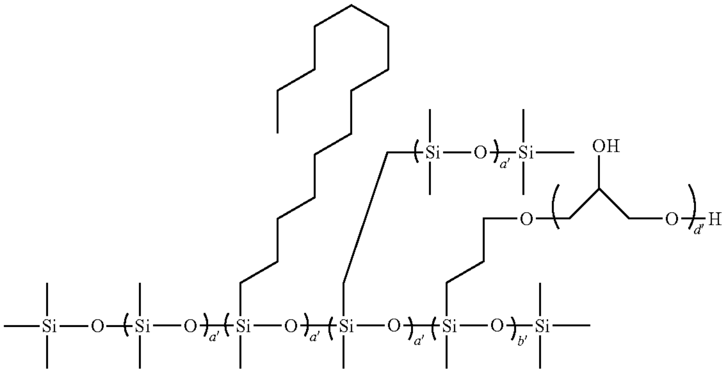
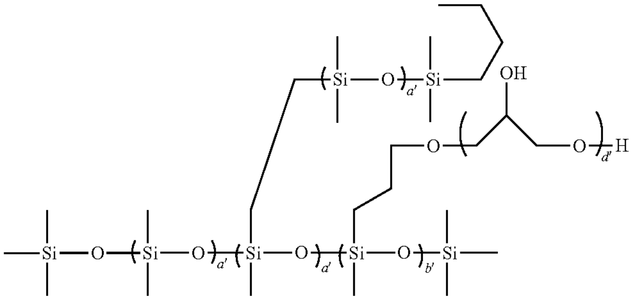
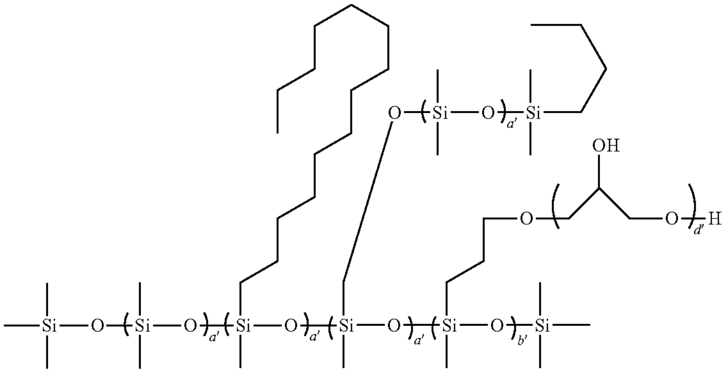
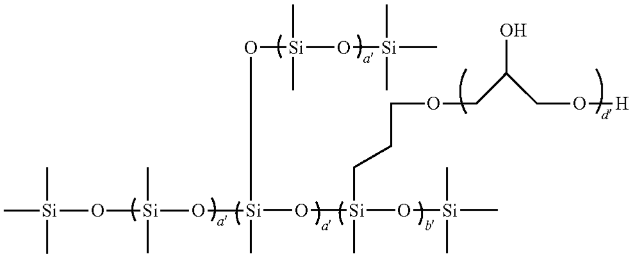
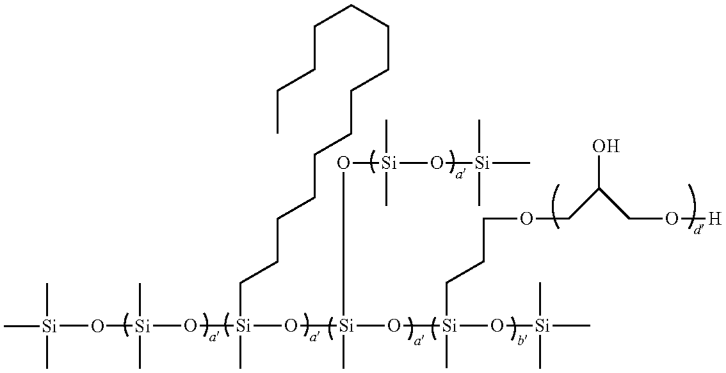

-continued
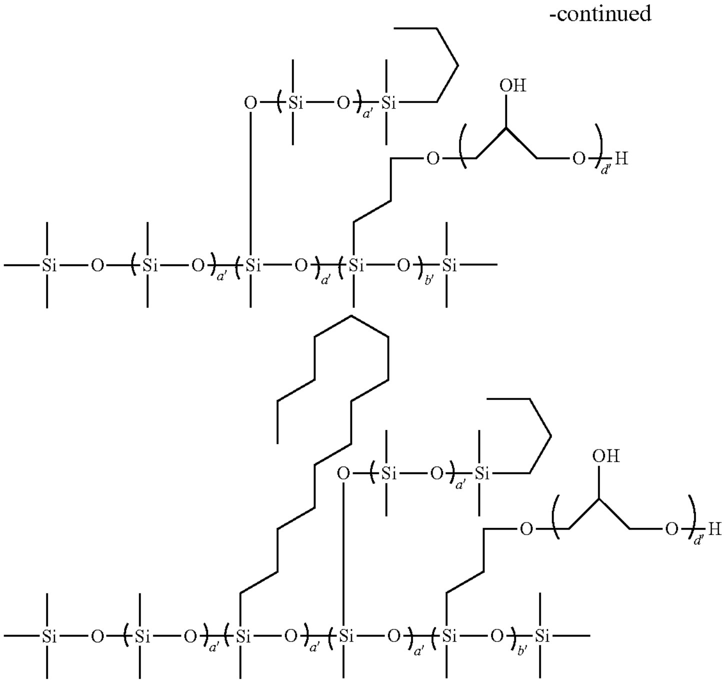
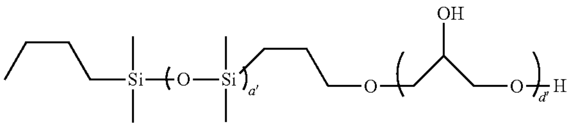
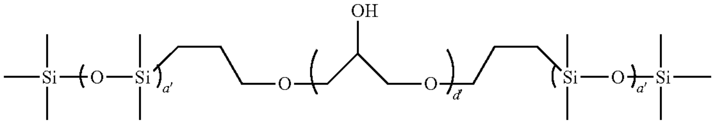
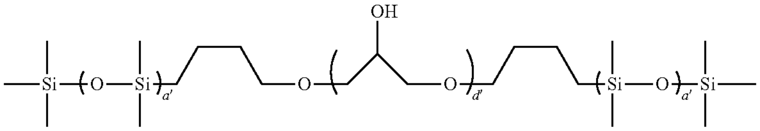
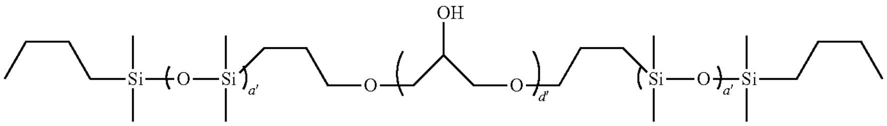
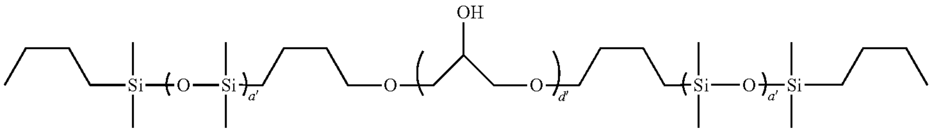
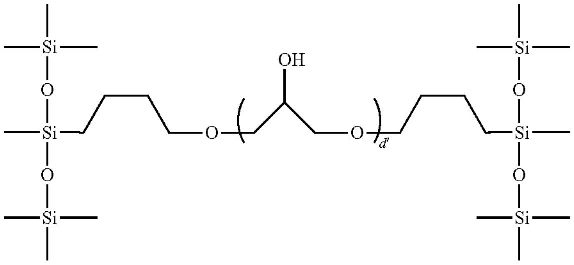

-continued

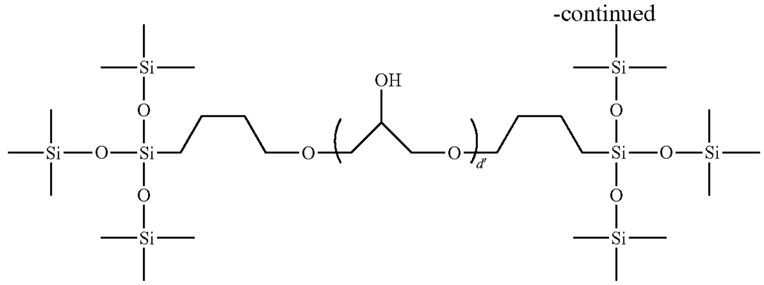

In the formulae, a', b', c', and d' are as defined above.

When such a silicone compound having a polyglycerin structure is incorporated, the resulting bio-electrode composition is capable of forming a living body contact layer that can exhibit more excellent moisture-holding property and consequently exhibit more excellent sensitivity to ions released from skin.

As has been described above, the inventive bio-electrode composition makes it possible to form a living body contact layer for a bio-electrode that is capable of efficiently conducting electric signals from skin to a device (i.e., excellent in electric conductivity), free from a risk of causing allergies even when the bio-electrode is attached to skin for a long period (i.e., excellent in biocompatibility), light-weight, manufacturable at low cost, and free from significant reduction in the electric conductivity even when the bio-electrode is wetted with water or dried. Moreover, it is possible to further enhance the electric conductivity by adding electro-conductive powder (carbon powder, metal powder), and it is possible to manufacture a bio-electrode with particularly high adhesive strength and high stretchability by combining the inventive bio-electrode composition with a resin having adhesion and stretchability. Further, the stretchability and adhesion to skin can be enhanced with an additive and so forth. The stretchability and adhesion can also be controlled by appropriately adjusting the composition of the resin and the thickness of the living body contact layer.

<Bio-Electrode>

The present invention also provides a bio-electrode including an electro-conductive base material and a living body contact layer formed on the electro-conductive base material, the living body contact layer being a cured product of the inventive bio-electrode composition described above.

Hereinafter, the inventive bio-electrode will be described in detail with reference to the drawings, but the present invention is not limited thereto.

FIG. 1 is a schematic sectional view showing an example of the inventive bio-electrode. In FIG. 1, a bio-electrode 1 has an electro-conductive base material 2 and a living body contact layer 3 formed on the electro-conductive base material 2. The living body contact layer 3 is formed from a cured product of the inventive bio-electrode composition. The living body contact layer 3 is constituted of an ion monomer-composite carbon particle 4 that is a reaction composite of a monomer having an ionic functional group and a carbon particle (e.g., the above-described carbon powder modified with an ion monomer). The living body contact layer 3 can further contain an adhesive resin 6 and an ionic polymer 5 other than the ion monomer-composite carbon particle 4. Hereinbelow, with reference to FIGS. 1 and 2, the living body contact layer 3 is described as a layer in which the ion monomer-composite carbon particle 4 and the ionic polymer 5 are dispersed in the adhesive resin 6. Nevertheless, the inventive bio-electrode is not limited to this embodiment.

When the bio-electrode 1 as shown in FIG. 1 is used, the living body contact layer 3 (i.e., the layer in which the ion monomer-composite carbon particle 4 and the ionic polymer 5 are dispersed in the adhesive resin 6) is brought into contact with a living body 7 as shown in FIG. 2. Electric signals are picked from the living body 7 through the ion monomer-composite carbon particle 4 and the ionic polymer 5, and then conducted to a sensor device or the like (not shown) via the electro-conductive base material 2. As described above, the inventive bio-electrode is capable of coping with both electric conductivity and biocompatibility by using the ion monomer-composite carbon particle 4 described above, and obtaining electric signals from skin stably in high sensitivity because the contact area with the skin is kept constant due to the adhesion thereof.

Hereinafter, each component of the inventive bio-electrode will be described more specifically.

[Electro-Conductive Base Material]

The inventive bio-electrode has an electro-conductive base material. This electro-conductive base material is usually connected electrically with a sensor device etc., and conducts electrical signals picked from a living body through the living body contact layer to the sensor device etc.

The electro-conductive base material is not particularly limited, as long as it has electric conductivity. The electro-conductive base material preferably contains one or more selected from the group consisting of gold, silver, silver chloride, platinum, aluminum, magnesium, tin, tungsten, iron, copper, nickel, stainless steel, chromium, titanium, carbon, and electro-conductive polymer, for example.

The electro-conductive base material may be a hard electro-conductive substrate, an electro-conductive film having flexibility, a cloth with the surface being coated with electro-conductive paste, a cloth into which electro-conductive polymer is kneaded, or the like without being limited to particular substrates. The electro-conductive base material may be flat, uneven, or mesh-form of woven metal wires, which can be appropriately selected in accordance with the use of the bio-electrode, and so forth.

[Living Body Contact Layer]

The inventive bio-electrode has a living body contact layer formed on the electro-conductive base material. This living body contact layer is a part to be actually in contact with a living body when using the bio-electrode. The living body contact layer has electric conductivity and adhesion. The living body contact layer is a cured product of the inventive bio-electrode composition described above; that is, an adherent resin layer formed from a cured composition containing: the component (A); and as necessary the component (B), the component (C), the component (D), the component (E), and the other component(s) (F).

The living body contact layer preferably has an adhesive strength in a range of 0.5 N/25 mm or more and 20 N/25 mm or less. The adhesive strength is commonly measured by the method described in JIS Z 0237, in which a metal substrate such as a stainless steel (SUS) substrate or a polyethylene terephthalate (PET) substrate can be used as a base material. Alternatively, human skin can be used for measuring. Human skin has lower surface energy than metals and various plastics, and the energy is as low as that of Teflon (registered trademark). Human skin is hard to adhere.

The living body contact layer of the bio-electrode has a thickness of preferably 1 μm or more and 5 mm or less, more preferably 2 μm or more and 3 mm or less. As the living body contact layer is thinner, the adhesive strength lowers, but the flexibility is improved, the weight decreases and the compatibility with skin is improved. The thickness of the living body contact layer can be selected based on the balance of adhesion and texture to the skin.

The inventive bio-electrode may be additionally provided with an adherent film on the living body contact layer as in conventional bio-electrodes (e.g., the bio-electrode described in JP 2004-033468A) in order to prevent peeling off of the bio-electrode from a living body during the use. When the adherent film is provided separately, the adherent film may be formed by using a raw material for the adherent film such as an acrylic type, a urethane type, and a silicone type. Particularly, the silicone type is suitable because of: the high oxygen permeability, which enables dermal respiration while the electrode is attached to the skin; the high water repellency, which suppresses lowering of adhesion due to perspiration; and the low irritation to skin. It is to be noted that the inventive bio-electrode does not necessarily require this adherent film that is provided separately, because peeling off from a living body can be prevented by adding a tackifier to the bio-electrode composition or using a resin having good adhesion to a living body as described above.

When the inventive bio-electrode is used as a wearable device, wiring between the bio-electrode and a sensor device, and other components are not limited to particular ones. For example, it is possible to employ ones described in JP 2004-033468A.

As described above, since the inventive bio-electrode includes the living body contact layer formed from the cured product of the aforementioned inventive bio-electrode composition, the inventive bio-electrode is capable of efficiently conducting electric signals from skin to a device (i.e., excellent in electric conductivity), does not cause allergies even after long-period attachment to skin (i.e., excellent in biocompatibility), is light-weight and manufacturable at low cost, and prevents significant reduction in the electric conductivity even when wetted with water or dried. In addition, it is possible to further improve the electric conductivity by adding an electro-conductive powder, and it is possible to manufacture a bio-electrode with particularly high adhesive strength and high stretchability by combining the inventive bio-electrode composition with a resin having adhesion and stretchability. Further, the stretchability and adhesion to skin can be improved with an additive and so forth. The stretchability and adhesion can also be controlled by appropriately adjusting the composition of the resin and the thickness of the living body contact layer. Accordingly, the inventive bio-electrode as described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, the method including:

applying the inventive bio-electrode composition onto the electro-conductive base material; and curing the bio-electrode composition to form the living body contact layer.

Note that the electro-conductive base material etc. used in the inventive method for manufacturing a bio-electrode may be the same as those described above.

The method for applying the bio-electrode composition onto the electro-conductive base material is not particularly limited. Examples of the suitable method include dip coating, spray coating, spin coating, roll coating, flow coating, doctor coating, screen printing, flexographic printing, gravure printing, inkjet printing, etc.

The method for curing the resin is not particularly limited and can be appropriately selected based on the kind of the components (A) and (B) used for the bio-electrode composition. For example, the bio-electrode composition is preferably cured by either or both of heat and light. The foregoing bio-electrode composition can also be cured by adding a catalyst in advance to generate acid or base to the bio-electrode composition, which causes a crosslinking reaction.

The heating temperature is not particularly limited and may be appropriately selected based on the kind of the components (A) and (B) used for the bio-electrode composition, but is preferably about 50 to 250° C., for example.

When the heating and light irradiation are combined, it is possible to perform the heating and the light irradiation simultaneously, to perform the light irradiation and then the heating, or to perform the heating and then the light irradiation. It is also possible to perform air-drying to evaporate the solvent before heating the coating film.

Water droplets may be attached to the surface of the cured film; alternatively, the film surface may be sprayed with water vapor or mist. These treatments improve the compatibility with skin, and enable quick collection of biological signals. Water mixed with alcohol can be used to reduce size of water droplets in water vapor or mist. The film surface may be wetted by bringing an absorbent cotton or cloth containing water into contact therewith.

The water for making the surface of the cured film wet may contain a salt. The water-soluble salt mixed with the water is selected from the group consisting of sodium salts, potassium salts, calcium salts, magnesium salts, and betaines.

Specifically, the water-soluble salt can be a salt selected from the group consisting of sodium chloride, potassium chloride, calcium chloride, magnesium chloride, saccharin sodium salt, acesulfame potassium, sodium carboxylate, potassium carboxylate, calcium carboxylate, sodium sulfonate, potassium sulfonate, calcium sulfonate, sodium phosphate, potassium phosphate, calcium phosphate, magnesium phosphate, and betaines. It should be noted that the components (A) and (C) described above are excluded from the water-soluble salt.

More specific examples of the water-soluble salt include, besides the aforementioned examples, sodium acetate, sodium propionate, sodium pivalate, sodium glycolate, sodium butyrate, sodium valerate, sodium caproate, sodium enanthate, sodium caprylate, sodium pelargonate, sodium caprate, sodium undecylate, sodium laurate, sodium tridecylate, sodium myristate, sodium pentadecylate, sodium palmitate, sodium margarate, sodium stearate, sodium benzoate, disodium adipate, disodium maleate, disodium phthalate, sodium 2-hydroxybutyrate, sodium 3-hydroxybutyrate, sodium 2-oxobutyrate, sodium gluconate, sodium methanesulfonate, sodium 1-nonanesulfonate, sodium 1-decanesulfonate, sodium 1-dodecanesulfonate, sodium 1-undecanesulfonate, sodium cocoyl isethionate, sodium lauroyl methylalanine, sodium methyl cocoyl taurate, sodium cocoyl glutamate, sodium cocoyl sarcosinate, sodium lauroyl methyl taurate, lauramidopropyl betaine, potassium isobutyrate, potassium propionate, potassium pivalate, potassium glycolate, potassium gluconate, potassium methanesulfonate, calcium stearate, calcium glycolate, calcium gluconate, calcium 3-methyl-2-oxobutyrate, and calcium methanesulfonate. The term betaines is a general term for inner salts. Specific examples thereof include amino acid compounds in each of which three methyl groups are added to an amino group. More specific examples include trimethylglycine, carnitine, and proline betaines.

The water for wetting the surface of the cured film can further contain a monohydric alcohol or polyhydric alcohol having 1 to 4 carbon atoms. The alcohol is preferably selected from the group consisting of ethanol, isopropyl alcohol, ethylene glycol, diethylene glycol, triethylene glycol, glycerin, polyethylene glycol, polypropylene glycol, polyglycerin, diglycerin, and a silicone compound having a polyglycerin structure. More preferably, the silicone compound having a polyglycerin structure is shown by the general formula (4)' or (5)'.

In the pretreatment methods with the aqueous solution containing the water-soluble salt, the cured bio-electrode film can be wetted by a spraying method, a droplet-dispensing method, etc. The bio-electrode film can also be wetted under a high-temperature, high-humidity condition like sauna. To prevent drying after the wetting, a protective film can be further stacked on the permeated layer to cover the surface. Since the protective film needs to be removed immediately before the bio-electrode is attached to skin, the protective film may be coated with a release agent, or a peelable Teflon (registered trademark) film may be used as the protective film. For long-time storage, the dry electrode covered with the peelable film is preferably sealed in a bag that is covered with aluminum etc. To prevent drying in the bag covered with aluminum, it is preferable to include water therein, too.

Before the inventive bio-electrode is attached to skin, the skin may be moisturized with water, alcohol, etc., or the skin may be wiped with a cloth or absorbent cotton containing water, alcohol, etc. The water and the alcohol may contain the above-described salts.

As has been described above, the inventive method for manufacturing a bio-electrode makes it possible to manufacture the inventive bio-electrode easily and at low cost, with the bio-electrode being excellent in electric conductivity and biocompatibility, light-weight, and capable of preventing significant reduction in the electric conductivity even when wetted with water or dried.

EXAMPLE

Hereinafter, the present invention will be specifically described with reference to Examples and Comparative Examples, but the present invention is not limited thereto. Incidentally, "Me" represents a methyl group, and "Vi" represents a vinyl group.

(Ionic Monomer)

Ionic monomers 1 to 14 used in Examples are shown below.

Ionic monomer 1

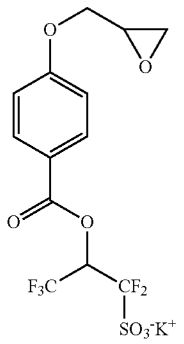

Ionic monomer 2

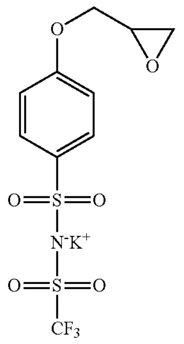

Ionic monomer 3

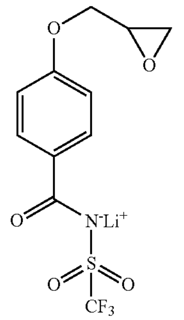

Ionic monomer 4

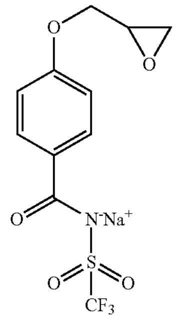

-continued

Ionic monomer 5

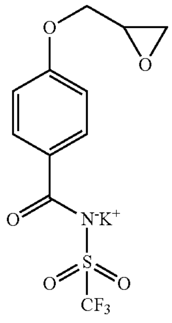

Ionic monomer 6

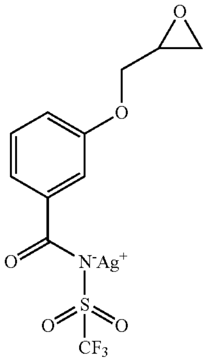

Ionic monomer 7

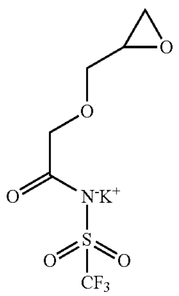

Ionic monomer 8

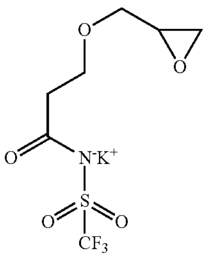

Ionic monomer 9

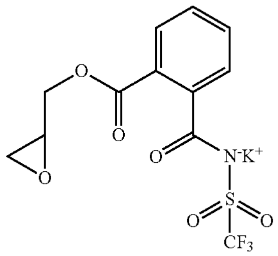

-continued

Ionic monomer 10

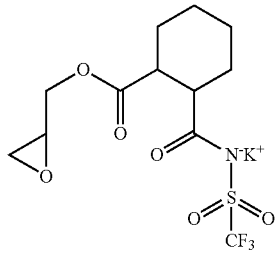

Ionic monomer 11

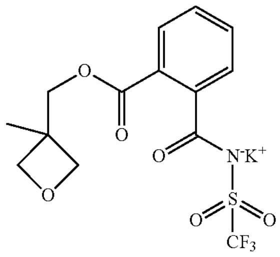

Ionic monomer 12

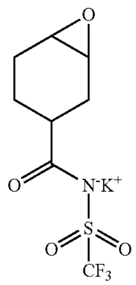

Ionic monomer 13

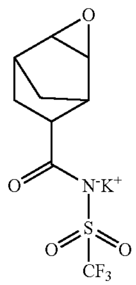

Ionic monomer 14

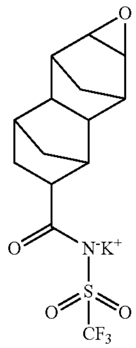

(Composite Carbon Particles)

Into 100 g of methyl isobutyl ketone (MIBK), 0.2 g of pyridine and 5 g of carbon black: DENKA BLACK Li-400 manufactured by Denka Co., Ltd. were added and stirred. Into the mixture, 1 g of Ionic monomer 1 was added dropwise and stirred at 60° C. for 20 hours. Then, the resultant was filtered, washed twice with a MIBK solution, and dried. Thus, Ionic monomer 1-composite carbon black was synthesized.

In the same way, Ionic monomer 2-composite carbon black to Ionic monomer 14-composite carbon black were synthesized.

Into 100 g of methyl isobutyl ketone (MIBK), 5 g of carboxylated multilayer carbon nanotube (manufactured by SIGMA-Aldrich Co., LLC., average diameter: 9.5 nm, average length: 1.5 μm) and 0.2 g of pyridine were added and stirred. Into the mixture, 1 g of Ionic monomer 5 was added dropwise and stirred at 60° C. for 20 hours. Then, the resultant was filtered, washed twice with a MIBK solution, and dried. Thus, Ionic monomer 5-composite multilayer carbon nanotube was synthesized.

Into 100 g of methyl isobutyl ketone (MIBK), 5 g of graphene oxide (manufactured by SIGMA-Aldrich Co., LLC.) and 0.2 g of pyridine were added and stirred. Into the mixture, 1 g of Ionic monomer 10 was added dropwise and stirred at 60° C. for 20 hours. Then, the resultant was filtered, washed twice with a MIBK solution, and dried. Thus, Ionic monomer 10-composite graphene oxide was synthesized.

Into 100 g of methyl isobutyl ketone (MIBK), 5 g of black lead (manufactured by SIGMA-Aldrich Co., LLC.) and 0.2 g of pyridine were added and stirred. Into the mixture, 1 g of Ionic monomer 10 was added dropwise and stirred at 60° C. for 20 hours. Then, the resultant was filtered, washed twice with a MIBK solution, and dried. Thus, Ionic monomer 10-composite black lead was synthesized.

(Ionic Polymer)

A solution of Ionic polymer 1, which was blended as a bio-electrode composition solution, was synthesized as follows. First, 20 mass % solutions of corresponding monomers in cyclopentanone were introduced into a reaction vessel and mixed. The reaction vessel was cooled to −70° C. under a nitrogen atmosphere, and subjected to vacuum degassing and nitrogen blowing, which were repeated three times. After the temperature was raised to room temperature, azobisisobutyronitrile (AIBN) was added thereto as a polymerization initiator in an amount of 0.01 moles per 1 mole of the whole monomers. The resultant was warmed to 60° C. and then allowed to react for 15 hours. The cyclopentanone was evaporated with an evaporator. After a portion of the polymer solution was dried, the composition of the resulting polymer was identified by 1H-NMR. The molecular weight (Mw) and the dispersity (Mw/Mn) of the obtained polymer were determined by gel permeation chromatography (GPC) using tetrahydrofuran (THF) as a solvent. Ionic polymer 1 is shown below.

Ionic Polymer 1

Mw=39, 100

Mw/Mn=1.91

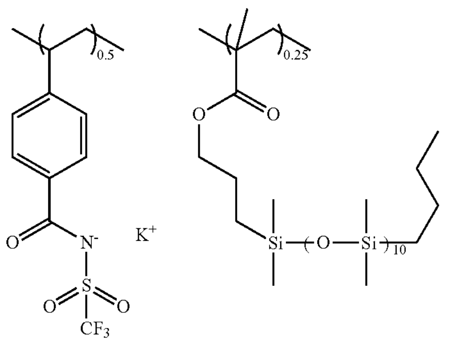

-continued

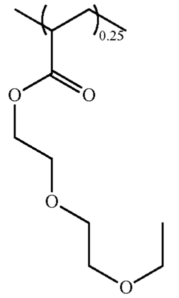

The repeating number in each formula shows the average value.

Ionic polymers 2 to 5 shown below were synthesized by the same method for synthesizing Ionic polymer 1.

Ionic Polymer 2

Mw=33, 300

Mw/Mn=1.83

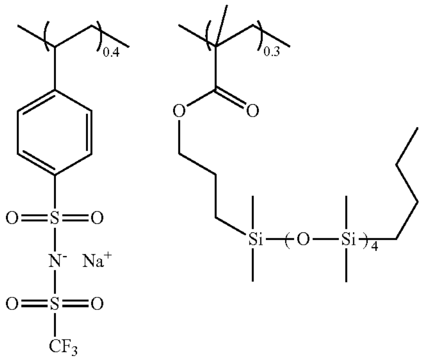

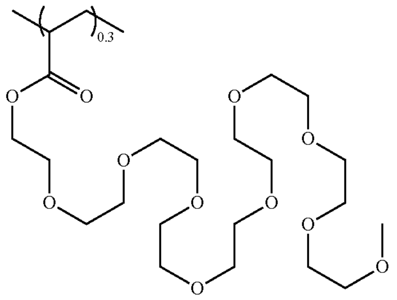

The repeating number in each formula shows the average value.

Ionic Polymer 3

Mw=87, 500

Mw/Mn=2.01

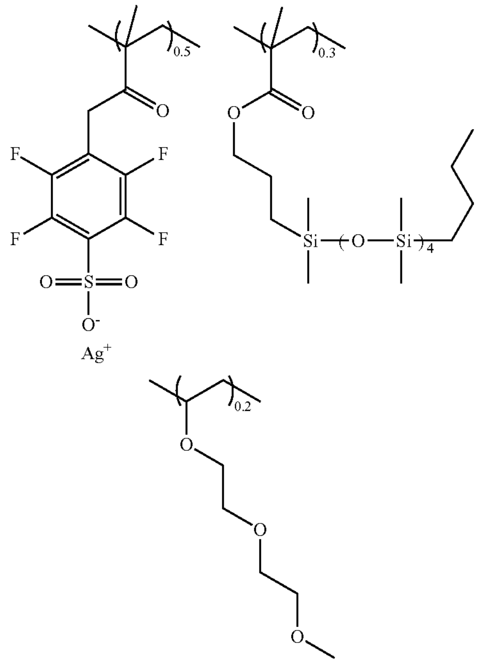

The repeating number in each formula shows the average value.

Ionic Polymer 4

Mw=36, 100

Mw/Mn=1.55

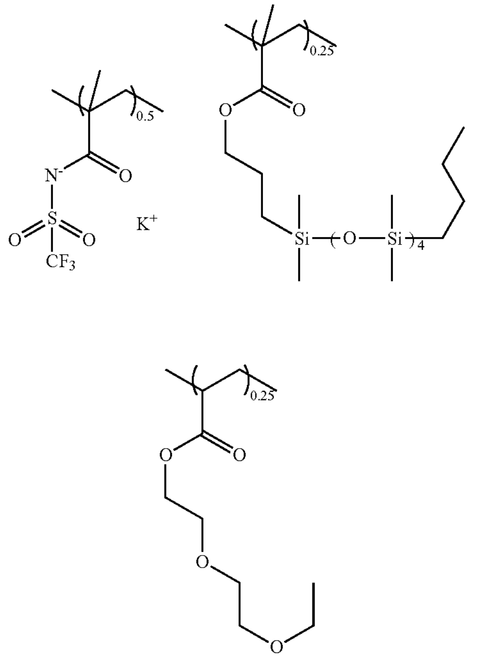

The repeating number in each formula shows the average value.

Ionic Polymer 5

Mw=38, 300

Mw/Mn=2.01

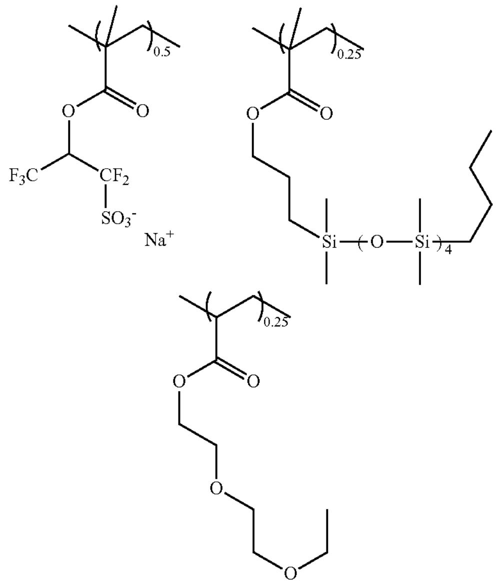

The repeating number in each formula shows the average value.

(Siloxane Compound)

Siloxane compounds 1 to 4, which were blended as silicone-based resin to the bio-electrode composition solutions, are shown below.

(Siloxane Compound 1)

Siloxane compound 1 was vinyl group-containing polydimethylsiloxane having an alkenyl group-content of 0.007 mol/100 g in which the terminals of molecular chain were capped with $SiMe_2Vi$ groups, with the 30% solution in toluene having a viscosity of 27,000 mPa-s.

(Siloxane Compound 2)

Siloxane compound 2 was a 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene.

(Siloxane Compound 3)

Siloxane compound 3 was polydimethylsiloxane-bonded MQ resin obtained by heating a solution (composed of 40 parts by mass of vinyl group-containing polydimethylsiloxane having an alkenyl group-content of 0.007 mol/100 g in which the terminals of molecular chain were capped with OH, with the 30% solution in toluene having a viscosity of 42,000 mPa-s; 100 parts by mass of 60% solution of polysiloxane of MQ resin composed of an $Me_3SiO_{0.5}$ unit and an $SiO_2$ unit ($Me_3SiO_{0.5}$ unit/$SiO_2$ unit=0.8) in toluene; and 26.7 parts by mass of toluene) with refluxing for 4 hours, followed by cooling.

(Siloxane Compound 4)

As methylhydrogensilicone oil, KF-99 manufactured by Shin-Etsu Chemical Co., Ltd. was used.

(Polyglycerin Silicone Compound)

Polyglycerin-silicone compounds (Polyglycerin compounds) 1 to 7 are shown below.

Polyglycerin-silicone compound 1
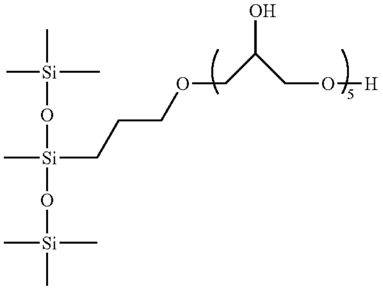
Polyglycerin-silicone compound 2
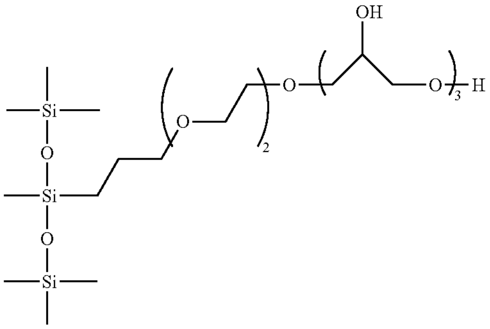
Polyglycerin-silicone compound 3
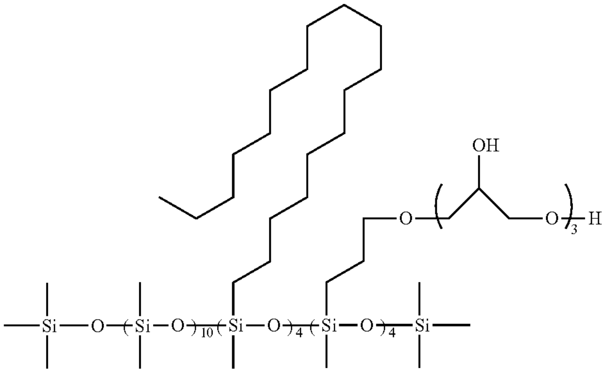
Polyglycerin-silicone compound 4
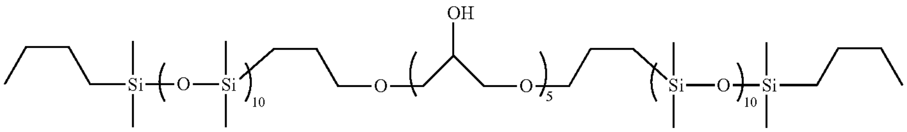
Polyglycerin-silicone compound 5
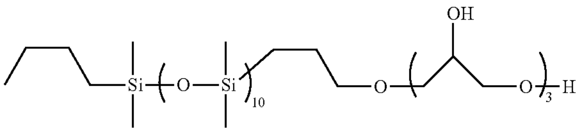
Polyglycerin-silicone compound 6
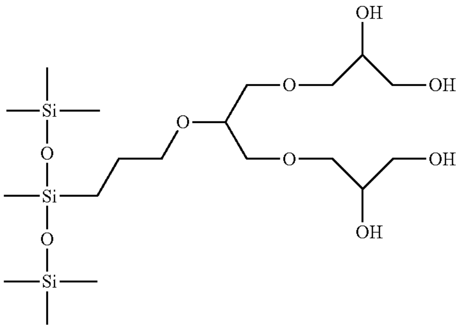

-continued

Polyglycerin-silicone compound 7

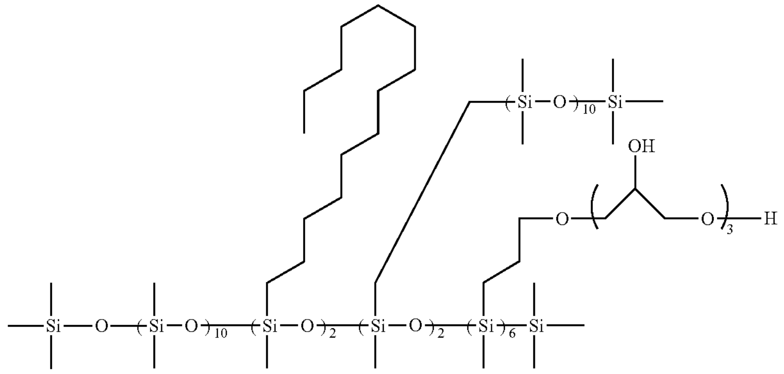

(Organic Solvent)

Organic solvents blended to the bio-electrode composition solutions are shown below.

ISOPAR G: isoparaffin base solvent manufactured by Standard Sekiyu CO., LTD.

ISOPAR M: isoparaffin base solvent manufactured by Standard Sekiyu CO., LTD.

(Additive)

Lithium titanate powder, platinum catalyst, and electric conductivity improver (carbon black, carbon nanotube, black lead, silver powder), which were blended as additives to the bio-electrode composition solutions, are shown below.

Metal powder: silver powder of silver flake with the diameter of 10 μm manufactured by Sigma-Aldrich Co., LLC.

Lithium titanate powder, spinel: with the size of 200 nm or less manufactured by Sigma-Aldrich Co., LLC.

Platinum catalyst: CAT-PL-50T manufactured by Shin-Etsu Chemical Co., Ltd.

Carbon black: DENKA BLACK Li-400 manufactured by Denka Co., Ltd.

Multilayer carbon nanotube: with the diameter of 110 to 170 nm and length of 5 to 9 μm manufactured by Sigma-Aldrich Co., LLC.

Black lead: with the diameter of 20 μm or less manufactured by Sigma-Aldrich Co., LLC.

Examples 1 to 17, Comparative Examples 1, 2

According to the compositions shown in Tables 1 to 3, the ionic monomer-composite carbon blacks, ionic monomer-composite multilayer carbon nanotube, ionic monomer-composite graphene oxide, ionic monomer-composite black lead, resins, ionic polymers, organic solvents, and additives (platinum catalyst, electric conductivity improver) were blended to prepare bio-electrode composition solutions (Bio-electrode composition solutions 1 to 17, Comparative bio-electrode composition solutions 1, 2).

TABLE 1

| Bio-electrode composition solution | Ionic monomer-composite carbon particle (parts by mass) | Resin (parts by mass) | Ionic polymer (parts by mass) | Organic solvent (parts by mass) | Additive (parts by mass) |
|---|---|---|---|---|---|
| Bio-electrode composition solution 1 | Ionic monomer 1-composite carbon black (20) | Siloxane compound 1(40) Siloxane compound 2(100) Siloxane compound 4(3) | — | ISOPAR G (100) | CAT-PL-50T(0.7) lithium titanate powder(12) silver flake(8) 1-ethynyl cyclohexanol(2) |
| Bio-electrode composition solution 2 | Ionic monomer 2-composite carbon black (10) | Siloxane compound 3(126) Siloxane compound 4(3) | Ionic polymer 1 (10) | n-octane(40) n-decane(20) cyclopentanone(70) | CAT-PL-50T(1.5) carbon black(5) 1-ethynyl cyclohexanol(2) |
| Bio-electrode composition solution 3 | Ionic monomer 3-composite carbon black (10) | Siloxane compound 3(126) Siloxane compound 4(3) | Ionic polymer 2 (10) | n-nonane(60) cyclopentanone(70) | CAT-PL-50T(1.5) carbon black(5) 1-ethynyl cyclohexanol(2) |
| Bio-electrode composition solution 4 | Ionic monomer 4-composite carbon black (12) | Siloxane compound 3(126) Siloxane compound 4(3) | Ionic polymer 3 (10) | ISOPAR G(60) cyclopentanone(70) | CAT-PL-50T(1.5) carbon black(6) 1-ethynyl cyclohexanol(2) |
| Bio-electrode composition solution 5 | Ionic monomer 5-composite carbon black (15) | Siloxane compound 3(126) Siloxane compound 4(3) | Ionic polymer 4 (10) | n-decane(30) n-octane(30) cyclopentanone(70) | CAT-PL-50T(1.5) 1-ethynyl cyclohexanol(2) |
| Bio-electrode composition solution 6 | Ionic monomer 6-composite carbon black (10) | Siloxane compound 3(126) Siloxane compound 4(3) | Ionic polymer 5 (10) | ISOPAR G(60) cyclopentanone(70) | CAT-PL-50T(1.5) multilayer carbon nanotube(3) 1-ethynyl cyclohexanol(2) |

TABLE 1-continued

| Bio-electrode composition solution | Ionic monomer-composite carbon particle (parts by mass) | Resin (parts by mass) | Ionic polymer (parts by mass) | Organic solvent (parts by mass) | Additive (parts by mass) |
|---|---|---|---|---|---|
| Bio-electrode composition solution 7 | Ionic monomer 7-composite carbon black (10) | Siloxane compound 3(126) Siloxane compound 4(3) | Ionic polymer 1 (10) | ISOPAR M(60) cyclopentanone(70) | CAT-PL-50T(1.5) carbon black(6) 1-ethynyl cyclohexanol(2) |

TABLE 2

| Bio-electrode composition solution | Ionic monomer-composite carbon particle (parts by mass) | Resin (parts by mass) | Ionic polymer (parts by mass) | Organic solvent (parts by mass) | Additive (parts by mass) |
|---|---|---|---|---|---|
| Bio-electrode composition solution 8 | Ionic monomer 8-composite carbon black (10) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 1(5) carbon black(6) 1-ethynyl cyclohexanol(2) |
| Bio-electrode composition solution 9 | Ionic monomer 9-composite carbon black (10) | Siloxane compound 3(126) Siloxane compound 4(3) | Ionic polymer 1 (10) | n-decane(30) n-octane(30) cyclo-pentanone(70) | CAT-PL-50T (1.5) Polyglycerin compound 2(5) carbon black(6) 1-ethynyl cyclohexanol(2) |
| Bio-electrode composition solution 10 | Ionic monomer 10-composite carbon black (10) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 3(5) carbon black(6) 1-ethynyl cyclohexanol(2) |
| Bio-electrode composition solution 11 | Ionic monomer 11-composite carbon black (8) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 4(5) carbon black(6) 1-ethynyl cyclohexanol(2) |
| Bio-electrode composition solution 12 | Ionic monomer 12-composite carbon black (10) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 5(5) 1-ethynyl cyclohexanol(2) |
| Bio-electrode composition solution 13 | Ionic monomer 13-composite carbon black (10) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 5(5) 1-ethynyl cyclohexanol(2) |
| Bio-electrode composition solution 14 | Ionic monomer 14-composite carbon black (10) | Siloxane compound 3(126) Siloxane compound 4(3) | Ionic polymer 1 (10) | n-decane(30) n-octane(30) cyclo-pentanone(70) | CAT-PL-50T(1.5) Polyglycerin compound 5(5) 1-ethynyl cyclohexanol(2) |
| Bio-electrode composition solution 15 | Ionic monomer 5-composite multilayer carbon nanotube (10) | Siloxane compound 3(126) Siloxane compound 4(3) | Ionic polymer 1 (10) | n-decane(30) n-octane(30) cyclo-pentanone(70) | CAT-PL-50T(1 .5) Polyglycerin compound 6(5) 1-ethynyl cyclohexanol(2) |
| Bio-electrode composition solution 16 | Ionic monomer 10-composite graphene oxide (15) | Siloxane compound 3(126) Siloxane compound 4(3) | — | n-decane(30) n-octane(30) cyclo-pentanone(70) | CAT-PL-50T(1.5) Polyglycerin compound 7(5) carbon black(4) 1-ethynyl cyclohexanol(2) |
| Bio-electrode composition solution 17 | Ionic monomer 10-composite black lead (15) | Siloxane compound 3(126) Siloxane compound 4(3) | — | n-decane(30) n-octane(30) cyclo-pentanone(70) | CAT-PL-50T(1.5) black lead (8) 1-ethynyl cyclohexanol(2) |

TABLE 3

| Bio-electrode composition solution | Ionic monomer-composite carbon particle (parts by mass) | Resin (parts by mass) | Ionic polymer (parts by mass) | Organic solvent (parts by mass) | Additive (parts by mass) |
|---|---|---|---|---|---|
| Comparative bio-electrode composition solution 1 | — | Siloxane compound 1(40) Siloxane compound 2 (100) Siloxane compound 4(3) | — | ISOPAR G(60) cyclo-pentanone(70) | CAT-PL-50T(1.5) carbon black(25) |
| Comparative bio-electrode composition solution 2 | — | Siloxane compound 1(40) Siloxane compound 2(100) Siloxane compound 4(3) | Ionic polymer 1 (20) | ISOPAR G(60) cyclo-pentanone(70) | CAT-PL-50T(1.5) carbon black(14) |

(Preparation of Bio-Electrodes)

As shown in FIG. 3, a thermoplastic urethane (TPU) film ST-604 (manufactured by Bemis Associates Inc.) designated by 20 was coated with an electro-conductive paste DOTITE FA-333 (manufactured by Fujikura Kasei Co., Ltd.) by screen printing. The coating film was baked in an oven at 120° C. for 10 minutes to print a keyhole-shaped electro-conductive pattern 2 including a circular portion with a diameter of 2 cm. Then, one of the bio-electrode composition solutions shown in Tables 1 to 3 was applied onto the circular portion by screen printing. After air-dried at room temperature for 10 minutes, the coating film was baked using an oven at 125° C. for 20 minutes to evaporate the solvent and form a living body contact layer 3 by curing. In this manner, bio-electrodes 1 were prepared. Next, as shown in FIG. 4, the urethane film having the bio-electrode 1 printed thereon was cut out and pasted on a double-sided tape 21. In this manner, three bio-electrode samples 10 were prepared for each of the composition solutions.

(Thickness Measurement of Living Body Contact Layer)

The thickness of the living body contact layer of each bio-electrode prepared as described above was measured with a micrometer. Table 4 shows the result.

(Biological Signal Measurement)

The electro-conductive wiring pattern formed from the electro-conductive paste of each bio-electrode sample was connected to a portable electrocardiograph HCG-901 (manufactured by OMRON HEALTHCARE Co., Ltd.) through an electro-conductive wire. A positive electrode of the electrocardiograph was attached to the location LA in FIG. 5 on a human body, a negative electrode was attached to the location LL, and an earth was attached to the location RA. Immediately after the attachments, the electrocardiogram measurement was started to measure the time until an electrocardiogram waveform including P, Q, R, S, and T waves appeared as shown in FIG. 6. Table 4 shows the result.

TABLE 4

| | Bio-electrode composition solution | Resin thickness (μm) | Time (min.) until ECG signal appeared |
|---|---|---|---|
| Example 1 | Bio-electrode composition solution 1 | 31 | 5 |
| Example 2 | Bio-electrode composition solution 2 | 31 | 2.5 |
| Example 3 | Bio-electrode composition solution 3 | 35 | 2.5 |
| Example 4 | Bio-electrode composition solution 4 | 34 | 2.3 |
| Example 5 | Bio-electrode composition solution 5 | 39 | 3.1 |
| Example 6 | Bio-electrode composition solution 6 | 36 | 2.4 |
| Example 7 | Bio-electrode composition solution 7 | 32 | 2.5 |
| Example 8 | Bio-electrode composition solution 8 | 34 | 1.2 |
| Example 9 | Bio-electrode composition solution 9 | 39 | 1.3 |
| Example 10 | Bio-electrode composition solution 10 | 43 | 1.2 |
| Example 11 | Bio-electrode composition solution 11 | 42 | 1.4 |
| Example 12 | Bio-electrode composition solution 12 | 32 | 1.5 |
| Example 13 | Bio-electrode composition solution 13 | 30 | 1.5 |
| Example 14 | Bio-electrode composition solution 14 | 29 | 1.6 |
| Example 15 | Bio-electrode composition solution 15 | 36 | 1.2 |
| Example 16 | Bio-electrode composition solution 16 | 37 | 1.3 |
| Example 17 | Bio-electrode composition solution 17 | 38 | 1.5 |
| Comparative Example 1 | Comparative bio-electrode composition solution 1 | 35 | not appeared |
| Comparative Example 9 | Comparative bio-electrode composition solution 2 | 34 | 30 |

As shown in Table 4, biological signals were detected within short times after the attachment to the body in Examples 1 to 17, in which the living body contact layers were each formed using the inventive bio-electrode composition including the composite of an ion monomer and a carbon powder. In contrast, no biological signals were detected in Comparative Example 1 simply containing the carbon particles. In Comparative Example 2 merely containing the ionic polymer and the carbon particles, it took longer time for the biological signal to appear after the attachment to the skin.

It should be noted that the present invention is not limited to the above-described embodiments. The embodiments are just examples, and any examples that substantially have the same feature and demonstrate the same functions and effects as those in the technical concept disclosed in claims of the present invention are included in the technical scope of the present invention.

The invention claimed is:

1. A bio-electrode composition comprising (A) a reaction composite comprising a monomer having an ionic functional group and a carbon particle, wherein the component (A) comprises the carbon particle bonded to the monomer having a structure selected from the group consisting of salts of ammonium, lithium, sodium, potassium, and silver formed with any of fluorosulfonic acid, fluorosulfonimide, and N-carbonyl-fluorosulfonamide.

2. The bio-electrode composition according to claim 1, wherein the carbon particle is selected from the group consisting of carbon black, carbon nanotube, graphite (black lead), and graphene.

3. The bio-electrode composition according to claim 1, wherein the monomer having a structure selected from the group consisting of salts of ammonium, lithium, sodium, potassium, and silver formed with any of fluorosulfonic acid, fluorosulfonimide, and N-carbonyl-fluorosulfonamide comprises a structure shown by any of the following general formulae (1)-1 to (1)-4, (1)-1

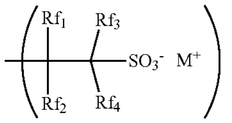

(1)-2

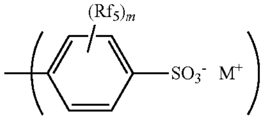

(1)-3

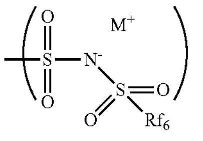

(1)-4

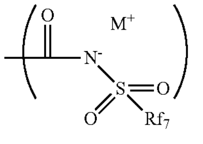

wherein $Rf_1$ and $Rf_2$ each represent a hydrogen atom, a fluorine atom, an oxygen atom, a methyl group, or a trifluoromethyl group, provided that when $Rf_1$ and $Rf_2$ represent an oxygen atom, the single oxygen atom represented by $Rf_1$ and $Rf_2$ bonds to a single carbon atom to form a carbonyl group; $Rf_3$ and $Rf_4$ each represent a hydrogen atom, a fluorine atom, or a trifluoromethyl group, provided that at least one of $Rf_1$ to $Rf_4$ is a fluorine atom or a trifluoromethyl group; $Rf_5$, $Rf_6$, and $Rf_7$ each represent a fluorine atom, or a linear or branched alkyl group having 1 to 4 carbon atoms, and have at least one fluorine atom; "m" represents an integer of 1 to 4; and $M^+$ represents an ion selected from the group consisting of an ammonium ion, a lithium ion, a sodium ion, a potassium ion, and a silver ion.

4. The bio-electrode composition according to claim 3, wherein the monomer having a structure selected from the group consisting of salts of ammonium, lithium, sodium, potassium, and silver formed with any of fluorosulfonic acid, fluorosulfonimide, and N-carbonyl-fluorosulfonamide is shown by any of the following general formulae (2)-1 to (2)-4, (2)-1

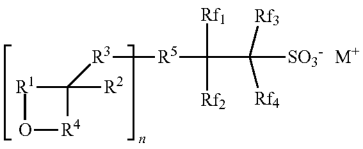

(2)-2

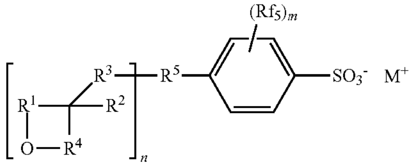

(2)-3

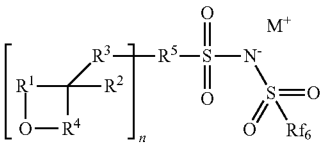

(2)-4

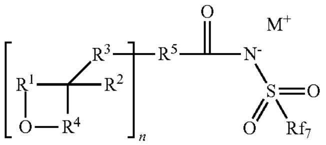

wherein $R^1$ represents an alkylene group having 1 to 8 carbon atoms, optionally bonded to $R^3$ to form a ring, and optionally having an ether group; $R^2$ represents a hydrogen atom, or an alkyl group having 1 to 4 carbon atoms; $R^3$ represents a single bond, or a linear, branched, or cyclic alkylene group having 1 to 20 carbon atoms, and optionally has an aromatic group, an ether bond, an ester bond, a hydroxy group, or a nitrogen atom; $R^4$ represents a single bond or a methylene group; $R^5$ represents a single bond, or a hydrocarbon group with a valency of (n+1) having 1 to 10 carbon atoms and optionally having an ether group or an ester group; "n" represents 1 or 2; and $Rf_1$ to $Rf_7$, $M^+$, and "m" are as defined above.

5. The bio-electrode composition according to claim 1, wherein the component (A) is a reaction product between 100 parts by mass of the carbon particle and 5 parts by mass or more of the monomer having an ionic functional group.

6. The bio-electrode composition according to claim 1, wherein the component (A) comprises an ammonium ion shown by the following general formula (3) as an ammonium ion for forming the ammonium salts, (3)

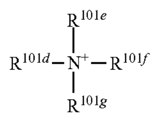

wherein $R^{101d}$, $R^{101e}$, $R^{101f}$, and $R^{101g}$ each represent a hydrogen atom, a linear, branched, or cyclic alkyl group having 1 to 13 carbon atoms, a linear, branched, or cyclic alkenyl group or alkynyl group having 2 to 12 carbon atoms, or an aromatic group having 4 to 20 carbon atoms, and optionally have one or more selected from the group consisting of an ether group, a carbonyl group, an ester group, a hydroxy group, an amino group, a nitro group, a sulfonyl group, a sulfinyl group, a halogen atom, and a sulfur atom; and $R^{101d}$ and $R^{101e}$, or $R^{101d}$, $R^{101e}$, and $R^{101f}$, are optionally bonded to each other together with a nitrogen atom bonded therewith to form a ring in which $R^{101d}$ and $R^{101e}$, or $R^{101d}$, $R^{101e}$, and $R^{101f}$, represent an alkylene group having 3 to 10 carbon atoms, or to form a heteroaromatic ring having the nitrogen atom in the formula within the ring.

7. The bio-electrode composition according to claim 1, further comprising a component (B) which is an adhesive resin.

8. The bio-electrode composition according to claim 7, wherein the component (B) is one or more selected from the group consisting of a silicone resin, a (meth)acrylate resin, and a urethane resin.

9. The bio-electrode composition according to claim 7, wherein the component (B) comprises diorganosiloxane having an alkenyl group, and organohydrogenpolysiloxane having an SiH group.

10. The bio-electrode composition according to claim 9, wherein the component (B) further comprises a silicone resin having an $SiO_2$ unit and an $R_xSiO_{(4-x)/2}$ unit, wherein R represents a substituted or unsubstituted monovalent hydrocarbon group having 1 to 10 carbon atoms, and "x" represents a number in a range of 2.5 to 3.5.

11. The bio-electrode composition according to claim 1, further comprising a component (C) which is a polymer compound having an ionic repeating unit.

12. The bio-electrode composition according to claim 11, wherein the ionic repeating unit of the component (C) comprises a repeating unit having a structure selected from the group consisting of salts of ammonium, lithium, sodium, potassium, and silver formed with any of fluorosulfonic acid, fluorosulfonimide, and N-carbonyl-fluorosulfonamide.

13. The bio-electrode composition according to claim 1, further comprising a component (D) which is a carbon powder and/or a metal powder.

14. The bio-electrode composition according to claim 13, wherein the carbon powder is one or both of carbon black and carbon nanotube.

15. The bio-electrode composition according to claim 13, wherein the metal powder is a powder of a metal selected from the group consisting of gold, silver, platinum, copper, tin, titanium, nickel, aluminum, tungsten, molybdenum, ruthenium, chromium, and indium.

16. The bio-electrode composition according to claim 15, wherein the metal powder is a silver powder.

17. The bio-electrode composition according to claim 1, further comprising a component (E) which is an organic solvent.

18. A bio-electrode comprising an electro-conductive base material and a living body contact layer formed on the electro-conductive base material, wherein the living body contact layer is a cured product of the bio-electrode composition according to claim 1.

19. The bio-electrode according to claim 18, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

20. A method for manufacturing a bio-electrode having an electro-conductive base material and a living body contact layer formed on the electro-conductive base material, comprising:

applying the bio-electrode composition according to claim 1 onto the electro-conductive base material; and curing the bio-electrode composition to form the living body contact layer.

21. The method for manufacturing a bio-electrode according to claim 20, wherein the electro-conductive base material comprises one or more selected from the group consisting of gold, silver, silver chloride, platinum, aluminum, magnesium, tin, tungsten, iron, copper, nickel, stainless steel, chromium, titanium, carbon, and electro-conductive polymer.

22. A reaction composite comprising a monomer having an ionic functional group and a carbon particle, wherein the reaction composite comprises the carbon particle bonded to the monomer having a structure selected from the group consisting of salts of ammonium, lithium, sodium, potassium, and silver formed with any of fluorosulfonic acid, fluorosulfonimide, and N-carbonyl-fluorosulfonamide.

23. The reaction composite according to claim 22, wherein the carbon particle is selected from the group consisting of carbon black, carbon nanotube, graphite (black lead), and graphene.

* * * * *